US010000753B2

(12) United States Patent
Suhy et al.

(10) Patent No.: US 10,000,753 B2
(45) Date of Patent: Jun. 19, 2018

(54) AGE-RELATED MACULAR DEGENERATION TREATMENT

(71) Applicant: Benitec Biopharma Limited, New South Wales (AU)

(72) Inventors: David Suhy, San Ramon, CA (US); Tin Mao, Castro Valley, CA (US); Shih-Chu Kao, Mountain View, CA (US)

(73) Assignee: BENITEC BIOPHARMA LIMITED, Balmain, New South Wales (AU)

( * ) Notice: Subject to any disclaimer, the term of this patent is extended or adjusted under 35 U.S.C. 154(b) by 0 days. days.

(21) Appl. No.: 14/759,401

(22) PCT Filed: Jan. 8, 2014

(86) PCT No.: PCT/AU2014/000007
§ 371 (c)(1),
(2) Date: Jul. 6, 2015

(87) PCT Pub. No.: WO2014/107763
PCT Pub. Date: Jul. 17, 2014

(65) Prior Publication Data
US 2016/0145611 A1    May 26, 2016

Related U.S. Application Data

(60) Provisional application No. 61/750,086, filed on Jan. 8, 2013.

(51) Int. Cl.
*C07H 21/02* (2006.01)
*C07H 21/04* (2006.01)
*C12N 15/113* (2010.01)

(52) U.S. Cl.
CPC ........ *C12N 15/113* (2013.01); *C12N 15/1136* (2013.01); *C12N 15/1137* (2013.01); *C12N 15/1138* (2013.01); *C12Y 304/21047* (2013.01); *C12N 2310/14* (2013.01); *C12N 2310/141* (2013.01); *C12N 2310/3519* (2013.01); *C12N 2310/531* (2013.01); *C12N 2330/51* (2013.01)

(58) Field of Classification Search
CPC .......................... C12N 15/113; C12N 2310/11
See application file for complete search history.

(56) References Cited

U.S. PATENT DOCUMENTS

| 7,939,505 | B2 * | 5/2011 | Quay | ................... | A61K 9/1272 |
| | | | | | 514/44 A |
| 8,282,921 | B2 * | 10/2012 | Glidden | ................ | A61K 38/53 |
| | | | | | 424/94.61 |
| 8,283,331 | B2 * | 10/2012 | Gregory | ................ | C12N 15/111 |
| | | | | | 514/44 A |

| 2009/0239816 | A1 | 9/2009 | Rivory et al. |
| 2012/0240245 | A1 | 9/2012 | Inana et al. |
| 2013/0029950 | A1 | 1/2013 | Bischoff et al. |

FOREIGN PATENT DOCUMENTS

| CN | 101437944 A | 5/2009 | |
| WO | WO 2004/009769 A2 | 1/2004 | |
| WO | WO 2005/087926 A2 | 9/2005 | |
| WO | WO 2006/084209 A2 | 8/2006 | |
| WO | WO 2006/116756 A1 | 11/2006 | |
| WO | WO 2007/056826 A1 * | 5/2007 | ........... C12N 15/113 |
| WO | WO 2007/067981 A2 | 6/2007 | |
| WO | WO 2010/065834 A1 | 6/2010 | |
| WO | WO 2012/015775 A2 | 2/2012 | |
| WO | WO 2013/126963 A1 | 9/2013 | |

OTHER PUBLICATIONS

Chang, et al. 2012 "Corneal neovascularization: An anti-VEGF therapy review" *Survey of Opthalmology* 57(5): 415-429.
McBride, et al. 2008 "Artificial miRNAs mitigate shRNA-mediated toxicity in the brain: Implications for the therapeutic development of RNAi" *Proceedings of the National Academy of Sciences* 105(15): 5868-5873.
Askou, A.L. et al., "Reduction of Choroidal Neovascularization in Mice by Adeno-Associated Virus-Delivered Anti-Vascular Endothelial Growth Factor Short Hairpin RNA," The Journal of Gene Medicine, 2012, pp. 632-641, vol. 14.
Cashman, S.M. et al., "Inhibition of Choroidal Neovascularization by Adenovirus-Mediated Delivery of Short Hairpin RNAs Targeting VEGF as a Potential Therapy for AMD," Investigative Ophthalmology & Visual Science, Aug. 2006, pp. 3496-3504, vol. 47, No. 6.
Chinese First Office Action, Chinese Application No. 201480010251.6, dated Jan. 11, 2017, 15 pages.
Chinese Second Office Action, Chinese Application No. 201480010251.6, dated Nov. 3, 2017, 17 pages.
European Partial Supplementary Search Report, European Application No. 14737958.0, dated Jul. 29, 2016, 7 pages.
European Extended Search Report, European Application No. 14737958.0, dated Nov. 3, 2016, 11 pages.
European Examination Report, European Application No. 14737958.0, dated Oct. 18, 2017, 7 pages.
Fang, A.M. et al., "Polymorphisms in the VEGFA and VEGFR-2 Genes and Neovascular Age-Related Macular Degeneration," Molecular Vision, 2009, pp. 2710-2719, vol. 15.
Pihlmann, M. et al., "Adeno-Associated Virus-Delivered Polycistronic MicroRNA-Clusters for Knockdown of Vascular Endothelial Growth Factor in Vivo," The Journal of Gene Medicine, 2012, pp. 328-338, vol. 14.

(Continued)

*Primary Examiner* — Amy H Bowman
(74) *Attorney, Agent, or Firm* — Fenwick & West LLP

(57) ABSTRACT

This invention is directed to an RNA interference (RNAi) agent and the use of that RNAi agent to treat Age-related Macular Degeneration, as well as pharmaceutical compositions containing the RNAi agents of the invention. The RNAi agent is a DNA-directed RNA interference (ddRNAi) agent (being an RNA molecule), together with an expression cassette or construct to express that agent in a cell (including in vivo), for inhibiting, preventing or reducing expression of an AMD associated gene. Preferably that AMD associated gene is one that is associated with wet AMD.

23 Claims, 68 Drawing Sheets

(56) References Cited

OTHER PUBLICATIONS

Figure 1E:
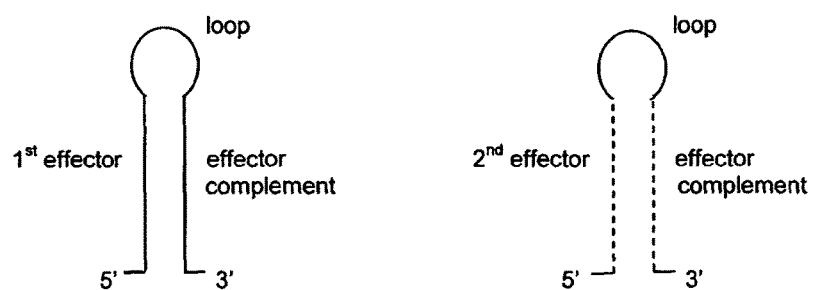

Yuan, M-K. et al., "Lentivirus-Mediated RNA Interference of Vascular Endothelial Growth Factor in Monkey Eyes with Iris Neovascularization," Molecular Vision, 2010, pp. 1743-1753, vol. 16.

Zhang, X. et al., "Recent Advance of the Study on Treatment for Age-Related Macular Degeneration," Int. J. Ophthalmol., 2007, pp. 1674-1674, vol. 7, No. 6.

Zhang, L. et al., "Vector-Based RNAi, a Novel Tool for Isoform-Specific Knock-Down of VEGF and Anti-Angiogenesis Gene Therapy of Cancer," Biochemical and Biophysical Research Communications, 2003, pp. 1169-1178, vol. 303.

PCT International Search Report and Written Opinion, PCT Application No. PCT/AU2014/000007, dated May 15, 2014, 48 pages.

* cited by examiner

Figure 1
Figure 1A
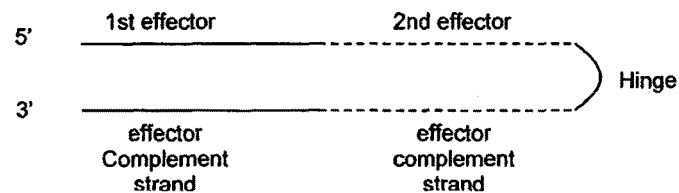
Figure 1B
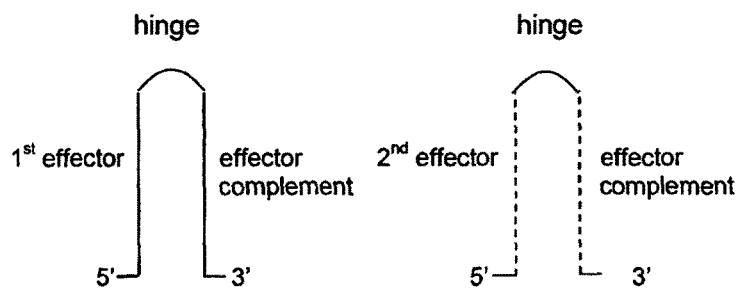
Figure 1C
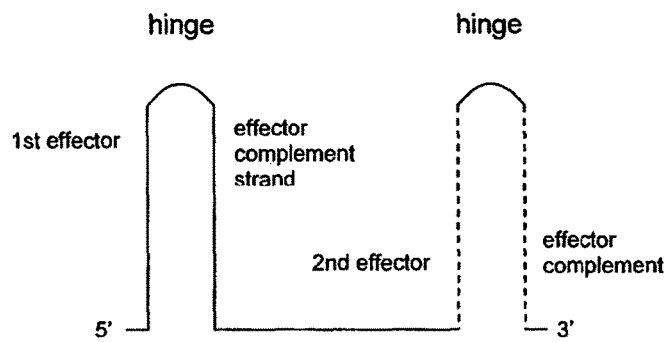
Figure 1D
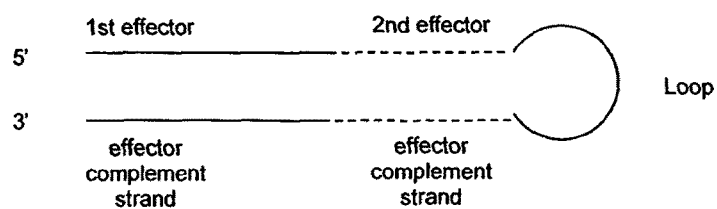

Figure 2
Figure 2A
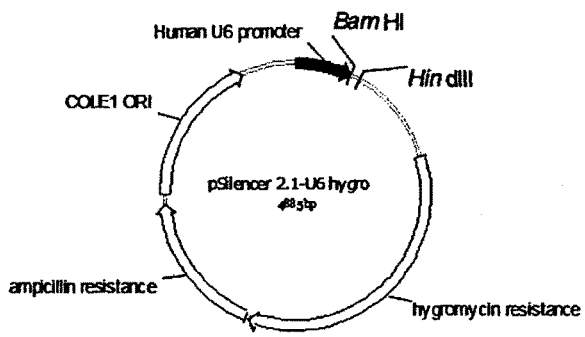
Figure 2B
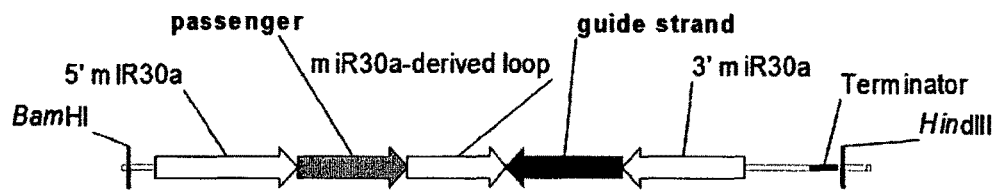
Figure 2C – DNA Sequence of B
ggatcc*ggtatattgctgttgacagtgagcga*TAGACACACCCACCCACATA*actgtga
agcagatgggt*TATGTGGGTGGGTGTGTCTACcgcctactgcctcggacttcaagctag
cggtacctttttaagctt (SEQ ID NO: 98)
Figure 2D Predicted RNA structure of B
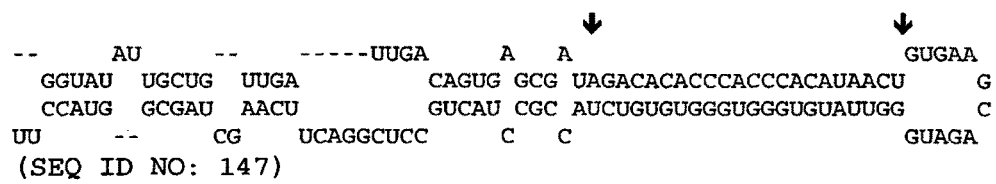
(SEQ ID NO: 147)

Figure 3
Figure 3A
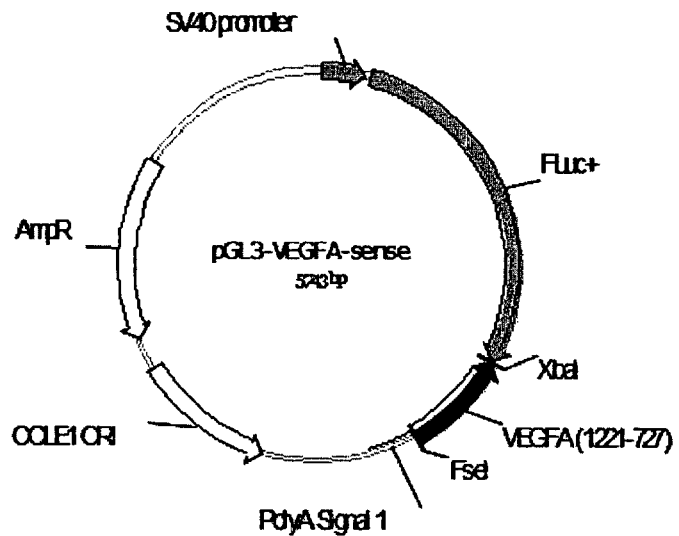
Figure 3B
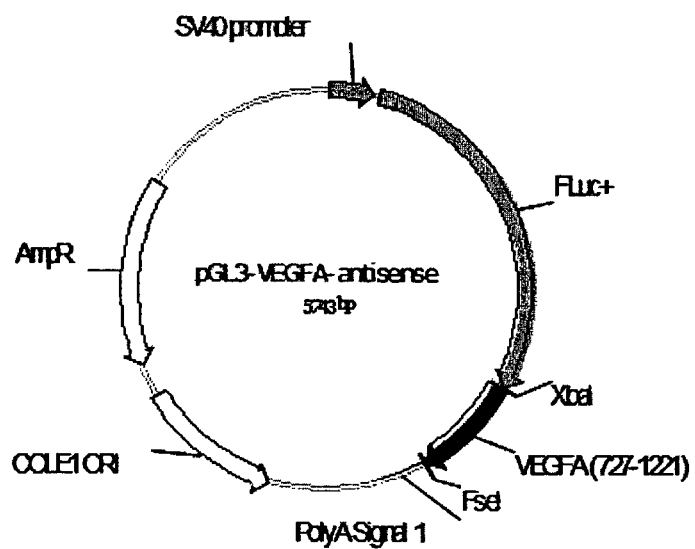

Figure 4
Figure 4A
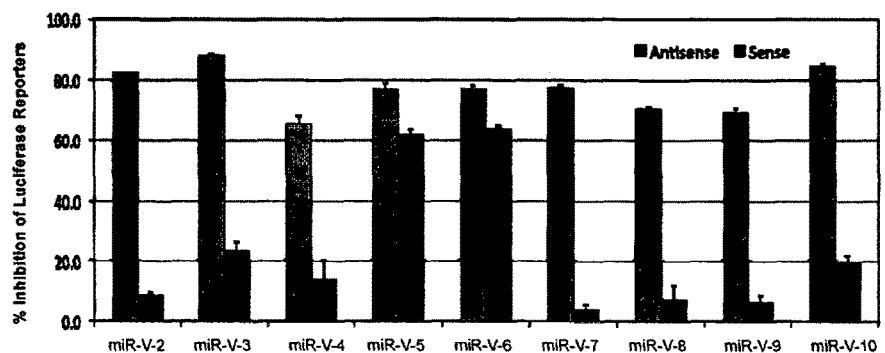
Figure 4B
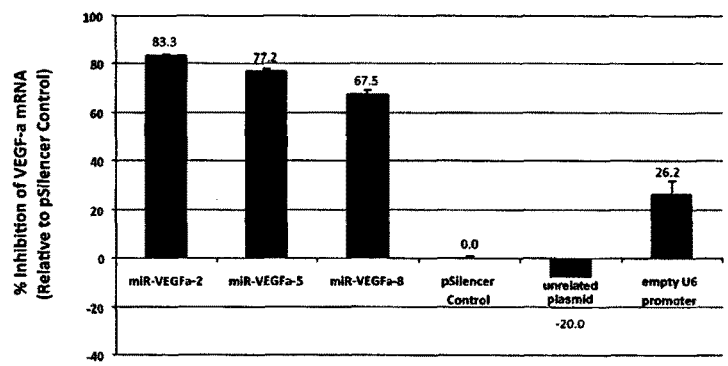
Figure 4C
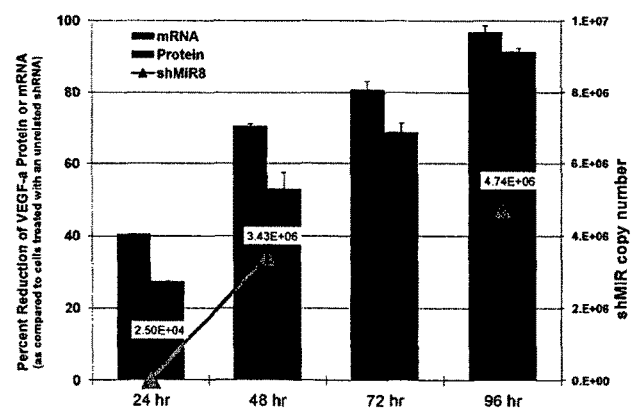

Figure 5
Figure 5A
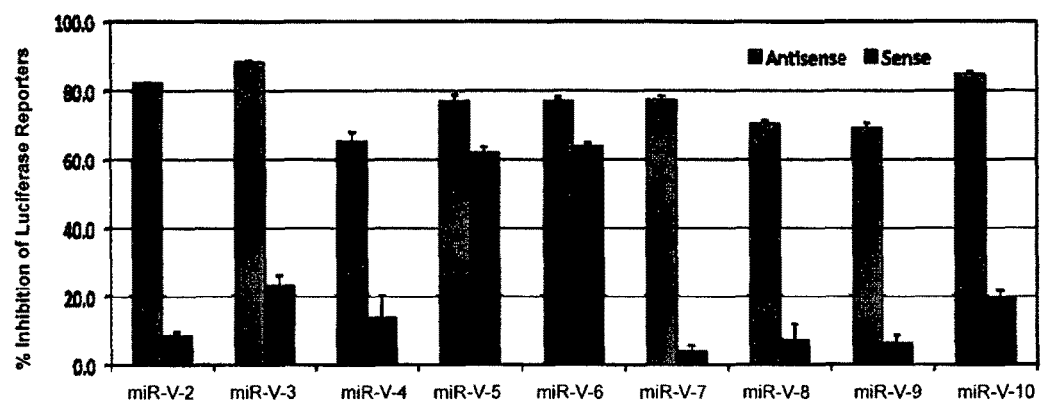
Figure 5B
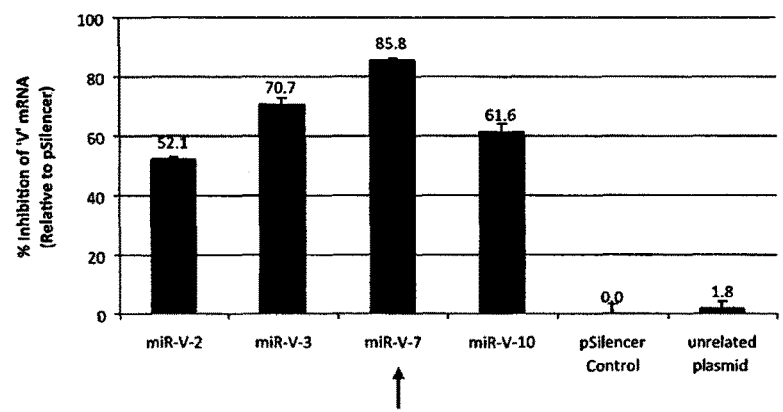

Figure 6
Figure 6A
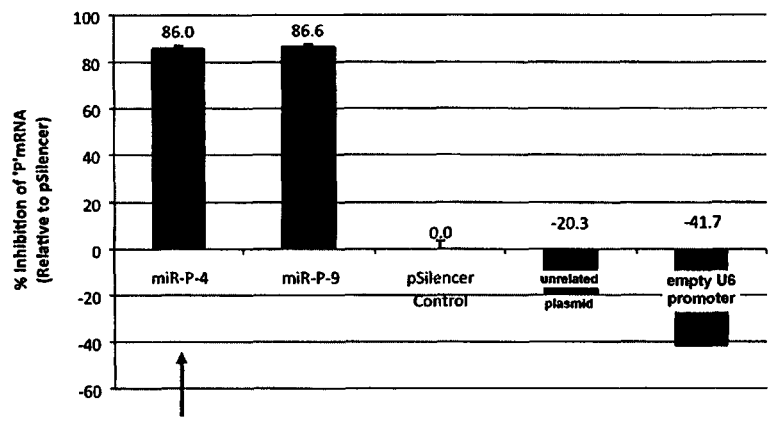
Figure 6B
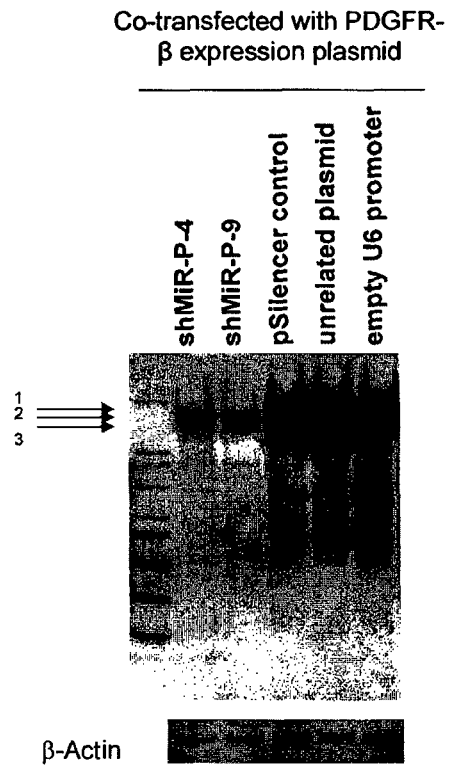

Figure 7
Figure 7A
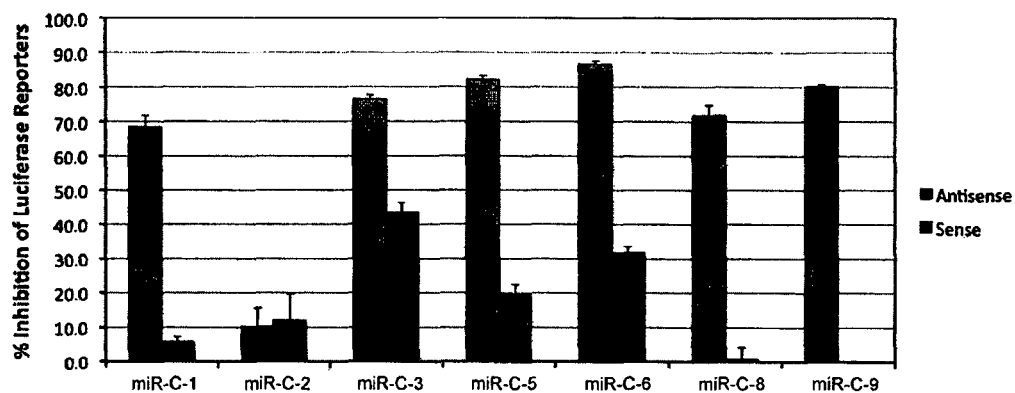
Figure 7B
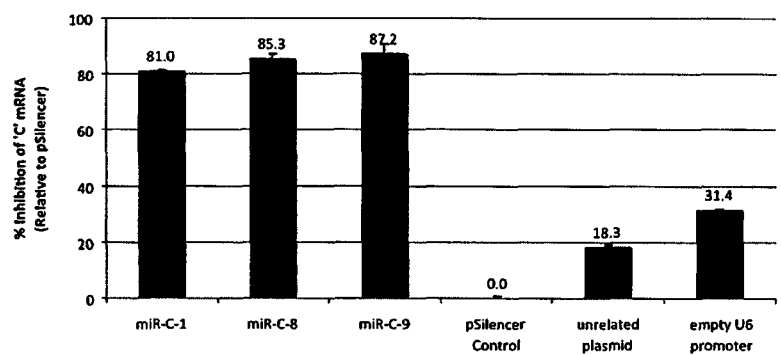

Figure 8
Figure 8A
Figure 8B
Figure 8C
Figure 8D
Figure 8E

Figure 9
Figure 9A
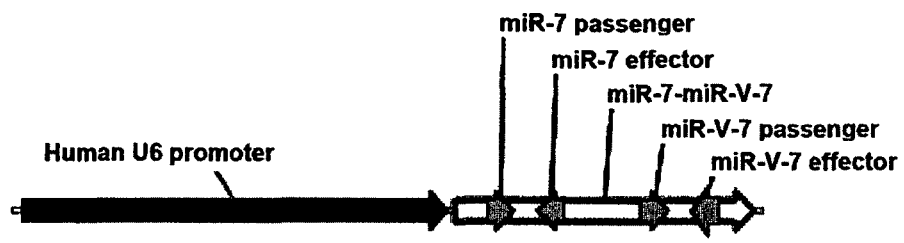
Figure 9B
Figure 9C
Figure 9D
Figure 9E

Figure 10
Figure 10A
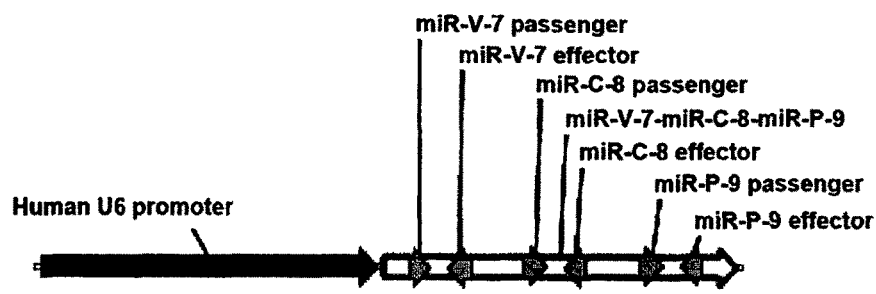
Figure 10B
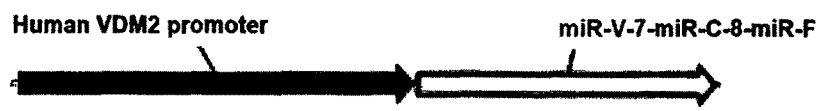
Figure 10C
Figure 10D
Figure 10E

Figure 11

VEGF-A target

SEQ ID NO:1  AGCAAGAGCTCCAGAGAGAAG

SEQ ID NO:2  GGCCTCCGAAACCATGAACTT

SEQ ID NO:3  CGAGACCCTGGTGGACATCTT

SEQ ID NO:4  GCACATAGGAGAGATGAGCTT

SEQ ID NO:5  TGAATGCAGACCAAAGAAAGA

SEQ ID NO:6  CAGAACAGTCCTTAATCCAGA

SEQ ID NO:7  TCTGGGATTCCTGTAGACACA

SEQ ID NO:8  GTAGACACACCCACCCACATA

SEQ ID NO:9  GGTGCTACTGTTTATCCGTAA

SEQ ID NO:10 CGAGATATTCCGTAGTACATA

VEGFR2 target

SEQ ID NO:11 TTGGACTGGCTTTGGCCCAAT

SEQ ID NO:12 CCCAGCTACATGATCAGCTAT

SEQ ID NO:13 GCCATGTTCTTCTGGCTACTT

SEQ ID NO:14 CGGACCGTTAAGCGGGCCAAT

SEQ ID NO:15 TCATGGTGATTGTGGAATTCT

SEQ ID NO:16 CCTGACCTTGGAGCATCTCAT

SEQ ID NO:17 TGGAGCATCTCATCTGTTACA

SEQ ID NO:18 GGCTAAGGGCATGGAGTTCTT

SEQ ID NO:19 ACCAGAAATGTACCAGACCAT

SEQ ID NO:20 ACCCCAAATTCCATTATGACA

Figure 11 (cont.)

PDGFR-β target

SEQ ID NO:21 ACTCCAGGTGTCATCCATCAA

SEQ ID NO:22 AGGTGTCATCCATCAACGTCT

SEQ ID NO:23 CCATGAGTACATCTACGTGGA

SEQ ID NO:24 GGACCTCGTGGGCTTCAGCTA

SEQ ID NO:25 AGGCAAGCTGGTCAAGATCTG

SEQ ID NO:26 GGAGAGCATCTTCAACAGCCT

SEQ ID NO:27 GCATCTTCAACAGCCTCTACA

SEQ ID NO:28 CCCAGAGCTGCCCATGAACGA

SEQ ID NO:29 GCAGTTCTACAATGCCATCAA

SEQ ID NO:30 CCATGCCTCCGACGAGATCTA

CFB target

SEQ ID NO:31 CTGCCAAGACTCCTTCATGTA

SEQ ID NO:32 GAACATCTACCTGGTGCTAGA

SEQ ID NO:33 CCGCCATGTCATCATCCTCAT

SEQ ID NO:34 GGAGGATTATCTGGATGTCTA

SEQ ID NO:35 GCAACATGTGTTCAAAGTCAA

SEQ ID NO:36 CATGTGTTCAAAGTCAAGGAT

SEQ ID NO:37 CAGGATATCAAAGCTCTGTTT

SEQ ID NO:38 TCGGAAGGAGGTCTACATCAA

SEQ ID NO:39 GAGGATTTGGGTTTTCTATAA

VEGF-A effector

SEQ ID NO:40 CUUCUCUCUGGAGCUCUUGCU

SEQ ID NO:41 AAGUUCAUGGUUUCGGAGGCC

Figure 11 (cont.)

SEQ ID NO:42 AAGAUGUCCACCAGGGUCUCG

SEQ ID NO:43 AAGCUCAUCUCUCCUAUGUGC

SEQ ID NO:44 UCUUUCUUUGGUCUGCAUUCA

SEQ ID NO:45 UCUGGAUUAAGGACUGUUCUG

SEQ ID NO:46 UGUGCUACAGGAAUCCCAGA

SEQ ID NO:47 UAUGUGGGUGGGUGUGUCUAC

SEQ ID NO:48 UUACGGAUAAACAGUAGCACC

SEQ ID NO:49 UAUGUACUACGGAAUAUCUCG

VEGFR2 effector

SEQ ID NO:50 AUUGGGCCAAAGCCAGUCCAA

SEQ ID NO:51 AUAGCUGAUCAUGUAGCUGGG

SEQ ID NO:52 AAGUAGCCAGAAGAACAUGGC

SEQ ID NO:53 AUUGGCCCGCUUAACGGUCCG

SEQ ID NO:54 AGAAUUCCACAAUCACCAUGA

SEQ ID NO:55 AUGAGAUGCUCCAAGGUCAGG

SEQ ID NO:56 UGUAACAGAUGAGAUGCUCCA

SEQ ID NO:57 AAGAACUCCAUGCCCUUAGCC

SEQ ID NO:58 AUGGUCUGGUACAUUUCUGGT

SEQ ID NO:59 UGUCAUAAUGGAAUUUGGGGT

PDGFR-β effector

SEQ ID NO:60 UUGAUGGAUGACACCUGGAGU

SEQ ID NO:61 AGACGUUGAUGGAUGACACCU

SEQ ID NO:62 UCCACGUAGAUGUACUCAUGG

SEQ ID NO:63 UAGCUGAAGCCCACGAGGUCC

Figure 11 (cont.)

SEQ ID NO:64 CAGAUCUUGACCAGCUUGCCU

SEQ ID NO:65 AGGCUGUUGAAGAUGCUCUCC

SEQ ID NO:66 UGUAGAGGCUGUUGAAGAUGC

SEQ ID NO:67 UCGUUCAUGGGCAGCUCUGGG

SEQ ID NO:68 UUGAUGGCAUUGUAGAACUGC

SEQ ID NO:69 UAGAUCUCGUCGGAGGCAUGG

<u>CFB effector</u>

SEQ ID NO:70 UACAUGAAGGAGUCUUGGCAG

SEQ ID NO:71 UCUAGCACCAGGUAGAUGUUC

SEQ ID NO:72 AUGAGGAUGAUGACAUGGCGG

SEQ ID NO:73 UAGACAUCCAGAUAAUCCUCC

SEQ ID NO:74 UUGACUUUGAACACAUGUUGC

SEQ ID NO:75 AUCCUUGACUUUGAACACAUG

SEQ ID NO:76 AAACAGAGCUUUGAUAUCCUG

SEQ ID NO:77 UUGAUGUAGACCUCCUUCCGA

SEQ ID NO:78 UUAUAGAAAACCCAAAUCCUC

SEQ ID NO:79 (Human VEGF-A)

TCGCGGAGGCTTGGGGCAGCCGGGTAGCTCGGAGGTCGTGGCGCTGGG
GGCTAGCACCAGCGCTCTGTCGGGAGGCGCAGCGGTTAGGTGGACCGGT
CAGCGGACTCACCGGCCAGGGCGCTCGGTGCTGGAATTTGATATTCATTG
ATCCGGGTTTTATCCCTCTTCTTTTTTCTTAAACATTTTTTTTTAAAACTGTAT
TGTTTCTCGTTTTAATTTATTTTTGCTTGCCATTCCCCACTTGAATCGGGCC
GACGGCTTGGGGAGATTGCTCTACTTCCCCAAATCACTGTGGATTTTGGAA
ACCAGCAGAAAGAGGAAAGAGGTAGCAAGAGCTCCAGAGAGAAGTCGAG
GAAGAGAGAGACGGGGTCAGAGAGAGCGCGCGGGCGTGCGAGCAGCGA

Figure 11 (cont.)

```
AAGCGACAGGGGCAAAGTGAGTGACCTGCTTTTGGGGGTGACCGCCGGA
GCGCGGCGTGAGCCCTCCCCCTTGGGATCCCGCAGCTGACCAGTCGCGC
TGACGGACAGACAGACAGACACCGCCCCCAGCCCCAGCTACCACCTCCT
CCCCGGCCGGCGGCGGACAGTGGACGCGGCGGCGAGCCGCGGGCAGG
GGCCGGAGCCCGCGCCCGGAGGCGGGGTGGAGGGGGTCGGGGCTCGC
GGCGTCGCACTGAAACTTTTCGTCCAACTTCTGGGCTGTTCTCGCTTCGGA
GGAGCCGTGGTCCGCGCGGGGGAAGCCGAGCCGAGCGGAGCCGCGAGA
AGTGCTAGCTCGGGCCGGGAGGAGCCGCAGCCGGAGGAGGGGGAGGAG
GAAGAAGAGAAGGAAGAGGAGAGGGGCCGCAGTGGCGACTCGGCGCT
CGGAAGCCGGGCTCATGGACGGGTGAGGCGGCGGTGTGCGCAGACAGT
GCTCCAGCCGCGCGCTCCCCAGGCCCTGGCCCGGGCCTCGGGCCGG
GGAGGAAGAGTAGCTCGCCGAGGCGCCGAGGAGAGCGGGCCGCCCCAC
AGCCCGAGCCGGAGAGGGAGCGCGAGCCGCGCCGGCCCCGGTCGGGC
CTCCGAAACCATGAACTTTCTGCTGTCTTGGGTGCATTGGAGCCTTGCCTT
GCTGCTCTACCTCCACCATGCCAAGTGGTCCCAGGCTGCACCCATGGCAG
AAGGAGGAGGGCAGAATCATCACGAAGTGGTGAAGTTCATGGATGTCTAT
CAGCGCAGCTACTGCCATCCAATCGAGACCCTGGTGGACATCTTCCAGGA
GTACCCTGATGAGATCGAGTACATCTTCAAGCCATCCTGTGTGCCCCTGAT
GCGATGCGGGGGCTGCTGCAATGACGAGGGCCTGGAGTGTGTGCCCACT
GAGGAGTCCAACATCACCATGCAGATTATGCGGATCAAACCTCACCAAGG
CCAGCACATAGGAGAGATGAGCTTCCTACAGCACAACAAATGTGAATGCA
GACCAAAGAAAGATAGAGCAAGACAAGAAAAAAAATCAGTTCGAGGAAAG
GGAAAGGGGCAAAAACGAAAGCGCAAGAAATCCCGGTATAAGTCCTGGAG
CGTGTACGTTGGTGCCCGCTGCTGTCTAATGCCCTGGAGCCTCCCTGGCC
CCCATCCCTGTGGGCCTTGCTCAGAGCGGAGAAAGCATTTGTTTGTACAA
GATCCGCAGACGTGTAAATGTTCCTGCAAAAACACAGACTCGCGTTGCAA
GGCGAGGCAGCTTGAGTTAAACGAACGTACTTGCAGATGTGACAAGCCGA
GGCGGTGAGCCGGGCAGGAGGAAGGAGCCTCCCTCAGGGTTTCGGGAA
CCAGATCTCTCACCAGGAAAGACTGATACAGAACGATCGATACAGAAACCA
CGCTGCCGCCACCACACCATCACCATCGACAGAACAGTCCTTAATCCAGA
AACCTGAAATGAAGGAAGAGGAGACTCTGCGCAGAGCACTTTGGGTCCGG
```

Figure 11 (cont.)

AGGGCGAGACTCCGGCGGAAGCATTCCCGGGCGGGTGACCCAGCACGG
TCCCTCTTGGAATTGGATTCGCCATTTTATTTTTCTTGCTGCTAAATCACCG
AGCCCGGAAGATTAGAGAGTTTTATTTCTGGGATTCCTGTAGACACACCCA
CCCACATACATACATTTATATATATATATATTATATATATATAAAAATAAATAT
CTCTATTTTATATATATAAAATATATATATTCTTTTTTTAAATTAACAGTGCTA
ATGTTATTGGTGTCTTCACTGGATGTATTTGACTGCTGTGGACTTGAGTTG
GGAGGGGAATGTTCCCACTCAGATCCTGACAGGGAAGAGGAGGAGATGA
GAGACTCTGGCATGATCTTTTTTTTGTCCCACTTGGTGGGGCCAGGGTCCT
CTCCCCTGCCCAGGAATGTGCAAGGCCAGGGCATGGGGGCAAATATGAC
CCAGTTTTGGGAACACCGACAAACCCAGCCCTGGCGCTGAGCCTCTCTAC
CCCAGGTCAGACGGACAGAAAGACAGATCACAGGTACAGGGATGAGGAC
ACCGGCTCTGACCAGGAGTTTGGGGAGCTTCAGGACATTGCTGTGCTTTG
GGGATTCCCTCCACATGCTGCACGCGCATCTCGCCCCCAGGGGCACTGC
CTGGAAGATTCAGGAGCCTGGGCGGCCTTCGCTTACTCTCACCTGCTTCT
GAGTTGCCCAGGAGACCACTGGCAGATGTCCCGGCGAAGAGAAGAGACA
CATTGTTGGAAGAAGCAGCCCATGACAGCTCCCCTTCCTGGGACTCGCCC
TCATCCTCTTCCTGCTCCCCTTCCTGGGGTGCAGCCTAAAAGGACCTATGT
CCTCACACCATTGAAACCACTAGTTCTGTCCCCCAGGAGACCTGGTTGT
GTGTGTGTGAGTGGTTGACCTTCCTCCATCCCCTGGTCCTTCCCTTCCCTT
CCCGAGGCACAGAGAGACAGGGCAGGATCCACGTGCCCATTGTGGAGGC
AGAGAAAAGAGAAAGTGTTTTATATACGGTACTTATTTAATATCCCTTTTTAA
TTAGAAATTAAAACAGTTAATTTAATTAAAGAGTAGGGTTTTTTTTCAGTATT
CTTGGTTAATATTTAATTTCAACTATTTATGAGATGTATCTTTTGCTCTCTCT
TGCTCTCTTATTTGTACCGGTTTTTGTATATAAAATTCATGTTTCCAATCTCT
CTCTCCCTGATCGGTGACAGTCACTAGCTTATCTTGAACAGATATTTAATTT
TGCTAACACTCAGCTCTGCCCTCCCCGATCCCCTGGCTCCCCAGCACACA
TTCCTTTGAAATAAGGTTTCAATATACATCTACATACTATATATATATTTGGC
AACTTGTATTTGTGTGTATATATATATATATGTTTATGTATATATGTGATT
CTGATAAAATAGACATTGCTATTCTGTTTTTTATATGTAAAAACAAAACAAGA
AAAAATAGAGAATTCTACATACTAAATCTCTCTCCTTTTTTAATTTTAATATTT
GTTATCATTTATTTATTGGTGCTACTGTTTATCCGTAATAATTGTGGGGAAA

Figure 11 (cont.)

AGATATTAACATCACGTCTTTGTCTCTAGTGCAGTTTTTCGAGATATTCCGT
AGTACATATTTATTTTTAAACAACGACAAAGAAATACAGATATATCTTAAAAA
AAAAAAAGCATTTTGTATTAAAGAATTTAATTCTGATCTCAAAAAAAAAAAAA
AAAAA

SEQ ID NO:80 (mouse VEGF-A)

AGCGCAGAGGCTTGGGGCAGCCGAGCTGCAGCGAGGCCGCGGCACTGG
GGGCGAGCTGAGCGGCGGCAGCGGAGCTCTGTCGCGAGACGCAGCGAC
AAGGCAGACTATTCAGCGGACTCACCAGCCCGGGAGTCTGTGCTCTGGGA
TTTGATATTCAAACCTCTTAATTTTTTTTTCTTAAACTGTATTGTTTTACGCTT
TAATTTATTTTTGCTTCCTATTCCCTCTTAAATCGTGCCAACGGTTTGAGG
AGGTTGGTTCTTCACTCCCTCAAATCACTTCGGATTGTGGAAATCAGCAGA
CGAAAGAGGTATCAAGAGCTCCAGAGAGAAGTCAAGGAAGAGAGAGA
GACCGGTCAGAGAGAGCGCGCTGGCGAGCGAACAGAGAGAGGGACAGG
GGCAAAGTGACTGACCTGCTTTTGGGGGTGACCGCCAGAGCGCGGCGTG
AGCCCTCCCCCTTGGGATCTTGCATCGGACCAGTCGCGCTGACGGACAGA
CAGACAGACACCGCCCCCAGCCCCAGCGCCCACCTCCTCGCCGGCGGGC
TGCCGACGGTGGACGCGGCGGCGAGCCGCGAGGAACCGAAGCCCGCGC
CCGGAGGCGGGGTGGAGGGGGTCGGGGCTCGCGGGATTGCACGGAAAC
TTTTCGTCCAACTTCTGGGCTCTTCTCGCTCCGTAGTAGCCGTGGTCTGCG
CCGCAGGAGACAAACCGATCGGAGCTGGGAGAAGTGCTAGCTCGGGCCT
GGAGAAGCCGGGGCCCGAGAAGAGAGGGGAGGAAGAGAAGGAAGAGGA
GAGGGGGCCGCAGTGGGCGCTCGGCTCTCAGGAGCCGAGCTCATGGAC
GGGTGAGGCGGCCGTGTGCGCAGACAGTGCTCCAGCCGCGCGCGCGCC
CCAGGCCCCGGCCCGGGCCTCGGTTCCAGAAGGGAGAGGAGCCCGCCA
AGGCGCGCAAGAGAGCGGGCTGCCTCGCAGTCCGAGCCGGAGAGGGAG
CGCGAGCCGCGCCGGCCCCGGACGGGCCTCCGAAACCATGAACTTTCTG
CTCTCTTGGGTGCACTGGACCCTGGCTTTACTGCTGTACCTCCACCATGC
CAAGTGGTCCCAGGCTGCACCCACGACAGAAGGAGAGCAGAAGTCCCAT
GAAGTGATCAAGTTCATGGATGTCTACCAGCGAAGCTACTGCCGTCCGATT
GAGACCCTGGTGGACATCTTCCAGGAGTACCCCGACGAGATAGAGTACAT

Figure 11 (cont.)

```
CTTCAAGCCGTCCTGTGTGCCGCTGATGCGCTGTGCAGGCTGCTGTAACG
ATGAAGCCCTGGAGTGCGTGCCCACGTCAGAGAGCAACATCACCATGCAG
ATCATGCGGATCAAACCTCACCAAAGCCAGCACATAGGAGAGATGAGCTT
CCTACAGCACAGCAGATGTGAATGCAGACCAAAGAAAGACAGAACAAAGC
CAGAAAAAAAATCAGTTCGAGGAAAGGGAAAGGGTCAAAAACGAAAGCGC
AAGAAATCCCGGTTTAAATCCTGGAGCGTTCACTGTGAGCCTTGTTCAGAG
CGGAGAAAGCATTTGTTTGTCCAAGATCCGCAGACGTGTAAATGTTCCTGC
AAAAACACAGACTCGCGTTGCAAGGCGAGGCAGCTTGAGTTAAACGAACG
TACTTGCAGATGTGACAAGCCAAGGCGGTGAGCCAGGCTGCAGGAAGGA
GCCTCCCTCAGGGTTTCGGGAACCAGACCTCTCACCGGAAAGACCGATTA
ACCATGTCACCACCACGCCATCATCGTCACCGTTGACAGAACAGTCCTTAA
TCCAGAAAGCCTGACATGAAGGAAGAGGAGACTCTTCGAGGAGCACTTTG
GGTCCGGAGGGCGAGACTCCGGCAGACGCATTCCCGGGCAGGTGACCAA
GCACGGTCCCTCGTGGGACTGGATTCGCCATTTTCTTATATCTGCTGCTAA
ATCGCCAAGCCCGGAAGATTAGGGTTGTTTCTGGGATTCCTGTAGACACA
CCCACCCACATACACACATATATATATTATATATATAAATAAATATATATG
TTTTATATATAAAATATATATATATTCTTTTTTTTAAATTAACTCTGCTAATGT
TATTGGTGTCTTCACTGGATATGTTTGACTGCTGTGGACTTGTGTTGGGAG
GAGGATGTCCTCACTCGGATGCCGACACGGGAGACAATGGGATGAAAGG
CTTCAGTGTGGTCTGAGAGAGGCCGAAGTCCTTTTGCCTGCCGGGGAGCA
AGCAAGGCCAGGGCACGGGGGCACATTGGCTCACTTCCAGAAACACGAC
AAACCCATTCCTGGCCCTGAGTCAAGAGGACAGAGAGACAGATGATGACA
GAGAAAGAGATAAAGATGCCGGTTCCAACCAGAAGTTTGGGGAGCCTCAG
GACATGGCATGCTTTGTGGATCCCCATGATAGTCTACAAAAGCACCCCGC
CCCTCTGGGCACTGCCTGGAAGAATCGGGAGCCTGGCCAGCCTTCAGCT
CGCTCCTCCACTTCTGAGGGGCCTAGGAGGCCTCCCACAGGTGTCCCGG
CAAGAGAAGACACGGTGGTGGAAGAAGAGGCCTGGTAATGGCCCCTCCT
CCTGGGACCCCTTCGTCCTCTCCTTACCCCACCTCCTGGGTACAGCCCAG
GAGGACCTTGTGTGATCAGACCATTGAAACCACTAATTCTGTCCCCAGGAG
ACTTGGCTGTGTGTGTGAGTGGCTTACCCTTCCTCATCTTCCCTTCCCAAG
GCACAGAGCAATGGGGCAGGACCCGCAAGCCCCTCACGGAGGCAGAGAA
```

Figure 11 (cont.)

AAGAGAAAGTGTTTTATATACGGTACTTATTTAATAGCCCTTTTTAATTAGAA
ATTAAAACAGTTAATTTAATTAAAGAGTAGGGTTTTTTTCAGTATTCTTGGTT
AATATTTAATTTCAACTATTTATGAGATGTATCTCTCGCTCTCTCTTATTTGT
ACTTGTGTGTGTGTGTGTGTGTGTGTGTGTGTGTGTGTGTGTGTATG
AAATCTGTGTTTCCAATCTCTCTCTCCCAGATCGGTGACAGTCACTAGCTT
GTCCTGAGAAGATATTTAATTTTGCTAACACTCAGCTCTGCCCTCCCTTGTC
CCCACCACACATTCCTTTGAAATAAGGTTTCAATATACATTTACATACTATAT
ATATATTTGGCAACTTGTGTTTGTATATAAATATATATATATATATATGTTT
ATGTATATATGTGATTCTGATAAAATAGACATTGCTATTCTGTTTTTTATATG
TAAAAACAAAACAAGAAAAATAGAGAATTCTACATACTAAATCTCTCTCCTT
TTTTAATTTTAATATTTGTTATCATTTATTTATTGGTGCTACTGTTTATCCGTA
ATAATTGTGGGGGAAAAAGATATTAACATCACGTCTTTGTCTCTAGAGCAG
TTTTCCGAGATATTCCGTAGTACATATTTATTTTTAAACAGCAACAAAGAAAT
ACAGATATATCTTAAAAAAAAAAGCATTTTGTATTAAAGAATTGAATTCTGAT
CTCAAAAAAAAAAAAAAAAAAA

SEQ ID NO:81 (macaque VEGF-A)

ATGAACTATGAGTCCCATATTGTGCTGAGGAGGGGTCTGTGGCCTGAGAG
GGGAAGGGCCCTGGCCTCTGCCGCCCTGGAAGGCAACATCATAGCCAGG
AATGGAGCCTGCTGCTCCTACTCCTTAACCGGTGCTCACCCCAGGCCTGG
CTGTGCCTGGAAGGCCTTGTTTCCATCCTGGGCCTTCACTTGCCTTCCCC
CTGCTTATTCCTGGGCCTCCAAAAAGCTTCTCTGTGCCCCAAGCTCTCCTC
TTCCAGGAAGTCTTCCTTTCCTGTTTGAGAAGGGGCTCCCTAACCTGCACC
CAGCCAGGCCAGCGGAACAGCCCCTGTCCACCTCCTACCTTCCTCTTGGG
CAGCTTCAAGGAGCCTGGAGGCTGCCCCTGCCAGCCCTGGGGAACTGTG
GCCCCGTTCTCGAGAGCCAGACATCCCTGAGGAGCTTTAGGACAGGAGA
GGAGGAAGTAGGCTATGCCAGCTGTAGACCAGACCCTGGCAAGATCCGG
GTGGACAATCAGACTGACTGGTCCCACTCTTCCCACAGGCATCAGAACCC
CAACTTTGTTCCCTGGAGCAGCCTGGAAATAGCCGGGTCAGAACCCAGTC
AGGAATTTTTCCAAGCTGGTTCCTATAGGCAAGAATGGGATAGGGGCCTTT
GGGAGCACTTCGGGAAGATGTGGAGAGTTGGAGGAAAAGGCAGCTTGGA

Figure 11 (cont.)

```
GATTGCTTTACTTCCCCAAATCACTGTGGATTTTGGAAACCAGCAGAAAGA
GGAAAGAGGTAGCAAGAGCTCCAGAGAGAAGTCGAGGAAGAGAGAGACG
GGGTCAGAGAGAGCGCGCGGGCGTGCGAGCAGCGAGAGGGACAGGGGC
AAAGTGAGTGACCTGCTTTTGGGGGTGACCGCCGGAGCGCGGCGTGAGC
CCTCCCCCTTGGGATCCCGCAGCGGACCAGTAGCGCTGACGGACAGACA
GACAGACACCGCCCCAGCCCCAGCGCCCACCTCCTCCCCGGCCGGCG
GCCGACAGTGGACGCGGCGGCGAGCCGCGGGCAGGGGCCGGAGCCCG
CGCCCGGAGGCGGGGTGGAGGGGGTCGGGGCTCGCGGCGTCGCACTGA
AACTTTTCGTCCAACTTCTGGGCTGTTCTCGCTTCGGAGGAGCCGTGGTC
CGCGCCGGGGAAGCCGAGCCGAGCGGAGCCGCGAGAAGTGCTAGCTCG
GGCCGGGAGGAGCCGCAGCCGGAGGAGGGGGAGGAGGAAGAAGAGAAG
GAAGAAGAGAGGGGGCCGCGGTGGCGACTCGGCGCTTGGAAGCCGGGC
TCATGGACGGGTGAGGCGGCGGTGTGCGCAGACAGTGCTCCAGCCGCGC
GCGCGCCCCAGGCCCTGGCCCGGGCCTCGGCCCGGGGAGGAAGAGGAG
CTCGCCGAGGCGCCGAAGAGAGCGGGCCGCCCCACAGCCCGAGCCGGA
GAGGGAGCGCGAGCCGCGCCGGCCCCGGTCGGGCCTCCGAAACCATGA
ACTTTCTGCTCTCTTGGGTGCATTGGAGCCTTGCCTTGCTGCTGTACCTCC
ACCATGCCAAGTGGTCCCAGGCTGCACCCATGGCAGAAGGAGGAGGGCA
GAATCATCACGAAGTGGTGAAGTTCATGGATGTCTATCAGCGCAGCTACTG
CCATCCAATCGAGACCCTGGTGGACATCTTCCAGGAGTACCCTGATGAGA
TTGAGTACATCTTCAAGCCATCCTGTGTGCCCTGATGCGATGTGGGGGC
TGCTGCAATGACGAGGGCCTGGAGTGTGTGCCCACTGAGGAGTCCAACAT
CACCATGCAGATTATGCGGATCAAACCTCACCAAGGCCAGCACATAGGAG
AGATGAGCTTCCTACAGCACAACAAATGTGAATGCAGACCAAAGAAAGATA
GAGCAAGACAAGAAAAAAAATCAGTTCGAGGAAAGGGAAGGGGCAAAAA
CGAAAGCGCAAGAAATCCCGGTATAAGTCCTGGAGCGTGTACGTTGGTGC
CCGCTGCTGTCTAATTCCCTGGAGCCTCCCTGGCCCCATCCCTGTGGGC
CTTGCTCAGAGCGGAGAAAGCATTTGTTTGTACAAGATCCGCAGACGTGTA
AATGTTCCTGCAAAAACACAGACTCGCGTTGCAAGGCGAGGCAGCTTGAG
TTAAACGAACGTACTTGCAGATGTGACAAGCCGAGGCGGTGAGCCGGGCA
GGAGGAAGGAGCCTCCCTCAGGGTTTCGGGAACCAGATCTCTCACCAGG
```

Figure 11 (cont.)

```
AAAGACAGATACAGAACGATCGATACAGAAACCACGCTGCCGCCACCACA
CCATCACCATCGACAGAACAGTCCTTAATCCAGAAGCCTGAAATGAAGGAA
GAGGAGACTCTGCGCAGAGCACTTTGGGTCCGGAGGGCGAGACTCCGGC
AGAAGCATTCCCGGGCGGGTGACCCAGCATGGTCCCTCTTGGAATTGGAT
TCGCCATTTTATTTTTCTTGCTGCTAAATCACCGAGCCCGGAAGATTAGAG
AGTTTTATTTCTGGGATTCCTGTAGACACACCCACCCACATACATACATTTA
TATATATATATATATTATATATATAAAAATAAATATCTATATTTTATATATATAA
AATATATATATTCTTTTTTTAAATTAACAGTGCTAATGTTATTGGTGTCTTCA
CTGGATGTATTTGACTGCTGTGGACTTGAGTTGGGAGGGGGAATGTTCCC
ACTCAGATCCTGACAGGGAAGAGGAGGAGATGAGAGACTCTGGCATGATC
TTTTTTTTTGTCCCACTTGGTGGGGCCAGGGTCCCCTCCCCTGCCCAGGA
ACGTGCAAGGCCAGGGTATGGGGGCAAATATGACCCACTTTTGGGAACAC
CGACAAACCCAGCCCTGGCACCGAGCCTCTACCCCGGGTCAGATGGACA
GAAAGACAGATGACAGGTACAGGGACGAGGACACTGGCTCTGACTAGGA
GTTTGGGGAGCTTCAGGACATTGCTGTGCTTTGGGGATTCCCTCCACATG
CTGCATGCGCATCTTGCCCCCAGGGGCAGCGCCTGGAAGATTCAGGAGC
CTGGGCGGCCTTCACTTACTCTCACCTGCTTCTGAGTTGCCCAGGAGGCC
ACTGGCAGATGGCCCGGCGAAGAGAAGAGACACATTGTTGGAAGAAGCA
GCTCATGACAGCTCCCCTTCCTGGGATTCACCCTCGTCCTCTTCCTGCTCC
CCTTCCTGGGGTGTAGCCTAAAAGGACCTGATGTCCTCACACCATTGAAAC
CACTAGTTCTGTCCCCCCAGGAGACCTGGTTGTGTGTGTGAGTGGTTG
ACCTTCCTCCATCCCCTGGTCCTTCCCTTCCCTTCCCGAGGCACAGAGAG
ACAGGGCAGGATCCACGTGCCCACTGTGGAGGCAGAGAAAGAGAAAGT
GTTTTATATACGGTACTTATTTAATATCCCTTTTTAATTAGAAATTAAAACAG
TTAATTTAATTAAAAAGTAGGGTTTTTTTCAGTATTCTTGGTTAATATTTAATT
TCAACTATTTATGAGATGTATCTTTTGCTCTCTCTCGCTCTCTTATTTGTACC
GGTTTTTGTATATAAAATTCATGTTTCCAATCTCTCTCTCCCTGATCGGTGA
CAGTCACTAGCTTATCTTGAACAGATATTTAATTTTGCTAACACTTAGCTCT
GCCCTCCCCGTTCCCCTGGCTCCCCAGCACACATTCCTTTGAAATAAGGTT
TCAATATACATCTACATACTATATATATATTTGGCAACTTGTATTTGTGTGTA
TATATATATATATGTTTATGTATATATGTGATTCTGATAAAATAGACATTGCT
```

Figure 11 (cont.)

ATTCTGTTTTTTATATGTAAAAACAAAACAAGAAAAAATAGAGAATTCTACAT
ACTAAATCTCTCTCCTTTTTTAATTTTAATATTTGTTATCATTTATTTATTGGT
GCTACTGTTTATCCGTAATAATTGTGGGGAAAAGATATTAACATCACGTCTT
TGTCTCTAGTGCAGTTTTTTGAGATATTCCGTAGTACATATTTATTTTTAAAC
AACAACAAAGAAATACAGATATATCTTAAAAAAAAAAGGATTTTGTATTAAA
GAATTTAATTCTGATCTCAAA

SEQ ID NO:82 (Human VEGFR2)

ACTGAGTCCCGGGACCCCGGGAGAGCGGTCAATGTGTGGTCGCTGCGTT
TCCTCTGCCTGCGCCGGGCATCACTTGCGCGCCGCAGAAAGTCCGTCTG
GCAGCCTGGATATCCTCTCCTACCGGCACCCGCAGACGCCCTGCAGCC
GCGGTCGGCGCCCGGGCTCCCTAGCCCTGTGCGCTCAACTGTCCTGCGC
TGCGGGGTGCCGCGAGTTCCACCTCCGCGCCTCCTTCTCTAGACAGGCG
CTGGGAGAAAGAACCGGCTCCCGAGTTCTGGGCATTTCGCCCGGCTCGA
GGTGCAGGATGCAGAGCAAGGTGCTGCTGGCCGTCGCCCTGTGGCTCTG
CGTGGAGACCCGGGCCGCCTCTGTGGGTTTGCCTAGTGTTTCTCTTGATC
TGCCCAGGCTCAGCATACAAAAGACATACTTACAATTAAGGCTAATACAA
CTCTTCAAATTACTTGCAGGGGACAGAGGGACTTGGACTGGCTTTGGCCC
AATAATCAGAGTGGCAGTGAGCAAAGGGTGGAGGTGACTGAGTGCAGCG
ATGGCCTCTTCTGTAAGACACTCACAATTCCAAAAGTGATCGGAAATGACA
CTGGAGCCTACAAGTGCTTCTACCGGGAAACTGACTTGGCCTCGGTCATT
TATGTCTATGTTCAAGATTACAGATCTCCATTTATTGCTTCTGTTAGTGACC
AACATGGAGTCGTGTACATTACTGAGAACAAAAACAAAACTGTGGTGATTC
CATGTCTCGGGTCCATTTCAAATCTCAACGTGTCACTTTGTGCAAGATACC
CAGAAAAGAGATTTGTTCCTGATGGTAACAGAATTTCCTGGGACAGCAAGA
AGGGCTTTACTATTCCCAGCTACATGATCAGCTATGCTGGCATGGTCTTCT
GTGAAGCAAAAATTAATGATGAAAGTTACCAGTCTATTATGTACATAGTTGT
CGTTGTAGGGTATAGGATTTATGATGTGGTTCTGAGTCCGTCTCATGGAAT
TGAACTATCTGTTGGAGAAAAGCTTGTCTTAAATTGTACAGCAAGAACTGA
ACTAAATGTGGGGATTGACTTCAACTGGGAATACCCTTCTTCGAAGCATCA
GCATAAGAAACTTGTAAACCGAGACCTAAAACCCAGTCTGGGAGTGAGAT

Figure 11 (cont.)

```
GAAGAAATTTTTGAGCACCTTAACTATAGATGGTGTAACCCGGAGTGACCA
AGGATTGTACACCTGTGCAGCATCCAGTGGGCTGATGACCAAGAAGAACA
GCACATTTGTCAGGGTCCATGAAAAACCTTTTGTTGCTTTTGGAAGTGGCA
TGGAATCTCTGGTGGAAGCCACGGTGGGGGAGCGTGTCAGAATCCCTGC
GAAGTACCTTGGTTACCCACCCCCAGAAATAAAATGGTATAAAAATGGAAT
ACCCCTTGAGTCCAATCACACAATTAAAGCGGGGCATGTACTGACGATTAT
GGAAGTGAGTGAAAGAGACACAGGAAATTACACTGTCATCCTTACCAATCC
CATTTCAAAGGAGAAGCAGAGCCATGTGGTCTCTGGTTGTGTATGTCCC
ACCCCAGATTGGTGAGAAATCTCTAATCTCTCCTGTGGATTCCTACCAGTA
CGGCACCACTCAAACGCTGACATGTACGGTCTATGCCATTCCTCCCCGC
ATCACATCCACTGGTATTGGCAGTTGGAGGAAGAGTGCGCCAACGAGCCC
AGCCAAGCTGTCTCAGTGACAAACCCATACCCTTGTGAAGAATGGAGAAG
TGTGGAGGACTTCCAGGGAGGAAATAAAATTGAAGTTAATAAAAATCAATT
TGCTCTAATTGAAGGAAAAAACAAAACTGTAAGTACCCTTGTTATCCAAGC
GGCAAATGTGTCAGCTTTGTACAAATGTGAAGCGGTCAACAAAGTCGGGA
GAGGAGAGAGGGTGATCTCCTTCCACGTGACCAGGGGTCCTGAAATTACT
TTGCAACCTGACATGCAGCCCACTGAGCAGGAGAGCGTGTCTTTGTGGTG
CACTGCAGACAGATCTACGTTTGAGAACCTCACATGGTACAAGCTTGGCC
CACAGCCTCTGCCAATCCATGTGGGAGAGTTGCCCACACCTGTTTGCAAG
AACTTGGATACTCTTTGGAAATTGAATGCCACCATGTTCTCTAATAGCACAA
ATGACATTTTGATCATGGAGCTTAAGAATGCATCCTTGCAGGACCAAGGAG
ACTATGTCTGCCTTGCTCAAGACAGGAAGACCAAGAAAAGACATTGCGTG
GTCAGGCAGCTCACAGTCCTAGAGCGTGTGGCACCCACGATCACAGGAAA
CCTGGAGAATCAGACGACAAGTATTGGGGAAAGCATCGAAGTCTCATGCA
CGGCATCTGGGAATCCCCCTCCACAGATCATGTGGTTTAAAGATAATGAGA
CCCTTGTAGAAGACTCAGGCATTGTATTGAAGGATGGGAACCGGAACCTC
ACTATCCGCAGAGTGAGGAAGGAGGACGAAGGCCTCTACACCTGCCAGG
CATGCAGTGTTCTTGGCTGTGCAAAAGTGGAGGCATTTTTCATAATAGAAG
GTGCCCAGGAAAAGACGAACTTGGAAATCATTATTCTAGTAGGCACGGCG
GTGATTGCCATGTTCTTCTGGCTACTTCTTGTCATCATCCTACGGACCGTT
AAGCGGGCCAATGGAGGGGAACTGAAGACAGGCTACTTGTCCATCGTCAT
```

Figure 11 (cont.)

```
GGATCCAGATGAACTCCCATTGGATGAACATTGTGAACGACTGCCTTATGA
TGCCAGCAAATGGGAATTCCCCAGAGACCGGCTGAAGCTAGGTAAGCCTC
TTGGCCGTGGTGCCTTTGGCCAAGTGATTGAAGCAGATGCCTTTGGAATT
GACAAGACAGCAACTTGCAGGACAGTAGCAGTCAAAATGTTGAAAGAAGG
AGCAACACACAGTGAGCATCGAGCTCTCATGTCTGAACTCAAGATCCTCAT
TCATATTGGTCACCATCTCAATGTGGTCAACCTTCTAGGTGCCTGTACCAA
GCCAGGAGGGCCACTCATGGTGATTGTGGAATTCTGCAAATTTGGAAACC
TGTCCACTTACCTGAGGAGCAAGAGAAATGAATTTGTCCCTACAAGACCA
AAGGGGCACGATTCCGTCAAGGGAAAGACTACGTTGGAGCAATCCCTGTG
GATCTGAAACGGCGCTTGGACAGCATCACCAGTAGCCAGAGCTCAGCCAG
CTCTGGATTTGTGGAGGAGAAGTCCCTCAGTGATGTAGAAGAAGAGGAAG
CTCCTGAAGATCTGTATAAGGACTTCCTGACCTTGGAGCATCTCATCTGTT
ACAGCTTCCAAGTGGCTAAGGGCATGGAGTTCTTGGCATCGCGAAAGTGT
ATCCACAGGGACCTGGCGGCACGAAATATCCTCTTATCGGAGAAGAACGT
GGTTAAAATCTGTGACTTTGGCTTGGCCCGGGATATTTATAAAGATCCAGA
TTATGTCAGAAAAGGAGATGCTCGCCTCCCTTTGAAATGGATGGCCCCAG
AAACAATTTTTGACAGAGTGTACACAATCCAGAGTGACGTCTGGTCTTTTG
GTGTTTTGCTGTGGGAAATATTTTCCTTAGGTGCTTCTCCATATCCTGGGG
TAAAGATTGATGAAGAATTTTGTAGGCGATTGAAAGAAGGAACTAGAATGA
GGGCCCCTGATTATACTACACCAGAAATGTACCAGACCATGCTGGACTGC
TGGCACGGGGAGCCCAGTCAGAGACCCACGTTTTCAGAGTTGGTGGAACA
TTTGGGAAATCTCTTGCAAGCTAATGCTCAGCAGGATGGCAAAGACTACAT
TGTTCTTCCGATATCAGAGACTTTGAGCATGGAAGAGGATTCTGGACTCTC
TCTGCCTACCTCACCTGTTTCCTGTATGGAGGAGGAGGAAGTATGTGACC
CCAAATTCCATTATGACAACACAGCAGGAATCAGTCAGTATCTGCAGAACA
GTAAGCGAAAGAGCCGGCCTGTGAGTGTAAAAACATTTGAAGATATCCCG
TTAGAAGAACCAGAAGTAAAAGTAATCCCAGATGACAACCAGACGGACAGT
GGTATGGTTCTTGCCTCAGAAGAGCTGAAAACTTTGGAAGACAGAACCAAA
TTATCTCCATCTTTTGGTGGAATGGTGCCCAGCAAAAGCAGGGAGTCTGTG
GCATCTGAAGGCTCAAACCAGACAAGCGGCTACCAGTCCGGATATCACTC
CGATGACACAGACACCACCGTGTACTCCAGTGAGGAAGCAGAACTTTTAA
```

Figure 11 (cont.)

```
AGCTGATAGAGATTGGAGTGCAAACCGGTAGCACAGCCCAGATTCTCCAG
CCTGACTCGGGGACCACACTGAGCTCTCCTCCTGTTTAAAAGGAAGCATC
CACACCCCCAACTCCTGGACATCACATGAGAGGTGCTGCTCAGATTTTCAA
GTGTTGTTCTTTCCACCAGCAGGAAGTAGCCGCATTTGATTTTCATTTCGA
CAACAGAAAAAGGACCTCGGACTGCAGGGAGCCAGTCTTCTAGGCATATC
CTGGAAGAGGCTTGTGACCCAAGAATGTGTCTGTGTCTTCTCCCAGTGTTG
ACCTGATCCTCTTTTTCATTCATTTAAAAAGCATTTATCATGCCCCCTGCTG
CGGGTCTCACCATGGGTTTAGAACAAAGACGTTCAAGAAATGGCCCCATC
CTCAAAGAAGTAGCAGTACCTGGGGAGCTGACACTTCTGTAAAACTAGAA
GATAAACCAGGCAATGTAAGTGTTCGAGGTGTTGAAGATGGGAAGGATTT
GCAGGGCTGAGTCTATCCAAGAGGCTTTGTTTAGGACGTGGGTCCCAAGC
CAAGCCTTAAGTGTGGAATTCGGATTGATAGAAAGGAAGACTAACGTTACC
TTGCTTTGGAGAGTACTGGAGCCTGCAAATGCATTGTGTTTGCTCTGGTGG
AGGTGGGCATGGGGTCTGTTCTGAAATGTAAAGGGTTCAGACGGGGTTTC
TGGTTTTAGAAGGTTGCGTGTTCTTCGAGTTGGGCTAAAGTAGAGTTCGTT
GTGCTGTTTCTGACTCCTAATGAGAGTTCCTTCCAGACCGTTACGTGTCTC
CTGGCCAAGCCCCAGGAAGGAAATGATGCAGCTCTGGCTCCTTGTCTCCC
AGGCTGATCCTTTATTCAGAATACCACAAAGAAAGGACATTCAGCTCAAGG
CTCCCTGCCGTGTTGAAGAGTTCTGACTGCACAAACCAGCTTCTGGTTTCT
TCTGGAATGAATACCCTCATATCTGTCCTGATGTGATATGTCTGAGACTGA
ATGCGGGAGGTTCAATGTGAAGCTGTGTGGTGTCAAAGTTTCAGGAAG
GATTTTACCCTTTTGTTCTTCCCCCTGTCCCCAACCCACTCTCACCCCGCA
ACCCATCAGTATTTTAGTTATTTGGCCTCTACTCCAGTAAACCTGATTGGGT
TTGTTCACTCTCTGAATGATTATTAGCCAGACTTCAAAATTATTTTATAGCC
CAAATTATAACATCTATTGTATTATTTAGACTTTTAACATATAGAGCTATTTC
TACTGATTTTTGCCCTTGTTCTGTCCTTTTTTTCAAAAAAGAAAATGTGTTTT
TTGTTTGGTACCATAGTGTGAAATGCTGGGAACAATGACTATAAGACATGC
TATGGCACATATATTTATAGTCTGTTTATGTAGAAACAAATGTAATATATTAA
AGCCTTATATATAATGAACTTTGTACTATTCACATTTTGTATCAGTATTATGT
AGCATAACAAAGGTCATAATGCTTTCAGCAATTGATGTCATTTTATTAAAGA
ACATTGAAAAACTTGAAGGAATCCCTTTGCAAGGTTGCATTACTGTACCCA
```

Figure 11 (cont.)

TCATTTCTAAAATGGAAGAGGGGGTGGCTGGGCACAGTGGCCGACACCTA
AAAACCCAGCACTTTGGGGGGCCAAGGTGGGAGGATCGCTTGAGCCCAG
GAGTTCAAGACCAGTCTGGCCAACATGGTCAGATTCCATCTCAAAGAAAAA
AGGTAAAAATAAAATAAAATGGAGAAGAAGGAATCAGA

SEQ ID NO:83 (mouse VEGFR2)

CTGTGTTTCCTTAGATCGCGCGGACCGCTACCCGGCAGGACTGAAAGCCC
AGACTGTGTCCCGCAGCCGGGATAACCTGGCTGACCCGATTCCGCGGAC
ACCGCTGCAGCCGCGGCTGGAGCCAGGGCGCCGGTGCCCCGCGCTCTC
CCCGGTCTTGCGCTGCGGGGGCGCATACCGCCTCTGTGACTTCTTTGCG
GGCCAGGGACGGAGAAGGAGTCTGTGCCTGAGAACTGGGCTCTGTGCCC
AGCGCGAGGTGCAGGATGGAGAGCAAGGCGCTGCTAGCTGTCGCTCTGT
GGTTCTGCGTGGAGACCCGAGCCGCCTCTGTGGGTTTGCCTGGCGATTTT
CTCCATCCCCCAAGCTCAGCACACAGAAAGACATACTGACAATTTTGGCA
AATACAACCCTTCAGATTACTTGCAGGGGACAGCGGGACCTGGACTGGCT
TTGGCCCAATGCTCAGCGTGATTCTGAGGAAAGGGTATTGGTGACTGAAT
GCGGCGGTGGTGACAGTATCTTCTGCAAAACACTCACCATTCCCAGGGTG
GTTGGAAATGATACTGGAGCCTACAAGTGCTCGTACCGGGACGTCGACAT
AGCCTCCACTGTTTATGTCTATGTTCGAGATTACAGATCACCATTCATCGC
CTCTGTCAGTGACCAGCATGGCATCGTGTACATCACCGAGAACAAGAACA
AAACTGTGGTGATCCCCTGCCGAGGGTCGATTTCAAACCTCAATGTGTCTC
TTTGCGCTAGGTATCCAGAAAAGAGATTTGTTCCGGATGGAAACAGAATTT
CCTGGGACAGCGAGATAGGCTTTACTCTCCCCAGTTACATGATCAGCTATG
CCGGCATGGTCTTCTGTGAGGCAAAGATCAATGATGAAACCTATCAGTCTA
TCATGTACATAGTTGTGGTTGTAGGATATAGGATTTATGATGTGATTCTGAG
CCCCCCGCATGAAATTGAGCTATCTGCCGGAGAAAAACTTGTCTTAAATTG
TACAGCGAGAACAGAGCTCAATGTGGGGCTTGATTTCACCTGGCACTCTC
CACCTTCAAAGTCTCATCATAAGAAGATTGTAAACCGGGATGTGAAACCCT
TTCCTGGGACTGTGGCGAAGATGTTTTTGAGCACCTTGACAATAGAAAGTG
TGACCAAGAGTGACCAAGGGGAATACACCTGTGTAGCGTCCAGTGGACGG
ATGATCAAGAGAAATAGAACATTTGTCCGAGTTCACACAAAGCCTTTTATTG

Figure 11 (cont.)

CTTTCGGTAGTGGGATGAAATCTTTGGTGGAAGCCACAGTGGGCAGTCAA
GTCCGAATCCCTGTGAAGTATCTCAGTTACCCAGCTCCTGATATCAAATGG
TACAGAAATGGAAGGCCCATTGAGTCCAACTACACAATGATTGTTGGCGAT
GAACTCACCATCATGGAAGTGACTGAAAGAGATGCAGGAAACTACACGGT
CATCCTCACCAACCCCATTTCAATGGAGAAACAGAGCCACATGGTCTCTCT
GGTTGTGAATGTCCCACCCCAGATCGGTGAGAAGCCTTGATCTCGCCTA
TGGATTCCTACCAGTATGGGACCATGCAGACATTGACATGCACAGTCTACG
CCAACCCTCCCCTGCACCACATCCAGTGGTACTGGCAGCTAGAAGAAGCC
TGCTCCTACAGACCCGGCCAAACAAGCCCGTATGCTTGTAAAGAATGGAG
ACACGTGGAGGATTTCCAGGGGGGAAACAAGATCGAAGTCACCAAAAACC
AATATGCCCTGATTGAAGGAAAAAACAAAACTGTAAGTACGCTGGTCATCC
AAGCTGCCAACGTGTCAGCGTTGTACAAATGTGAAGCCATCAACAAAGCG
GGACGAGGAGAGAGGGTCATCTCCTTCCATGTGATCAGGGGTCCTGAAAT
TACTGTGCAACCTGCTGCCCAGCCAACTGAGCAGGAGAGTGTGTCCCTGT
TGTGCACTGCAGACAGAAATACGTTTGAGAACCTCACGTGGTACAAGCTTG
GCTCACAGGCAACATCGGTCCACATGGGCGAATCACTCACACCAGTTTGC
AAGAACTTGGATGCTCTTTGGAAACTGAATGGCACCATGTTTTCTAACAGC
ACAAATGACATCTTGATTGTGGCATTTCAGAATGCCTCTCTGCAGGACCAA
GGCGACTATGTTTGCTCTGCTCAAGATAAGAAGACCAAGAAAAGACATTGC
CTGGTCAAACAGCTCATCATCCTAGAGCGCATGGCACCCATGATCACCGG
AAATCTGGAGAATCAGACAACAACCATTGGCGAGACCATTGAAGTGACTTG
CCCAGCATCTGGAAATCCTACCCCACACATTACATGGTTCAAAGACAACGA
GACCCTGGTAGAAGATTCAGGCATTGTACTGAGAGATGGGAACCGGAACC
TGACTATCCGCAGGGTGAGGAAGGAGGATGGAGGCCTCTACACCTGCCA
GGCCTGCAATGTCCTTGGCTGTGCAAGAGCGGAGACGCTCTTCATAATAG
AAGGTGCCCAGGAAAAGACCAACTTGGAAGTCATTATCCTCGTCGGCACT
GCAGTGATTGCCATGTTCTTCTGGCTCCTTCTTGTCATTGTCCTACGGACC
GTTAAGCGGGCCAATGAAGGGGAACTGAAGACAGGCTACTTGTCTATTGT
CATGGATCCAGATGAATTGCCCTTGGATGAGCGCTGTGAACGCTTGCCTT
ATGATGCCAGCAAGTGGGAATTCCCCAGGGACCGGCTGAAACTAGGAAAA
CCTCTTGGCCGCGGTGCCTTCGGCCAAGTGATTGAGGCAGACGCTTTTGG

Figure 11 (cont.)

```
AATTGACAAGACAGCGACTTGCAAAACAGTAGCCGTCAAGATGTTGAAAGA
AGGAGCAACACACAGCGAGCATCGAGCCCTCATGTCTGAACTCAAGATCC
TCATCCACATTGGTCACCATCTCAATGTGGTGAACCTCCTAGGCGCCTGCA
CCAAGCCGGGAGGGCCTCTCATGGTGATTGTGGAATTCTGCAAGTTTGGA
AACCTATCAACTTACTTACGGGGCAAGAGAAATGAATTTGTTCCCTATAAG
AGCAAAGGGGCACGCTTCCGCCAGGGCAAGGACTACGTTGGGGAGCTCT
CCGTGGATCTGAAAAGACGCTTGGACAGCATCACCAGCAGCCAGAGCTCT
GCCAGCTCAGGCTTTGTTGAGGAGAAATCGCTCAGTGATGTAGAGGAAGA
AGAAGCTTCTGAAGAACTGTACAAGGACTTCCTGACCTTGGAGCATCTCAT
CTGTTACAGCTTCCAAGTGGCTAAGGGCATGGAGTTCTTGGCATCAAGGA
AGTGTATCCACAGGGACCTGGCAGCACGAAACATTCTCCTATCGGAGAAG
AATGTGGTTAAGATCTGTGACTTCGGCTTGGCCCGGGACATTTATAAAGAC
CCGGATTATGTCAGAAAAGGAGATGCCCGACTCCCTTTGAAGTGGATGGC
CCCGGAAACCATTTTTGACAGAGTATACACAATTCAGAGCGATGTGTGGTC
TTTCGGTGTGTTGCTCTGGGAAATATTTTCCTTAGGTGCCTCCCCATACCC
TGGGGTCAAGATTGATGAAGAATTTTGTAGGAGATTGAAAGAAGGAACTAG
AATGCGGGCTCCTGACTACACTACCCCAGAAATGTACCAGACCATGCTGG
ACTGCTGGCATGAGGACCCCAACCAGAGACCCTCGTTTTCAGAGTTGGTG
GAGCATTTGGGAAACCTCCTGCAAGCAAATGCGCAGCAGGATGGCAAAGA
CTATATTGTTCTTCCAATGTCAGAGACACTGAGCATGGAAGAGGATTCTGG
ACTCTCCCTGCCTACCTCACCTGTTTCCTGTATGGAGGAAGAGGAAGTGT
GCGACCCCAAATTCCATTATGACAACACAGCAGGAATCAGTCATTATCTCC
AGAACAGTAAGCGAAAGAGCCGGCCAGTGAGTGTAAAAACATTTGAAGAT
ATCCCATTGGAGGAACCAGAAGTAAAAGTGATCCCAGATGACAGCCAGAC
AGACAGTGGGATGGTCCTTGCATCAGAAGAGCTGAAAACTCTGGAAGACA
GGAACAAATTATCTCCATCTTTTGGTGGAATGATGCCCAGTAAAAGCAGGG
AGTCTGTGGCCTCGGAAGGCTCCAACCAGACCAGTGGCTACCAGTCTGG
GTATCACTCAGATGACACAGACACCACCGTGTACTCCAGCGACGAGGCAG
GACTTTTAAAGATGGTGGATGCTGCAGTTCACGCTGACTCAGGGACCACA
CTGCGCTCACCTCCTGTTTAAATGGAAGTGGTCCTGTCCCGGCTCCGCCC
CCAACTCCTGGAAATCACGAGAGAGGTGCTGCTTAGATTTTCAAGTGTTGT
```

Figure 11 (cont.)

```
TCTTTCCACCACCCGGAAGTAGCCACATTTGATTTTCATTTTTGGAGGAGG
GACCTCAGACTGCAAGGAGCTTGTCCTCAGGGCATTTCCAGAGAAGATGC
CCATGACCCAAGAATGTGTTGACTCTACTCTCTTTTCCATTCATTTAAAAGT
CCTATATAATGTGCCCTGCTGTGGTCTCACTACCAGTTAAAGCAAAAGACT
TTCAAACAGTGGCTCTGTCCTCCAAGAAGTGGCAACGGCACCTCTGTGAA
ACTGGATCGAATGGGCAATGCTTTGTGTGTTGAGGATGGGTGAGATGTCC
CAGGGCCGAGTCTGTCTACCTTGGAGGCTTTGTGGAGGATGCGGGCTATG
AGCCAAGTGTTAAGTGTGGGATGTGGACTGGGAGGAAGGAAGGCGCAAG
CTCGCTCGGAGAGCGGTTGGAGCCTGCAGATGCATTGTGCTGGCTCTGGT
GGAGGTGGGCTTGTGGCCTGTCAGGAAACGCAAAGGCGGCCGGCAGGGT
TTGGTTTTGGAAGGTTTGCGTGCTCTTCACAGTCGGGTTACAGGCGAGTTC
CCTGTGGCGTTTCCTACTCCTAATGAGAGTTCCTTCCGGACTCTTACGTGT
CTCCTGGCCTGGCCCCAGGAAGGAAATGATGCAGCTTGCTCCTTCCTCAT
CTCTCAGGCTGTGCCTTAATTCAGAACACCAAAAGAGAGGAACGTCGGCA
GAGGCTCCTGACGGGGCCGAAGAATTGTGAGAACAGAACAGAAACTCAG
GGTTTCTGCTGGGTGGAGACCCACGTGGCTGCCCTGGTGGCAGTGTCTG
AGGGTTCTCTGTCAAGTGGCGGTAAAGGCTCAGGCTGGTGTTCTTCCTCT
ATCTCCACTCCTGTCAGGCCCCAAGTCCTCAGTATTTTAGCTTTGTGGCT
TCCTGATGGCAGAAAAATCTTAATTGGTTGGTTTGCTCTCCAGATAATCACT
AGCCAGATTTCGAAATTACTTTTTAGCCGAGGTTATGATAACATCTACTGTA
TCCTTTAGAATTTTAACCTATAAAACTATGTCTACTGGTTTCTGCCTGTGTG
CTTATGTTAAAAAAAAAAAAAAAAAAAA
```

SEQ ID NO:84 (macaque VEGFR2)

```
TCCCGGGACCCCGGGAGAGCAGGCGGTGTGTGGTCACTGCGTTTCCTCT
GCCTGCGCCGGGCATCACTTGCGCGCCGCAGAGAGCCAGTCTGGCAGCC
GGGATATCCTCTCCTACTGGCATCCGCAGACGCCCTGCAGCCGCGGTC
GGCACCCGGGCTCCCAAGCCGTGTGCGCTCAACGGTCCTGCGCTGCGCG
GTGGCGCGGATTCCGTCTCCGCGCCTCCTTCTCTAGACAGGCGCTGGGA
GAAAGAATCGGCTTCAGAGTTCTGGGCATTTTGCCCAGCTCGAGGTGCAG
GATGGCGAGCAAGGTGCTGCTGGCCGTCGCCCTGTGGCTCTGCGTGGAG
```

Figure 11 (cont.)

```
ACCCGGGCCGCCTCTGTGGGTTTGCCTAGTGTTTCTCTTGATCTGCCCAG
GCTCAGCATACAAAAAGACATACTTACAATTAAGGCTAATACAACTCTTCAA
ATTACTTGCAGGGGACAGAGGGACTTGGACTGGCTTTGGCCCAATAATCA
GAGTGGCAGTGAGCAAAGGGTGGAGGTGACTGAGTGCAGCGATGGCCTC
TTCTGTAAGACACTCACAATTCCAAAAGTGATCGGAAATGACACTGGAGCC
TACAAGTGCTTCTACCGGGAAACTGACTTGGCCTCGGTCATTTATGTCTAT
GTTCAAGATTACAGATCTCCATTTATTGCTTCTGTTAGTGACCAACATGGAG
TCGTGTACATTACTGAGAACAAAACAAAACTGTGGTGATTCCATGTCTCG
GGTCCATTTCAAATCTCAACGTGTCACTTTGTGCAAGGTACCCAGAAAAGA
GATTTGTTCCTGATGGTAACAGAATTTCCTGGGACAGCAAGAAGGGCTTTA
CTATTCCCAGCTATATGATCAGCTATGCTGGCATGGTCTTCTGTGAAGCAA
AAATTAATGATGAAAGTTACCAGTCTATTATGTACATAGTTGTGGTTGTAGG
GTATAGGATTTATGATGTGGTTCTGAGTCCGTCTCATGGAGTTGAACTATC
TGTTGGAGAGAAGCTTGTCTTAAATTGTACAGCAAGAACTGAACTAAATGT
GGGGATTGACTTCAACTGGGAATACCCTTCTTCGAAGCATCAGCATAAGAA
ACTTGTAAACCGAGATCTAAAAACCCAGTCTGGGAGTGAGATGAAGAAATT
TTTGAGCACCTTAACTATAGATGGTGTAACCCGGAGTGACCAAGGATTGTA
CACCTGTGCAGCGTCCAGTGGGCTGATGACCAAGAAGAACAGCACATTTG
TCAGGGTCCATGAAAAACCTTTTGTTGCTTTTGGAAGTGGCATGGAATCTC
TGGTGGAAGCCACGGTGGGGGAGCGTGTCAGAATCCCTGTGAAGTACCTT
GGTTACCCGCCCCCAGAAATAAAATGGTATAAAAATGGAATACCCCTTGAG
TCCAATCACACAGTTAAAGTGGGGCATGTGCTGACGATCATGGAAGTGAG
CGAAAGAGACACAGGAAATTACACTGTCATCCTTACCAATCCCATTTCAAA
GGAGAAGCAGAGTCACGTGGTCTCTCTGGTTGTGTATGTCCCACCCCAGA
TTGGTGAGAAATCTCTGATCTCTCCTGTGGATTCCTACCAGTACGGCACCA
CTCAAACGCTGACATGTACGGTCTACGCTATTCCTCCCCGCATCACATCC
ACTGGTATTGGCAGTTGGAGGAAGAGTGCCCCAACGAGCCCAGCCAAGCT
GTCTCAGTGACAAACCCATACCCTTGTGAAGAATGGAGAAGTGTGGAGGA
CTTCCAGGGAGGAAATAAAATTGAAGTCAATAAAAATCAATTTGCTCTAATT
GAAGGAAAAAACAAAACTGTAAGTACCCTTGTTATCCAAGCGGCAAATGTG
TCAGCTTTGTACAAATGTGAAGCGGTCAACAAAGTCGGGAGAGGAGAGAG
```

Figure 11 (cont.)

```
GGTGATCTCCTTCCATGTTACCAGGGGTCCTGAAATTACTTTGCAACCTGA
CTTGCAGCCCACTGAACAGGAGAGCGTGTCTTTGTGGTGCACTGCAGACA
AATCTACATTTGAGAACCTCACATGGTACAAGCTTGGCCCACAGCCTCTGC
CAGTCCACGTGGGAGAGTTGCCCACACCTGTTTGCAAGAACTTGGATACT
CTTTGGAAATTGAATGCCACTATATTCTCTAATAGCACAAATGACATTTTGA
TCATGGAGCTTAAGAATGCATCCTTGCAGGACCAAGGAGACTATGTCTGC
GTTGCTCAAGACAGGAAGACCAAGAAAAGACATTGCGTGGTCAGGCAGCT
CACAGTCCTCGAGCGCGTGGCACCCATGATCACAGGAAACCTGGAGAATC
AGACGACGAGTATTGGGGAAACCATTGAAGTCTCATGCACGGCATCTGGG
AATCCCCCTCCACAGATCATGTGGTTTAAAGATAATGAGACCCTTGTAGAA
GACTCAGGCATTGTATTGAAGGATGGGAACCGGAACCTCACTATCCGCAG
AGTGAGGAAGGAGGACGAAGGCCTCTACACCTGCCAGGCATGCAGTGTT
CTTGGCTGTGCAAAAGTGGAGGCATTTTTCATAATAGAAGGTGCCCAGGAA
AAGACGAACTTGGAAATCATTATTCTAGTAGGCACAGCAGTGATTGCCATG
TTCTTCTGGCTACTTCTTGTCATCATTCTACGGACCGTTAAGCGGGCCAAT
GGAGGGGAACTGAAGACAGGCTACTTGTCCATCGTCATGGATCCTGATGA
ACTCCCATTGGATGAACACTGTGAACGACTGCCTTATGATGCCAGCAAATG
GGAATTCCCCAGAGACCGGCTGAAGCTAGGTAAGCCGCTTGGCCGTGGT
GCCTTTGGCCAAGTGATTGAAGCAGATGCCTTTGGAATTGACAAGACAGC
AACTTGCAGGACAGTAGCAGTCAAAATGTTGAAAGAAGGAGCGACACACA
GTGAGCATCGAGCCCTCATGTCTGAACTCAAGATCCTCATTCATATTGGTC
ACCATCTCAATGTGGTCAACCTTCTAGGTGCCTGTACCAAGCCAGGAGGG
CCACTCATGGTGATTGTGGAATTCTGCAAGTTTGGAAACCTATCCACTTAC
CTGAGGAGCAAGAGAAATGAATTTTTTGTTTTTTCCTTTGCTTTTTTATAGA
CCAAAGGGGCACGATTCCGTCAAGGGAAAGACTATGTTGGAGCAATCCCT
GTGGATCTGAAACGGCGCTTGGACAGCATCACCAGTAGCCAGAGCTCAGC
CAGCTCTGGATTTGTGGAGGAGAAGTCCCTCAGTGATGTAGAAGAAGAGG
AAGCTCCTGAAGACCTGTATAAGGACTTCCTGACCTTGGAGCATCTCATCT
GTTACAGCTTCCAAGTGGCTAAGGGCATGGAGTTCTTGGCATCACGAAAG
TGTATCCACAGGGACCTGGCGGCACGAAATATCCTCTTATCGGAGAAGAA
CGTGGTTAAAATCTGTGACTTTGGCTTGGCCCGGGATATTTATAAAGATCC
```

Figure 11 (cont.)

```
AGATTATGTCAGAAAAGGAGATGCTCGCCTCCCTTTGAAATGGATGGCCC
CAGAAACAATTTTTGACAGAGTGTACACAATCCAGAGTGACGTCTGGTCTT
TTGGCGTGTTGCTGTGGGAAATATTTTCCTTGGGTGCTTCTCCATATCCTG
GGGTAAAGATTGATGAAGAATTTTGTAGGCGATTGAAAGAAGGAACTAGAA
TGAGGGCCCCGATTATACTACACCAGAAATGTACCAGACCATGCTGGAC
TGCTGGCACGGGGAGCCCAGTCAGAGACCCACGTTTTCAGAGTTGGTGG
AACATTTGGGAAATCTCTTGCAAGCTAATGCTCAGCAGGACGGCAAAGACT
ATATTGTTCTTCCGATATCAGAGACTTTGAGCATGGAAGAGGATTCTGGAC
TCTCTCTGCCTACCTCACCTGTTTCCTGTATGGAGGAGGAGGAAGTATGTG
ACCCCAAATTCCATTATGACAACACAGCAGGAATCAGTCAGTATCTGCAGA
ACAGTAAGCGAAAGAGCCGGCCTGTGAGTGTAAAAACATTTGAAGACATC
CCATTAGAAGAACCAGAAGTAAAAGTAATCCCAGATGACAACCAGACGGA
CAGTGGTATGGTTCTTGCCTCAGAAGAGCTGAAAACTTTGGAAGACAGAAC
CAAATTAGCTCCATCTTTTAGTGGAATGGTGTCCAGCAAAAGCAGGGAGTC
TGTGGCATCTGAGGGCTCAAACCAGACAAGTGGCTACCAGTCCGGATATC
ACTCCGACGACACAGACACCACTGTGTACTCCAGTGAGGAAGCAGAACTT
TTAAAGCTGATAGAGATCGGAGTGCAAACCGGCAGCACAGCCCAGATTCT
CCAGCCTGACTCGGGGACCACATTGAGCTCCCTCCTGTTTAAAAGGAAG
CACCCACGCCCCCAACTCCTGGACATCACATAAGAGGTGCTGCTCAGATT
TTCAAGTGTTGTTCTTTCCACCAGCAGGAAGTAGCCGCATTTGATTTTCATT
TCAACAACAAAAAAGGACCTCGGACTGCAGGGAGCTAGTCTTCTAGGCA
TATCCTGGAAGAGGCTTGTGACCCAAGAATGTGTCCGTGTATTCTCCAGT
GTTAACCTGATCCTCTTTTTCATTCATTTAAAAAGCATTTATCATGCTGCCTA
CTGCGGGTCTCACCATGGGTTAGAACAAAGACGTTCAAGAAATGGCCCCA
TCCTCAAAGAAGTAGCAGTACCTGGGGAGTTGACACTTCTGTAAAACTAGA
AGATAAACCAGGCAATGTAAGTGTTTGGGGTGTTGCAGATGGGAAGGATT
TGCAGGGCTCAGTCTATCCAAGAGGCTTTGTTTAGGACGTCGGTCCCAAG
CCAAGCCTTAAGTGTGGAATTCAGATTGACAGAAAGGAAGACTAACATTAA
CTTGCTCTGAGAGAGTACTGGAGCCTGCAAATGCATTGTGTTGGCTCCGG
TGGAGGTGGGCATGGGGTCTGTTCTGAAATGTAAAGGCTTCAGATGGGGT
TTCTGGTTTTAGAAGGTTGCGTGTTCTTCGCAGTTGGGCTGAAGGAGAGTT
```

Figure 11 (cont.)

CCTTGTGCTGTTTCCGACTCCTAATGAGAGTTCCTTCCAGACCCTTACGTG
TCTCCTGGCCAAGCCCCAGGAAGGAAATTATGCAGCTCTGGCTCCTTGTC
TCTCAGGCTGATCCTTTATTCAGAACACCACAAAGTAAGGACATTCAGCTC
GAGGCTCCCTGCCGTGTTGAAGAGTTCTGACTGCACAAACCAGCTTCTGG
TTTCTTCTGGATGAATACCCTCATCTCTATCCTGATGTGATATGTCTGAGAC
TGAAGGCGGGAGGTTCAATGTCAAGCTGTGTGTAGTGTCAAAGCTTCAGG
AAGGATTTTACCCTTTTGTTCTTCCCCCGTCCCCAACCCACTCTCACCCC
ACAACCCATCAGGATTTTAGTTATTTGGCCTCTACACTCCAGTAAACCTCTA
CACTCCAGTAAACAAACTCCAGAGAGTTTGTTCACTCTCTGAATGATTATTA
GCCAGACTTCAAAATTACTTTATAGCCCAAATTATAACATCTATTGTATTGTT
TAGACTTTTAACATATAGAGCTATTTCTACTGATTTTTGCCCTTTTTCTGTCC
TTTTTTTCAAAAAAGAAAATGTGTTTTTTGTTTGGTACCATAGTGTGAAATGC
TGGGAACAATGACTATAAGACATGCTATGGCACATATATTTATAGTCTGTTT
ATGTAGAAACAAATGTAATATATTAAAGCCTTATATTATATATAATGAACTTT
GTACTATTCACATTTTGTATCAGTATTATGTAGCATAACAAAGGTCATAATG
CTTTCAGCAATCGATGTCATTTTATTAAAAAACATTGAAAAACTTGAA

SEQ ID NO:85 (Human PDGFR- β)

CTCCTGAGGCTGCCAGCAGCCAGCAGTGACTGCCCGCCCTATCTGGGAC
CCAGGATCGCTCTGTGAGCAACTTGGAGCCAGAGAGGAGATCAACAAGGA
GGAGGAGAGAGCCGGCCCCTCAGCCCTGCTGCCCAGCAGCAGCCTGTGC
TCGCCCTGCCCAACGCAGACAGCCAGACCCAGGGCGGCCCCTCTGGCGG
CTCTGCTCCTCCCGAAGGATGCTTGGGGAGTGAGGCGAAGCTGGGCCGC
TCCTCTCCCCTACAGCAGCCCCCTTCCTCCATCCCTCTGTTCTCCTGAGCC
TTCAGGAGCCTGCACCAGTCCTGCCTGTCCTTCTACTCAGCTGTTACCCAC
TCTGGGACCAGCAGTCTTTCTGATAACTGGGAGAGGGCAGTAAGGAGGAC
TTCCTGGAGGGGGTGACTGTCCAGAGCCTGGAACTGTGCCCACACCAGAA
GCCATCAGCAGCAAGGACACCATGCGGCTTCCGGGTGCGATGCCAGCTC
TGGCCCTCAAAGGCGAGCTGCTGTTGCTGTCTCCTGTTACTTCTGGAAC
CACAGATCTCTCAGGGCCTGGTCGTCACACCCCGGGGCCAGAGCTTGT
CCTCAATGTCTCCAGCACCTTCGTTCTGACCTGCTCGGGTTCAGCTCCGG

Figure 11 (cont.)

TGGTGTGGGAACGGATGTCCCAGGAGCCCCCACAGGAAATGGCCAAGGC
CCAGGATGGCACCTTCTCCAGCGTGCTCACACTGACCAACCTCACTGGGC
TAGACACGGGAGAATACTTTTGCACCCACAATGACTCCCGTGGACTGGAG
ACCGATGAGCGGAAACGGCTCTACATCTTTGTGCCAGATCCCACCGTGGG
CTTCCTCCCTAATGATGCCGAGGAACTATTCATCTTTCTCACGGAAATAACT
GAGATCACCATTCCATGCCGAGTAACAGACCCACAGCTGGTGGTGACACT
GCACGAGAAGAAGGGGACGTTGCACTGCCTGTCCCTATGATCACCAAC
GTGGCTTTTCTGGTATCTTTGAGGACAGAAGCTACATCTGCAAAACCACCA
TTGGGGACAGGGAGGTGGATTCTGATGCCTACTATGTCTACAGACTCCAG
GTGTCATCCATCAACGTCTCTGTGAACGCAGTGCAGACTGTGGTCCGCCA
GGGTGAGAACATCACCCTCATGTGCATTGTGATCGGGAATGAGGTGGTCA
ACTTCGAGTGGACATACCCCGCAAAGAAAGTGGGCGGCTGGTGGAGCC
GGTGACTGACTTCCTCTTGGATATGCCTTACCACATCCGCTCCATCCTGCA
CATCCCCAGTGCCGAGTTAGAAGACTCGGGGACCTACACCTGCAATGTGA
CGGAGAGTGTGAATGACCATCAGGATGAAAAGGCCATCAACATCACCGTG
GTTGAGAGCGGCTACGTGCGGCTCCTGGGAGAGGTGGGCACACTACAAT
TTGCTGAGCTGCATCGGAGCCGGACACTGCAGGTAGTGTTCGAGGCCTAC
CCACCGCCCACTGTCCTGTGGTTCAAAGACAACCGCACCCTGGGCGACTC
CAGCGCTGGCGAAATCGCCCTGTCCACGCGCAACGTGTCGGAGACCCGG
TATGTGTCAGAGCTGACACTGGTTCGCGTGAAGGTGGCAGAGGCTGGCCA
CTACACCATGCGGGCCTTCCATGAGGATGCTGAGGTCCAGCTCTCCTTCC
AGCTACAGATCAATGTCCCTGTCCGAGTGCTGGAGCTAAGTGAGAGCCAC
CCTGACAGTGGGGAACAGACAGTCCGCTGTCGTGGCCGGGGCATGCCCC
AGCCGAACATCATCTGGTCTGCCTGCAGAGACCTCAAAAGGTGTCCACGT
GAGCTGCCGCCCACGCTGCTGGGGAACAGTTCCGAAGAGGAGAGCCAGC
TGGAGACTAACGTGACGTACTGGGAGGAGGAGCAGGAGTTTGAGGTGGT
GAGCACACTGCGTCTGCAGCACGTGGATCGGCCACTGTCGGTGCGCTGC
ACGCTGCGCAACGCTGTGGGCCAGGACACGCAGGAGGTCATCGTGGTGC
CACACTCCTTGCCCTTTAAGGTGGTGGTGATCTCAGCCATCCTGGCCCTG
GTGGTGCTCACCATCATCTCCCTTATCATCCTCATCATGCTTTGGCAGAAG
AAGCCACGTTACGAGATCCGATGGAAGGTGATTGAGTCTGTGAGCTCTGA

Figure 11 (cont.)

```
CGGCCATGAGTACATCTACGTGGACCCCATGCAGCTGCCCTATGACTCCA
CGTGGGAGCTGCCGCGGGACCAGCTTGTGCTGGGACGCACCCTCGGCTC
TGGGGCCTTTGGGCAGGTGGTGGAGGCCACGGCTCATGGCCTGAGCCAT
TCTCAGGCCACGATGAAAGTGGCCGTCAAGATGCTTAAATCCACAGCCCG
CAGCAGTGAGAAGCAAGCCCTTATGTCGGAGCTGAAGATCATGAGTCACC
TTGGGCCCCACCTGAACGTGGTCAACCTGTTGGGGGCCTGCACCAAAGG
AGGACCCATCTATATCATCACTGAGTACTGCCGCTACGGAGACCTGGTGG
ACTACCTGCACCGCAACAAACACACCTTCCTGCAGCACCACTCCGACAAG
CGCCGCCCGCCCAGCGCGGAGCTCTACAGCAATGCTCTGCCCGTTGGGC
TCCCCCTGCCCAGCCATGTGTCCTTGACCGGGGAGAGCGACGGTGGCTA
CATGGACATGAGCAAGGACGAGTCGGTGGACTATGTGCCCATGCTGGACA
TGAAAGGAGACGTCAAATATGCAGACATCGAGTCCTCCAACTACATGGCC
CCTTACGATAACTACGTTCCCTCTGCCCCTGAGAGGACCTGCCGAGCAAC
TTTGATCAACGAGTCTCCAGTGCTAAGCTACATGGACCTCGTGGGCTTCAG
CTACCAGGTGGCCAATGGCATGGAGTTTCTGGCCTCCAAGAACTGCGTCC
ACAGAGACCTGGCGGCTAGGAACGTGCTCATCTGTGAAGGCAAGCTGGTC
AAGATCTGTGACTTTGGCCTGGCTCGAGACATCATGCGGGACTCGAATTA
CATCTCCAAAGGCAGCACCTTTTTGCCTTTAAAGTGGATGGCTCCGGAGA
GCATCTTCAACAGCCTCTACACCACCCTGAGCGACGTGTGGTCCTTCGGG
ATCCTGCTCTGGGAGATCTTCACCTTGGGTGGCACCCCTTACCCAGAGCT
GCCCATGAACGAGCAGTTCTACAATGCCATCAAACGGGGTTACCGCATGG
CCCAGCCTGCCCATGCCTCCGACGAGATCTATGAGATCATGCAGAAGTGC
TGGGAAGAGAAGTTTGAGATTCGGCCCCCCTTCTCCCAGCTGGTGCTGCT
TCTCGAGAGACTGTTGGGCGAAGGTTACAAAAGAAGTACCAGCAGGTGG
ATGAGGAGTTTCTGAGGAGTGACCACCCAGCCATCCTTCGGTCCCAGGCC
CGCTTGCCTGGGTTCCATGGCCTCCGATCTCCCCTGGACACCAGCTCCGT
CCTCTATACTGCCGTGCAGCCCAATGAGGGTGACAACGACTATATCATCC
CCCTGCCTGACCCCAAACCCGAGGTTGCTGACGAGGGCCCACTGGAGGG
TTCCCCCAGCCTAGCCAGCTCCACCCTGAATGAAGTCAACACCTCCTCAA
CCATCTCCTGTGACAGCCCCCTGGAGCCCAGGACGAACCAGAGCCAGA
GCCCCAGCTTGAGCTCCAGGTGGAGCCGGAGCCAGAGCTGGAACAGTTG
```

Figure 11 (cont.)

```
CCGGATTCGGGGTGCCCTGCGCCTCGGGCGGAAGCAGAGGATAGCTTCC
TGTAGGGGGCTGGCCCCTACCCTGCCCTGCCTGAAGCTCCCCCCTGCC
AGCACCCAGCATCTCCTGGCCTGGCCTGACCGGGCTTCCTGTCAGCCAG
GCTGCCCTTATCAGCTGTCCCCTTCTGGAAGCTTTCTGCTCCTGACGTGTT
GTGCCCCAAACCCTGGGGCTGGCTTAGGAGGCAAGAAAACTGCAGGGGC
CGTGACCAGCCCTCTGCCTCCAGGGAGGCCAACTGACTCTGAGCCAGGG
TTCCCCAGGGAACTCAGTTTTCCCATATGTAAGATGGGAAAGTTAGGCTT
GATGACCCAGAATCTAGGATTCTCTCCCTGGCTGACAGGTGGGGAGACCG
AATCCCTCCCTGGGAAGATTCTTGGAGTTACTGAGGTGGTAAATTAACTTT
TTTCTGTTCAGCCAGCTACCCCTCAAGGAATCATAGCTCTCTCCTCGCACT
TTTATCCACCCAGGAGCTAGGGAAGAGACCCTAGCCTCCCTGGCTGCTGG
CTGAGCTAGGGCCTAGCCTTGAGCAGTGTTGCCTCATCCAGAAGAAAGCC
AGTCTCCTCCCTATGATGCCAGTCCCTGCGTTCCCTGGCCCGAGCTGGTC
TGGGGCCATTAGGCAGCCTAATTAATGCTGGAGGCTGAGCCAAGTACAGG
ACACCCCAGCCTGCAGCCCTTGCCCAGGGCACTTGGAGCACACGCAGC
CATAGCAAGTGCCTGTGTCCCTGTCCTTCAGGCCCATCAGTCCTGGGGCT
TTTTCTTTATCACCCTCAGTCTTAATCCATCCACCAGAGTCTAGAAGGCCA
GACGGGCCCCGCATCTGTGATGAGAATGTAAATGTGCCAGTGTGGAGTGG
CCACGTGTGTGTGCCAGTATATGGCCCTGGCTCTGCATTGGACCTGCTAT
GAGGCTTTGGAGGAATCCCTCACCCTCTCTGGGCCTCAGTTTCCCCTTCA
AAAAATGAATAAGTCGGACTTATTAACTCTGAGTGCCTTGCCAGCACTAAC
ATTCTAGAGTATTCCAGGTGGTTGCACATTTGTCCAGATGAAGCAAGGCCA
TATACCCTAAACTTCCATCCTGGGGGTCAGCTGGGCTCCTGGGAGATTCC
AGATCACACATCACACTCTGGGGACTCAGGAACCATGCCCCTTCCCCAGG
CCCCCAGCAAGTCTCAAGAACACAGCTGCACAGGCCTTGACTTAGAGTGA
CAGCCGGTGTCCTGGAAAGCCCCAGCAGCTGCCCCAGGGACATGGGAA
GACCACGGGACCTCTTTCACTACCCACGATGACCTCCGGGGGTATCCTGG
GCAAAAGGGACAAAGAGGGCAAATGAGATCACCTCCTGCAGCCCACCACT
CCAGCACCTGTGCCGAGGTCTGCGTCAAGACAGAATGGACAGTGAGGA
CAGTTATGTCTTGTAAAAGACAAGAAGCTTCAGATGGGTACCCCAAGAAGG
ATGTGAGAGGTGGGCGCTTTGGAGGTTTGCCCCTCACCCACCAGCTGCCC
```

Figure 11 (cont.)

CATCCCTGAGGCAGCGCTCCATGGGGGTATGGTTTTGTCACTGCCCAGAC
CTAGCAGTGACATCTCATTGTCCCCAGCCCAGTGGGCATTGGAGGTGCCA
GGGGAGTCAGGGTTGTAGCCAAGACGCCCCGCACGGGGAGGGTTGGG
AAGGGGGTGCAGGAAGCTCAACCCTCTGGGCACCAACCCTGCATTGCA
GGTTGGCACCTTACTTCCCTGGGATCCCCAGAGTTGGTCCAAGGAGGGAG
AGTGGGTTCTCAATACGGTACCAAAGATATAATCACCTAGGTTTACAAATAT
TTTTAGGACTCACGTTAACTCACATTTATACAGCAGAAATGCTATTTTGTAT
GCTGTTAAGTTTTTCTATCTGTGTACTTTTTTTTAAGGGAAAGATTTTAATAT
TAAACCTGGTGCTTCTCACTCACAAAAA

SEQ ID NO:86 (mouse PDGFR- β)

GGGGCAGAGAAAGCCCACAGTGGTGTGAGCTCTGGGGCTGTCTGTGGCC
ACAGTCCCGGCTACCCTATCTGGGACCTAGGATTGCTCTGGGAGTAACTT
TGAGAGAGAGGAGAACAGAGAGGAAACAGTCCAGAGCCAGAGCGGGCCC
AGACCAGTCGTCAGTCTCCTGCCTGCCAGCTAGACCTAGGGCGGCCCCTC
GGGCTGCTCCGCTCCTCCCGGAGGATGCTTTTGGAGTGAGGAGGGGCCG
GGCTGCTTCTCACCCCTGAGCACCCTCTCCATTCCCCTGATTCTCTCAGG
GTTTTCCGCAATCAGGCCAGCCCTTCTACTGCTGTCCGTTTTTGGGTCCA
GCAAAATAACAGAAGACAGCGAGGTGGACTTCCTGGAGGGGGTGATAGCT
CACATCAGAAGCCATCTGTAGCCCGGACACCATGGGGCTTCCAGGAGTGA
TACCAGCTTTAGTCCTCAGAGGCCAGTTGTTGCTGTCCGTGTTATGGCTCC
TGGGACCGCAGACCTCCCGGGGCCTAGTCATCACGCCCCTGGGCCAGA
GTTTGTTCTCAACATCTCCAGCACCTTTGTTCTGACCTGCTCGGGCTCAGC
TCCGGTGATGTGGGAACAGATGTCCCAGGTGCCCTGGCAAGAAGCGGCC
ATGAATCAGGACGGCACCTTCTCCAGTGTGCTGACACTGACCAATGTCACT
GGGGGAGACACTGGGGAATACTTTTGTGTCTACAACAACTCACTAGGGCC
GGAGCTCAGTGAGAGGAAGCGTATCTATATCTTTGTGCCAGATCCCACCAT
GGGCTTCCTCCCTATGGACTCCGAGGACCTGTTCATTTTTGTCACGGATGT
CACTGAGACGACAATTCCGTGCCGAGTGACAGACCCCAGCTGGAGGTG
ACGCTACATGAGAAGAAGTGGATATCCCCCTACACGTACCCTACGACCA
CCAGCGAGGTTTCACTGGTACTTTTGAGGACAAGACTTACATTTGCAAAAC

Figure 11 (cont.)

```
CACCATTGGGGACAGGGAAGTGGACTCCGATACTTACTACGTCTACAGCC
TCCAGGTGTCATCCATCAACGTCTCTGTGAATGCCGTGCAGACTGTGGTC
CGCCAGGGCGAGAGCATCACCATCCGGTGCATTGTGATGGGCAATGATGT
GGTGAACTTCCAATGGACGTACCCCGCATGAAGAGTGGGCGGCTGGTG
GAGCCAGTGACAGACTACCTCTTTGGAGTGCCCTCCCGCATTGGCTCCAT
CCTGCATATCCCCACGGCTGAGCTGAGTGATTCGGGCACCTATACTTGCA
ACGTGTCAGTGAGTGTGAACGACCATGGCGATGAGAAAGCCATCAACATC
TCTGTGATCGAGAATGGCTACGTGCGGCTGCTGGAGACACTGGGAGATGT
AGAAATTGCTGAGCTGCACCGGAGTCGGACGCTGCGGGTGGTGTTCGAG
GCTTATCCGATGCCTTCTGTCCTGTGGCTCAAGGACAACCGTACCTTGGG
TGACTCCGGCGCTGGCGAGTTAGTTTTGTCTACTCGCAACATGTCTGAGA
CCCGGTACGTGTCAGAACTGATCCTGGTACGTGTGAAGGTGTCAGAAGCG
GGCTACTATACTATGCGAGCCTTCCACGAGGACGATGAGGTCCAGCTCTC
CTTCAAGCTGCAGGTCAATGTCCCCGTCCGTGTGCTGGAGCTGAGTGAGA
GTCACCCTGCCAATGGGGAGCAGACAATCCGCTGTCGTGGCCGGGGCAT
GCCTCAGCCAAATGTCACCTGGTCTACCTGCAGAGACCTCAAAAGTAGGT
GTCCACGAAAACTGTCACCCACACCCTTGGGGAATAGTTCCAAGGAGGAG
AGCCAGCTAGAAACGAATGTGACTTTCTGGGAGGAAGATCAGGAATACGA
GGTGGTGAGCACACTGCGCCTGCGCCACGTGGATCAGCCACTGTCCGTA
CGCTGCATGCTGCAGAACTCCATGGGTGGAGATTCGCAGGAGGTCACCGT
GGTCCCACATTCCTTGCCCTTCAAAGTGGTGGTGATCTCAGCCATCCTGG
CCTTAGTGGTCCTTACCGTCATCTCTCTCATCATCCTCATCATGCTGTGGC
AGAAGAAGCCACGCTATGAGATCCGATGGAAGGTCATTGAGTCTGTGAGC
TCTGACGGTCATGAGTACATCTACGTGGACCCTGTGCAGTTGCCTTACGA
CTCCACCTGGGAGCTGCCACGGGACCAGCTTGTTCTGGGACGCACTCTTG
GCTCTGGGGCTTTCGGACAGGTGGTGGAGGCCACAGCTCACGGTCTGAG
CCATTCGCAGGCCACCATGAAAGTGGCTGTCAAGATGCTGAAATCGACAG
CCAGAAGTAGCGAGAAGCAAGCCTTAATGTCCGAGCTGAAGATTATGAGT
CATCTTGGACCCCACCTGAACGTGGTCAACCTGCTGGGGCCTGCACCAA
AGGAGGGCCCATCTACATCATCACGGAATACTGCCGATACGGTGATCTGG
TGGACTACCTGCACCGGAACAAACACACCTTCTTGCAGCGACACTCCAAC
```

Figure 11 (cont.)

AAGCATTGTCCGCCCAGTGCTGAGCTCTACAGCAACGCCCTGCCAGTGGG
GTTCTCCCTACCCAGCCACTTGAACCTGACTGGGGAGAGTGACGGTGGCT
ACATGGATATGAGCAAGGATGAATCTATAGATTACGTGCCCATGTTGGACA
TGAAAGGAGACATCAAATACGCAGACATTGAGTCCCCAGCTACATGGCC
CCTTATGATAACTATGTCCCATCTGCCCCTGAAAGGACCTATCGCGCCACC
TTAATCAACGACTCACCAGTGCTCAGCTACACAGACCTCGTGGGCTTCAG
CTACCAAGTGGCCAACGGCATGGACTTCTTAGCCTCTAAGAACTGTGTTCA
CCGAGACTTGGCGGCCAGGAATGTGCTCATCTGCGAGGGCAAGCTGGTC
AAGATCTGTGACTTCGGCCTGGCTCGAGACATCATGAGGGACTCAAACTA
CATCTCCAAAGGCAGCACCTTCCTGCCTCTGAAGTGGATGGCCCCAGAGA
GCATCTTCAACAGCCTCTACACCACTTTGAGTGATGTCTGGTCTTTTGGGA
TCCTACTCTGGGAGATCTTCACACTGGGTGGCACCCCTTACCCAGAGCTG
CCCATGAACGACCAGTTCTACAATGCCATCAAGAGGGGCTACCGCATGGC
CCAGCCTGCTCATGCCTCCGACGAGATCTATGAGATCATGCAGAAATGCT
GGGAAGAAAAGTTTGAGACTCGACCCCCCTTCTCCCAGCTGGTGCTGCTC
CTGGAGAGGCTTCTGGGTGAAGGCTATAAAAAGAAGTACCAGCAGGTAGA
TGAGGAGTTCCTGAGGAGTGACCATCCTGCCATCCTGAGGTCCCAAGCCC
GCTTTCCGGGGATCCACAGCCTCCGATCCCTCTGGACACCAGCTCTGTT
CTCTACACTGCCGTGCAGCCCAATGAGAGTGACAATGACTACATCATCCC
CTTACCTGACCCCAAGCCTGACGTTGCTGATGAAGGTCTCCCAGAGGGGT
CCCCCAGCCTTGCCAGTTCCACCTTGAATGAAGTCAACACTTCCTCCACCA
TCTCCTGCGACAGTCCCCTGGAGCTCCAAGAAGAGCCACAGCAAGCAGAG
CCTGAGGCACAACTGGAGCAGCCACAGGATTCAGGCTGCCCAGGACCTC
TGGCTGAAGCAGAGGACAGCTTCCTGTAGGAACTGACATCACTCCATTTTG
CCCGAATCTCCCTTCTGCCTCCCAGAACCCAACCCTCTTGGCCTGGCCTG
GCCTGGCCTGGCCTCCCAGCAGCTACACTGCCACAAGCTGTCCCCTCGA
GGAAAGCCCTTGGTTTGCAGCACTCAAGGTCCAGGGACCCAGCTTAGCTT
AGGAGGCAAGAGAACTCTGCCTCGGGAAGGTCATGGACTCTGAACCAG
GGTTCCTCCAGGGGACTCAGTTTCCCCAAATGTAAGAGGAAGAGTTGTAC
TTGGCTACAGGACAGGTCTGGAGCCCGGATTCCTGCAGAAATCCACGACT
GTACGGTGGTGTGTTCATATCCTCCTGTGTAGCAGCTGCCCCTCAGCTGG

Figure 11 (cont.)

ATTGCTCTACTTTGATCTTCCTAAGAATCAGGCAAGGACCTGGTGTCTGGC
TCCTGGCCAAACTGTAACCAGCCTTGGACAAGGTCTTTTCATTCAGAGCCC
ACCTCCCCTGGTCTTAGCTTTCCCAGGCCCGAGCTGGTCTGGGGCCAGCC
ATGCTTAATGAATGCTGTTAGTGGTGAAGGTAGGCCGAGTACAGAATGCTC
TGGCCTGCAGCCCTGCCTGGGCACTCAGGGCACACCTGGCCACAGGAAG
CACCCACTCCTTTCAGCCCCACCAGTCCTAGAATAGTCCCCAGGTCACTCT
CAGCTGACCCACCCACCAGAGTCTGCAGGGCCATTGTCCACGCCTGTGAT
AGGCTAAGCATCTGCCTGAAGTGTGTACCTACCACTAGGAGCCCTGGCTC
TGCGCTGGACCTGCTATGAGACCTTGGGGGCTTTCCTTGTTCTCTCTGGG
GACCAGTTTTCTTTCCCCTTTGAAAAGCAAGTTGGACACATAGACTCTGAG
TACCCTGTCAATAGTACAATTCTTGTATGTTCTGGGAGTTTGCTCTTGTCCC
GAGGAAGCAGGGTCAAGTCCTTAAACTGATCTTTCTAGGGGTCAGCTGAG
CTCTTGGAAGATCCTGATACACTTCACACTCTGGGGGTTCAGGAACCGA
GCCTCTTCTTCAAGTCTCCAAGTGCAACTGCCCAGACCTTGACTTGGAGTG
ACAGTGAGTGTCCTAGGAAACCCCCTTACAGCTGTCCTGAGGACACAGAA
GAGACCACGAGACCCTTTTTTCATATCATGAAGCCAGCAAGAGTGGCAGA
GAAGGCAAGCCAGGTTACCTCGGGCCACTGTCACCAGCAGCGTGTGGAC
AGACATGATGGACAGTGAGGACAGACGTCCCATGCAGGACAAGAGACTTG
AGATGGGCAATGAGAGGAAGATGCTGACGGGATTACCACCTCAACTGCCA
GCTGCCCCGTCCCCAGGGAGCACCCCACAGAAACAGTTCTAACCCTGAA
CCAATGAACATTGCAAGTGCCTGGGGACTAGGGAGTGGGGGGAAGTCAG
CCTTTCTGGGGACCCTCCCTGCTAGCTGGTTGGCTAGCTGGCATCTCCCC
GCTTGGAGCAGCAGAGGCTGGGGAGTACTGCTCACAATGGTACCAAAGAT
AGAATCACCTAGGTTTACAAGTACTTGTAGGACTCGAGATAACCCACATTT
AGACACCGGAAGTGCTATTTTATATGCTGTTAAGTTTTCCTATCTGTACTTT
TTTTTTAAATGGGAAAGATTTTAATATTAAACTTGGTGCTTCTCACTGAATAA
CCG

SEQ ID NO:87 macaque PDGFR-β

CTCCTGAGGCTGCCAGCAGCCAGCAGTGACTGCCCGCCCTATCTGGGAC
CCAGGATCGCTCTGTGAGCAACTTGGAGCCAGAGAGGAGATCAACAACGA

Figure 11 (cont.)

GGAGGAGAGAGCCGGCCCCTCAGCCCAGCTGCCCAGCAGCAGCCTGCG
CTCGCCCTGCCCAACGCAGACAGCCAGACCCAGGGCGGCCCCTCTGGCG
GCTCTGCTCCTCCCGAAGGATGCTTGGGGAGTGAGGCGAAGCTGGGCCG
CTCCTCTTCCCTGCAGCAGTCCCCTCCCTCCATCCCTCCGTTCTCCTGAGC
CTTCAGGAGCCTGCAACGGTCCTGCCTGGCCTTCTACCCAGCTGTTACCC
ACTCTGGGACCAGCAGTCTTTCTGATAACAGAAACTCCAAACTTGATAACA
GGCAGAGGGCAGTAAGGAGGACTTCCTGGAGGGGGTGACTGTCCAGAGC
CTGGAACTCTGCCCACACCAGAAGCCATCAGCAGCAAGGACACCATGCGG
CTTCCGGGTGCGATGCCAGCTCTGGCCCTCAAAGGCCAGCTGCTGTTGCT
GCCCCTGCTGTTACTGCTGGAACCGCAGGTCTCTCAGGGCCTGGTCATCA
CACCCCCGGGGCCAGAGCTTATCCTCAATGTCTCCAGCACCTTTGTTCTG
ACCTGCTCGGGTTCAGCTCCCGTGGTGTGGGAGCGGATGTCCCAGGAGC
TCCCACAGGAAATGGCCAAGGCCCAGGACAATACCTTCTCCAGTGTGCTG
ACACTGACCAACCTCACTGGGCTAGACACGGGAGAATACTTTTGCACCTA
CAATGACTCCCGTGGACTGGAGCCTGATGAGCGGAAACGGCTCTACATCT
TTGTGCCAGATCCCACCATGGGCTTCCTCCCTAATGACGCCGAGGAACTA
TTCATCTTTCTTACGGAAATAACTGAGATCACCATTCCATGCCGAGTAACA
GACCCACAACTGGTGGTGACACTGCACGAGAAGAAAGGGGACATTGCACT
GCCTGTCCCCTACGATCACCAGCGTGGCTTTTCTGGTATCTTTGAGGACA
GAAGCTACATCTGCAAAACCACCATTGGGGACAGGGAGGTGGATTCCGAC
GCCTACTATGTCTACAGACTCCAGGTGTCATCCATCAACGTCTCCGTGAAT
GCAGTGCAGACGGTGGTCCGCCAGGGTGAGAACATTACCCTCATGTGCAT
TGTGATCGGGAATGAGGTGGTCAACTTCGAGTGGATGTACCCCCGCAAAG
AAAGTGGGCGGCTGGTGGAGCCGGTGACCGACTTCCTCTTGGATATGCCT
TACCACATCCGCTCCATCCTGCACATCCCCAGTGCCGAGTTAGAAGACTC
GGGGACCTACACCTGCAATGTGACAGAGAGTGTGAATGACCATCAGGATG
AAAAGGCCATCAACATCACTGTGGTTGAGAGTGGCTACGTGCGGCTCCTG
GGAGAGGTGGGAGCACTACAATTTGCTGAGCTGCACCGGAGCCGGACAC
TGCAGGTAGTGTTCGAGGCCTACCCTCCGCCCACCGTCCTGTGGTTCAAA
GACAACCGCACCTTGGGCGACTCCAGCGCAGGCGAGATCGCCCTGTCCA
CGCGCAACGTGTCAGAGACCAGGTATGTGTCAGAGCTGACACTCGTTCGG

Figure 11 (cont.)

GTGAAGGTGGCAGAGGCTGGCCACTACACCATGCGGGCCTTCCATGAGG
ACGCTGAGGTCCAGCTCTCCTTCCAGCTACAGATCAATGTCCCTGTCCGC
GTGCTGGAGCTAAGTGAGAGCCACCCAGACAGCGGGGAACAGACAGTCC
GCTGTCGTGGCCGGGGCATGCCCCAGCCGAACATCATCTGGTCTGCCTG
CAGAGACCTCAAAAGGTGTCCACGCGAGCTGCCGCCCATGCTGCTGGGG
AACAGTTCTGAAGAGGAGAGCCAGCTGGAGACGAACGTGACATACTGGGA
GGAGGAGCAGGAGTTTGAGGTGGTGAGCACACTGCGTCTGCAGCACGTG
GATCGGCCACTGTCGGTGCGCTGCACGCTGCGCAACGCTGTGGGCCAGG
ACATGCAGGAGGTCATCGTGGTGCCACACTCTTTGCCCTTCAAGGCAGTG
GTGATCTCAGCCATCCTGGCCCTGGTGGTCCTCACCATCATCTCCCTTATC
ATCCTCATCATGCTTTGGCAGAAGAAGCCACGTTACGAGATCCGATGGAA
GGTGATTGAGTCTGTGAGCTCTGATGGCCATGAGTACATCTACGTGGACC
CCATGCAGCTGCCCTATGACTCCACGTGGGAGCTGCCGCGGGACCAGCT
TGTGCTGGGACGCACCCTCGGCTCTGGGGCCTTTGGGCAGGTGGTGGAG
GCCACGGCTCATGGCCTGAGCCATTCTCAGGCCACGATGAAAGTGGCCGT
CAAGATGCTTAAATCCACAGCCCGCAGCAGTGAGAAGCAAGCCCTCATGT
CGGAGCTGAAGATCATGAGTCACCTTGGGCCCCACCTGAACGTGGTCAAC
CTGTTGGGGGCCTGCACCAAAGGAGGACCCATCTATATCATCACTGAGTA
CTGCCGCTACGGAGACCTGGTGGACTACCTGCACCGCAACAAGCACACGT
TCCTGCAGCACCATTCCGACAAGCGCCGCCCGCCCAGCGCGGAGCTCTA
CAGCAATGCGCTGCCCGTTGGGCTCCCCTGCCCAGCCACGTGTCCCTG
ACTGGGGAGAGCGATGGTGGCTACATGGACATGAGCAAGGACGAGTCGG
TGGACTACGTGCCCATGCTGGACATGAAAGGAGATGTCAAATATGCCGAC
ATCGAGTCCTCCAACTACATGGCCCCCTACGATAACTACGTTCCCTCTGCC
CCTGAGAGGACCTGTCGGGCAACTTTAATCAATGAGTCTCCGGTGCTAAG
CTACATGGACCTTGTGGGCTTCAGCTACCAGGTGGCCAATGGCATGGAGT
TCCTGGCCTCCAAGAACTGCGTGCACCGAGACCTGGCGGCCAGGAACGT
GCTCATCTGCGAGGGCAAGCTGGTCAAGATCTGTGACTTTGGCCTGGCTC
GAGACATCATGCGGGATTCGAATTACATCTCCAAAGGCAGTACCTTTTTGC
CTTTGAAGTGGATGGCTCCAGAGAGCATCTTCAACAGCCTCTACACCACC
CTGAGCGACGTGTGGTCCTTCGGGATCCTGCTCTGGGAGATCTTCACTTT

Figure 11 (cont.)

```
GGGTGGCACCCCTTACCCAGAGCTGCCCATGAATGAGCAGTTCTACAATG
CCATCAAACGGGGTTACCGCATGGCCCAGCCTGCCCACGCCTCCGACGA
GATCTATGAGATCATGCAGAAGTGCTGGGAAGAGAAGTTTGAGATTCGGC
CCCCTTTCTCCCAGCTGGTGCTGCTTCTCGAGAGACTGTTGGGCGAAGGT
TACAAAAAGAAGTACCAGCAGGTGGATGAGGAGTTTCTGAGGAGTGACCA
CCCAGCCATCCTTCGGTCCCAGGCCCGCTTGCCTGGGTTCCATGGCCTCC
GATCTCCCCTGGACAGCAGCTCCGTCCTCTATACCGCCGTGCAGCCCAAT
GAGGGTGACAACGACTATATCATCCCCCTGCCTGACCCCAAACCCGAGGT
TGCTGACGAGGGCCCACTGGAGGGTTCCCCCAGCCTAGCCAGCTCCACC
CTGAATGAAGTCAACACCTCCTCGACCATCTCCTGTGACAGCCCTCTGGA
GCCCCAGGAGGAACCAGAGCCAGAGCCCCAGCTTGAGCGCCAGGTGGAA
CCAGAGCCAGAGCTGGAACAGCTGCCGGATTCAGGGTGCCCCGCGCCTC
GAGCGGAAGCAGAGGACAGCTTCCTGTAGGGGGCTGGCCCCCACCCTGC
CCTGCCCAAAGCTTCCCCTCTGCCAGCACCCAGCACCTCCTGGCCTGGCC
GGGTCTCCTGTCAGCCAGGCTGCCCTTATCAGCTGTCCCCTTCTGGAAGC
TTTCTGCTCCTGACGTGTTGTGCCCCAAACCCTGGGGCTGGCTTAGGAGG
CAAGAAAACTGCAGGGGCCATGACCAGCCCTGTGCCTCCAGGGAGGCTA
ACTGACTCTGAGCCAGGGTTCCGCCCAGGGGACTCCGTTTTCCCATATGT
AAGATGGTAAAGTTGGGCTTGATGCCCAGAATCTAGGATTCTCTCCCTGGC
TGATAGGTAGGGAGGTCAAATCCCTCCCTGGAAAGATTCTTGGGGTTATTG
AGGTGGTAAATTAACTTTTTTCTGTTCAGCCAGCTACCCCTCAAGGAATCAT
AGCTCTCCTCGCACTTTTATCCACCCAGGAGCTAGGAAAGGGACCCTA
GCATCCCTGGCTGCTGCCTGAGCTGGGGCCTAGCCTTGGGCAGTGTTGC
CTCATCCAGAAGAAAGCCAGTCTCCTCCCTATGATGCCAGTCCCTGCTTTC
CCTGGCCCAAGCTGGTCTGGGGCCATTAGGCAGCCTAATTAATGCTGGAG
GCTGAGCCAAGTACAGGACACCCCAGCCTGCAGCCCCTGCCCAGGGCA
CTTGGAGCACATGTGGCCATAGCAAGTGCCCGTGTCCCTGTCCTTCAGGC
CCATCAGTCCTGGAGCTTTTTCTTTATCACCCTCAGTCTTAATCCATCCACC
AGAGTCTGGAAGGCCAGACGGGCCCCGCATCTGTGATGAGAATGTAAATG
TGCCAGTGTGGAGTGGCCACATGTGTGTTCCAATATATGGCCCTGGCTCT
GCACTGGATCTGCTATGAGACTTTGGAGGAATCCCTCGCCCTCTCTGGGC
```

Figure 11 (cont.)

CTCAGTTTTCCCCTTGAAAAAATGAACAAGTCGGACTTATTAACTCCAAGTG
CCTTGCCAGCACTAACATTCTAGAATATTCCAGGTGGTCGCACATTTGTCC
AGATGAAGCAAGGTCATATACCCTAAACTTCCATCCTGGGGGGTCAGCTG
GGCTCCTGGGAGATTCCAGATCACACATCACACTCTGGGGACACAGGAAC
CATGCCCCTTCCCCAGGCCTCCAGCAAGTCTCAAGAACGCAGCTGTCCAG
GCCTTGACTTAAGAATGACAGCCGGTGTCTTGGAAAGCCCCAGCAGCTG
CCCCAGGGACATGGGAAGACCACGGGACCTCTTTCACTACCCCGATGAC
CTCTGAGGGTATCCCGGGCAAAAGAGACAGAGGGCAAATGAGATCACCTC
CTGCAGCCCACCACTCCAGCACCTGCGCCGAGGTCTGCGTCAGTTATGTC
TTGTAAAGGACAAGAAGCTTCAGATGGGTACTCCAAGAAGGATATGAGAG
GTGGGCGCTTTGGAGGTTTCCTCCTCAACCACCAGCTGCCCCATCCCTGA
GGCAGCACTCCGTGGGGGTATGGTTTTGTCACTGCCCAGACCTAGCAGTG
ACATCTCATTGTCCCCAGCCCAGTGAGCATTGGAGGTGCCAGGGGAGTCG
GTTGTAGCCAAGGCGTCCAGCACGGGGAGGGTTGGGAAGGGGGTGCA
GGAAGGGCACCAGCCCTGCATTGCAGGTTGGCACCTTACTTCCCTGAGAT
CCCCAAAGTTGGTCCAAGGAGGGAGAGTGGGCTCTCAATACGGTACCAAA
GATATAATCACCTAGGTTTACAAATATTTTTAGGACTCACGTTAACTCACAT
TTATACAGCAGAAGTGCTATTTTGTATGCTGTTAAGTTTTTCTATCTGTGTA
CTTTTTTAAGGGAAAGATTTTAATATTAAACCTGGTGCTTCTCACTCACAG
A

SEQ ID NO:88 (Human CFB)

GACTTCTGCAGTTTCTGTTTCCTTGACTGGCAGCTCAGCGGGGCCCTCCC
GCTTGGATGTTCCGGGAAAGTGATGTGGGTAGGACAGGCGGGGCGAGCC
GCAGGTGCCAGAACACAGATTGTATAAAAGGCTGGGGGCTGGTGGGGAG
CAGGGGAAGGGAATGTGACCAGGTCTAGGTCTGGAGTTTCAGCTTGGACA
CTGAGCCAAGCAGACAAGCAAAGCAAGCCAGGACACACCATCCTGCCCCA
GGCCCAGCTTCTCTCCTGCCTTCCAACGCCATGGGGAGCAATCTCAGCCC
CCAACTCTGCCTGATGCCCTTTATCTTGGGCCTCTTGTCTGGAGGTGTGAC
CACCACTCCATGGTCTTTGGCCCGGCCCCAGGGATCCTGCTCTCTGGAGG
GGGTAGAGATCAAAGGCGGCTCCTTCCGACTTCTCCAAGAGGGCCAGGC

Figure 11 (cont.)

```
ACTGGAGTACGTGTGTCCTTCTGGCTTCTACCCGTACCCTGTGCAGACAC
GTACCTGCAGATCTACGGGGTCCTGGAGCACCCTGAAGACTCAAGACCAA
AAGACTGTCAGGAAGGCAGAGTGCAGAGCAATCCACTGTCCAAGACCACA
CGACTTCGAGAACGGGGAATACTGGCCCCGGTCTCCCTACTACAATGTGA
GTGATGAGATCTCTTTCCACTGCTATGACGGTTACACTCTCCGGGGCTCTG
CCAATCGCACCTGCCAAGTGAATGGCCGATGGAGTGGGCAGACAGCGAT
CTGTGACAACGGAGCGGGGTACTGCTCCAACCCGGGCATCCCCATTGGC
ACAAGGAAGGTGGGCAGCCAGTACCGCCTTGAAGACAGCGTCACCTACCA
CTGCAGCCGGGGGCTTACCCTGCGTGGCTCCAGCGGCGAACGTGTCAG
GAAGGTGGCTCTTGGAGCGGGACGGAGCCTTCCTGCCAAGACTCCTTCAT
GTACGACACCCCTCAAGAGGTGGCCGAAGCTTTCCTGTCTTCCCTGACAG
AGACCATAGAAGGAGTCGATGCTGAGGATGGGCACGGCCCAGGGGAACA
ACAGAAGCGGAAGATCGTCCTGGACCCTTCAGGCTCCATGAACATCTACC
TGGTGCTAGATGGATCAGACAGCATTGGGGCCAGCAACTTCACAGGAGCC
AAAAAGTGTCTAGTCAACTTAATTGAGAAGGTGGCAAGTTATGGTGTGAAG
CCAAGATATGGTCTAGTGACATATGCCACATACCCCAAAATTTGGGTCAAA
GTGTCTGAAGCAGACAGCAGTAATGCAGACTGGGTCACGAAGCAGCTCAA
TGAAATCAATTATGAAGACCACAAGTTGAAGTCAGGGACTAACACCAAGAA
GGCCCTCCAGGCAGTGTACAGCATGATGAGCTGGCCAGATGACGTCCCTC
CTGAAGGCTGGAACCGCACCCGCCATGTCATCATCCTCATGACTGATGGA
TTGCACAACATGGGCGGGGACCCAATTACTGTCATTGATGAGATCCGGGA
CTTGCTATACATTGGCAAGGATCGCAAAAACCCAAGGGAGGATTATCTGGA
TGTCTATGTGTTTGGGGTCGGGCCTTTGGTGAACCAAGTGAACATCAATGC
TTTGGCTTCCAAGAAAGACAATGAGCAACATGTGTTCAAAGTCAAGGATAT
GGAAAACCTGGAAGATGTTTTCTACCAAATGATCGATGAAAGCCAGTCTCT
GAGTCTCTGTGGCATGGTTTGGGAACACAGGAAGGGTACCGATTACCACA
AGCAACCATGGCAGGCCAAGATCTCAGTCATTCGCCCTTCAAAGGGACAC
GAGAGCTGTATGGGGGCTGTGGTGTCTGAGTACTTTGTGCTGACAGCAGC
ACATTGTTTCACTGTGGATGACAAGGAACACTCAATCAAGGTCAGCGTAGG
AGGGGAGAAGCGGGACCTGGAGATAGAAGTAGTCCTATTTCACCCCAACT
ACAACATTAATGGGAAAAAGAAGCAGGAATTCCTGAATTTTATGACTATGA
```

Figure 11 (cont.)

CGTTGCCCTGATCAAGCTCAAGAATAAGCTGAAATATGGCCAGACTATCAG
GCCCATTTGTCTCCCCTGCACCGAGGGAACAACTCGAGCTTTGAGGCTTC
CTCCAACTACCACTTGCCAGCAACAAAAGGAAGAGCTGCTCCCTGCACAG
GATATCAAAGCTCTGTTTGTGTCTGAGGAGGAGAAAAAGCTGACTCGGAA
GGAGGTCTACATCAAGAATGGGGATAAGAAAGGCAGCTGTGAGAGAGATG
CTCAATATGCCCCAGGCTATGACAAAGTCAAGGACATCTCAGAGGTGGTC
ACCCCTCGGTTCCTTTGTACTGGAGGAGTGAGTCCCTATGCTGACCCCAA
TACTTGCAGAGGTGATTCTGGCGGCCCCTTGATAGTTCACAAGAGAAGTC
GTTTCATTCAAGTTGGTGTAATCAGCTGGGGAGTAGTGGATGTCTGCAAAA
ACCAGAAGCGGCAAAAGCAGGTACCTGCTCACGCCCGAGACTTTCACATC
AACCTCTTTCAAGTGCTGCCCTGGCTGAAGGAGAAACTCCAAGATGAGGA
TTTGGGTTTTCTATAAGGGGTTTCCTGCTGGACAGGGGCGTGGGATTGAA
TTAAAACAGCTGCGACAACAAAAAAAAAAAAAAAAAAAAA

SEQ ID NO:89 (mouse CFB)

GCTCCATCACACAGTCCATGGAAAGACTGATCTTTTAAATTGGGGGTAGTG
GAGGTGGTGGTCTGTGCTTGTTAGGAGGGGTCTGGGGGCTAAGAGGGAG
CTTTGAAAGGGAAGTTCTGGCCCTTGGTCAGTCAAGGGTGGGGCTCACAT
AGTTTCTGTTTCCTCAGTTGGCAGTTCAGCTGGGGCCCTCCTTCATGAATG
TTCCGGGAAGCAGTGGCTGCGTGCGCAGGGTAGGCTGGCCAGGCTGCAG
ATGCCAGAGCAGATTGCATAAAAGGTTAGGGGACAGTGGGAAGGGGTGT
AGCCAGATCCAGCATTTGGGTTTCAGTTTGGACAGGAGGTCAAATAGGCA
CCCAGAGTGACCTGGAGAGGGCTTTGGGCCACTGGACTCTCTGGTGCTTT
CCATGACAATGGAGAGCCCCCAGCTCTGCCTCGTCCTCTTGGTCTTAGGC
TTCTCCTCTGGAGGTGTGAGCGCAACTCCAGTGCTTGAGGCCCGGCCCCA
AGTCTCCTGCTCTCTGGAGGGAGTAGAGATCAAAGGCGGCTCCTTTCAAC
TTCTCCAAGGCGGTCAGGCCCTGGAGTACCTATGTCCCTCTGGCTTCTAC
CCATACCCCGTGCAGACTCGAACCTGCAGATCCACAGGCTCCTGGAGCGA
CCTGCAGACCCGAGACCAAAGATTGTCCAGAAGGCGGAATGCAGAGCAA
TACGCTGCCCACGACCGCAGGACTTTGAAAATGGGGAATTCTGGCCCCGG
TCCCCCTTCTACAACCTGAGTGACCAGATTTCTTTTCAATGCTATGATGGTT

Figure 11 (cont.)

```
ACGTTCTCCGGGGCTCTGCTAATCGCACCTGCCAAGAGAATGGCCGGTGG
GATGGGCAAACAGCAATTTGTGATGATGGAGCTGGATACTGTCCCAATCC
CGGTATTCCTATTGGGACAAGGAAGGTGGGTAGCCAATACCGCCTTGAAG
ACATTGTTACTTACCACTGCAGCCGGGGACTTGTCCTGCGTGGCTCCCAG
AAGCGAAAGTGTCAAGAAGGTGGCTCATGGAGTGGGACAGAGCCTTCCTG
CCAAGATTCCTTCATGTATGACAGCCCTCAAGAAGTGGCCGAAGCATTCCT
ATCCTCCCTGACAGAGACCATCGAAGGAGCCGATGCTGAGGATGGGCACA
GCCCAGGAGAACAGCAGAAGAGGAAGATTGTCCTAGACCCCTCGGGCTC
CATGAATATCTACCTGGTGCTAGATGGATCAGACAGCATCGGAAGCAGCA
ACTTCACAGGGGCTAAGCGGTGCCTCACCAACTTGATTGAGAAGGTGGCG
AGTTACGGGGTGAGGCCACGATATGGTCTCCTGACATATGCTACAGTCCC
CAAAGTGTTGGTCAGAGTGTCTGATGAGAGGAGTAGCGATGCCGACTGGG
TCACAGAGAAGCTCAACCAAATCAGTTATGAAGACCACAAGCTGAAGTCAG
GGACCAACACCAAGAGGGCTCTCCAGGCTGTGTATAGCATGATGAGCTGG
GCAGGGGATGCCCCGCCTGAAGGCTGGAATAGAACCCGCCATGTCATCAT
CATTATGACTGATGGCTTGCACAACATGGGTGGAAACCCTGTCACTGTCAT
TCAGGACATCCGAGCCTTGCTGGACATCGGCAGGGATCCCAAAAATCCCA
GGGAGGATTACCTGGATGTGTATGTGTTTGGGGTCGGGCCTCTGGTGGAC
TCCGTGAACATCAATGCCTTAGCTTCCAAAAAGGACAATGAGCATCATGTG
TTTAAAGTCAAGGATATGGAAGACCTGGAGAATGTTTTCTACCAAATGATT
GATGAAACCAAATCTCTGAGTCTCTGTGGCATGGTGTGGGAGCATAAAAAA
GGCAACGATTATCATAAGCAACCATGGCAAGCCAAGATCTCAGTCACTCG
CCCTCTGAAAGGACATGAGACCTGTATGGGGGCCGTGGTGTCTGAGTACT
TCGTGCTGACAGCAGCGCACTGCTTCATGGTGGATGATCAGAAACATTCC
ATCAAGGTCAGCGTGGGGGGTCAGAGGCGGGACCTGGAGATTGAAGAGG
TCCTGTTCCACCCCAAATACAATATTAATGGGAAAAAGGCAGAAGGGATCC
CTGAGTTCTATGATTATGATGTGGCCCTAGTCAAGCTCAAGAACAAGCTCA
AGTATGGCCAGACTCTCAGGCCCATCTGTCTCCCTGCACGGAGGGAACC
ACACGAGCCTTGAGGCTTCCTCAGACAGCCACCTGCAAGCAGCACAAGGA
ACAGTTGCTCCCTGTGAAGGATGTCAAAGCTCTGTTTGTATCTGAGCAAGG
GAAGAGCCTGACTCGGAAGGAGGTGTACATCAAGAATGGGGACAAGCCA
```

Figure 11 (cont.)

GTTGTGAGAGAGATGCTACAAAGGCCCAAGGCTATGAGAAGGTCAAAGAT
GCCTCTGAGGTGGTCACTCCACGGTTCCTCTGCACAGGAGGGGTGGATC
CCTATGCTGACCCCAACACATGCAAAGGAGATTCCGGGGGCCCTCTCATT
GTTCACAAGAGAAGCCGCTTCATTCAAGTTGGTGTGATTAGCTGGGGAGT
AGTAGATGTCTGCAGAGACCAGAGGCGGCAACAGCTGGTACCCTCTTATG
CCCGGGACTTCCACATCAACCTCTTCCAGGTGCTGCCCTGGCTAAAGGAC
AAGCTCAAAGATGAGGATTTGGGTTTTCTATAAAGAGCTTCCTGCAGGGAG
AGTGTGAGGACAGATTAAAGCAGTTACAATAACAAAAAAAAAAAAAAAAAA
AAA

SEQ ID NO:90 (macaque CFB)

ATAGATATATTAGCATCAGGGAGACAGGGCAAAGGTTCCACCCTTCAGCTC
AGTCCCCAGTCCCTGCTTATTATTTCCCTAACAGAAGACCATCCCCCTTGC
CACTCCCTGGGTTTTCTTCTCTGGCAGCAATGAAGCAGCTGCTGAGCCAG
CTCTGGTTTTCGGGAAGTCAGATGACCTTTTCCCTCCCGCGGCTCTCTGC
CTCTCGCTGTCCCTAGGGAGGACACCATGGACCCACTGATGGTTCTTTTTT
GCCTGCTGTTCCTGTACCCAGGTCCGGCAGACTCGGCTACCTCCTGCCCT
CAGAACGTGAATATCTCTGGTGGCACCTTCACCCTCAGCCATGGCTGGGC
CCCTGGGAGCCTTCTCATCTACTCCTGTCCCCAGGGCCTGTACCCATCCC
CAGCGTCACGGCTGTGCAAGAGCAGCGGACAGTGGCAGACCCCAAGAGC
CACCCGGTCTCTGACTAAGGCGGTCTGCAAACCTGGCCACTGCCCCAACC
CCGGCATTTCGCTGGGCGCGGTGCGGACAGGCTCCCGCTTTGGTCATGG
GGACAAGGTCCGCTATCGCTGCTCCTCGAATCTTGTGCTCACGGGGTCTG
CGGAGCGGGAGTGCCAGGGCAACGGGGTCTGGAGTGGAACGGAGCCCA
TCTGCCGCCAGCCCTACTCTTATGACTTCCCTGAGGACGTGGCCCCTGCC
CTGGGCACCTCCTTCTCCCACATGCTTGGGGCCACCAATCCCACCCAGAG
GACAAAGGATCATGAAAATGGAACTGGGACTAACACCTATGCAGCCCTAAA
CAGTGTCTATCTCATGATGAACAATCAAATGCAACTCCTTGGCATGAAAAC
GATGGCCTGGCAGGAAATCCGACATGCCATCATCCTTCTGACAGATGGAA
AGTCCAATATGGGTGGCTCTCCCAAAACAGCTGTTGACCAAATCAGAGAG
ATCTTGAATATCAACCAGAAGAGGAATGACTATCTGGACATCTATGCCATC

Figure 11 (cont.)

GGGGTGGGCAAGCTGGATGTGGACTGGAGAGAACTGAATGAGCTGGGGT
CCAAGAAGGATGGCGAGAGGCATGCCTTCATTCTGCAGGACACAAAGGCT
CTGCACCAGGTCTTTGAACATATGCTGGATGTCTCCAAGCTCACAGACACC
ATCTGCGGGGTGGGGAACATGTCAGCAAACGCCTCTGACCAAGAGAGGA
CACCCTGGCATGTCACTATTAAGCCCAAGAGCCAAGAGACCTGCCGGGGA
GCCCTCATCTCCGACCAATGGGTCCTGACAGCGGCTCACTGCTTCCGCGA
TGGCAACGACCACTCCCTATGGAGGGTCAATGTGGGAGACCCCAAATCCC
AGTGGGGCAAAGAATTCCTTATTGAGAAGGCAGTGATTTCCCCAGGATTTG
ATGTCTTTGCCAAAAAGAACCAGGGAATCCTGGAGTTCTATGGTGATGACA
TCGCCCTGCTGAAGCTGGCCCAGAAAGTAAAGATGTCCACCCATGCCAGG
CCCATCTGCCTTCCCTGCACCATGGAGGCCAATCTGGCTCTGCGGAGACC
TCAAGGCAGCACCTGTAGGGACCATGAGAATGAACTGCTGAACAAACAGA
GTGTTCCTGCTCATTTTGTCGCCTTGAATGGGAGCAAACTGAACATTAACC
TTAAGATGGGAGTGGAGTGGACAAGCTGTGCCGAGGTCGTCTCCCAAGAA
AAAACCATGTTCCCCAACTTGACAGATGTCAGGGAGGTGGTGACAGACCA
GTTTCTATGCAGTGGGACCCAGGAGGATGAGAGTCCCTGCAAGGGTGTGA
CCACCACTCCATTGTCTTCGGCCCAGCCTCAAGGATCCTGCTCTCTGGAG
GGGGTAGAGATCAAAGGTGGCTCCTTCCGACTTCTCCAAGAGGGCCAGG
CACTGGAATACGTGTGTCCTTCTGGCTTCTACCCGTACCCTGTGCAGACAC
GTACCTGCAGATCCACGGGGTCCTGGAGCACCCTGCAGACTCAAGATCGA
AAAACTGTCAAGAAGGCAGAGTGCAGAGCAATCCGCTGTCCACGACCACA
GGACTTCGAGAACGGGGAATACCGGCCCCGGTCTCCCTACTACAATGTGA
GTGATGAGATCTCTTTCCACTGCTATGACGGTTACACTCTCCGGGGCTCTG
CCAATCGCACCTGCCAAGTGAATGGCCGGTGGAGTGGGCAGACAGCGAT
CTGTGACAACGGAGCGGGGTACTGCTCCAACCCAGGCATCCCCATTGGCA
CAAGGAAGGTGGGCAGCCGGTACCGCCTTGAAGACAGCGTCACCTACCA
CTGCAGCCGGGGGCTTACCCTGCGTGGCTCCCAGCGGCGAACATGTCAG
GAAGGTGGCTCTTGGAGCGGGACGGAGCCTTCCTGCCAAGACTCCTTCAT
GTACGACACCCCTCAAGAGGTGGCCGAAGCTTTCCTGTCTTCCCTGACGG
AGACCATAGAAGGAGTCGATGCCGAGGATGGGCACAGCCCAGGGGAACA
ACAGAAGCGGAGGATCATCCTAGACCCTTCAGGCTCCATGAACATCTACC

Figure 11 (cont.)

TGGTGCTAGATGGATCAGACAGCATTGGGGCCGGCAACTTCACAGGAGCC
AAAAAGTGTCTAGTCAACTTAATTGAGAAGGTGGCAAGTTATGGTGTGAAG
CCAAGATATGCTCTAGTGACATATGCCACATACCCCAGAATTTGGGTCAAA
GTGTCTGACCAAGAGAGCAGCAATGCAGACTGGGTCACGAAGAAGCTCAG
TGAAATCAATTATGAAGACCACAAGTTGAAGTCAGGGACTAACACCAAGAG
GGCCCTCCAGGCAGTGTACAGCATGATGAGTTGGCCAGAGGACATCCCTC
CTGAAGGCTGGAACCGCACCCGCCATGTCATCATCCTCATGACCGATGGA
TTGCACAACATGGGCGGGGACCCAATTACTGTCATTGATGAGATCCGGGA
CTTGTTATACATCGGCAAGGATCGTAAAAACCCGAGGGAGGATTATCTGGA
TGTCTATGTGTTTGGGGTTGGACCTTTGGTGGACCAAGTGAACATCAATGC
TTTGGCTTCCAAGAAAGACAATGAGCAACATGTGTTCAAAGTCAAGGATAT
GGAAAACCTGGAAGACGTTTTCTTCCAAATGATTGATGAAAGCCAGTCTCT
GAGTCTCTGTGGCATGGTTTGGGAACACAGCAAGGGTACCGATTACCACA
AGCAACCATGGCAGGCCAAGATCTCAGTCACTCGCCCTTCGAAGGGACAT
GAGAGCTGTATGGGGGCTGTGGTGTCTGAGTACTTTGTGCTGACAGCAGC
ACATTGTTTTACTGTGGACGACAAGGAACACTCAATCAAGGTCAGCGTGG
GAGGGAAGAAGCGGGACCTGGAGATAGAAAAGTCCTATTTCACCCCGAC
TACAACATTAGCGAGAAAAAGAAGCAGGAATTCCTGAATTTTATGACTAT
GACGTTGCCCTGATCAAGCTCAAGAATAAGTTGAATTATGACCCGACTATC
AGGCCCATTTGTCTCCCCTGCACCGAGGGAACAACTCGAGCTTTGAGGCT
TCCTCCAACTACCACTTGCCAGCAACAGAAGGAAGAGCTGCTCCCTGCAC
AGGATATCAAAGCTCTGTTTGTGTCTGAGGAGGAGAAGAAGCTGACTCGG
AAGGAGGTCTACATCAAGAATGGGGATAAGAAAGGCAGCTGTGAGAGAGA
TGCTCAATATGCCCCAGGCTATGACAAAGTCAAGGACATCTCGGAGGTGG
TCACCCCTCGGTTCCTTTGTACTGGAGGAGTGAGTCCCTATGCTGACCCC
AATACTTGCAGAGGTGATTCTGGCGGCCCCTTGATAGTTCACAAGAGAAGT
CGTTTCATTCAAGTTGGTGTCATCAGCTGGGGAGTAGTGGATGTCTGCAAA
AACCAGAAGCGGCAAAAGCAGGTACCTGCTCACGCCCGAGACTTTCACGT
CAACCTCTTCCAAGTGCTGCCCTGGCTGAAGGAGAAACTCCAAGATGAGG
ATTTGGGTTTTCTCTAAGGGGTTTCCTGCTGGACAGGGGCGCGGGATTGA
ATTAAAACAGCTGCGACAACACTT

Figure 11 (cont.)

SEQ ID NO:91 (miR-1)

GGATCCGGTATATTGCTGTTGACAGTGAGCGTGCAAGAGCTCCAGAGAGA
AGACTGTGAAGCAGATGGGTCTTCTCTCTGGAGCTCTTGCTCGCCTACTG
CCTCGGACTTCAAGCTAGCGGTACCTTTTTAAGCTT

SEQ ID NO:92 (miR-12)

GGATCCGGTATATTGCTGTTGACAGTGAGCGAGCCTCCGAAACCATGAAC
TTACTGTGAAGCAGATGGGTAAGTTCATGGTTTCGGAGGCCCGCCTACTG
CCTCGGACTTCAAGCTAGCGGTACCTTTTTAAGCTT

SEQ ID NO:93 (miR-3)

GGATCCGGTATATTGCTGTTGACAGTGAGCGAGAGACCCTGGTGGACATC
TTACTGTGAAGCAGATGGGTAAGATGTCCACCAGGGTCTCGCGCCTACTG
CCTCGGACTTCAAGCTAGCGGTACCTTTTTAAGCTT

SEQ ID NO:94 (miR-4)

GGATCCGGTATATTGCTGTTGACAGTGAGCGACACATAGGAGAGATGAGC
TTACTGTGAAGCAGATGGGTAAGCTCATCTCTCCTATGTGCCGCCTACTGC
CTCGGACTTCAAGCTAGCGGTACCTTTTTAAGCTT

SEQ ID NO:95 (miR-5)

GGATCCGGTATATTGCTGTTGACAGTGAGCGAGAATGCAGACCAAAGAAA
GAACTGTGAAGCAGATGGGTTCTTTCTTTGGTCTGCATTCACGCCTACTGC
CTCGGACTTCAAGCTAGCGGTACCTTTTTAAGCTT

SEQ ID NO:96 (miR-6)

GGATCCGGTATATTGCTGTTGACAGTGAGCGAAGAACAGTCCTTAATCCAG
AACTGTGAAGCAGATGGGTTCTGGATTAAGGACTGTTCTGCGCCTACTGC
CTCGGACTTCAAGCTAGCGGTACCTTTTTAAGCTT

Figure 11 (cont.)

SEQ ID NO:97 (miR-7)

GGATCCGGTATATTGCTGTTGACAGTGAGCGACTGGGATTCCTGTAGACA
CAACTGTGAAGCAGATGGGTTGTGTCTACAGGAATCCCAGACGCCTACTG
CCTCGGACTTCAAGCTAGCGGTACCTTTTTAAGCTT

SEQ ID NO:98 (miR-8)

GGATCCGGTATATTGCTGTTGACAGTGAGCGATAGACACACCCACCCACA
TAACTGTGAAGCAGATGGGTTATGTGGGTGGGTGTGTCTACCGCCTACTG
CCTCGGACTTCAAGCTAGCGGTACCTTTTTAAGCTT

SEQ ID NO:99 (miR-9)

GGATCCGGTATATTGCTGTTGACAGTGAGCGAGTGCTACTGTTTATCCGTA
AACTGTGAAGCAGATGGGTTTACGGATAAACAGTAGCACCCGCCTACTGC
CTCGGACTTCAAGCTAGCGGTACCTTTTTAAGCTT

SEQ ID NO:100 (miR-10)

GGATCCGGTATATTGCTGTTGACAGTGAGCGAGAGATATTCCGTAGTACAT
AACTGTGAAGCAGATGGGTTATGTACTACGGAATATCTCGCGCCTACTGCC
TCGGACTTCAAGCTAGCGGTACCTTTTTAAGCTT

SEQ ID NO:101 (miR-V-1)

GGATCCGGTATATTGCTGTTGACAGTGAGCGATGGACTGGCTTTGGCCCA
ATACTGTGAAGCAGATGGGTATTGGGCCAAAGCCAGTCCAACGCCTACTG
CCTCGGACTTCAAGCTAGCGGTACCTTTTTAAGCTT

SEQ ID NO:102 (miR-V-2)

GGATCCGGTATATTGCTGTTGACAGTGAGCGACCAGCTACATGATCAGCT
ATACTGTGAAGCAGATGGGTATAGCTGATCATGTAGCTGGGCGCCTACTG
CCTCGGACTTCAAGCTAGCGGTACCTTTTTAAGCTT

Figure 11 (cont.)

SEQ ID NO:103 (miR-V-3)

GGATCCGGTATATTGCTGTTGACAGTGAGCGACCATGTTCTTCTGGCTACT
TACTGTGAAGCAGATGGGTAAGTAGCCAGAAGAACATGGCCGCCTACTGC
CTCGGACTTCAAGCTAGCGGTACCTTTTTAAGCTT

SEQ ID NO:104 (miR-V-4)

GGATCCGGTATATTGCTGTTGACAGTGAGCGAGGACCGTTAAGCGGGCCA
ATACTGTGAAGCAGATGGGTATTGGCCCGCTTAACGGTCCGCGCCTACTG
CCTCGGACTTCAAGCTAGCGGTACCTTTTTAAGCTT

SEQ ID NO:105 (miR-V-5)

GGATCCGGTATATTGCTGTTGACAGTGAGCGACATGGTGATTGTGGAATTC
TACTGTGAAGCAGATGGGTAGAATTCCACAATCACCATGACGCCTACTGCC
TCGGACTTCAAGCTAGCGGTACCTTTTTAAGCTT

SEQ ID NO:106 (miR-V-6)

GGATCCGGTATATTGCTGTTGACAGTGAGCGACTGACCTTGGAGCATCTC
ATACTGTGAAGCAGATGGGTATGAGATGCTCCAAGGTCAGGCGCCTACTG
CCTCGGACTTCAAGCTAGCGGTACCTTTTTAAGCTT

SEQ ID NO:107 (miR-V-7)

GGATCCGGTATATTGCTGTTGACAGTGAGCGAGGAGCATCTCATCTGTTAC
AACTGTGAAGCAGATGGGTTGTAACAGATGAGATGCTCCACGCCTACTGC
CTCGGACTTCAAGCTAGCGGTACCTTTTTAAGCTT

SEQ ID NO:108 (miR-V-8)

GGATCCGGTATATTGCTGTTGACAGTGAGCGAGCTAAGGGCATGGAGTTC
TTACTGTGAAGCAGATGGGTAAGAACTCCATGCCCTTAGCCCGCCTACTG
CCTCGGACTTCAAGCTAGCGGTACCTTTTTAAGCTT

Figure 11 (cont.)

SEQ ID NO:109 (miR-V-9)

GGATCCGGTATATTGCTGTTGACAGTGAGCGACCAGAAATGTACCAGACC
ATACTGTGAAGCAGATGGGTATGGTCTGGTACATTTCTGGACGCCTACTGC
CTCGGACTTCAAGCTAGCGGTACCTTTTTAAGCTT

SEQ ID NO:110 (miR-V-10)

GGATCCGGTATATTGCTGTTGACAGTGAGCGACCCCAAATTCCATTATGAC
AACTGTGAAGCAGATGGGTTGTCATAATGGAATTTGGGGACGCCTACTGC
CTCGGACTTCAAGCTAGCGGTACCTTTTTAAGCTT

SEQ ID NO:111 (miR-P-1)

GGATCCGGTACCGGTATATTGCTGTTGACAGTGAGCGTCTCCAGGTGTCA
TCCATCAAACTGTGAAGCAGATGGGTTTGATGGATGACACCTGGAGTCGC
CTACTGCCTCGGACTTCAACAATTGTTTTTAAGCTT

SEQ ID NO:112 (miR-P-2)

GGATCCGGTACCGGTATATTGCTGTTGACAGTGAGCGTGGTGTCATCCAT
CAACGTCTACTGTGAAGCAGATGGGTAGACGTTGATGGATGACACCTCGC
CTACTGCCTCGGACTTCAACAATTGTTTTTAAGCTT

SEQ ID NO:113 (miR-P-3)

GGATCCGGTACCGGTATATTGCTGTTGACAGTGAGCGACATGAGTACATC
TACGTGGAACTGTGAAGCAGATGGGTTCCACGTAGATGTACTCATGGCGC
CTACTGCCTCGGACTTCAACAATTGTTTTTAAGCTT

SEQ ID NO:114 (miR-P-4)

GGATCCGGTACCGGTATATTGCTGTTGACAGTGAGCGAGACCTCGTGGGC
TTCAGCTAACTGTGAAGCAGATGGGTTAGCTGAAGCCCACGAGGTCCCGC
CTACTGCCTCGGACTTCAACAATTGTTTTTAAGCTT

Figure 11 (cont.)

SEQ ID NO:115 (miR-P-5)

GGATCCGGTACCGGTATATTGCTGTTGACAGTGAGCGTGGCAAGCTGGTC
AAGATCTGACTGTGAAGCAGATGGGTCAGATCTTGACCAGCTTGCCTCGC
CTACTGCCTCGGACTTCAACAATTGTTTTTAAGCTT

SEQ ID NO:116 (miR-P-6)

GGATCCGGTACCGGTATATTGCTGTTGACAGTGAGCGAGAGAGCATCTTC
AACAGCCTACTGTGAAGCAGATGGGTAGGCTGTTGAAGATGCTCTCCCGC
CTACTGCCTCGGACTTCAACAATTGTTTTTAAGCTT

SEQ ID NO:117 (miR-P-7)

GGATCCGGTACCGGTATATTGCTGTTGACAGTGAGCGACATCTTCAACAG
CCTCTACAACTGTGAAGCAGATGGGTTGTAGAGGCTGTTGAAGATGCCGC
CTACTGCCTCGGACTTCAACAATTGTTTTTAAGCTT

SEQ ID NO:118 (miR-P-8)

GGATCCGGTACCGGTATATTGCTGTTGACAGTGAGCGACCAGAGCTGCCC
ATGAACGAACTGTGAAGCAGATGGGTTCGTTCATGGGCAGCTCTGGGCGC
CTACTGCCTCGGACTTCAACAATTGTTTTTAAGCTT

SEQ ID NO:119 (miR-P-9)

GGTACCGGTATATTGCTGTTGACAGTGAGCGACAGTTCTACAATGCCATCA
AACTGTGAAGCAGATGGGTTTGATGGCATTGTAGAACTGCCGCCTACTGC
CTCGGACTTCAACAATTGTTTTT

SEQ ID NO:120 (miR-P-10)

GGATCCGGTACCGGTATATTGCTGTTGACAGTGAGCGACATGCCTCCGAC
GAGATCTAACTGTGAAGCAGATGGGTTAGATCTCGTCGGAGGCATGGCGC
CTACTGCCTCGGACTTCAACAATTGTTTTTAAGCTT

Figure 11 (cont.)

SEQ ID NO:121 (miR-C-1)

GGATCCGCTAGCGGTATATTGCTGTTGACAGTGAGCGATGCCAAGACTCC
TTCATGTAACTGTGAAGCAGATGGGTTACATGAAGGAGTCTTGGCAGCGC
CTACTGCCTCGGACTTCAAGGTACCTTTTTAAGCTT

SEQ ID NO:122 (miR-C-2)

GGATCCGCTAGCGGTATATTGCTGTTGACAGTGAGCGAAACATCTACCTG
GTGCTAGAACTGTGAAGCAGATGGGTTCTAGCACCAGGTAGATGTTCCGC
CTACTGCCTCGGACTTCAAGGTACCTTTTTAAGCTT

SEQ ID NO:123 (miR-C-3)

GGATCCGCTAGCGGTATATTGCTGTTGACAGTGAGCGAGGTGCTAGATGG
ATCAGACAACTGTGAAGCAGATGGGTTGTCTGATCCATCTAGCACCACGC
CTACTGCCTCGGACTTCAAGGTACCTTTTTAAGCTT

SEQ ID NO:124 (miR-C-4)

GGATCCGCTAGCGGTATATTGCTGTTGACAGTGAGCGACTAGATGGATCA
GACAGCATACTGTGAAGCAGATGGGTATGCTGTCTGATCCATCTAGCCGC
CTACTGCCTCGGACTTCAAGGTACCTTTTTAAGCTT

SEQ ID NO:125 (miR-C-5)

GGATCCGCTAGCGGTATATTGCTGTTGACAGTGAGCGAGAGGATTATCTG
GATGTCTAACTGTGAAGCAGATGGGTTAGACATCCAGATAATCCTCCCGCC
TACTGCCTCGGACTTCAAGGTACCTTTTTAAGCTT

SEQ ID NO:126 (miR-C-6)

GGATCCGCTAGCGGTATATTGCTGTTGACAGTGAGCGATCTCTGAGTCTCT
GTGGCATACTGTGAAGCAGATGGGTATGCCACAGAGACTCAGAGACCGCC
TACTGCCTCGGACTTCAAGGTACCTTTTTAAGCTT

Figure 11 (cont.)

SEQ ID NO:127 (miR-C-7)

GGATCCGCTAGCGGTATATTGCTGTTGACAGTGAGCGAGCTGTGGTGTCT
GAGTACTTACTGTGAAGCAGATGGGTAAGTACTCAGACACCACAGCCCGC
CTACTGCCTCGGACTTCAAGGTACCTTTTTAAGCTT

SEQ ID NO:128 (miR-C-8)

GGATCCGCTAGCGGTATATTGCTGTTGACAGTGAGCGAAGGATATCAAAG
CTCTGTTTACTGTGAAGCAGATGGGTAAACAGAGCTTTGATATCCTGCGCC
TACTGCCTCGGACTTCAAGGTACCTTTTTAAGCTT

SEQ ID NO:129 (miR-C-9)

GGATCCGCTAGCGGTATATTGCTGTTGACAGTGAGCGACGGAAGGAGGTC
TACATCAAACTGTGAAGCAGATGGGTTTGATGTAGACCTCCTTCCGACGCC
TACTGCCTCGGACTTCAAGGTACCTTTTTAAGCTT

SEQ ID NO:130 (qRT PCR RNA)

UGGGUUAUGUGGGUGGGUGUGUCUACCGCCU

SEQ ID NO:131 (Primer for qRT PCR)

TATGTGGGTGGGTGTGTCTAC

SEQ ID NO: 132 (U6-miR-7)

CCTAAGGCCCAGTGGAAAGACGCGCAGGCAAAACGCACCACGTGACGGA
GCGTGACCGCGCGCCGAGCGCGCGCCAAGGTCGGGCAGGAAGAGGGCC
TATTTCCCATGATTCCTTCATATTTGCATATACGATACAAGGCTGTTAGAGA
GATAATTAGAATTAATTTGACTGTAAACACAAAGATATTAGTACAAAATACG
TGACGTAGAAAGTAATAATTTCTTGGGTAGTTTGCAGTTTTAAAATTATGTT
TTAAAATGGACTATCATATGCTTACCGTAACTTGAAAGTATTTCGATTTCTT
GGGTTTATATATCTTGTGGAAAGGACGCGGGATCCGGTATATTGCTGTTGA
CAGTGAGCGACTGGGATTCCTGTAGACACAACTGTGAAGCAGATGGGTTG
TGTCTACAGGAATCCCAGACGCCTACTGCCTCGGACTTCAAGCTAGCGGT
ACCTTTTTAAGCTT

Figure 11 (cont.)

SEQ ID NO: 133 (VDM2-miR-7)

CCTAAGGCATTCTTTCCATAGCCCACAGGGCTGTCAAAGACCCCAGGGCC
TAGTCAGAGGCTCCTCCTTCCTGGAGAGTTCCTGGCACAGAAGTTGAAGC
TCAGCACAGCCCCCTAACCCCCAACTCTCTCTGCAAGGCCTCAGGGGTCA
GAACACTGGTGGAGCAGATCCTTTAGCCTCTGGATTTTAGGGCCATGGTA
GAGGGGGTGTTGCCCTAAATTCCAGCCCTGGTCTCAGCCCAACACCCTCC
AAGAAGAAATTAGAGGGGCCATGGCCAGGCTGTGCTAGCCGTTGCTTCTG
AGCAGATTACAAGAAGGGACTAAGACAAGGACTCCTTTGTGGAGGTCCTG
GCTTAGGGAGTCAAGTGACGGCGGCTCAGCACTCACGTGGGCAGTGCCA
GCCTCTAAGAGTGGGCAGGGGCACTGGCCACAGAGTCCCAGGGAGTCCC
ACCAGCCTAGTCGCCAGACCGGATCCGGTATATTGCTGTTGACAGTGAGC
GACTGGGATTCCTGTAGACACAACTGTGAAGCAGATGGGTTGTGTCTACA
GGAATCCCAGACGCCTACTGCCTCGGACTTCAAGCTAGCGGTACCTTTTA
AGCTT

SEQ ID NO: 134 (ICAM2-miR-7)

CCTAAGGATGGGATTTGGGGTTCCCCAGATCTGGGGCTTGTAGGCCTGAC
TCTCCCCTGTGCACACGTCTCATACACGCATGCGTGCACCCATTGCCTGC
CCCGCCCCTTGCACAGGGAGTCAGCAGGGAGGACTGGGTTATGCCCTGC
TTATCAGCAGCTTCCCAGCTTCCTCTGCCTGGATTCTTAGAGGCCTGGGGT
CCTAGAACGAGCTGGTGCACGTGGCTTCCCAAAGATCTCTCAGATAATGA
GAGGAAATGCAGTCATCAGTTTGCAGAAGGCTAGGGATTCTGGGCCATAG
CTCAGACCTGCGCCCACCATCTCCCTCCAGGCAGCCCTTGGGGATCCGGT
ATATTGCTGTTGACAGTGAGCGACTGGGATTCCTGTAGACACAACTGTGAA
GCAGATGGGTTGTGTCTACAGGAATCCCAGACGCCTACTGCCTCGGACTT
CAAGCTAGCGGTACCTTTTAAGCTT

SEQ ID NO: 135 (RPE65-miR-7)

CCTAAGGTTCCAAGGACTTCTTTGGGCAGTACCTTGTCTGTGCTGGCAAG
CAACTGAGACTTAATGAAAGAGTATTGGAGATATGAATGAATTGATGCTGT
ATACTCTCAGAGTGCCAAACATATACCAATGGACAAGAAGGTGAGGCAGA

Figure 11 (cont.)

GAGCAGACAGGCATTAGTGACAAGCAAAGATATGCAGAATTTCATTCTCAG
CAAATCAAAAGTCCTCAACCTGGTTGGAAGAATATTGGCACTGAATGGTAT
CAATAAGGTTGCTAGAGAGGGTTAGAGGTGCACAATGTGCTTCCATAACAT
TTTATACTTCTCCAATCTTAGCACTAATCAAACATGGTTGAATACTTTGTTTA
CTATAACTCTTACAGAGTTATAAGATCTGTGAAGACAGGGACAGGGACAAT
ACCCATCTCTGTCTGGTTCATAGGTGGTATGTAATAGATATTTTTAAAAATA
AGTGAGTTAATGAATGAGGGTGAGAATGAAGGCACAGAGGTATTAGGGGG
AGGTGGGCCCCAGAGAATGGTGCCAAGGTCCAGTGGGGTGACTGGGATC
AGCTCAGGCCTGACGCTGGCCACTCCACCTAGCTCCTTTCTTTCTAATCT
GTTCTCATTCTCCTTGGGAAGGATTGAGGTCTCTGGAAAACAGCCAAACAA
CTGTTATGGGAACAGCAAGCCCAAATAAAGCCAAGCATCAGGGGGATCTG
AGAGCTGAAAGCAACTTCTGTTCCCCCTCCCTCAGCTGAAGGGGTGGGGA
AGGGCTCCCAAAGCCATAACTCCTTTTAAGGGATTTAGAAGGCATAAAAAG
GCCCCTGGCTGAGAACTTCCTTCTTCATTCTGCAGTGGATCCGGTATATTG
CTGTTGACAGTGAGCGACTGGGATTCCTGTAGACACAACTGTGAAGCAGA
TGGGTTGTGTCTACAGGAATCCCAGACGCCTACTGCCTCGGACTTCAAGC
TAGCGGTACCTTTTTAAGCTT

SEQ ID NO: 136 (FLT-miR-7)

CCTAAGGGCGCTCCCGGGCCCGCGTCGCCAGCACCTCCCCACGCGCGCT
CGGCCCCGGGCCACCCGCCCTCGTCGGCCCCGCCCCTCTCCGTAGCC
GCAGGGAAGCGAGCCTGGGAGGAAGAAGAGGGTAGGTGGGGAGGCGGA
TGAGGGGTGGGGGACCCCTTGACGTCACCAGAAGGAGGTGCCGGGGTAG
GAAGTGGGCTGGGGAAAGGTTATAAATCGCCCCGCCCTCGGCTGCTCTT
CATCGAGGTCCGCGGGAGGCTCGGAGCGCGCCAGGCGGACACTCCTGG
ATCCGGTATATTGCTGTTGACAGTGAGCGACTGGGATTCCTGTAGACACAA
CTGTGAAGCAGATGGGTTGTGTCTACAGGAATCCCAGACGCCTACTGCCT
CGGACTTCAAGCTAGCGGTACCTTTTTAAGCTT

Figure 11 (cont.)

SEQ ID NO: 137 (U6-miR-7-MiR-V-7)

CCTAAGGCCCAGTGGAAAGACGCGCAGGCAAAACGCACCACGTGACGGA
GCGTGACCGCGCGCCGAGCGCGCGCCAAGGTCGGGCAGGAAGAGGGCC
TATTTCCCATGATTCCTTCATATTTGCATATACGATACAAGGCTGTTAGAGA
GATAATTAGAATTAATTTGACTGTAAACACAAAGATATTAGTACAAAATACG
TGACGTAGAAAGTAATAATTTCTTGGGTAGTTTGCAGTTTTAAAATTATGTT
TTAAAATGGACTATCATATGCTTACCGTAACTTGAAAGTATTTCGATTTCTT
GGGTTTATATATCTTGTGGAAAGGACGCGGGATCCGGTATATTGCTGTTGA
CAGTGAGCGACTGGGATTCCTGTAGACACAACTGTGAAGCAGATGGGTTG
TGTCTACAGGAATCCCAGACGCCTACTGCCTCGGACTTCAAGCTAGCGGT
ACCGGTATATTGCTGTTGACAGTGAGCGAGGAGCATCTCATCTGTTACAAC
TGTGAAGCAGATGGGTTGTAACAGATGAGATGCTCCACGCCTACTGCCTC
GGACTTCAATTTTTAAGCTT

SEQ ID NO: 138 (VDM2-miR-7-miR-V-7)

CCTAAGGCATTCTTTCCATAGCCCACAGGGCTGTCAAAGACCCCAGGGCC
TAGTCAGAGGCTCCTCCTTCCTGGAGAGTTCCTGGCACAGAAGTTGAAGC
TCAGCACAGCCCCCTAACCCCCAACTCTCTCTGCAAGGCCTCAGGGGTCA
GAACACTGGTGGAGCAGATCCTTTAGCCTCTGGATTTTAGGGCCATGGTA
GAGGGGGTGTTGCCCTAAATTCCAGCCCTGGTCTCAGCCCAACACCCTCC
AAGAAGAAATTAGAGGGGCCATGGCCAGGCTGTGCTAGCCGTTGCTTCTG
AGCAGATTACAAGAAGGGACTAAGACAAGGACTCCTTTGTGGAGGTCCTG
GCTTAGGGAGTCAAGTGACGGCGGCTCAGCACTCACGTGGGCAGTGCCA
GCCTCTAAGAGTGGGCAGGGGCACTGGCCACAGAGTCCCAGGGAGTCCC
ACCAGCCTAGTCGCCAGACCGATCCGGTATATTGCTGTTGACAGTGAGCG
ACTGGGATTCCTGTAGACACAACTGTGAAGCAGATGGGTTGTGTCTACAG
GAATCCCAGACGCCTACTGCCTCGGACTTCAAGCTAGCGGTACCGGTATA
TTGCTGTTGACAGTGAGCGAGGAGCATCTCATCTGTTACAACTGTGAAGCA
GATGGGTTGTAACAGATGAGATGCTCCACGCCTACTGCCTCGGACTTCAA
AAGCTT

Figure 11 (cont.)

SEQ ID NO: 139 (ICAM2-miR-7-miR-V-7)

CCTAAGGATGGGATTTGGGGTTCCCCAGATCTGGGGCTTGTAGGCCTGAC
TCTCCCCTGTGCACACGTCTCATACACGCATGCGTGCACCCATTGCCTGC
CCCGCCCCTTGCACAGGGAGTCAGCAGGGAGGACTGGGTTATGCCCTGC
TTATCAGCAGCTTCCCAGCTTCCTCTGCCTGGATTCTTAGAGGCCTGGGGT
CCTAGAACGAGCTGGTGCACGTGGCTTCCCAAAGATCTCTCAGATAATGA
GAGGAAATGCAGTCATCAGTTTGCAGAAGGCTAGGGATTCTGGGCCATAG
CTCAGACCTGCGCCCACCATCTCCTCCAGGCAGCCCTTGGGATCCGGTA
TATTGCTGTTGACAGTGAGCGACTGGGATTCCTGTAGACACAACTGTGAAG
CAGATGGGTTGTGTCTACAGGAATCCCAGACGCCTACTGCCTCGGACTTC
AAGCTAGCGGTACCGGTATATTGCTGTTGACAGTGAGCGAGGAGCATCTC
ATCTGTTACAACTGTGAAGCAGATGGGTTGTAACAGATGAGATGCTCCACG
CCTACTGCCTCGGACTTCAAAAGCTT

SEQ ID NO: 140 (RPE65-miR-7-miR-V-7)

CCTAAGGTTCCAAGGACTTCTTTGGGCAGTACCTTGTCTGTGCTGGCAAG
CAACTGAGACTTAATGAAAGAGTATTGGAGATATGAATGAATTGATGCTGT
ATACTCTCAGAGTGCCAAACATATACCAATGGACAAGAAGGTGAGGCAGA
GAGCAGACAGGCATTAGTGACAAGCAAAGATATGCAGAATTTCATTCTCAG
CAAATCAAAAGTCCTCAACCTGGTTGGAAGAATATTGGCACTGAATGGTAT
CAATAAGGTTGCTAGAGAGGGTTAGAGGTGCACAATGTGCTTCCATAACAT
TTTATACTTCTCCAATCTTAGCACTAATCAAACATGGTTGAATACTTTGTTTA
CTATAACTCTTACAGAGTTATAAGATCTGTGAAGACAGGGACAGGGACAAT
ACCCATCTCTGTCTGGTTCATAGGTGGTATGTAATAGATATTTTTAAAAATA
AGTGAGTTAATGAATGAGGGTGAGAATGAAGGCACAGAGGTATTAGGGGG
AGGTGGGCCCCAGAGAATGGTGCCAAGGTCCAGTGGGGTGACTGGGATC
AGCTCAGGCCTGACGCTGGCCACTCCCACCTAGCTCCTTTCTTTCTAATCT
GTTCTCATTCTCCTTGGGAAGGATTGAGGTCTCTGGAAAACAGCCAAACAA
CTGTTATGGGAACAGCAAGCCCAAATAAAGCCAAGCATCAGGGGGATCTG
AGAGCTGAAAGCAACTTCTGTTCCCCCTCCCTCAGCTGAAGGGGTGGGGA
AGGGCTCCCAAAGCCATAACTCCTTTTAAGGGATTTAGAAGGCATAAAAAG

Figure 11 (cont.)

GCCCCTGGCTGAGAACTTCCTTCTTCATTCTGCAGTGATCCGGTATATTGC
TGTTGACAGTGAGCGACTGGGATTCCTGTAGACACAACTGTGAAGCAGAT
GGGTTGTGTCTACAGGAATCCCAGACGCCTACTGCCTCGGACTTCAAGCT
AGCGGTACCGGTATATTGCTGTTGACAGTGAGCGAGGAGCATCTCATCTG
TTACAACTGTGAAGCAGATGGGTTGTAACAGATGAGATGCTCCACGCCTAC
TGCCTCGGACTTCAAAAGCTT

SEQ ID NO: 141 (FLT-miR-7-miR-V-7)

CCTAAGGGCGCTCCCGGGCCCGCGTCGCCAGCACCTCCCCACGCGCGCT
CGGCCCCGGGCCACCCGCCCTCGTCGGCCCCGCCCCTCTCCGTAGCC
GCAGGGAAGCGAGCCTGGGAGGAAGAAGAGGGTAGGTGGGGAGGCGGA
TGAGGGGTGGGGGACCCCTTGACGTCACCAGAAGGAGGTGCCGGGGTAG
GAAGTGGGCTGGGGAAAGGTTATAAATCGCCCCCGCCCTCGGCTGCTCTT
CATCGAGGTCCGCGGGAGGCTCGGAGCGCGCCAGGCGGACACTCCTGG
ATCCGGTATATTGCTGTTGACAGTGAGCGACTGGGATTCCTGTAGACACAA
CTGTGAAGCAGATGGGTTGTGTCTACAGGAATCCCAGACGCCTACTGCCT
CGGACTTCAAGCTAGCGGTACCAAGCTT

SEQ ID NO: 142 (U6-miR-V-7-miR-C-8-miR-P9)

CCTAAGGCCCAGTGGAAAGACGCGCAGGCAAAACGCACCACGTGACGGA
GCGTGACCGCGCGCCGAGCGCGCGCCAAGGTCGGGCAGGAAGAGGGCC
TATTTCCCATGATTCCTTCATATTTGCATATACGATACAAGGCTGTTAGAGA
GATAATTAGAATTAATTTGACTGTAAACACAAAGATATTAGTACAAAATACG
TGACGTAGAAAGTAATAATTTCTTGGGTAGTTTGCAGTTTTAAAATTATGTT
TTAAAATGGACTATCATATGCTTACCGTAACTTGAAAGTATTTCGATTTCTT
GGGTTTATATATCTTGTGGAAAGGACGCGGGATCCGGTATATTGCTGTTGA
CAGTGAGCGAGGAGCATCTCATCTGTTACAACTGTGAAGCAGATGGGTTG
TAACAGATGAGATGCTCCACGCCTACTGCCTCGGACTTCAAGCTAGCGGT
ATATTGCTGTTGACAGTGAGCGAAGGATATCAAAGCTCTGTTTACTGTGAA
GCAGATGGGTAAACAGAGCTTTGATATCCTGCGCCTACTGCCTCGGACTT
CAAGGTACCGGTATATTGCTGTTGACAGTGAGCGACAGTTCTACAATGCCA

Figure 11 (cont.)

TCAAACTGTGAAGCAGATGGGTTTGATGGCATTGTAGAACTGCCGCCTACT
GCCTCGGACTTCAACAATTGTTTTTAAGCTT

SEQ ID NO: 143 (VDM2-miR-V-7-miR-C-8-miR-P-9)

CCTAAGGCATTCTTTCCATAGCCCACAGGGCTGTCAAAGACCCCAGGGCC
TAGTCAGAGGCTCCTCCTTCCTGGAGAGTTCCTGGCACAGAAGTTGAAGC
TCAGCACAGCCCCTAACCCCAACTCTCTCTGCAAGGCCTCAGGGGTCA
GAACACTGGTGGAGCAGATCCTTTAGCCTCTGGATTTTAGGGCCATGGTA
GAGGGGGTGTTGCCCTAAATTCCAGCCCTGGTCTCAGCCCAACACCCTCC
AAGAAGAAATTAGAGGGGCCATGGCCAGGCTGTGCTAGCCGTTGCTTCTG
AGCAGATTACAAGAAGGGACTAAGACAAGGACTCCTTTGTGGAGGTCCTG
GCTTAGGGAGTCAAGTGACGGCGGCTCAGCACTCACGTGGGCAGTGCCA
GCCTCTAAGAGTGGGCAGGGGCACTGGCCACAGAGTCCCAGGGAGTCCC
ACCAGCCTAGTCGCCAGACCGGATCCGGTATATTGCTGTTGACAGTGAGC
GAGGAGCATCTCATCTGTTACAACTGTGAAGCAGATGGGTTGTAACAGATG
AGATGCTCCACGCCTACTGCCTCGGACTTCAAGCTAGCGGTATATTGCTGT
TGACAGTGAGCGAAGGATATCAAAGCTCTGTTTACTGTGAAGCAGATGGG
TAAACAGAGCTTTGATATCCTGCGCCTACTGCCTCGGACTTCAAGGTACCG
GTATATTGCTGTTGACAGTGAGCGACAGTTCTACAATGCCATCAAACTGTG
AAGCAGATGGGTTTGATGGCATTGTAGAACTGCCGCCTACTGCCTCGGAC
TTCAACAATTGTTTTTAAGCTT

SEQ ID NO: 144 (ICAM2-miR-V-7-miR-C-8-miR-P-9)

CCTAAGGATGGGATTTGGGGTTCCCCAGATCTGGGGCTTGTAGGCCTGAC
TCTCCCCTGTGCACACGTCTCATACACGCATGCGTGCACCCATTGCCTGC
CCCGCCCCTTGCACAGGGAGTCAGCAGGGAGGACTGGGTTATGCCCTGC
TTATCAGCAGCTTCCCAGCTTCCTCTGCCTGGATTCTTAGAGGCCTGGGGT
CCTAGAACGAGCTGGTGCACGTGGCTTCCCAAAGATCTCTCAGATAATGA
GAGGAAATGCAGTCATCAGTTTGCAGAAGGCTAGGGATTCTGGGCCATAG
CTCAGACCTGCGCCCACCATCTCCCTCCAGGCAGCCCTTGGGGATCCGGT
ATATTGCTGTTGACAGTGAGCGAGGAGCATCTCATCTGTTACAACTGTGAA

Figure 11 (cont.)

GCAGATGGGTTGTAACAGATGAGATGCTCCACGCCTACTGCCTCGGACTT
CAAGCTAGCGGTATATTGCTGTTGACAGTGAGCGAAGGATATCAAAGCTCT
GTTTACTGTGAAGCAGATGGGTAAACAGAGCTTTGATATCCTGCGCCTACT
GCCTCGGACTTCAAGGTACCGGTATATTGCTGTTGACAGTGAGCGACAGT
TCTACAATGCCATCAAACTGTGAAGCAGATGGGTTTGATGGCATTGTAGAA
CTGCCGCCTACTGCCTCGGACTTCAACAATTGTTTTTAAGCTT

SEQ ID NO: 145 (RPE65-miR-V-7-miR-C-8-miR-P-9)

CCTAAGGTTCCAAGGACTTCTTTGGGCAGTACCTTGTCTGTGCTGGCAAG
CAACTGAGACTTAATGAAAGAGTATTGGAGATATGAATGAATTGATGCTGT
ATACTCTCAGAGTGCCAAACATATACCAATGGACAAGAAGGTGAGGCAGA
GAGCAGACAGGCATTAGTGACAAGCAAAGATATGCAGAATTTCATTCTCAG
CAAATCAAAAGTCCTCAACCTGGTTGGAAGAATATTGGCACTGAATGGTAT
CAATAAGGTTGCTAGAGAGGGTTAGAGGTGCACAATGTGCTTCCATAACAT
TTTATACTTCTCCAATCTTAGCACTAATCAAACATGGTTGAATACTTTGTTTA
CTATAACTCTTACAGAGTTATAAGATCTGTGAAGACAGGGACAGGGACAAT
ACCCATCTCTGTCTGGTTCATAGGTGGTATGTAATAGATATTTTTAAAAATA
AGTGAGTTAATGAATGAGGGTGAGAATGAAGGCACAGAGGTATTAGGGGG
AGGTGGGCCCCAGAGAATGGTGCCAAGGTCCAGTGGGGTGACTGGGATC
AGCTCAGGCCTGACGCTGGCCACTCCCACCTAGCTCCTTTCTTTCTAATCT
GTTCTCATTCTCCTTGGGAAGGATTGAGGTCTCTGGAAAACAGCCAAACAA
CTGTTATGGGAACAGCAAGCCCAAATAAAGCCAAGCATCAGGGGGATCTG
AGAGCTGAAAGCAACTTCTGTTCCCCCTCCCTCAGCTGAAGGGGTGGGGA
AGGGCTCCCAAAGCCATAACTCCTTTTAAGGGATTTAGAAGGCATAAAAAG
GCCCCTGGCTGAGAACTTCCTTCTTCATTCTGCAGTGGATCCGGTATATTG
CTGTTGACAGTGAGCGAGGAGCATCTCATCTGTTACAACTGTGAAGCAGAT
GGGTTGTAACAGATGAGATGCTCCACGCCTACTGCCTCGGACTTCAAGCT
AGCGGTATATTGCTGTTGACAGTGAGCGAAGGATATCAAAGCTCTGTTTAC
TGTGAAGCAGATGGGTAAACAGAGCTTTGATATCCTGCGCCTACTGCCTC
GGACTTCAAGGTACCGGTATATTGCTGTTGACAGTGAGCGACAGTTCTACA

Figure 11 (cont.)

ATGCCATCAAACTGTGAAGCAGATGGGTTTGATGGCATTGTAGAACTGCC
GCCTACTGCCTCGGACTTCAACAATTGTTTTTAAGCTT

SEQ ID NO: 146 (FLT-miR-V-7-miR-C-8-miR-P-9)

CCTAAGGGCGCTCCCGGGCCCGCGTCGCCAGCACCTCCCCACGCGCGCT
CGGCCCCGGGCCACCCGCCCTCGTCGGCCCCGCCCTCTCCGTAGCC
GCAGGGAAGCGAGCCTGGGAGGAAGAAGAGGGTAGGTGGGGAGGCGGA
TGAGGGGTGGGGGACCCCTTGACGTCACCAGAAGGAGGTGCCGGGGTAG
GAAGTGGGCTGGGGAAAGGTTATAAATCGCCCCGCCCTCGGCTGCTCTT
CATCGAGGTCCGCGGGAGGCTCGGAGCGCGCCAGGCGGACACTCCTGG
ATCCGGTATATTGCTGTTGACAGTGAGCGAGGAGCATCTCATCTGTTACAA
CTGTGAAGCAGATGGGTTGTAACAGATGAGATGCTCCACGCCTACTGCCT
CGGACTTCAAGCTAGCGGTATATTGCTGTTGACAGTGAGCGAAGGATATC
AAAGCTCTGTTTACTGTGAAGCAGATGGGTAAACAGAGCTTTGATATCCTG
CGCCTACTGCCTCGGACTTCAAGGTACCGGTATATTGCTGTTGACAGTGA
GCGACAGTTCTACAATGCCATCAAACTGTGAAGCAGATGGGTTTGATGGC
ATTGTAGAACTGCCGCCTACTGCCTCGGACTTCAACAATTGTTTTTAAGCTT

SEQ ID NO: 147 (Predicted RNA of miR-8)

GGUAUAUUGCUGUUGACAGUGAGCGAUAGACACACCCACCCACAUAACU
GUGAAGCAGAUGGGUUAUGUGGGUGGGUGUGUCUACCGCCUACUGCCU
CGGACUUCAAGCUAGCGGUACCUU

AGE-RELATED MACULAR DEGENERATION TREATMENT

CROSS-REFERENCE TO RELATED APPLICATIONS

This application is the U.S. National Phase under 35 U.S.C. § 371 of International Application PCT/AU2014/000007, filed Jan. 8, 2014, which claims priority to U.S. 61/750,086, filed Jan. 8, 2013.

REFERENCE TO SEQUENCE LISTING

This application incorporates by reference the sequence listing submitted as ASCII text filed via EFS-Web on Jul. 6, 2015. The Sequence Listing is provided as a file entitled "seqlstUS_FBRIC80_004APC.txt," created on Jul. 6, 2015, and which is approximately 113 kilobytes in size.

FIELD OF THE INVENTION

This invention is directed to an RNA interference (RNAi) agent and the use of that RNAi agent to treat Age-related Macular Degeneration, as well as pharmaceutical compositions containing the RNAi agents of the invention.

BACKGROUND OF THE INVENTION

Age related macular degeneration (AMD) is the leading cause of irreversible vision loss in the United States and many other industrialised countries. "Dry" AMD is the most common type of macular degeneration and affects 90% of the people who have the condition. The dry form is characterized by the formation of drusen within the macula, a specialized structural region of the retina which capture the light that enters the eye. Typically, drusen is formed under the retinal pigment epithelial (RPE) cells and its presence is thought to lead to atrophy of photoreceptors due to a breakdown or thinning of the RPE layer of that supports the photoreceptor cells. It is also thought that persistence of drusen within the retina leads to a persistent inflammatory reaction and results in a cascade of secondary responses that eventually can lead to wet AMD.

The "wet" form of AMD is characterized by an abnormal outgrowth of blood vessels from the vasculature situated behind the retina in a process that is often referred to as choroidal neovascularization (CNV). While not as prevalent as the dry form, it has a more rapid onset and is more severe phenotype, often leading to reduction of a substantial portion of the visual field.

The current standard of care for wet AMD is Ranibizumab (RAN), a monoclonal antibody fragment with strong affinity to the vascular endothelial growth factor-A (VEGF-A), a molecular moiety secreted from cells and known to cause the formation or growth of nascent blood vessels. RAN binds to and inhibits the biologic activity of VEGF-A, thereby preventing the interaction of VEGF-A with its receptors (VEGFR1 and VEGFR2) on the surface of endothelial cells. This results in a reduction in endothelial cell proliferation, less vascular leakage, and a reduction in new blood vessel formation characteristic of CNV.

The ocular half-life of RAN, however, is only nine days following intravitreal injection, thus therapeutic doses must be administered monthly to patients to remain effective at suppressing vascular proliferation. Although useful at stabilizing visual acuity in nearly 95% of patients, improved vision was noted in only 29%-40% of patients. RAN acts as a molecular sponge to mop-up secreted VEGF-A. Inefficiencies in this process may be one reason why vision is only stabilized, not improved in most patients. In other words, it treats the symptoms but not the cause.

The principal drawback with existing monoclonal antibody wet AMD therapies is the requirement for frequent, continuous treatment, typically involving monthly injections into the eye. Combined with a rapidly aging population and correspondingly low numbers of clinicians who are qualified to administer intravitreal injections, application of this therapy This has placed enormous strain on healthcare systems. Thus there is clearly a need for longer lasting treatments and/or treatments that can reverse the symptoms. Alternative treatments for wet AMD have been similarly unsatisfactory, also as a result of their frequency of administration, but as well as their side effects or poor efficacy.

One of the newer drugs to commence clinical trials is that of the VEGF Trap Eye (VTE) which incorporates the second binding domain of the VEGFR-1 receptor and the third domain of the VEGFR2 receptor 1. By fusing these extracellular protein sequences to the Fc segment of a human IgG backbone, developers have created a chimeric protein with a very high VEGF binding affinity (Stewart M W. Br J Ophthalmol (2012). doi:10.1136/bjophthalmol-2011-300654). As well as binding all isomers of the VEGF-A family, it also binds VEGF-B and placental growth factor.

Given the fact that the chimera protein still has a relatively short half-life, VTE however must still be regularly administered—every 2 months.

AAV2-sFLT01 is a gene therapy vector that expresses a modified soluble Flt1 receptor coupled to a human IgG1 Fc. As a high affinity VEGF binding protein, AAV2-sFLT01 functions to neutralize the pro-angiogenic activities of VEGF for treatment of wet AMD via an intravitreal injection. (Wasworth et al. Molecular Therapy vol. 19 no. 2 Feb. 2011; 326-334). The use of an AAV vector is expected to ensure long-term expression, lasting for many months or even years, from a single injection. However, in order to accommodate the sFLT01 and IgG1 Heavy Chain Fc fusion protein, single stranded AAV must be used, which in turn requires high quantities of vector for efficient transduction and thus increases the risk of an immune response to the viral capsid proteins. Moreover, a high prevalence of the normal adult population has been exposed to serotype 2 variant of AAV, and may have pre-existing immunity against it.

The molecule PF-04523655 is a 19 nucleotide siRNA that inhibits the expression of the hypoxia-inducible gene RTP801 (Nguyen et al. Ophthalmology. 2012 September; 119(9):1867-73). In clinical studies conducted to date, it has been found to prevent neovascularization and vessel leakage, although does so via a different pathway than VEGF. It has been demonstrated that the siRNA only persists in the eye for several weeks, meaning that like so many of the other existing and developing therapies, patients will require regular intravitreal injections for treatment. A failure to do so with many treatments has seen a continued loss of visual acuity, and a progression of degeneration.

More generally, previous siRNA-based approaches for treating and managing wet AMD have failed. Although initial pre-clinical experimental results were encouraging, it was subsequently demonstrated that mode of action of these molecules was not through a sequence specific RNAi-based mechanism, but rather through induction of a non-specific interferon response mediated by the interaction of siRNAs with Toll-like receptor TLR3 (Kleinmann et al 2008). Toll-like receptors are transmembrane proteins that play a key role in the innate immune system. Often positioned on either the cell surface or on intracellular vesicles such as the endosome, some family members of this family recognize double stranded RNA, not normally present in the endogenous cell, as foreign substance and triggers a cascade of molecule responses. This leads to interferon activation, which has a transitory therapeutic effect in mouse models. However interferon has a much lower efficacy in humans which explains the poor efficacy of this treatment in human clinical testing.

Retinostat is an equine infectious anaemia virus (EIAV) based lentivirus vector expressing angiostatin and endostatin, both of which are naturally occurring angiogenesis inhibitors in the ocular compartment. Endostatin blocks VEGF signalling, reduces vascular permeability, decreases cell matrix adhesion and promotes endothelial cell apoptosis. Angiostatin prevents endothelial cell proliferation and migration. The genes are delivered via a subretinal injection and inhibit the formation of new blood vessels. Sub-retinal delivery however requires an intensive surgical procedure, which, unlike intravitreal delivery, does not lend itself to outpatient treatments or treatment at a local doctor.

Despite the large amount of development activity in the field of AMD therapeutics, and wet AMD in particular, there remains a need to create more effective therapies that are also patient friendly with respect to side effects, the mode of treatment and the frequency thereof. This invention is directed to a RNA interference (RNAi) agent and the use of that RNAi agent to manage and treat wet AMD in individuals.

The RNAi pathway is initiated by the enzyme Dicer, which cleaves double-stranded RNA (dsRNA) molecules into short fragments (commonly referred to as siRNAs) of ~20-25 nucleotides. One of the two strands of each fragment, known as the guide strand or active strand, is then incorporated into the RNA-induced silencing complex (RISC) through binding to a member of the Argonaute protein family. After integration into the RISC, the guide strand base-pairs with its target mRNA and is thought to either inhibit a target by inhibiting translation (by stalling the translational machinery) and/or inducing cleavage of the mRNA, thereby preventing it from being used as a translation template.

While the fragments produced by Dicer are double-stranded, only the guide strand, directs gene silencing. The anti-guide strand (referred to commonly as a passenger strand, carrier strand or * strand) is frequently degraded during RISC activation (Gregory R et al., 2005). RISC assembly is thought to be governed by an enzyme that selects which strand of a dsRNA Dicer product is loaded into RISC. This strand is usually the one whose 5' end is less tightly paired to its complement. There also appears to be a clear bias for A, and to a lesser extent U, at the 5' position to facilitate binding to some Argonaute proteins (Schwarz D S et al., 2003; Frank F et al., 2010).

The present invention seeks to overcome the problems associated with other therapies as already discussed above, while overcoming the previous challenges faced by RNAi therapeutics in this field.

Reference to any prior art in the specification is not, and should not be taken as, an acknowledgment or any form of suggestion that this prior art forms part of the common general knowledge in Australia or any other jurisdiction or that this prior art could reasonably be expected to be ascertained, understood and regarded as relevant by a person skilled in the art.

SUMMARY OF THE INVENTION

There is an unmet need for long term therapy for AMD, and in particular, wet AMD. It has been discovered by the current inventors that particular RNAi constructs have the ability to down-regulate the expression of genes associated with the development of AMD (collectively referred to as 'AMD associated genes'). This in turn can slow the progression of AMD and the accompanying vision loss, and in some instances, result in an improvement in visual acuity. By utilising RNAi technology to achieve long term suppression of those target sequences, together with the use of a vector delivery vehicle that directs the RNAi agent to the target cells in a non-invasive manner, this need can be met and it can be met in a patient convenient and friendly manner. Moreover, because RNA agents expressed from DNA directed RNAi (ddRNAi) constructs are produced in the nucleus and do not interact with Toll-like receptors on either the cell surface or within the endomal compartment, ddRNAi agents can be produced without activating an interferon response via the TLRs.

In one aspect of the invention, there is provided a DNA-directed RNA interference (ddRNAi) agent (being an RNA molecule), and an expression cassette or construct to express that agent in a cell (including in vivo), for inhibiting, preventing or reducing expression of one or more target sequences in an AMD associated gene, preferably a wet AMD associated gene, where the agent comprises
   an effector sequence (described further below) of at least 17 nucleotides in, and
   an effector complement sequence
wherein the effector sequence is complementary or substantially complementary to one or more target regions in a transcript of the one or more target sequences.

The target region can be selected from the group consisting of any 10 or more contiguous nucleotides within a transcript of a target sequence selected from any one or more of SEQ ID NOS: 1-39. The effector complement sequence is substantially complementary to the effector sequence such that it will tend to anneal so as to form a double stranded RNA segment.

The effector sequence is directed to a target region within a transcript of a target sequence of a target gene. Thus the effector sequence is 'directed to' a target region by being substantially complementary (as 'substantial complementarity' is defined below) in sequence to a transcript from a target gene containing the target region. An RNAi agent, such as a ddRNAi agent, having a double-stranded portion containing the effector sequence, can therefore "inhibit expression of a target gene sequence" by virtue of the target gene sequence containing the target region. Accordingly, within a cell having an AMD associated gene, the RNAi agent is capable of inhibiting expression of a target gene sequence because the sequence of the effector (as 'effector' is defined below) is substantially complementary to (at least) a region of the mRNA target sequence of the target gene. This can be illustrated by considering the following random, hypothetical short sequence:
   5'GG<u>CATTGCG</u>3'—target region within target sequence
   5'GG<u>CAUUGCG</u>3'—transcript of target sequence
   3'<u>GUAACG</u>5'—effector sequence, which is substantially complementary to the target region in the transcript of the target sequence.

Typically, a target region is a region of nucleic acid sequence within the mRNA of a gene that is intended to be silenced or to have its expression (at the level of transcription or translation) reduced, inhibited or prevented.

As can be seen in the explanatory comparison above, 'substantial complementarity' between the effector sequence and the effector complement sequence can be 100% complementarity. However as more particularly explained and defined further below, substantial complementarity can be 80% to 100% complementary. So in an effector sequence having a length of, for example, 20 nucleotides, the effector sequence is substantially complementary to the effector complement sequence if 17 of the 20 nucleotides are complementary ie 85% complementarity. Moreover, usually one end of the double stranded segment will be linked by a loop sequence so as to form a 'hairpin' shaped structure referred to as shRNA. This is also known as an 'interrupted inverted repeat' structure, as the DNA encoding such an RNA sequence contains an inverted repeat of the region of the target gene that is transcribed to the effector sequence, interrupted by a stuffer or spacer sequence encoding the loop.

The concept of substantial complementary described in the paragraph above applies equally to the substantial complementarity between the effector sequence and the target sequence where substantial complementarity can be 80% to 100% complementarity. That is, if the target region within a target sequence is 20 nucleotides long, and the effector sequence is 20 nucleotides long, then the effector sequence may have, for example, 16, 17, 18 or 20 nucleotides that are complementary with the target, equating to 80%, 85%, 90% and 100% complementarity respectively.

In both situations, one will appreciate that substantial complementarity may not equate to a whole number. For example, at least 85% complementarity to a sequence of 22 nucleotides would be 18.7 nucleotides, so is effectively a requirement for 19 of 22 to be complementary.

Alternatively, substantial complementarity of 80 to 100% complementarity (both in the context of substantial complementarity between the effector and target, and effector and its complement) can be described with reference to the number of nucleotides that will not G-C/A-U base pair (except for wobble pairs as described below). There may be 1, 2, 3, 4 or 5 nucleotides within the complementary region between the 2 RNAs that are not themselves complementary with a nucleotide on the other strand when considering at least 80% complementarity across a nucleotide sequence. As to whether there can be 1, 2, 3, 4 or 5 nucleotides that do not base pair is dependent on the length of the relevant sequence. For example, if the effector sequence is 17 nucleotides long, it cannot have 5 nucleotides that will not base pair, as this would equate to only 71% complementarity. In a 17 nucleotide sequence, there must be complementarity between 14 of the 17 nucleotides for at least 80% complementarity.

In a preferred embodiment of the invention, the double stranded region formed by the effector sequence and its complement is expressed as part of a microRNA (miRNA) structure similar to the structure of endogenous miRNAs which are a natural substrate for endogenous RNAi processing pathways. Processing of double stranded RNAs expressed from ddRNAi constructs can be imprecise, and can result in toxicity. McBride et al. (2008) designed "artificial miRNA" constructs which expressed sequences from the base and loop of endogenous miRNAs, and suggested that more precise processing of expressed shRNAs from the miR-backbone led to reduced toxicity from the constructs. Wu et al. (2011) showed that mismatched duplexes (containing mismatches in the passenger strand) sometimes showed increased silencing activity, due possibly to their greater structural resemblance to endogenous miRNAs.

In one aspect of the invention, there is provided a ddRNAi agent and an expression cassette to express that agent in a cell, for inhibiting, preventing or reducing expression of an AMD associated gene, preferably a wet AMD associated gene, where the agent comprises
an effector sequence of at least 17 nucleotides in length complementary to or substantially complementary to one or more target regions in a transcript of a target region, and an effector complement sequence
wherein the effector sequence and the effector complement sequence are expressed within a miRNA structure. The target region may be selected from the group consisting of any 10 or more contiguous nucleotides within a transcript of a sequence selected from any one or more of SEQ ID NOS: 1-39.

In some forms of the invention, the agent has more than one effector sequence. Multiple effectors may target the same region of a wet AMD associated gene (typically variants of the same region), different regions of a wet AMD associated gene, more than one wet AMD associated gene, or a combination of all of the above.

RNAi agents, such as ddRNAi agents, can contain 2 or 3 or more effector sequences. As explained above, the ddRNAi agent comprises an effector complement sequence for each effector sequence, thus forming effector—effector complement pairs (ie a first effector—first effector complement pair, a second effector—second effector complement pair, etc). These pairs may be, but need not be, contiguous to one another, as long as the RNAi agent can fold so as to permit each pair to anneal. Various other considerations suggest one order or another of the effectors and effector complements along the length of the RNAi agent. In addition, as would be understood by one skilled in the art, and as illustrated in the Figures, any particular effector sequence may be swapped in position with its complement in the agent. The important feature, as exemplified in the various embodiments below, is that the effector sequence is able to anneal with its complement to form a double stranded region. For example:

ddRNAi agent comprising, in a 5' to 3' direction, a first effector sequence; a second effector sequence; second effector complement sequence; and a first effector complement sequence;

a ddRNAi agent comprising, in a 5' to 3' direction, a first effector sequence; a second effector sequence; a third effector sequence; a third effector complement sequence; a second effector complement sequence; and a first effector complement sequence;

a ddRNAi agent comprising, in a 5' to 3' direction, a first effector; a first effector complement sequence; a second effector sequence; and a second effector complement sequence;

a ddRNAi agent comprising, in a 5' to 3' direction, a first effector sequence; a first effector complement sequence; a second effector sequence; a second effector complement sequence; a third effector sequence; and a third effector complement sequence;

a ddRNAi agent comprising, in a 5' to 3' direction, a first effector sequence; a second effector sequence; a loop sequence of 2 to 100 non-self-complementary nucleotides; a second effector complement sequence; and a first effector complement sequence;

a ddRNAi agent comprising, in a 5' to 3' direction, a first effector sequence; a loop sequence of 2 to 100 non-self-complementary nucleotides; a first effector complement sequence; a sequence of 2 to 100 non-self-complementary nucleotides; a second effector sequence; a loop sequence of 2 to 100 non-self-complementary nucleotides; and a second effector complement sequence;

a ddRNAi agent comprising, in a 5' to 3' direction, a first effector sequence; a loop sequence of 2 to 100 non-self-complementary nucleotides; a first effector complement sequence; a spacer sequence of 2 to 100 non-self-complementary nucleotides; a second effector sequence; a loop sequence of 2 to 100 non-self-complementary nucleotides; and a second effector complement sequence;

a ddRNAi agent comprising, in a 5' to 3' direction, a first effector sequence; a first effector complement sequence; a spacer sequence of 2 to 100 non-self-complementary nucleotides; a second effector sequence; a second effector complement sequence; a spacer sequence of 2 to 100 non-self-complementary nucleotides; a third effector sequence; and a third effector complement sequence.

The non-self-complementary nucleotides act as loop sequences when located between an effector and its complement, and as spacer sequences when located between the complement of one effector sequence, and the next effector sequence. In each of these embodiments, the effector sequence, and its complement, as well as any additional sequence such as a sequence of 2 to 100 non-self-complementary nucleotides, is expressed within or part of a miRNA structure.

In particular forms of each of the embodiments described above, each effector sequence is at least 17 nucleotides in length, preferably 17 to 30 nucleotides in length, and more preferably 17 to 21 nucleotides in length, and comprises a nucleotide sequence selected from the group consisting of any 10 or more contiguous nucleotides from a sequence from any one of SEQ ID NOS: 40-78. The effector sequences may all be the same, or may all be different, or may be a combination, e.g. 2 effector sequences of at least 10 contiguous nucleotides of SEQ ID NO:47 and one effector sequence of at least 10 contiguous nucleotides of SEQ ID NO: 56.

Preferably, the effector sequence is selected from the group consisting of any contiguous 11, 12, 13, 14, 15 or 16 nucleotides within any one of SEQ ID NOS: 40-78, and preferably 17 or more contiguous nucleotides within any one of SEQ ID NOS: 40-78 and most preferably 17 to 21 contiguous nucleotides within any one of SEQ ID NOS: 40-78. Typically, the effector complement will be the same length, or about the same length (ie ±15% nucleotide length, or 1 to 3 nucleotides depending on the total length) as its corresponding effector sequence.

In particular embodiments the effector sequence of the ddRNAi agent consists of, or consists essentially of, a nucleotide sequence selected from the group consisting of any one of SEQ ID NOS: 40-78 inclusive. In these embodiments, a ddRNAi agent SEQ ID NOS: 40-78 as well as additional nucleotides or other chemical modifications would "consist essentially of" SEQ ID NOS: 40-78 as long as it exhibits activity for inhibiting, reducing or preventing the expression of the target gene, as may be determined in accordance with the assays described below. Similarly, an RNAi agent "consists essentially of" one of SEQ ID NOS: 40-78 where it is shorter than the corresponding SEQ ID as long as it exhibits activity for inhibiting, reducing or preventing the expression of the target gene, as may be determined in accordance with the assays described below.

In alternative embodiments, the dsRNA is comprised of 2 separate RNA strands that are annealed to form a duplex. That duplex may then be embedded in a miRNA backbone.

ddRNAi agents may be expressed from a DNA expression cassette inserted into any suitable vector or ddRNAi construct. Accordingly, in aspects of the invention there is provided a ddRNAi expression cassette comprising (in no particular order):

one or more promoter sequences
one or more DNA sequences that encode for one or more effector sequences, preferably being DNA sequences that encode for any 10 or more and preferably any 17 or more contiguous nucleotides within a sequence from any one of SEQ ID NOS: 40-78,
one or more DNA sequences that encode for one or more effector complement sequences and optionally
one or more terminator sequences
one or more DNA sequences that encode for spacer sequences, loop sequences, or both; and
one or more enhancer sequences.

In some embodiments, one promoter is operably linked to multiple effector-encoding regions such that a ddRNAi agent with multiple effector sequences is produced. In alternative embodiments, where each effector-encoding region is operably linked to its own promoter, multiple ddRNAi agents are produced from a single expression cassette. In constructs where there are multiple promoters, these may be all the same or different. Preferred promoters are poi III promoters such as U6 and H1; pol II promoters such as the RPE cell specific promoter RPE-65 (Boye et al. 2012) and VMD2 (Zhu et al. 2010), and choroid endothelial-specific promoters FLT-1 or ICAM2 can also be used to drive expression of ddRNAi constructs.

In embodiments where the effector sequence and its complement, are expressed within a miRNA structure, the ddRNAi expression cassette additionally comprises sequences that, encode for the miRNA structure referred to herein as miRNA encoding (ME) sequences. The ME sequences may also encode for loop sequences.

There is also provided ddRNAi expression constructs, into which the ddRNAi expression cassettes are inserted for expression. In addition, when the vector backbone of the construct is compatible with a delivery system, the ddRNAi expression constructs are also delivery constructs. A particularly preferred delivery construct is a viral vector, such as a modified adeno-associated virus (AAV) vector (Petrs-Silva et al. 2011) that allows delivery of ddRNAi expression cassettes to appropriate cells deep in the retina following intravitreal injection. Use of a modified AAV to deliver an expression construct that produces the therapeutic ddRNAi agent from within the cell avoids an interferon response often caused by direct interactions of nucleic acids with surface-expressed toll-like receptor 3. This is hypothesised to be the reason for a number of failures of siRNA-based ocular drugs in clinical trials.

Accordingly, in this embodiment there is provided a ddRNAi expression construct comprising a ddRNAi expression cassette for expressing a ddRNAi agent for inhibiting expression of one or more target sequences in an AMD associated gene, the expression cassette comprising (in no particular order)

one or more promoter sequences
one or more DNA sequences that encode for one or more effector sequences,
one or more DNA sequences that encode for one or more effector complement sequences;

and optionally
  one or more terminator sequences
    one or more DNA sequences that encode for loop sequences, spacer sequences or both,
  one or more enhancer sequences,
wherein the construct is a viral vector delivery vehicle.

Preferably the expression cassette further comprises ME sequence so that the ddRNAi agent is expressed as part of or within a miRNA structure.

In one embodiment, the expression cassette of the viral vector delivery construct comprises one DNA sequences that encodes a first effector sequence of any 10 or more contiguous nucleotides within 5' UAUGUGGGUGGGUGUGUCUAC 3' of the AMD-associated gene VEGF-A (SEQ ID NO:47).

In a further embodiment, the expression cassette of the viral vector delivery construct comprises two DNA sequences that encode a first effector sequence of any 10 or more contiguous nucleotides within 5' UGUAACAGAUGAGAUGCUCCA 3' of the AMD-associated gene VEGRF-2 (SEQ ID NO:56) and a second effector sequence of any 10 or more contiguous nucleotides within 5' UAUGUGGGUGGGUGUGUCUAC 3' of the AMD-associated gene VEGFA (SEQ ID NO:47).

In yet another alternative embodiment, the expression cassette of the viral vector delivery construct comprises three DNA sequences that encode a first effector sequence of any 10 or more contiguous nucleotides within 5' AAGUAGCCAGAAGAACAUGGC 3' of the AMD-associated gene VEGRF-2 (SEQ ID NO:52); a second effector sequence of any 10 or more contiguous nucleotides within 5' UUAUAGAAAACCCAAAUCCUC 3' of the AMD-associated gene CFB (SEQ ID NO:78); and a third effector sequence of any 10 or more contiguous nucleotides within 5' UAGCUGAAGCCCACGAGGUCC 3' of the AMD-associated gene PDGFR-β (SEQ ID NO:63).

The invention also provides for siRNA agents that comprise a sequence of at least 17 nucleotides in length selected from the group consisting of any 10 or more contiguous nucleotides within a sequence from any one of SEQ ID NOS: 40-78 and a sequence complement with which the sequence forms a duplex, and that are capable of inhibiting expression of a wet AMD associated gene.

In accordance with some embodiments, there is provided a method of inhibiting the expression of an mRNA or polypeptide encoded by an AMD associated gene in a subject comprising administering to the subject a composition of the invention comprising a ddRNAi agent that consists essentially of or consists of a nucleotide sequence selected from the group consisting of any one of SEQ ID NOS: 40-78 and sequences that vary from SEQ ID NOS: 40-78 by 1, 2, 3, 4 or 5 nucleotides. A ddRNAi expression cassette or ddRNAi expression construct for expressing the ddRNAi agent may also be administered.

In another embodiment the invention provides a composition for the treatment of AMD in a subject, preferably wet AMD, or treatment of other diseases that are caused by inappropriate vascularisation within the retina, comprising as an active ingredient, a ddRNAi agent, ddRNAi expression cassette or ddRNAi expression construct of the invention for inhibiting, preventing or reducing expression of one or more target sequences in an AMD associated gene.

In another embodiment the invention provides a pharmaceutical composition comprising an effective amount of a ddRNAi agent, ddRNAi expression cassette or ddRNAi expression construct of the invention as a main ingredient for inhibiting, preventing or reducing expression of one or more target sequences in an AMD associated gene. The composition may be used for example for the treatment of AMD in a subject, preferably wet AMD, or treatment of other diseases that are caused by inappropriate vascularisation within the retina. In some embodiments, the composition further comprises a pharmaceutically acceptable carrier or diluent.

In another embodiment the invention provides a composition for the treatment of AMD in a subject, preferably wet AMD, or treatment of other diseases that are caused by inappropriate vascularisation' within the retina, comprising as an active ingredient a ddRNAi agent, ddRNAi expression cassette or ddRNAi expression construct of the invention for inhibiting, preventing or reducing expression of one or more target sequences in an AMD associated gene.

In another embodiment the invention provides a composition for inhibiting, preventing or reducing expression of one or more target sequences in an AMD associated gene comprising a ddRNAi agent, ddRNAi expression cassette or ddRNAi expression construct of the invention for use in the treatment of wet AMD in a subject. In some embodiments, the composition further comprises a pharmaceutically acceptable carrier or diluent.

In another embodiment, the invention provides a ddRNAi agent, ddRNAi expression cassette or ddRNAi expression construct for inhibiting, preventing or reducing expression of one or more target sequences in an AMD associated gene in the preparation of a medicament for the treatment of AMD in a subject. Preferably the medicament is for wet AMD.

In another embodiment the invention provides an AMD treatment composition comprising an effective amount of a ddRNAi agent, ddRNAi expression cassette or ddRNAi expression construct of the invention for inhibiting, preventing or reducing expression of one or more target sequences in an AMD associated gene as a main ingredient, optionally with a pharmaceutically acceptable carrier or diluent.

The invention also provides a method for treating or delaying the progression of diseases that are caused by inappropriate vascularisation within the retina in a subject, comprising administering to the subject a ddRNAi agent, ddRNAi expression cassette or ddRNAi expression construct or composition of the invention for inhibiting, preventing or reducing expression of one or more target sequences in an AMD associated gene, thereby reducing the severity of AMD.

Yet a further aspect of the invention provides a method for reducing the progression of AMD in a subject, preferably wet AMD, comprising administering to the subject a ddRNAi agent, ddRNAi expression cassette or ddRNAi expression construct or composition of the invention for inhibiting, preventing or reducing expression of one or more target sequences in an AMD associated gene, thereby reducing the severity of AMD.

In each of the methods of the invention, the ddRNAi agent, ddRNAi expression cassette or ddRNAi expression construct or composition of the invention is preferably delivered to the subject's eye/s by intravitreal injection or subretinal injection.

In a further aspect, the present invention provides a kit of parts including (a) a ddRNAi agent, ddRNAi expression cassette or ddRNAi expression construct or composition of the invention and (b) a pharmaceutically acceptable carrier or diluent.

In certain embodiments an RNAi agent or pharmaceutical composition of the invention may be provided in the form of a device, disposable or reusable, including a receptacle for holding the RNAi agent or pharmaceutical composition. In one embodiment, the device is a syringe, preferably a syringe suitable for intravitreal injection or subretinal injection. The RNAi agent or pharmaceutical composition may be provided in the device in a state that is ready for use or in a state requiring mixing or addition of further components.

Although the invention finds application in humans, the invention is also useful for veterinary purposes. The invention is useful for the treatment of AMD or other diseases caused by inappropriate vascularisation in domestic animals such as cattle, sheep, horses and poultry; companion animals such as cats and dogs; and zoo animals.

BRIEF DESCRIPTION OF THE DRAWINGS/FIGURES

FIG. 1A-G illustrates some of the ddRNAi agent structures of the invention.

FIG. 2: A. Map of pSilencer (Invitrogen). This expression cassette contains the human U6 promoter (black arrow) and was designed to express shRNA sequences cloned into this vector as BamHI/Hind III fragments. B. A generalized map showing the schematic layout of a BamHI/Hind III shRNA fragment designed to silence AMD associated genes. The positions of BamHi/Hind III restriction sites are shown; the white arrows denote sequences from the 5' stem of miR30a, a sequence derived from the loop of mir30a and the 3' stem of miR30a. The grey arrow represents the predicted passenger strand and the black arrow the predicted guide strand. The relative positioning of the predicted guide strand and the predicted passenger strand may be interchangeable. The black line denotes a pol III termination signal. C. DNA sequence of the miR-8 fragment, which potently silences VEGF-A, is shown and corresponds to SEQ ID NO: 98. The lowercase letters denote restriction sites, mir30a-related sequences and pol III terminator sequences. The underlined sequences are derived from the base of human miR30a pre-cursor RNA (both 5' and 3'); sequences in italics are derived from the loop sequences of miR30a. The upper case sequences indicate the predicted passenger strand sequence, the bold uppercase sequences denote the predicted effector sequence (SEQ ID NO: 47). D. Predicted RNA secondary structure of miR-8, determined using the M-fold program (SEQ ID NO:147); the predicted Dicer and Drosha processing sites are indicated by arrows.

FIG. 3: A. Map of pGL3-VEGFA-sense reporter. The plasmid encodes firefly luciferase (Fluc+) driven by the SV40 promoter (grey arrows) and a eukaryotic transcriptional terminator. A portion of the non-coding strand of the VEGF-A gene was inserted into the 3' UTR of FLuc+ transcriptional unit using Xba I and Fse I restriction sites present in the 3'UTR of the parent plasmid (pGL3; Promega). This plasmid was used to quantify inhibitory activity of the passenger strand of miR-2 in dual luciferase assays. B. Map of pGL3-VEGFa-antisense reporter, features are shown as in FIG. 3A. The corresponding portion of the VEGF-A gene used in FIG. 3A was inserted into the 3' UTR of FLuc+ transcriptional unit using Xba I and Fse I restriction sites, but used the coding strand of the VEGF-A gene. This plasmid was used to quantify inhibitory activity of the effector strand of miR-2 in dual luciferase assays.

FIG. 4: A. The graph shows the percent inhibition of VEGF-A expression determined using dual luciferase assays; activities against both sense and antisense targets in sensor constructs are shown (n=3±SD). B. The graph shows percent inhibition of VEGF-A mRNA levels determined by qRT PCR in HEK293T cells co-transfected with either miR-2, miR-5 and miR-8 along with a full length cDNA that expresses the full length VEGF-A protein. Percent inhibition is calculated to untransfected cells and empty vector controls (pSilencer and an empty U6 expression cassette). C. The graph shows levels of VEGF-A mRNA and protein in ARPE-19 cells that have been transduced with an adenovirus vector expressing miR-8. Samples of RNA and protein were collected at 24, 48, 72 and 96 hours post transduction. The triangles show intracellular levels of mature, processed miR-8 in which the loop sequences have been cleaved.

FIG. 5: A. The graph shows the percent inhibition of VEGFR2 determined using firefly luciferase reporters as previously described; activities against both sense and antisense reporter constructs are shown (n=3±SD). B. The graph shows percent inhibition of VEGFR2 mRNA levels determined by RT QPCR in HEK203T cells that were co-transfected with miR-V-2, miR-V-3, miR-V-7 or miR-V-10 and a plasmid expressing a full length cDNA to VEGFR2. Percent inhibition was calculated as mRNA remaining as compared to empty vector controls (pSilencer; Invitrogen and an unrelated plasmid). C. Western blot analysis of cells transfected in parallel conditions as in 5B and showing reductions in VEGFR2 (arrow). Protein extracts from HUVEC cells were run in parallel to show positioning of VEGFR2 on the gel.

FIG. 6: A. The graph shows percent inhibition of PDGFR-β mRNA levels in HEK293T cells that were co-transfected with either miR-V-4 or miR-V-9 and a plasmid expressing a full length cDNA to PDGFR-β. Percent inhibition was calculated as mRNA remaining as compared to controls (pSilencer, Invitrogen and an unrelated plasmid and an empty U6 expression cassette). B. Western blot analysis of cells transfected in parallel conditions as in 6B and showing reductions in PDGFR-β (arrows).

FIG. 7: A. The graph shows the percent inhibition of CFB expression determined using firefly luciferase reporters as previously described; activities against both sense and antisense reporter constructs are shown (n=3±SD). B. The graph shows percent inhibition of CFB mRNA levels in HEK293T cells co-transfected with miR-C-1, miR-C-8 or miR-C-9 and a plasmid expressing a full length cDNA to CFB. Percent inhibition was calculated as compared to controls (pSilencer, Invitrogen, an unrelated plasmid and an empty U6 expression cassette). C. Western blot analysis performed on parallel treated wells as in 7B showed reductions in CFB (arrows).

FIG. 8: A. Map of U6-miR-7. This uses the human U6 promoter (black arrow) to drive expression of miR-7 which targets VEGF-A. The miR-7 coding sequences are identical to those in FIG. 2A and are shown as a white arrow, the positions of miR-7 passenger And miR-7 effector sequences are shown as grey arrows. The sequence of the U6-miR-7 fragment is listed as SEQ ID NO: 132. B. Map of VMD2-miR-7. This uses the human VMD2 promoter (black arrow) to drive expression of miR-7 (white arrow), which targets VEGF-A. The sequence of the VMD2-miR-7 fragment is listed as SEQ ID NO: 133. C. Map of ICAM2-miR-7. This uses the human ICAM2 promoter (black arrow) to drive expression of miR-7 (white arrow), which targets VEGF-A. The sequence of the ICAM2-miR-7 fragment is listed as SEQ ID NO: 134. D. Map of RPE-65-miR-7. This uses the human RPE65 promoter (black arrow) to drive expression of miR-7 (white arrow), which targets VEGF-A. The sequence of the RPE65-miR-7 fragment is listed as SEQ ID NO: 135. E. Map of FLT-miR-7. This uses the human FLT promoter (black arrow) to drive expression of miR-7 (white arrow), which targets VEGF-A. The sequence of the FLT-miR-7 fragment is listed as SEQ ID NO: 136.

FIG. 9: A. Map of U6-miR-7-miR-V-7. This uses the human U6 promoter (black arrow) to drive expression of miR-7-miR-V-7 which targets VEGF-A and VEGFR2. The miR-7-miR-V-7 coding sequences are shown as a white arrow, the positions of miR-7 passenger and miR-7 effector sequences and miR-V-7 passenger and miR-V-7 effector sequences are shown as grey arrows. The sequence of the U6-miR-7 fragment is listed as SEQ ID NO: 137. B. Map of VMD2-miR-7 miR-V-7. This uses the human VMD2 promoter (black arrow) to drive expression of miR-7 miR-V-7 (white arrow), which targets VEGF-A and VEGFR2. The sequence of the VMD2-miR-7 miR-V-7 fragment is listed as SEQ ID NO: 138. C. Map of ICAM2-miR-7 miR-V-7. This uses the human ICAM2 promoter (black arrow) to drive expression of miR-7 miR-V-7 (white arrow), which targets VEGF-A and VEGFR2. The sequence of the ICAM2-miR-7 miR-V-7 fragment is listed as SEQ ID NO: 139. D. Map of RPE-65-miR-7 miR-V-7. This uses the human RPE65 promoter (black arrow) to drive expression of miR-7 miR-V-7 (white arrow), which targets VEGF-A and VEGFR2. The sequence of the RPE65-miR-7 miR-V-7 fragment is listed as SEQ ID NO: 140. E. Map of FLT-miR-7 miR-V-7. This uses the human FLT promoter (black arrow) to drive expression of miR-7 miR-V-7 (white arrow), which targets VEGF-A and VEGFR2. The sequence of the FLT-miR-7 fragment is listed as SEQ ID NO: 141.

FIG. 10: A. Map of U6-miR-V-7-miR-C-8-miR-P-9. This uses the human U6 promoter (black arrow) to drive expression of miR-V-7-miR-C-8-miR-P-9 which targets VEGFR2, CFB and PDGFR-β. The miR-V-7-miR-C-8-miR-P-9 coding sequences are shown as a white arrow, the positions of miR-V-7 passenger and miR-V-7 effector sequences, miR-C-8 passenger and miR-C-8 effector sequences, and miR-P-9 passenger and miR-P-9 effector sequences are shown as grey arrows. The sequence of the U6-miR-V-7-miR-C-8-miR-P-9 fragment is listed as SEQ ID NO: 142. B. Map of VMD2-miR-V-7-miR-C-8-miR-P-9. This uses the human VMD2 promoter (black arrow) to drive expression of miR-V-7-miR-C-8-miR-P-9 (white arrow), which targets VEGFR2, CFB and PDGFR-β. The sequence of the VMD2-miR-V-7-miR-C-8-miR-P-9 fragment is listed as SEQ ID NO: 143. C. Map of ICAM2-miR-V-7-miR-C-8-miR-P-9. This uses the human ICAM2 promoter (black arrow) to drive expression of miR-V-7-miR-C-8-miR-P-9 (white arrow), which targets VEGFR2, CFB and PDGFR-β. The sequence of the ICAM2 miR-V-7-miR-C-8-miR-P-9 fragment is listed as SEQ ID NO: 144. D. Map of RPE65-miR-V-7-miR-C-8-miR-P-9. This uses the human RPE65 promoter (black arrow) to drive expression of miR-V-7-miR-C-8-miR-P-9 (white arrow), which targets VEGFR2, CFB and PDGFR-β. The sequence of the RPE65-miR-V-7-miR-C-8-miR-P-9 fragment is listed as SEQ ID NO: 145. E. Map of FLT-miR-V-7-miR-C-8-miR-P-9. This uses the human FLT promoter (black arrow) to drive expression of miR-V-7-miR-C-8-miR-P-9 (white arrow), which targets VEGFR2, CFB and PDGFR-β. The sequence of the FLT-miR-V-7-miR-C-8-miR-P-9 fragment is listed as SEQ ID NO: 146.

FIG. 11: sequences referred to throughout the specification.

DETAILED DESCRIPTION OF THE EMBODIMENTS

Reference will now be made in detail to certain embodiments of the invention. While the invention will be described in conjunction with the embodiments, it will be understood that the intention is not to limit the invention to those embodiments. On the contrary, the invention is intended to cover all alternatives, modifications, and equivalents, which may be included within the scope of the present invention as defined by the claims.

One skilled in the art will recognize many methods and materials similar or equivalent to those described herein, which could be used in the practice of the present invention. The present invention is in no way limited to the methods and materials described.

It will be understood that the invention disclosed and defined in this specification extends to all alternative combinations of two or more of the individual features mentioned or evident from the text or drawings. All of these different combinations constitute various alternative aspects of the invention.

For purposes of interpreting this specification, the following definitions will apply and whenever appropriate, terms used in the singular will also include the plural and vice versa. In the event that any definition set forth conflicts with any document incorporated herein by reference, the definition set forth below shall prevail.

Definitions

As used herein, except where the context requires otherwise, the term "comprise" and variations of the term, such as "comprising", "comprises" and "comprised", are not intended to exclude further additives, components, integers or steps.

The term "RNA interference" or "RNAi" refers generally to a RNA dependent gene silencing process that is initiated by double stranded RNA (dsRNA) molecules in a cell's cytoplasm. The dsRNA reduces the expression of a target nucleic acid sequence, which may be a DNA whose RNA expression products are reduced, or an RNA, with which the dsRNA molecule shares substantial or total homology.

By "double stranded RNA" or "dsRNA" it is meant a double stranded RNA molecule that is capable of inhibiting expression of a target nucleic acid sequence with which it shares homology. In some embodiments the dsRNA is a hairpin or stem loop structure, with a duplex region optionally linked by at least 1 nucleotide, and is referred to as a "hairpin RNA" or "short hairpin RNAi agent" or "shRNA". The duplex is formed between an effector sequence and a sequence complementary to the effector sequence herein referred to as an "effector complement". Typically, the effector complement will be the same length as its corresponding effector sequence. As will be explained below, the effector sequence is complementary to the target nucleic acid sequence.

An "effector sequence" is the nucleotide sequence that, when part of the RISC complex, binds to the target nucleotide sequence, thereby targeting that sequence for destruction by the cell. It is analogous to the "guide" strand discussed in the background section. The effector sequence is 'directed to' a target region by being complementary or substantially complementary in sequence to the transcript from the target region such that an RNA agent having a double stranded portion containing the effector sequence inhibits expression of the target gene sequence.

The "effector complement", which is analogous to the passenger strand discussed in the background is of sufficient complementarity to the effector such that it anneals to the effector sequence. It is likely that the effector complement will be of a similar sequence to the target gene sequence, but does not necessarily have to be.

As already detailed in the sections above "substantially complementary", or "substantial complementarity", it is meant that the sequences are of sufficient complementarity to enable hybridisation of annealing (as later defined). Briefly, substantial complementarity as described above may be described in terms of:

percentage identity (being 80 to 100%) between an effector and its complement, or between an effector and the target region of a target sequence; or number of nucleotides that are not complementary, being 1, 2, 3, 4 or 5, provided that number is consistent with the percentage identity requirement of 80 to 100%.

Substantial complementarity therefore includes 100% complementarity, but 100% complementarity may also be referred to throughout the specification as "complementary", or "being complementary". A sequence complementary to or substantially complementary to a region of a target gene has the degree of sequence complementarity across a contiguous target sequence. Generally, a double stranded RNA region of the invention may be subjected to mutagenesis to produce single or several nucleotide substitutions, deletions or additions. It is believed that this level of difference between an effector and its complement, or between an effector and the target region of a target sequence will not negatively impact on the ability of the ddRNAi agent to be able to inhibit expression of the target sequence.

When the first effector sequence does have 1, 2, 3, 4 or 5 nucleotides that will not G-C/A-U base pair with the target sequence, it is preferred that the differences are in the first or last 5 nucleotides of the first effector sequence, with only 1 or 2 nucleotide changes in the centre portion of the effector sequence.

As noted above, substantial complementarity is intended to mean that the sequences are hybridisable or annealable. The terms "hybridising" and "annealing" (and grammatical equivalents) are used interchangeably in this specification in respect of nucleotide sequences and refer to nucleotide sequences that are capable of forming Watson-Crick base pairs due to their complementarity. Preferably the substantially complementary sequences are able to hybridise under conditions of medium or high stringency:

high stringency conditions: 0.1×SSPE (or 0.1×SSC), 0.1% SDS, 65° C.

medium stringency conditions: 0.2×SSPE (or 1.0×SSC), 0.1% SDS, 50° C.

Alternatively, "substantially complementary" would also be understood by the person skilled in the art to involve non-Watson-Crick base-pairing, especially in the context of RNA sequences, such as a so-called "wobble pair" which can form between guanosine and uracil residues in RNA. "Complementary" is used herein in its usual way to indicate Watson-Crick base pairing, and "non-complementary" is used to mean non-Watson-Crick base pairing, even though such non-complementary sequences may form wobble pairs or other interactions. In the context of the present invention, reference to "non-pairing" sequences relates specifically to sequences between which Watson-Crick base pairs do not form.

The term "RNAi agent" refers to a dsRNA sequence that elicits RNAi. This term may be used interchangeably with "small interfering RNAs" (siRNA agents) and small hairpin RNA (shRNAi or hpRNAi agents), wherein a hairpin has a stem-loop structure.

The "loop" of a hairpin structure is an additional sequence wherein at least some of the nucleotides are non-complementary to either itself, the target sequence, the effector sequence or the effector complement. The loop can be a sequence of 2 to 100 nucleotides which are capable of forming a loop. Not all of the nucleotides of the loop sequence need be non-annealed. For example, in a loop sequence of ACUGUGAAGCAGAUGAGU, nucleotides ACU may be annealed with AGU, while the intervening GUGAAGCAGAUG sequence remains non-annealed.

In embodiments in which the ddRNAi agent is expressed as part of a miRNA structure, the loop sequence may be derived from the miRNA, and is encoded by the ME sequence.

A "microRNA" or "miRNA" is a naturally occurring, small non-coding RNA molecule present in organisms that functions in the post-transcriptional regulation of gene expression. miRNA transcripts are capable of forming hairpin-like structures; typically contain mismatches and bulges within or adjacent to the double stranded RNA regions. The miRNA structure in which the ddRNAi agents of the invention are preferably expressed contains mismatches and insertions, as detailed above. Wu et al. (2011) showed that mismatched duplexes (containing mismatches in the passenger strand) sometimes showed increased silencing activity, due possibly to their greater structural resemblance to endogenous miRNAs. Similarly Gu et al. (2012) showed the introduction of bulges adjacent to loop sequences in shRNA molecules can result in increased precision of Dicer processing.

In the double stranded, folded miRNA structure, at least 50% of the nucleotides on the top strand are annealed to nucleotides of the bottom strand. Of the non-annealed (ie unpaired) nucleotides, they may be insertions ie they lack a complementary nucleotide on the opposing strand, or they may be mismatches such that they do not anneal. For example, a G and an A. The double stranded, folded miRNA structure can contain 2 or more annealed nucleotides, separated by 1 or more non-annealed nucleotides, to give a double stranded RNA structure with "bubbles" or 'bulges" where the nucleotides are not annealed.

By "miRNA encoding sequence" or "ME sequence", it is meant the DNA sequence contained within a ddRNAi expression cassette (see below for definition and description) that encodes for RNA which is capable of folding in to a miRNA structure. The effector sequence and the effector complement of a ddRNAi agent is expressed within or as part of that miRNA structure. The ME sequence has a first and second part. In an expression cassette for expressing a single hairpin (having one or more effector/effector complement pairs), the first part of the ME sequence is located upstream (ie 5') of the 5' most effector or effector complement encoding sequence, and the second part is located downstream (ie 3') to the 3' most effector or effector complement encoding sequence.

In the case of an expression cassette for a multiple hairpin structure, each effector/effector complement pair has a corresponding first and second ME sequence, wherein the first ME sequence is upstream of the effector or effector complement encoding sequence and the second part is downstream of the corresponding effector or effector complement encoding sequence. In an expression cassette having the following exemplary structure, in a 5' to 3' direction:

a promoter
a first ME sequence;
a first effector;
a first effector complement sequence;
a second ME sequence;
a third ME sequence;

a second effector sequence;
a second effector complement sequence; and
a fourth ME sequence it will be appreciated that the second and third ME sequence can either be (using exemplary sequences to illustrate the point) consecutive, can have intervening sequence between them, or can be a single ME sequence that serves the same function as the second and third ME sequence.

i) Consecutive:

(SEQ ID NO: 148)
ggtatattgctgttgacagtgagcga
ME sequence 2 ggtatattgctggggacagtgagccc
ME sequence 3 ii) Intervening:

(SEQ ID NO: 149)
ggtatattgctgttgacagtgagcgaATTGCCATG
ME sequence 2        INTERVENING ggtatattgctggggacagtgaaccc
ME sequence 3 iii) Single:

(SEQ ID NO: 150)
ggtatattgctgttgacagtgagcgaggtatattgctgg
ME sequence ggacagtgagccc The double stranded or duplex region of the RNAi agent is at least 17 base pairs long, and usually in the range of 17 to 30 base pairs. RNAi agents can be synthesized chemically or enzymatically outside of cells and subsequently delivered to cells or can be expressed in vivo by an appropriate vector in cells (see, e.g., U.S. Pat. No. 6,573,099, WO 2004/106517 and WO1999/49029, all of which are incorporated herein by reference).

The term "DNA-directed RNAi agent" or "ddRNAi agent" refers to an RNAi agent that is transcribed from a DNA expression cassette ("ddRNAi expression cassette"). Depending on the arrangement of terminators and promoters within the ddRNAi expression cassettes, they may express ddRNAi agents with single or multiple effector sequences, or may express multiple ddRNAi agents. A ddRNAi agent transcribed from the expression cassette may be transcribed as a single RNA that is capable of self-annealing into a single hairpin structure with a duplex region linked by at least 2 nucleotides. The single hairpin may include one effector sequence and its complement (see FIG. 1B or E) or multiple effector sequences and their complements (see FIG. 1A or D). Alternatively, the agent may be a single RNA with multiple shRNA domains (ie multiple hairpin structures formed by the effector sequences and their complement—see FIG. 1C or F).

The ddRNAi expression cassette can be ligated into vectors referred to as ddRNAi vectors or ddRNAi constructs. The vectors may provide sequences specifying transcription of the ddRNAi expression cassette in vivo or in vitro. The vector may additionally serve as the delivery vehicle for the ddRNAi expression cassette. Viral based vectors for example will generate a ddRNAi construct that is useful for expression of the ddRNAi expression cassette as well as being compatible with viral delivery.

A cell has been "transformed", "transduced" or "transfected" by an exogenous or heterologous nucleic acid or vector when such nucleic acid has been introduced into the cell. The transforming DNA may or may not be integrated (covalently linked) into the genome of the cell. With respect to eukaryotic cells, a stably transformed cell is one in which the transforming DNA has become integrated into a host cell chromosome or is maintained extra-chromosomally (episomally) so that the transforming DNA is inherited by daughter cells during cell replication. In non-replicating, differentiated cells the transforming DNA may persist as an episome.

"Gene expression" can be a reference to either or both transcription or translation.

"Inhibition of expression" refers to the absence or observable decrease in the level of protein and/or mRNA product from the target gene. The inhibition does not have to be absolute, but may be partial inhibition sufficient for there to a detectable or observable change as a result of the administration of a RNAi or ddRNAi agent or siRNA agent or ddRNAi expression cassette or expression construct of the invention. Inhibition may be measured by determining a decrease in the level of mRNA and/or protein product from a target nucleic acid relative to a cell lacking the ddRNAi agent or construct, and may be as little as 1%, 5% or 10%, or may be absolute ie 100% inhibition. The effects of inhibition may be determined by examination of the outward properties ie quantitative and/or qualitative phenotype of the cell or organism.

"Off-target" effects is a term used to describe unintentional side-effects of treatment with an RNAi reagent. This is frequently thought to involve unintended knockdown of a target sequence as a consequence of chance homology with the passenger or effector sequences and another target gene, although subtler effects arising from metabolic compensation of a knockdown can also occur. Processing of miRNAs by endogenous RNAi pathways frequently results in the loading of only the effector strand into RISC, and degradation of the passenger strand. One potential source of off-target effects is the unanticipated incorporation of the passenger strand into RISC such that passenger sequences can consequently silence genes which they fortuitously share homology with. There is evidence that a step in RISC loading "senses" the predicted thermodynamic stability of an RNA duplex across a potential target site in dsRNA precursors and preferentially loads the strand whose 5' end is from the less stable end of the duplex. One strategy to minimise the potential for off-target effects is to screen ddRNAi molecules for activity of the passenger strand using Dual Luciferase assays. Loading of this strand into RISC is undesirable.

As used herein, a "vascular endothelial growth factor-A gene" or "VEGF-A gene", includes a gene that encodes a protein that stimulates angiogenesis. In one embodiment the VEGF-A gene encodes a nucleotide sequence as shown in Genbank with accession number NM_001025366 (SEQ ID NO:79) which encodes human VEGF-A. In another embodiment, a VEGF-A gene is an orthologous or paralogous gene to the VEGF-A gene, including but not limited to a nucleotide sequence as shown in Genbank with accession number NM_001025250 (*Mus musculus*, SEQ ID NO:80) or XM_001089925 (*Macaca mulatta*, SEQ ID NO:81). In another embodiment, the VEGF-A gene may be a human gene or gene from an animal as described herein and includes allelic variants.

As used herein, a "vascular endothelial growth factor receptor 2 gene" or "VEGFR2 gene" includes a gene that encodes a receptor for VEGF. In one embodiment the VEGFR2 gene encodes a nucleotide sequence as shown in Genbank with accession number NM_002253 (SEQ ID NO: 82) which encodes human VEGFR2. In another embodiment, a VEGFR2 gene is an orthologous or paralogous gene to the VEGFR2, including but not limited to a nucleotide sequence as shown in Genbank with accession number NM_010612 (*Mus musculus*, SEQ ID NO:83) or XM_001086814 (*Macaca mulatta*, SEQ ID NO:84). In another embodiment, VEGFR2 gene may be a human gene or gene from an animal as described herein and includes allelic variants.

As used herein, a "Beta-type platelet-derived growth factor receptor gene" or "PDGFR-β gene" includes a gene that encodes the PDGFR-β protein. In one embodiment the PDGFR-β gene encodes a nucleotide sequence as shown in Genbank with accession number NM_002609 (SEQ ID NO:85) which encodes human PDGFR-β. In another embodiment, a PDGFR-β gene is an orthologous or paralogous gene to the PDGFR-β, including but not limited to a nucleotide sequence as shown in Genbank with accession number NM_001142706 (*Mus musculus*, SEQ ID NO:86) or XM_00110759 (*Macaca mulatta*, SEQ ID NO:87). In another embodiment, PDGFR-β gene may be a human gene or gene from an animal as described herein and includes allelic variants.

As used herein, a "Complement Factor B gene" or "CFB gene" includes a gene that encodes the CFB protein, a component of drusen. In one embodiment the CFB gene encodes a nucleotide sequence as shown in Genbank with accession number NM_001710 (SEQ ID NO: 88) which encodes human CFB. In another embodiment, a CFB gene is an orthologous or paralogous gene to the CFB, including but not limited to a nucleotide sequence as shown in Genbank with accession number NM_00114270 (*Mus musculus*, SEQ ID NO:89) or XM_001113553 (*Macaca mulatta*, SEQ ID NO:90). In another embodiment, CFB gene may be a human gene or gene from an animal as described herein and includes allelic variants.

Sequences are "paralogous" if they are separated by a gene duplication event: if a gene in an organism is duplicated to occupy two different positions in the same genome, then the two copies are paralogous.

Sequences are "orthologous" if they are separated by a speciation event: when a species diverges into two separate species, the divergent copies of a single gene in the resulting species are said to be orthologous.

As used herein, "a quantitative phenotypic trait" refers to a trait associated with the molecular expression of a nucleic acid in a host cell and may thus include the quantity of RNA molecules transcribed or replicated, the quantity of post-transcriptionally modified RNA molecules, the quantity of translated peptides or proteins, or the activity of such peptides or proteins.

A reduction of phenotypic expression of a nucleic acid where the phenotype is a qualitative trait means that in the presence of the RNAi agent of the invention, the phenotypic trait switches to a different state when compared to a situation in which the RNAi agent is absent. A reduction of phenotypic expression of a nucleic acid may thus be measured as a reduction in steady state levels of (part of) that nucleic acid, a reduction in translation of (part of) that nucleic acid or a reduction in the effect the presence of the transcribed RNA(s) or translated polypeptide(s) have on the eukaryotic cell or the organism, and will ultimately lead to altered phenotypic traits. It is clear that the reduction in phenotypic expression of a nucleic acid of interest may be accompanied by or correlated to an observable change in phenotype. The assessment may be by way of biochemical techniques such as Northern hybridisation, quantitative realtime PCR assays, gene expression assays, antibody binding, ELISA, RIA, western blotting and other assays and techniques known in the art.

"Target nucleic acids" may be either RNA or DNA, whose transcription products are targeted, coding or non-coding sequence, endogenous or exogenous.

A "therapeutic composition" or "pharmaceutical composition" or "composition for treating" refers to a composition including a ddRNAi agent, ddRNAi expression cassette, ddRNAi construct or siRNA agent.

The words "treat" or "treatment" refer to therapeutic treatment wherein the object is to slow down (lessen) an undesired physiological change or disorder. For purposes of this invention, beneficial or desired clinical results include, but are not limited to, alleviation of symptoms of AMD, stabilised (i.e., not worsening or progressing) AMD, and stabilised CNV.

The phrase "therapeutically effective amount" means an amount of a compound of the present invention that (i) treats the particular disease, condition, or disorder, (ii) attenuates, ameliorates, or eliminates one or more symptoms of the particular disease, condition, or disorder, (iii) prevents or delays the onset of one or more symptoms of the particular disease, condition, or disorder described herein, (iv) prevents or delays progression of the particular disease, condition or disorder, or (v) reverses damage caused prior to treatment to some extent. The reversal does not have to absolute, but any clinically relevant return of visual acuity post-treatment is considered a reversal of damage.

The current invention provides a new RNAi agent, and use of the RNAi agent for reducing the regression of visual acuity associated with AMD in affected individuals, particularly those with wet AMD. Treatment is aimed at one or more of:

i. controlling angiogenesis associated with choroidal neo-vascularisation (CNV) by long-term knock down of VEGF-A translation and subsequent secretion from retina cells using a DNA construct containing one or more sequences aimed at silencing specific genes associated with VEGF-A expression. VEGF-A stimulates angiogenesis, and therefore the abnormal outgrowth of blood vessels from the vasculature behind the retina. A number of existing therapies only serve to "mop up" secreted VEGF-A, which may stabilise vision, but does not necessarily improve vision in all patients.

ii. Additional control of angiogenesis might be obtained by knockdown of both VEGF-A and its receptor VEGFR2, since this strategy would be expected to interfere with the process at two distinct steps.

iii. Reversal of AMD might be achieved by knockdown of three targets, namely VEGFR2, PDGFR-β and CFB. VEGFR2 knockdown would be expected to control angiogenesis, PDGFR-β knockdown would be expected to inhibit or reverse nascent blood vessel formation and CFB knockdown would be expected to inhibit or even reverse drusen deposition iv) limiting treatment frequency, and limiting treatment to RPE cells via localised injection of the therapeutic molecules.

Identifying appropriate target sequences within target genes, and designing RNAi agents that work based on those sequences, is not routine. As will be demonstrated in the results section, target sequences that look like good candidates on paper, may not necessarily effectively silence the target, or may not do so to an effective level for therapeutic purposes. Some effector sequences work much more effectively than others to silence a target in particular incorporation of passenger strands into RISC is undesirable since this may lead to significant off-target effects and consequent toxicity. But it is not predictable which sequences are able to be silenced by mere visual inspection of the sequence itself, let alone to what extent they may be silenced, and if that would be sufficient for the purposes of the invention. Even more so when you are seeking to silence 2 or more unrelated targets.

Despite the recognition in the art that VEGF-A is a suitable target for AMD therapies, efforts to create an effective therapy to date have been plagued by the problems summarised in the background. With respect to silencing by RNAi techniques in particular, previous efforts using in vitro produced siRNA agents have been unsuccessful due to siRNA interaction with membrane bound TLR3 and subsequent activation of interferon. In addition, cells which secrete the majority of VEGF-A are the RPE cells, generally found buried underneath layers of specialized cells towards the back of the eye. RNAi moieties are highly charged complexes and can be difficult to traverse across multiple layers of cells because of this physical property. The new range of targets, the ddRNAi agents and the viral delivery agents utilised seek to overcome these issues.

In addition to VEGF-A these targets include one or more of:
VEGFR2: the receptor for VEGF-A; silencing VEGFR2 is expected to have similar consequences to silencing VEGF-A
PDGFR-β: the receptor for PDGFR-β. This molecule plays a role in recruitment and stabilisation of endothelial cells, which is critical for stabilisation of nascent blood vessels.
CFB: This is a major component of drusen, the hallmark extracellular deposit associated with AMD. (Anderson et al 2010). Silencing CFB may inhibit the formation of drusen.

RNA interference (RNAi) is an RNA-dependent gene silencing process that is initiated by short double-stranded RNA molecules in a cell's cytoplasm. In mammals, RNAi is mediated by double-stranded RNA molecules referred to as small interfering RNAs (siRNA). The double stranded, or duplex region of the RNAi agent is at least 17 base pairs long, and usually in the range of 17 to 30 base pairs. RNAi agents can be synthesised chemically or enzymatically outside of cells and subsequently delivered to cells or can be expressed in vivo by an appropriate vector in cells (such as AAV, adenovirus, lentivirus, or non-viral liposome-based delivery systems).

Pre-clinical testing of RNAi agents as AMD therapeutics requires the extensive use of animal models. Mouse (*Mus muscularis*) and primate (eg macaques, *Macaca fascicularis*) models are widely used to test the efficacy of treatments, and other species such as dogs (*Canis familiaris*) are commonly used as models to determine the clinical safety of therapeutic compounds. For RNAi therapeutics it is advantageous to design reagents that target nucleotide sequences of AMD-associated genes that are highly conserved between humans and the various pre-clinical test species since a single RNAi reagent can be used at all stages of pre-clinical testing. For poorly conserved genes multiple RNAi reagents with sequences that differ slightly between the different test species must be tested in parallel to accurately determine potential toxicity.

Accordingly, the RNAi reagents described in this application are, where possible, designed to target sequences conserved between humans and the potential test species (mice, dogs and primates such as macaques), since this provides significant advantages for a drug development program.

ddRNAi Agent

RNAi agents may be expressed from DNA vectors, referred to as DNA-directed RNAi, or ddRNAi. They can directly target the activity of genes with minimum off-target events. In the case of AMD, this offers a unique opportunity to address the unmet clinical treatment needs. Accordingly, in one aspect of the invention, there is provided a DNA-directed RNA interference (ddRNAi) agent for inhibiting expression of one or more target sequences in an AMD-associated gene, the ddRNAi agent comprising at least:

a first effector sequence of at least 17 nucleotides in length; and a first effector complement sequence;

wherein the first effector sequence is complementary or substantially complementary to one or more target regions in a transcript of the one or more target sequences.

Typically, the first effector sequence forms a double stranded region with the first effector complement sequence.

The sequences of the ddRNAi agents of the invention have to have a sufficient identity to the AMD-associated gene, such as the VEGF-A, VEGFR2, CFB and PDGFR-β genes, in order to mediate target specific RNAi.

The first effector sequence is at least 17 nucleotides long, preferably 17 to 30 nucleotides and more preferably 17 to 21 nucleotides. It may be 17, 18, 19, 20, 21, 22, 23, 24, 25, 26, 27, 28, 29 or 30 nucleotides in length. When the first effector sequence is longer than 17 nucleotides, it is preferred that at least 17 contiguous nucleotides of the first effector sequence forms the double stranded region with the complementary strand. A ddRNAi agent according to this embodiment of the invention therefore has a maximum length determined by the length and number of effector sequence/s ie each effector sequence is not comprised within a longer sequence.

The ddRNAi agents of the invention inhibit expression of AMD-associated target genes. Preferably the AMD-associated gene is VEGF-A, or one or more of VEGFR2, CFB and PDGFR-β, and each effector sequence is selected from the group consisting of any 10 or more contiguous nucleotides within a sequence from any one of SEQ ID NOS: 40-78.

As illustrated in the table below, when the AMD-associated gene to be inhibited, prevented or reduced is VEGF-A, each effector sequence is selected from SEQ ID NOS: 40-49. When the AMD-associated gene to be inhibited, prevented or reduced is VEGFR2 each effector sequence is selected from SEQ ID NOS: 50-59. When the AMD-associated gene to be inhibited, prevented or reduced is PDGFR-β, each effector sequence is selected from SEQ ID NOS: 60-69. When the AMD-associated gene to be inhibited, prevented or reduced is CFB, each effector sequence is selected from SEQ ID NOS: 70-78.

TABLE 1

VEGF-A, VEGFR2, CFB and PDGFR-β gene target sequences and their corresponding ddRNAi effector sequences

| Target[a] | Target position[b] | SEQ ID NO | Target sequence in 5' to 3' direction[c] | SEQ ID NO | Corresponding effector sequence in 5' to 3' direction[d] |
|---|---|---|---|---|---|
| VEGF-A miR-1 | 328-348 | 1 | AGCAAGAGCTCCAGAGAGAAG | 40 | CUUCUCUCUGGAGCUCUUGCU |
| VEGF-A miR-2 | 1026-1046 | 2 | GGCCTCCGAAACCATGAACTT | 41 | AAGUUCAUGGUUUCGGAGGCC |
| VEGF-A miR-3 | 1203-1223 | 3 | CGAGACCCTGGTGGACATCTT | 42 | AAGAUGUCCACCAGGGUCUCG |
| VEGF-A miR-4 | 1383-1403 | 4 | GCACATAGGAGAGATGAGCTT | 43 | AAGCUCAUCUCUCCUAUGUGC |
| VEGF-A miR-5 | 1422-1442 | 5 | TGAATGCAGACCAAAGAAAGA | 44 | UCUUUCUUUGGUCUGCAUUCA |
| VEGF-A miR-6 | 1858-1878 | 6 | CAGAACAGTCCTTAATCCAGA | 45 | UCUGGAUUAAGGACUGUUCUG |
| VEGF-A miR-7 | 2055-2075 | 7 | TCTGGGATTCCTGTAGACACA | 46 | UGUGUCUACAGGAAUCCCAGA |
| VEGF-A miR-8 | 2067-2087 | 8 | GTAGACACACCCACCCACATA | 47 | UAUGUGGGUGGGUGUGUCUAC |
| VEGF-A miR-9 | 3480-3500 | 9 | GGTGCTACTGTTTATCCGTAA | 48 | UUACGGAUAAACAGUAGCACC |
| VEGF-A miR-10 | 3554-3574 | 10 | CGAGATATTCCGTAGTACATA | 49 | UAUGUACUACGGAAUAUCUCG |
| VEGFR2 miR-V-1 | 477-497 | 11 | TTGGACTGGCTTTGGCCCAAT | 50 | AUUGGGCCAAAGCCAGUCCAA |
| VEGFR2 miR-V-2 | 864-884 | 12 | CCCAGCTACATGATCAGCTAT | 51 | AUAGCUGAUCAUGUAGCUGGG |
| VEGFR2 miR-V-3 | 2625-2645 | 13 | GCCATGTTCTTCTGGCTACTT | 52 | AAGUAGCCAGAAGAACAUGGC |
| VEGFR2 miR-V-4 | 2661-2681 | 14 | CGGACCGTTAAGCGGGCCAAT | 53 | AUUGGCCCGCUUAACGGUCCG |
| VEGFR2 miR-V-5 | 3037-3057 | 15 | TCATGGTGATTGTGGAATTCT | 54 | AGAAUUCCACAAUCACCAUGA |
| VEGFR2 miR-V-6 | 3299-3319 | 16 | CCTGACCTTGGAGCATCTCAT | 55 | AUGAGAUGCUCCAAGGUCAGG |
| VEGFR2 miR-V-7 | 3307-3327 | 17 | TGGAGCATCTCATCTGTTACA | 56 | UGUAACAGAUGAGAUGCUCCA |
| VEGFR2 miR-V-8 | 3338-3358 | 18 | GGCTAAGGGCATGGAGTTCTI | 57 | AAGAACUCCAUGCCCUUAGCC |
| VEGFR2 miR-V-9 | 3698-3718 | 19 | ACCAGAAATGTACCAGACCAT | 58 | AUGGUCUGGUACAUUUCUGG<u>T</u> |
| VEGFR2 miR-V-10 | 3928-3948 | 20 | ACCCCAAATTCCATTATGACA | 59 | UGUCAUAAUGGAAUUUGGGG<u>T</u> |
| PDGFR-β miR-P-1 | 1093-1113 | 21 | ACTCCAGGTGTCATCCATCAA | 60 | UUGAUGGAUGACACCUGGAGU |
| PDGFR-β miR-P-2 | 1098-1118 | 22 | AGGTGTCATCCATCAACGTCT | 61 | AGACGUUGAUGGAUGACACCU |

TABLE 1-continued

VEGF-A, VEGFR2, CFB and PDGFR-β gene target sequences and their corresponding ddRNAi effector sequences

| Target[a] | Target position[b] | SEQ ID NO | Target sequence in 5' to 3' direction[c] | SEQ ID NO | Corresponding effector sequence in 5' to 3' direction[d] |
|---|---|---|---|---|---|
| PDGFR-β miR-P-3 | 2197-2217 | 23 | CCATGAGTACATCTACGTGGA | 62 | UCCACGUAGAUGUACUCAUGG |
| PDGFR-β miR-P-4 | 2872-2892 | 24 | GGACCTCGTGGGCTTCAGCTA | 63 | UAGCUGAAGCCCACGAGGUCC |
| PDGFR-β miR-P-5 | 2977-2997 | 25 | AGGCAAGCTGGTCAAGATCTG | 64 | CAGAUCUUGACCAGCUUGCCU |
| PDGFR-β miR-P-6 | 3085-3105 | 26 | GGAGAGCATCTTCAACAGCCT | 65 | AGGCUGUUGAAGAUGCUCUCC |
| PDGFR-β miR-P-7 | 3090-3110 | 27 | GCATCTTCAACAGCCTCTACA | 66 | UGUAGAGGCUGUUGAAGAUGC |
| PDGFR-β miR-P-8 | 3181-3202 | 28 | CCCAGAGCTGCCCATGAACGA | 67 | UCGUUCAUGGGCAGCUCUGGG |
| PDGFR-β miR-P-9 | 3202-3222 | 29 | GCAGTTCTACAATGCCATCAA | 68 | UUGAUGGCAUUGUAGAACUGC |
| PDGFR-β miR-P-10 | 3250-3270 | 30 | CCATGCCTCCGACGAGATCTA | 69 | UAGAUCUCGUCGGAGGCAUGG |
| CFB miR-C-1 | 929-949 | 31 | CTGCCAAGACTCCITCATGTA | 70 | UACAUGAAGGAGUCUUGGCAG |
| CFB miR-C-2 | 1085-1105 | 32 | GAACATCTACCTGGTGCTAGA | 71 | UCUAGCACCAGGUAGAUGUUC |
| CFB miR-C-3 | 1096-1116 | 33 | TGGTGCTAGATGGATCAGACA | 72 | UGUCUGAUCCAUCUAGCACCA |
| CFB miR-C-4 | 1100-1120 | 34 | GCTAGATGGATCAGACAGCAT | 73 | AUGCUGUCUGAUCCAUCUAGC |
| CFB miR-C-5 | 1535-555 | 35 | GGAGGATTATCTGGATGTCTA | 74 | UAGACAUCCAGAUAAUCCUCC |
| CFB miR-C-6 | 1697-1717 | 36 | GTCTCTGAGTCTCTGTGGCAT | 75 | AUGCCACAGAGACUCAGAGAC |
| CFB miR-C-7 | 1817-1837 | 37 | GGCTGTGGTGTCTGAGTACTT | 76 | AAGUACUCAGACACCACAGCC |
| CFB miR-C-8 | 2154-2174 | 38 | CAGGATATCAAAGCTCTGTTT | 77 | AAACAGAGCUUUGAUAUCCUG |
| CFB miR-C-9 | 2201-2221 | 39 | TCGGAAGGAGGTCTACATCAA | 78 | UUGAUGUAGACCUCCUUCCGA |

[a]Target genes are human VEGF-A (NM_0010253660), VEGFR2 (NM_002253), PDGFR-β (NM_002609) and CFB (NM_001710); designations below gene names refer to versions of ddRNAi constructs targeting the particular genes.
[b]Target positions for human sequences listed.
[c]Target sequences are the DNA sequences recognised by the effector sequence.
[d]Effector sequences are the predicted RNA sequences produced by dicer processing of the ddRNAi agents that target AMD-associated genes; T refers to constructs where effector is modified to maintain structure of the expressed RNAs.

The ddRNAi agents of the invention are preferably expressed within or as part of a miRNA structure. These miRNA structures have the sequences shown as "miR sequences" and are listed in Table 2 (SEQ ID NOS: 91-129), which were designed to express the indicated effector sequences (SEQ ID NOS: 40-78). The corresponding constructs containing the expression cassettes for expressing the miRNA structures is also shown as "miR-designations".

TABLE 2 miR constructs displaying strong, sequence-specific silencing of AMD-associated genes

| AMD Target | miR designations[a] | SEQ ID NO: miR sequence[b] | SEQ ID NO: effector sequence[c] |
|---|---|---|---|
| VEGF-A | miR-1 | 91 | 40 |
|  | miR-2 | 92 | 41 |

TABLE 2-continued miR constructs displaying strong, sequence-specific silencing of AMD-associated genes

| AMD Target | miR designations[a] | SEQ ID NO: miR sequence[b] | SEQ ID NO: effector sequence[c] |
|---|---|---|---|
|  | miR-3 | 93 | 42 |
|  | miR-4 | 94 | 43 |
|  | miR-5 | 95 | 44 |
|  | miR-6 | 96 | 45 |
|  | miR-7 | 97 | 46 |
|  | miR-8 | 98 | 47 |
|  | miR-9 | 99 | 48 |
|  | miR-10 | 100 | 49 |
| VEGFR2 | miR-V-1 | 101 | 50 |
|  | miR-V-2 | 102 | 51 |
|  | miR-V-3 | 103 | 52 |
|  | miR-V-4 | 104 | 53 |
|  | miR-V-5 | 105 | 54 |
|  | miR-V-6 | 106 | 55 |
|  | miR-V-7 | 107 | 56 |
|  | miR-V-8 | 108 | 57 |
|  | miR-V-9 | 109 | 58 |
|  | miR-V-10 | 110 | 59 |
| PDGFR-β | miR-P-1 | 111 | 60 |
|  | miR-P-2 | 112 | 61 |
|  | miR-P-3 | 113 | 62 |
|  | miR-P-4 | 114 | 63 |
|  | miR-P-5 | 115 | 64 |
|  | miR-P-6 | 116 | 65 |
|  | miR-P-7 | 117 | 66 |
|  | miR-P-8 | 118 | 67 |
|  | miR-P-9 | 119 | 68 |
|  | miR-P-10 | 120 | 69 |
| CFB | miR-C-1 | 121 | 70 |
|  | miR-C-2 | 122 | 71 |
|  | miR-C-3 | 123 | 72 |
|  | miR-C-4 | 124 | 73 |
|  | miR-C-5 | 125 | 74 |
|  | miR-C-6 | 126 | 75 |
|  | miR-C-7 | 127 | 76 |
|  | miR-C-8 | 128 | 77 |
|  | miR-C-9 | 129 | 78 |

[a]miR constructs tested for silencing activity and favourable strand specificities against the indicated human target genes (see FIGS. 4-7).
[b]SEQ ID NOS corresponding to inserts of miR constructs.
[c]SEQ ID NOS of predicted effector sequences produced by indicated miR constructs.

Any of the ddRNAi agents of the invention can be expressed within or as part of a miRNA structure. As will be explained throughout the specification, this can assist with more accurate processing of the ddRNAi agent, and lower toxicity within the cell.

In one embodiment of the invention, the ddRNAi agent of the invention inhibits expression of one or more target sequences in a VEGF-A gene. A target sequence is preferably selected from the ddRNAi VEGF-A target sequences listed in Table 1 (SEQ ID NOS: 1-10); the corresponding effector sequences that would be produced by dicer processing of a ddRNAi agent targeting those sequences is shown in SEQ ID NOS: 40-49 respectively. Note that the VEGF-A target sequences and effector sequences have been chosen to show conservation of nucleotide sequences between human and the pre-clinical test species mouse, dog and macaque.

In an alternative embodiment of the invention, the ddRNAi agent of the invention inhibits expression of one or more target sequences in a VEGFR2 gene. A target sequence is preferably selected from the ddRNAi a VEGFR2 target sequences listed in Table 2 (SEQ ID NOS: 11-20); the corresponding effector sequences are therefore selected from SEQ ID NOS: 50-59 respectively as shown in Table 2. Note that the VEGFR2 target (SEQ ID NOS: 11-20) and effector sequences (SEQ ID NOS: 50-59) are identical to, or differ by only a single nucleotide between human and the pre-clinical test species mouse and macaque.

In an alternative embodiment of the invention, the ddRNAi agent of the invention inhibits expression of one or more target sequences in a PDGFR-β gene. A target sequence is preferably selected from the ddRNAi PDGFR-β target sequences listed in Table 2 (SEQ ID NOS: 21-30); the corresponding effector sequences are therefore selected from SEQ ID NOS: 60-69 respectively as shown in Table 2. Note that the PDGFR-β target (SEQ ID NOS: 21-30) and effector sequences (SEQ ID NOS: 60-69) are identical to, or differ by only a single nucleotide between human and the pre-clinical test species mouse and macaque.

In an alternative embodiment of the invention, the ddRNAi agent of the invention inhibits expression of one or more target sequences in a CFB gene. A target sequence is preferably selected from the ddRNAi CFB target sequences listed in Table 1 (SEQ ID NOS: 31-39); the corresponding effector sequences are therefore selected from SEQ ID NOS: 70-78 respectively as shown in Table 2. Note that the CFB target (SEQ ID NOS: 31-39) and effector sequences (SEQ ID NOS: 70-78) are identical to, or differ by only a single nucleotide between human and the pre-clinical test species mouse and macaque.

In accordance with the explanation provided earlier, the relationship between the DNA target sequence and the corresponding effector sequence of the ddRNAi agent can be shown as (using the target SEQ ID NO:2 and its corresponding effector sequence SEQ ID NO:41 from Table 1):

5'   GGCCTCCGAAACCATGAACTT   3'—target sequence of VEGF-A (SEQ ID NO:2)

5' GGCCUCCGAAACCAUGAACUU 3'—mRNA transcript of SEQ ID NO:2

3'   AAGUUCAUGGUUUCGGAGGCC   5'—effector sequence of ddRNAi agent (SEQ ID NO:41) to target SEQ ID NO:2, which when read in the 5' to 3' direction, can be seen to be substantially complementary to the transcript of the target sequence.

As explained in the background section, both strands of the ddRNAi agent have the potential to be the effector sequence. However there is evidence that particular features of a sequence can favour one strand to enter the RISC and the other strand to be destroyed. There is evidence that a step in RISC loading "senses" thermodynamic stability of an RNA duplex across a potential target site in dsRNA precursors and preferentially loads the strand whose 5' end is from the less stable end of the duplex. Therefore target site sequences were typically adjusted to maximise the number of AT base pairs at the 3' end of the target site, i.e. maximising the number of A or U bases in the 5' end of the effector strand. The list of refined target sites was then screened for conservation between likely test species, specifically mice and monkeys. Target site sequences were then screened against the human transcriptome, using BLAST, and those showing high homology to other human genes (>3 mismatches) were discarded.

Constructs based on these target sequences were prepared in a miRNA backbone and tested empirically for activity and strand selectivity as described below. These sequence preferences are reflected in preferred embodiments, and data is provided in the examples section showing the advantages of some sequences over other.

For example, in one embodiment of this aspect of the invention, there is provided a DNA-directed RNA interference (ddRNAi) agent for inhibiting expression of one or more target sequences in an AMD-associated gene, the ddRNAi agent comprising at least:

a first effector sequence of any 10 or more contiguous nucleotides within 5' UAUGUGGGUGGGUGUGUC-UAC 3' (SEQ ID NO:47); and a first effector complement sequence.

The first effector sequence is substantially complementary to a target region in a transcript of one or more target sequences in an AMD-associated gene. In this example, the target gene is VEGF-A.

Preferably the first effector sequence is at least 17 or more contiguous nucleotides within 5' UAUGUGGGUGGGU-GUGUCUAC 3' (SEQ ID NO:47).

When the first effector sequence has 1, 2, 3, 4 or 5 nucleotides different to SEQ ID NO:47, the differences are preferably present in the first and/or last 5 nucleotides, and preferably at least the centre 10 nucleotides are 100% complementary to a target region in a transcript of one or more target sequences.

In alternative embodiments, the ddRNAi agent comprises a first effector sequence of any 10 or more, preferably any 17 or more, contiguous nucleotides within SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, SEQ ID NO:64, SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO:74, SEQ ID NO:75, SEQ ID NO:76, SEQ ID NO:77 or SEQ ID NO:78.

In particularly preferred embodiments, the ddRNAi agent comprises a first effector sequence of any 10 or more, preferably any 17 or more, contiguous nucleotides within sequences able to inhibit the expression of a target gene region by at least 70%. Preferably, in this embodiment, the first effector is selected from SEQ ID NO:47, which targets a sequence of SEQ ID NO:8.

The first effector sequence may comprise a sequence selected from any 10 or more and preferably any 17 or more contiguous nucleotides within a sequence from the group consisting of SEQ ID NOS: 40-78, or alternatively, each effector sequence may be a variant of SEQ ID NOS:40-78, having 1, 2, 3, 4 or 5 nucleotide variations. In yet a further embodiment, each effector sequence may consist of 20 nucleotides, of which 17, 18, 19, or all 20 nucleotides are contiguous nucleotides from a sequence selected from the group consisting of SEQ ID NOS: 40-78.

Multiple Targeting ddRNAi Agents ddRNAi agents with multiple effector sequences have the advantage of being able to target a range of molecular targets and naturally occurring variants thereof that may exist between individuals, as well as the advantage of the additive or synergistic effects achieved with multiple effector sequences as opposed to single effector sequences. In the present invention, where in one embodiment there are 2 or 3 different target genes selected from VEGF-A, VEGFR2, CFB and PDGFR-β, it is particularly advantageous for a single construct to be utilised to target the 2 or 3 genes. This eliminates the need to deliver multiple ddRNAi agents each targeting a different gene. As would be appreciated by the person skilled in the art, it would be difficult to ensure that delivery would result in equal and sufficient concentrations of each of the agents.

In one embodiment of the invention, the ddRNAi agent comprises two or more effector sequences to enable targeting of more than one target sequence of the AMD-associated gene. The multiple target sequences may be in the same region of the one gene. For example, a 17 to 30 nucleotide region, preferably a 17 to 21 nucleotide region, within VEGF-A, VEGFR2, CFB or PDGFR-β that has natural variation in the sequence between individuals. Alternatively, the target sequences may be in different regions of the one target gene, where the target gene may be VEGF-A, VEGFR2, CFB or PDGFR-β.

As noted above the target sequences may also be in different AMD-associated genes. For example, a first effector sequence targets a sequence in VEGFR2, whereas a second effector sequence in the same ddRNAi agent targets a sequence in a VEGF-A gene. In a preferred embodiment, there are at least 2 effector sequences, each one targeting a sequence in each of VEGF-A and VEGFR. In an alternative embodiment, there are at least 3 effector sequences, each one targeting a sequence in each of VEGFR2, CFB and PDGFR-β.

To provide greater specificity the ddRNAi agent comprises the following (in no particular order):

a first effector sequence of at least 17 nucleotides in length;

a second effector sequence of at least 17 nucleotides in length;

a first effector complement sequence; and a second effector complement sequence.

The first and second effector sequences of a multiple targeting ddRNAi agent form a double stranded region with their respective effector complements. Preferably, the first and second effector sequences are 17 to 30 nucleotides in length. More preferably, the first and second effector sequence are both selected from any 10 or more and preferably any 17 or more contiguous nucleotides within any one of the sequences of SEQ ID NOS: 40-78 listed in Table 1 above, or are sequences having 1, 2, 3, 4 or 5 nucleotides difference from those sequences listed in Table 1.

In one embodiment, the first effector sequence is selected from any 10 or more and preferably any 17 or more contiguous nucleotides within a sequence from any one of the group consisting of SEQ ID NOS:40-78, and the second effector sequence is selected from any 10 or more and preferably any 17 or more contiguous nucleotides within a sequence from any one of the group consisting of SEQ ID NOS: 40-78. The first and second effector sequence may both be the same sequence or may alternatively be different sequences.

The first and second effector sequence may each comprise a sequence selected from any 10 or more contiguous nucleotides within a sequence from the group consisting of SEQ ID NOS: 40-78, or alternatively, each effector sequence may also be a variant of SEQ ID NOS: 40-78, having 1, 2, 3, 4 or 5 nucleotide variations. In yet a further embodiment, each effector sequence may consist of 20 nucleotides, of which 17, 18, 19, or all 20 nucleotides are contiguous nucleotides from a sequence selected from the group consisting of SEQ ID NOS: 40-78. When there are two or more effector sequences, they may represent a combination of the 3 types described above.

In particularly preferred embodiments, the first and second effector sequence comprise any 10 or more, preferably any 17 or more, contiguous nucleotides within sequences able to inhibit the expression of a target gene region by at least 70%. Preferably in this embodiment, each effector sequence is selected from any 10 or more and preferably any 17 or more contiguous nucleotides within a sequence consisting of SEQ ID NO:47 and SEQ ID NO:56 such that there is provided a DNA-directed RNA interference (ddRNAi)

agent for inhibiting expression of one or more target sequences in an AMD associated gene, the ddRNAi agent comprising, in a 5' to 3' direction
    a first effector sequence of any 10 or more contiguous nucleotides within 5' UAUGUGGGUGGGUGUGUC-UAC 3' (SEQ ID NO:47);
    a first effector complement sequence;
    a second effector sequence of any 10 or more contiguous nucleotides within 5' UGUAACAGAUGAGAUG-CUCCA 3' (SEQ ID NO:56); and
    a second effector complement sequence
wherein each effector sequence is substantially complementary one or more target regions in a transcript of the one or more target sequences.

Long Hairpin Version

When the ddRNAi agent contains more than one effector sequence, and the ddRNAi agent is expressed as a single strand of RNA, it will fold to form different structures depending on the order of the effector sequences and the sequences complementary to the effector sequences. In one embodiment, there is provided a DNA-directed RNA interference (ddRNAi) agent for inhibiting expression of one or more target sequences in an AMD-associated gene, preferably a VEGF-A gene and/or one or more of a VEGFR2, CFB and PDGFR-β gene, the ddRNAi agent comprising, in a 5' to 3' direction, at least:
    a first effector sequence of at least 17 nucleotides in length;
    a second effector sequence of at least 17 nucleotides in length;
    a second effector complement sequence; and
    a first effector complement sequence
wherein each effector sequence is substantially complementary to one or more target regions in a transcript of the one or more target sequences. This will result in a ddRNAi agent with a structure as shown in FIG. 1A. See also WO2004/106517, incorporated herein by reference.

Alternatively, at least one effector, and preferably both, effector sequences, are 100% complementary one or more target regions in a transcript of the one or more target sequences. Preferably the first and second effector sequences are both selected from the group consisting of any 10 or more and preferably any 17 or more contiguous nucleotides within any one of SEQ ID NOS: 40-78. For example, in one embodiment, there is provided a DNA-directed RNA interference (ddRNAi) agent for inhibiting expression of one or more target sequences in an AMD-associated gene, the ddRNAi agent comprising, in a 5' to 3' direction, at least:
    a first effector sequence of 5' AAGUUCAUGGUUUCG-GAGGCC 3' (SEQ ID NO:41);
    a second effector sequence 5' UCUUUCUUUGGUCUG-CAUUCA 3' (SEQ ID NO:44);
    a second effector complement; and
    a first effector complement
wherein the AMD-associated gene is VEGF-A.

Each effector sequence is substantially complementary to one or more target regions in a transcript of the one or more target sequences.

Alternatively, at least one effector, and preferably both effector sequences, are 100% complementary to one or more target regions in a transcript of the one or more target sequences.

In particularly preferred embodiments, the first and second effector sequence comprise any 10 or more, preferably any 17 or more, contiguous nucleotides within sequences able to inhibit the expression of a target gene region by at least 70%. Preferably, in this embodiment, each effector sequence is selected from SEQ ID NOS: 40-78, more preferably from SEQ ID NOS: 40-59 and most preferably SEQ ID NOS: 40-49.

In yet another embodiment, being an embodiment where the ddRNAi agent has 3 effector sequences, there is provided a DNA-directed RNA interference (ddRNAi) agent for inhibiting expression of one or more target sequences in the target gene, the ddRNAi agent comprising, in a 5' to 3' direction, at least:
    a first effector sequence of 5' AAGUUCAUGGUUUCG-GAGGCC 3' (SEQ ID NO:41);
    a second effector sequence of 5' UCUUUCUUUGGU-CUGCAUUCA 3' (SEQ ID NO:44);
    a third effector sequence of 5' UAUGUGGGUGGGUGU-GUCUAC 3' (SEQ ID NO:47);
    a third effector complement sequence;
    a second effector complement sequence; and
    a first effector complement sequence.

Each effector sequence is substantially complementary to one or more target regions in a transcript of the one or more target sequences.

Alternatively, at least one effector, and optionally 2 out of the 3 or all 3 of the effectors, are 100% complementary to one or more target regions in a transcript of the one or more target sequences.

In particularly preferred embodiments, the first, second and third effector sequence comprise any 10 or more, preferably any 17 or more, contiguous nucleotides within sequences able to inhibit the expression of a target gene region by at least 70%. Preferably, in this embodiment, each effector sequence is selected from SEQ ID NOS:40-78, more preferably from SEQ ID NOS: 40-59, and most preferably from SEQ ID NOS: 40-49.

It will also be appreciated by the skilled person that the order of effector and effector complements can be altered, provided that a single, long hairpin structure is formed by annealing of the effector sequence with its effector complement to form dsRNA. For example, in a 2-effector sequence ddRNAi agent, the sequences may be arranged in the following exemplary 5' to 3' orders:
    first effector-second effector-second effector complement-first effector complement;
    second effector-first effector-first effector complement-second effector complement;
    first effector-second effector complement-second effector-first effector complement;
    first effector complement-second effector complement-second effector-first effector;
    first effector complement-second effector-second effector complement-first effector.

In a 3-effector sequence ddRNAi agent, the sequences may be arranged in the following exemplary 5' to 3' orders:
    first effector-second effector-third effector-third effector complement-second effector complement-first effector complement
    first effector-second effector complement-third effector-third effector complement-second effector-first effector complement;
    first effector-second effector-third effector complement-third effector-second effector complement-first effector complement
    first effector-third effector-second effector complement-second effector-third effector complement-first effector complement
    first effector complement-second effector complement-third effector complement-third effector-second effector-first effector complement first effector complement-second effector complement-third effector-third effector complement-second effector-first effector.

In yet further embodiments, the first effector sequence may be selected from any 10 or more and preferably any 17 or more contiguous nucleotides within a sequence from the group consisting of SEQ ID NOS:40-78; the second effector sequence may be selected from any 10 or more and preferably any 17 or more contiguous nucleotides within a sequence from the group consisting of SEQ ID NOS:40-78; the third effector sequence may be selected from any 10 or more and preferably any 17 or more contiguous nucleotides within a sequence from the group consisting of SEQ ID NOS:40-78; and any further effector sequences may be selected from any 10 or more and preferably any 17 or more contiguous nucleotides within a sequence from the group consisting of SEQ ID NOS:40-78. Alternatively, each effector sequence may also be a variant of SEQ ID NOS:40-78, having 1, 2, 3, 4 or 5 nucleotide variations. Preferably, the differences are present in the first and/or last 5 nucleotides, and at least the centre 11-12 nucleotides are 100% complementary to one or more target regions in a transcript, of the one or more target sequences. In each of the embodiments, wherein only VEGF-A is to be targeted, each effector sequence is selected from SEQ ID NOS: 40-49; wherein only VEGFR2 is to be targeted, each effector sequence is selected from SEQ ID NOS: 50-59; wherein only PDGFR-β is to be targeted, each effector sequence is selected from SEQ ID NOS: 60-69; and wherein only CFB is to be targeted, each effector sequence is selected from SEQ ID NOS: 70-78.

The first, second and third effector sequence may each comprise a sequence selected from any 10 or more contiguous nucleotides within a sequence from the group consisting of SEQ ID NOS: 40-78, or alternatively; each effector sequence may also be a variant of SEQ ID NOS:40-78, having 1, 2, 3, 4 or 5 nucleotide variations. In yet a further embodiment, each effector sequence may consist of 20 nucleotides, of which 17, 18, 19, or all 20 nucleotides are contiguous nucleotides from a sequence selected from the group consisting of SEQ ID NOS: 40-78. When there are multiple effector sequences, they may represent a combination of the 3 types described above.

Multiple Hairpin Version

In an alternative embodiment, there is provided a DNA-directed RNA interference (ddRNAi) agent for inhibiting expression of one or more target sequences in one or more AMD-associated genes, preferably a VEGF-A, VEGFR2, CFB or PDGFR-β genes, the ddRNAi agent comprising, in a 5' to 3' direction, at least:
  a first effector sequence of at least 17 nucleotides in length;
  a first effector complement;
  a second effector sequence of at least 17 nucleotides in length; and
  a second effector complement
wherein each effector sequence is substantially complementary to one or more target regions in a transcript of the one or more target sequences.

Alternatively, at least one effector, and preferably both effector sequences, is 100% complementary to the one or more target regions of a transcript of the one or more target sequences.

This will result in a ddRNAi agent with a structure as shown in FIG. 1B or C, depending on the type of expression cassette used to express it (see later in the specification). See also WO2005/087926 and WO2006/084209, incorporated herein by reference.

In either embodiment, where there are 2 target sequences, it is preferable that the first and second effector sequences are both substantially complementary to the one or more target regions of a transcript of their respective target sequences.

Preferably the first and second effector sequences are both selected from any 10 or more and preferably any 17 or more contiguous nucleotides within a sequence from the group consisting of SEQ ID NOS: 40-78. For example, in one embodiment, there is provided a DNA-directed RNA interference (ddRNAi) agent for inhibiting expression of one or more target sequences in an AMD-associated gene, the ddRNAi agent comprising, in a 5' to 3' direction, at least:
  a first effector sequence of any 10 or more contiguous nucleotides within 5' UAUGUGGGUGGGUGUGUC-UAC 3' (SEQ ID NO:47);
  a first effector complement sequence;
  a second effector sequence any 10 or more contiguous nucleotides within 5' AAGUUCAUGGUUUCGGAG-GCC 3' (SEQ ID NO:41) or 5' UCUUUCUUUGGU-CUGCAUUCA 3' (SEQ ID NO:44); and
  a second effector complement sequence,
wherein the AMD-associated gene is VEGF-A.

Each effector sequence is substantially complementary to one or more target regions in a transcript of the one or more target sequences.

Alternatively, at least one effector, and preferably both effector sequences, have 100% complementarity to one or more target, regions in a transcript of the one or more target sequences.

In particularly preferred embodiments, the first and second effector sequence comprise any 10 or more, preferably any 17 or more, contiguous nucleotides within sequences able to inhibit the expression of a target region by at least 70%. Preferably, in this embodiment, each effector sequence is selected from SEQ ID NOS: 40-78, more preferably SEQ ID NOS: 40-59, and most preferably SEQ ID NOS: 40-49.

In yet another embodiment, being an embodiment where the ddRNAi agent has 3' effector sequences, there is provided a DNA-directed RNA interference (ddRNAi) agent for inhibiting expression of one or more target sequences in one or more AMD-associated genes, the ddRNAi agent comprising, in a 5' to 3' direction, at least:
  a first effector sequence of any 10 or more contiguous nucleotides within 5' AAGUUCAUGGUUUCGGAG-GCC 3' (SEQ ID NO:41);
  a first effector complement sequence;
  a second effector sequence of any 10 or more contiguous nucleotides within 5' UCUUUCUUUGGUCUG-CAUUCA 3' (SEQ ID NO:44);
  a second effector complement sequence;
  a third effector sequence of any 10 or more contiguous nucleotides within 5' UAUGUGGGUGGGUGUGUC-UAC (SEQ ID NO:47); and
  a third effector complement sequence,
wherein the AMD-associated gene is VEGF-A.

In yet another embodiment, being an embodiment where the ddRNAi agent has 2 effector sequences, there is provided a DNA-directed RNA interference (ddRNAi) agent for inhibiting expression of one or more target sequences in one or more AMD-associated genes, the ddRNAi agent comprising, in a 5' to 3' direction, at least:

a first effector sequence of any 10 or more contiguous nucleotides within 5' UGUAACAGAUGAGAUG-CUCCA 3' of the AMD-associated gene VEGRF-2 (SEQ ID NO:56);
a first effector complement sequence;
a second effector sequence of any 10 or more contiguous nucleotides within 5' UAUGUGGGUGGGUGUGUC-UAC 3' of the AMD-associated gene VEGFA (SEQ ID NO:47); and
a second effector complement sequence.

Each effector sequence in these embodiments is substantially complementary to one or more target regions in a transcript of the one or more target sequences.

It will be appreciated by the skilled person that the VEGFA sequence can be first and the VEGFR2 sequence can be second. This is an equivalent embodiment.

In yet another embodiment, being an embodiment where the ddRNAi agent has 3 effector sequences, there is provided a DNA-directed RNA interference (ddRNAi) agent for inhibiting expression of one or more target sequences in one or more AMD-associated genes, the ddRNAi agent comprising, in a 5' to 3' direction, at least:
a first effector sequence of any 10 or more contiguous nucleotides within 5' AAGUAGCCA-GAAGAACAUGGC 3' of the AMD-associated gene VEGRF-2 (SEQ ID NO:52);
a first effector complement sequence;
a second effector sequence of any 10 or more contiguous nucleotides within 5' UUAUAGAAAACCCAAAUC-CUC 3' of the AMD-associated gene CFB (SEQ ID NO:78);
a second effector complement sequence;
a third effector sequence of any 10 or more contiguous nucleotides within 5' UAGCUGAAGCCCACGAG-GUCC 3' of the AMD-associated gene PDGFR-β (SEQ ID NO:63); and
a third effector complement sequence.

Each effector sequence in both of these embodiments is substantially complementary to one or more target regions in a transcript of the one or more target sequences. It will be appreciated by the skilled person that the sequence can be in a different 5' to 3' order and represent equivalent embodiments. For example, PDGFR-β can be first, VEGFR2 can be second and CFB can be third. Alternatively, at least one effector, and optionally 2 out of the 3 or all 3 of the effectors, is 100% complementary to one or more target regions in a transcript of the one or more target sequences.

In particularly preferred embodiments, the first, second and third effector sequence comprise any 10 or more, preferably any 17 or more, contiguous nucleotides within sequences able to inhibit the expression of a target gene region by at least 70%. Preferably, in this embodiment, each effector sequence is selected from SEQ ID NOS: 40-78, more preferably SEQ ID NOS: 40-59, and most preferably SEQ ID NOS: 40-49.

In yet further embodiments, the first effector sequence may be any 10 or more contiguous nucleotides within a sequence selected from the group consisting of SEQ ID NOS:40-78; the second effector sequence may be any 10 or more contiguous nucleotides within a sequence selected from the group consisting of SEQ ID NOS:40-78; the third effector sequence may be any 10 or more contiguous nucleotides within a sequence selected from the group consisting SEQ ID NOS:40-78; and any further effector sequences may be any 10 or more contiguous nucleotides within a sequence selected from the group consisting of SEQ ID NOS:40-78. Preferably, each effector sequence is at least 17 contiguous nucleotides.

Each effector sequence may also be a variant of SEQ ID NOS:40-78, having 1, 2, 3, 4 or 5 nucleotide variations. Preferably, the differences are present in the first and/or last 5 nucleotides, and at least the centre 10-12 nucleotides are 100% complementary to one or more target regions in a transcript of the one or more target sequences.

The first, second and third effector sequence may each comprise a sequence selected from any 10 or more contiguous nucleotides within a sequence from the group consisting of SEQ ID NOS: 40-78, or alternatively, each effector sequence may also be a variant of SEQ ID NOS:40-78, having 1, 2, 3, 4 or 5 nucleotide variations. In yet a further embodiment, each effector sequence may consist of 20 nucleotides, of which 17, 18, 19, or all 20 nucleotides are contiguous nucleotides from a sequence selected from the group consisting of SEQ ID NOS: 40-78. When there are multiple effector sequences, they may represent a combination of the 3 types described above.

Furthermore, in the long hairpin structure or the multiple hairpin structure the ddRNAi agent may include additional effector sequences and corresponding complementary sequences according to one of the following formula:
Long hairpin:
[effector sequence]$_{1-10}$[effector complement sequence]$_{1-10}$
Multiple hairpin:
[effector sequence-effector complement sequence]$_{1-10}$ Preferably, in the long hairpin formula, the number of effector sequences is equal to the number of effector complement sequences. Typically, there are 2, 3, 4 or 5 effector sequences, and accordingly, 2, 3, 4 or 5 effector complement sequences respectively.

When the ddRNAi agent does contain more than one effector sequence, the effector sequences may be the same or different. For example, if a ddRNAi agent has 3 effector sequences, 2 effector sequences may have the same sequence, while 1 is different. Alternatively, all 3 effector sequences may be different. Preferably, the effector sequences are any 10 or more and preferably any 17 or more contiguous nucleotides within a sequence selected from the group consisting of SEQ ID NOS:40-78, or variants thereof which have 1, 2, 3, 4 or 5 nucleotide variations. Preferably, the differences are present in the first and/or last 5 nucleotides, and at least the centre 10-12 nucleotides are 100% complementary to one or more target regions in a transcript of the one or more target sequences.

When targeting a single region of a target sequence that has naturally occurring variants, or single nucleotide polymorphisms, it is preferably that at least one effector sequence is chosen from any 10 or more and preferably any 17 or more contiguous nucleotides within a sequence selected from the group consisting of SEQ ID NOS:40-78, whereas other effector sequences are variants of that chosen sequence. For example, a first effector sequence may comprise 20 nucleotides of SEQ ID NO: 47; the second effector sequence should therefore be a variant of SEQ ID NO:47.

Hairpin Structures

In the above embodiments, the effector sequence hybridises with its corresponding effector complement sequence to form a hairpin structure. At the end of the hairpin, two or more unbound nucleotides form the 'hinge' or 'loop'. In one embodiment, the unbound nucleotides are part of the effector sequence and the effector complement, such that only a portion of the at least 17 nucleotides of the effector sequence will form a duplex with its corresponding complementary sequence. For example, when the effector sequence and its complement are both 20 nucleotides long, 18 of the nucleotides may base pair to form a double stranded region, leaving a total of 4 nucleotides to form a single stranded loop between and joining the effector sequence and its effector complement sequence.

In an alternative embodiment, an additional sequence that is non-complementary to itself, the target sequence, the effector sequence or the effector complement may be included in the ddRNAi in order to create a 'loop'. As such, in yet another embodiment of the invention, the ddRNAi agent further includes a sequence of 2 to 100 unpaired nucleotides capable of forming a loop, more preferably, 2 to 10 unpaired nucleotides. In a preferred embodiment the loop includes the nucleotide sequence AA, UU, UUA, UUAG, UUACAA, CAAGAGA or $N_1AAN_2$, where $N_1$ and $N_2$ are any of C, G, U and A and may be the same or different. Otherwise, specific loop sequences include ACU-GUGAAGCAGAUGGGU. In these loops, not all of the loop sequence has to remain non-annealed. In a loop of, for example, 18 nucleotides, the first and last 3 nucleotides for example may anneal with each other, leaving the intervening 15 nucleotides non-annealed.

In embodiments in which the ddRNAi agent is expressed as part of a miRNA structure the loop sequence may be derived from the miRNA, and is encoded by the miRNA encoding (ME) sequence.

There may be one or more loops depending on the ddRNAi agent structure. When a ddRNAi agent has a structure based on formula [effector sequence]$_{1-10}$ [effector complement sequence]$_{1-10}$ additional non-self-complementary sequence to give rise to a single loop structure is contained between the last effector sequence and the effector complement sequence of that last effector sequence, as illustrated in FIG. 1D. In this embodiment, there is therefore provided a DNA-directed RNA interference (ddRNAi) agent for inhibiting expression of one or more target sequences in an AMD-associated' gene selected from VEGF-A, VEGFR2, CFB and PDGFR-β, the ddRNAi agent comprising, in a 5' to 3' direction, at least:
 a first effector sequence of at least 17 nucleotides in length;
 a second effector sequence of at least 17 nucleotides in length;
 a loop sequence of 2 to 100 non-self-complementary nucleotides;
 a second effector complement sequence; and
 a first effector complement sequence
wherein each effector sequence is substantially complementary to one or more target regions in a transcript of the one or more target sequences.

Figure 1F:
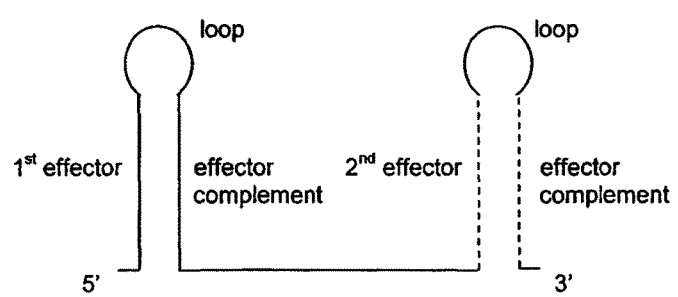
Figure 1G:
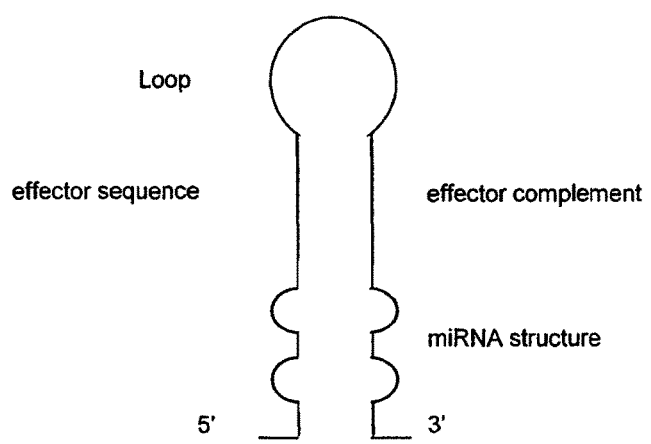

When the ddRNAi agent has a multiple hairpin structure based on formula [effector sequence-effector complement sequence]$_{1-10}$ additional non-self-complementary sequence is contained between each effector sequence and its complementary sequence to give rise to a loop structure, as illustrated in FIGS. 1E and F (depending on the type of expression cassette used to express it—see later in the specification). In this embodiment, there is provided a DNA-directed RNA interference (ddRNAi) agent for inhibiting expression of one or more target sequences in an AMD-associated gene, the ddRNAi agent comprising, in a 5' to 3' direction, at least:
 a first effector sequence of at least 17 nucleotides in length;
 a loop sequence of 2 to 100 non-self-complementary nucleotides;
 a first effector complement sequence;
 a second effector sequence of at least 17 nucleotides in length;
 a loop sequence of 2 to 100 non-self-complementary nucleotides; and
 a second effector complement sequence
wherein each effector sequence is substantially complementary to one or more target regions in a transcript of the one or more target sequences in the AMD-associated gene, and gene is selected from one or more of VEGF-A, VEGFR2, CFB and PDGFR-β.

In this embodiment where there are more than two effector and complementary sequences, and therefore more than two hairpin structures, the length of additional non-self-complementary sequence that forms each loop structure does not have to be the same. For example, one loop structure may have 5 nucleotides, while another loop structure may have 9 nucleotides.

In addition, when there are two or more hairpin structures, there may be additional non-self-complementary sequence that acts as a spacer sequence between each loop. In this embodiment, there is provided a DNA-directed RNA interference (ddRNAi) agent for inhibiting expression of one or more target sequences in an AMD-associated gene, the ddRNAi agent comprising, in a 5' to 3' direction, at least:
 a first effector sequence of at least 17 nucleotides in length;
 a loop sequence of 2 to 100 non-self-complementary nucleotides;
 a first effector complement sequence;
 a spacer sequence of 2 to 100 non-self-complementary nucleotides;
 a second effector sequence of at least 17 nucleotides in length;
 a loop sequence of 2 to 100 non-self-complementary nucleotides; and
 a second effector complement sequence
wherein each effector sequence is substantially complementary to one or more target regions in a transcript of the one or more target sequences in the AMD-associated gene, and gene is selected from one or more of VEGF-A, VEGFR2, CFB and PDGFR-13.

2 Strand ddRNAi Agents

As will be appreciated by one skilled in the art, it is not necessary that the entire ddRNAi agent is expressed as one sequence. For example, in one embodiment of the invention, the first effector sequence may be generated (e.g., transcribed by one DNA sequence), and the first effector complement sequence may be generated (e.g., transcribed from a separate DNA sequence). Optionally, a loop sequence may be attached to either transcript or part of the loop attached to the 3' end of one transcript and the 5' end of the other transcript, and that loop sequence may be derived from a miRNA when the effector or effector complement sequence is expressed as part of a miRNA structure. Within the cell, the two transcripts then form the ddRNAi agent by hybridising through annealing between the first effector sequences and its complement.

In Vitro Expressed ddRNAi Agents of Chemically Synthesised siRNA

While it is envisaged that effective treatment of wet AMD will require ddRNAi agents to be expressed in vivo from ddRNAi constructs (as will be outlined below), there may be circumstances where it is desirable to administer ddRNAi agents that are expressed in vitro or to administer siRNAs that are chemically synthesised, thereby functioning as therapy with transient duration of effect. Screening the patient for their reaction to the treatment for example may benefit from a short term treatment with siRNAs that do not integrate and replicate in the cells before commencing long term therapy with in vivo expressed ddRNAi agents.

The ddRNAi agents of the invention may therefore be expressed in vitro and then delivered to target cells. Alternatively, siRNAs may be chemically synthesised and then delivered to the target cells. In light of this, in another aspect of the invention, there is provided a small interfering RNAi agent (siRNA agent) for inhibiting expression of one or more target sequences in an AMD-associated gene, the siRNA comprising
 a first effector sequence of at least 17 nucleotides in length; and
 a first effector complement sequence;
wherein the effector sequence is substantially complementary to one or more target regions in a transcript of the one or more target sequences.

Similarly to the ddRNAi agents described above, the siRNA agent may also include more than one effector sequence for multiple targeting, be that multiple targets in a single gene such as VEGF-A, or targets in more than one gene, such as VEGFR2, CFB and PDGFR-β. The effector sequences are preferably selected from any 10 or more and preferably any 17 or more contiguous nucleotides within a sequence from the group consisting of SEQ ID NOS: 40-78.

Considerable flexibility is possible in the design of siRNAs. Typically siRNAs consist of dsRNA molecules with 5'-phosphate and 3'-hydroxyl residues, strand lengths can vary from 20-29 nucleotides and may optionally be designed to include 2 nucleotide 3' overhangs. In some embodiments each strand can be synthesised as $N_{19-27}TT$ (where TT can be deoxyribonucleotides). siRNAs can be readily designed based on regions of SEQ ID NOS: 40-78 as described above and can be used therapeutically as single sequences or in any combinations. Alternatively siRNA agents can consist of single RNA molecules containing effector and effector complement sequences similar or identical to those expressed from ddRNAi expression cassettes. These sequences can be based on SEQ ID NOS: 40-78 and can be used therapeutically as single sequences or in any combination with one another. The siRNAs can be chemically synthesized with appropriately protected ribonucleoside phosphoramidates and a conventional synthesiser and thus are widely available commercially and able to be designed and synthesised according to routine methods in the art. In preferred embodiments, the siRNAs have the sequences of any 10 or more contiguous nucleotides within a sequence from one or more of SEQ ID NOS: 40-78.

Expression Cassettes and miRNA Backbones

The ddRNAi agents of the invention are expressed from DNA expression cassettes. The expression cassettes comprise the regulatory sequences required for expression, such as the promoter, together with the DNA sequence that encodes the ddRNAi agent itself. In embodiments in which the ddRNAi agent is expressed as part of a miRNA structure, the expression cassette also includes the DNA sequence that encodes for that miRNA structure.

The ddRNAi expression cassettes comprise (in no particular order):
 one of more promoter sequences
 one or more DNA sequences that encode for one or more effector sequences
 one or more DNA sequences that encode for one or more effector complement sequences;
and optionally
 one or more terminator sequences
 one or more DNA sequences that encode for loop sequences, spacer sequences or both
 one or more enhancer sequences.

The first promoter sequence and last terminator sequence may be derived from the vector in to which the expression cassette is cloned.

In one embodiment, there is provided a DNA-directed RNA interference (ddRNAi) expression cassette for expressing a ddRNAi agent, wherein the ddRNAi agent inhibits expression of one or more target sequences in an AMD-associated gene, the ddRNAi constructs comprising, in a 5' to 3' direction:
 a promoter sequence
 a DNA sequence that encodes for a first effector sequence
 a DNA sequence that encodes for a first effector complement sequence; and
 a terminator sequence.

The DNA sequence that encodes for the first effector sequence is preferably a DNA that encodes for 10 or more, preferably 17 or more, contiguous nucleotides within a sequence from any one of SEQ ID NOS: 40-78. In a particularly preferred embodiment, the first effector sequence comprise any 10 or more, preferably any 17 or more, contiguous nucleotides within sequences able to inhibit the expression of a target gene region by at least 70%. Preferably, in this embodiment, the first effector sequence is selected from SEQ ID NOS: 40-78, more preferably SEQ ID NOS: 40-59, and most preferably SEQ ID NOS: 40-49.

Alternatively, as outlined above in relation to the ddRNAi agent itself, the sequence that encodes for the effector sequence may encode an effector sequence that varies by 1, 2, 3, 4 or 5 nucleotides from SEQ ID NOS: 40-78 without effecting the ability of the sequence encoded to base pair with the transcript of the target sequence and inhibit expression of the target sequence.

The skilled person would appreciate that a DNA sequence encoding any given RNA sequence is the same sequence as the RNA but having thymine (T) bases instead of uracil (U) bases. The ddRNAi expression cassettes encoding ddRNAi agents having more than one effector sequence in a long hairpin structure comprise, in a 5' to 3' direction:
 a promoter sequence;
 a DNA sequence that encodes for a first effector sequence;
 a DNA sequence that encodes for a second effector sequence;
 optionally a sequence that encodes for sequence capable of forming a loop;
 a DNA sequence that encodes for a second effector complement sequence;
 a DNA sequence that encodes for a first effector complement sequence; and
 optionally a terminator sequence.

Preferably the DNA sequences encode first and second effector sequence selected from any 10 or more and preferably any 17 or more contiguous nucleotides within a sequence from the group consisting of SEQ ID NOS: 40-78. Preferably, the first and second effector sequence is selected from SEQ ID NOS: 40-59. Alternatively, the DNA sequences encode for an effector sequence that varies from SEQ ID NOS: 40-78 by 1, 2, 3, 4 or 5 nucleotides without affecting the ability of the effector sequence encoded to base pair with a transcript of the target sequence and inhibit expression of the target sequence.

When the ddRNAi agent has more than one effector sequence and a multiple hairpin structure based on formula

[effector sequence-effector complement sequence]$_{1-10}$ expression of each [effector sequence-effector complement sequence] pair may be controlled by a single promoter, or alternatively by a separate promoter. When separate promoters are contemplated, the ddRNAi expression cassette comprises, in a 5' to 3' direction:

a promoter sequence
a DNA sequence that encodes for a first effector sequence
a DNA sequence that encodes for a first effector complement sequence;
optionally a terminator sequence;
a promoter sequence;
a DNA sequence that encodes for a second effector sequence;
a DNA sequence that encodes for a second effector complement sequence; and
optionally a terminator sequence.

In this embodiment, multiple ddRNAi agents are produced from the one expression cassette, as each effector/effector complement is expressed as a single hairpin structure.

When a single promoter is contemplated, the ddRNAi expression cassette comprises, in a 5' to 3' direction:

a promoter sequence
a DNA sequence that encodes for a first effector sequence
a DNA sequence that encodes for a first effector complement sequence;
a DNA sequence that encodes for a second effector sequence;
a DNA sequence that encodes for a second effector complement sequence; and
optionally a terminator sequence.

Similarly to the above embodiments, the DNA sequences preferably encode first and second effector sequence selected from any 10 or more and preferably any 17 or more contiguous nucleotides within a sequence from the group consisting of SEQ ID NOS:40-78, or, effector sequences that vary in sequence from SEQ ID NOS: 40-78 by 1, 2, 3, 4 or 5 nucleotides. Preferably, the first and second effector sequence is selected from SEQ ID NOS: 40-78, more preferably SEQ ID NOS: 40-59, and most preferably SEQ ID NOS: 40-49.

Any of the abovementioned ddRNAi agents are preferably expressed in a miRNA structure from an expression cassette.

Processing of shRNAs expressed from ddRNAi constructs can be imprecise. The expression of the ddRNAi within or as part of an RNA structure like a miRNA, which is a natural substrate for RNAi processing pathways, is one way to minimise this. McBride et al. (2008) designed "artificial miRNA" constructs which expressed sequences from the base and loop of endogenous miRNAs; these showed reduced toxicity suggesting more precise processing of expressed shRNAs. Wu et al. (2011) showed that mismatched duplexes (containing mismatches in the passenger strand) sometimes showed increased silencing activity, due possibly to their greater structural resemblance to endogenous miRNAs. Similarly Gu et al. (2012) showed the introduction of bulges adjacent to loop sequences in shRNA molecules can result in increased precision of dicer processing.

In embodiments where the effector and effector complement are expressed as a miRNA structure, the ddRNAi expression cassette further includes sequence that encodes for the miRNA structure referred to herein as "miRNA encoding sequence" or "ME sequence". This is the DNA sequence contained within a ddRNAi expression cassette that encodes for RNA which, once expressed, folds in to a miRNA structure. The effector sequence and the effector complement therefore are expressed as part of or within that miRNA structure. As will be appreciated from the Figures illustrating a ddRNAi agent expressed in a miRNA structure, and as detailed earlier in the specification, the ME sequences will be located upstream and downstream of the effector sequence and the effector complement sequence as required. Using an expression cassette that expresses a ddRNAi agent with a single effector-effector complement pair as an example, there is provided a DNA-directed RNA interference (ddRNAi) expression cassette for expressing a ddRNAi agent, wherein the ddRNAi agent inhibits expression of one or more target sequences in an AMD-associated gene, the ddRNAi cassette comprising, in a 5' to 3' direction:

a promoter sequence
a first ME sequence
a DNA sequence that encodes for a first effector sequence
optionally a sequence that encodes for sequence capable of forming a loop
a DNA sequence that encodes for a first effector complement sequence;
a second ME sequence; and
optionally a terminator sequence, wherein the sequence encoded by the first and second ME sequences is capable of forming a miRNA structure. The effector sequence and the effector complement therefore are expressed as part of or within that miRNA structure.

The optional sequence that encodes for sequence capable of forming a loop may also be ME sequence. For example, if a particular miRNA structure is being utilised as the structure in which the ddRNAi agent is expressed within or as part of, the loop sequence of the ddRNAi agent may come from the same miRNA. In alternative embodiments, the loop sequence may come from a different miRNA than the miRNA structure encoded by the ME sequences, but nonetheless, is still miRNA derived or originating sequence.

The ddRNAi expression cassette may alternatively be described by reference to the total length of the ddRNAi agent expressed, which is a product of the total length of sequence between the promoter and terminator. For example, when the length of the effector sequence in a single effector ddRNAi consists of 17, 18, 19, 20, 21, 22, 23, 24, 25, 26, 27, 28, 29, or 30 nucleotides, the ddRNAi expression cassette will have a length of 34 to 60 nucleotides between the promoter and terminator. This length may further include 2 to 100 nucleotides of "loop" or "hinge" sequence, giving a length of between 36 to 160 nucleotides. For ddRNAi agents having multiple effector sequences, where each effector sequence consists of 17, 18, 19, 20, 21, 22, 23, 24, 25, 26, 27, 28, 29, or 30 nucleotides, the overall length is increased proportionally.

The presence of ME sequence for encoding the miRNA structure/s will also add to overall length.

One useful way of designing ddRNAi expression cassettes of the invention is to assume Dicer cuts every 22 nucleotides (also referred to as '22 nt phasing'), and effector sequences can therefore be designed to encode any 10 or more, and preferably any 17 or more contiguous nucleotides within a sequence from the group consisting of SEQ ID NOS:40-78, together with appropriate spacers and other sequence requirements for the appropriate promoter.

Agents targeting different sites of mRNA are suitable for shRNA construction, because they can avoid the influence of secondary structures of mRNA, and thus perform their functions independently.

When a U6 promoter is used, it is preferable but not essential that the DNA sequence operably linked to the promoter starts with a guanine (G) base; when a H1 promoter is used, it is preferable but not essential that the DNA sequence operably linked to the promoter starts with an adenine (A) base. The effector encoding sequence can therefore be modified accordingly.

The use of miRNA-derived sequences to drive expression of shRNAs is particularly advantageous when using pol II promoters. Transcriptional initiation sites for poi II promoters are frequently imprecise. Since dicer processing of an shRNA is largely dependent on the structure of the shRNA, processing will not be greatly affected by slight variations in transcriptional start sites in most instances. The use of miRNA derived sequences therefore permits greater flexibility in designing ddRNAi constructs that utilise pol II promoters.

In some instances it may be advantageous to increase the length of shRNAs. One way to accomplish this is to extend the length of the effector sequence in an shRNA to maximise its complementarity to the target sequence, in either a 5' or 3' direction, and also extend the length of the effector complement to maximise base pairing within the stem of the shRNA. For example an shRNA based on SEQ ID NO: 47 could be readily extended in a 5' or 3' direction to target additional sequences adjacent to those in SEQ ID NO:8 to produce an shRNA with a 30 nucleotide stem. The effector sequence could share substantial homology to the target as defined elsewhere in this specification.

In some instances it may be desirable to avoid the DNA sequence TTTT within effector, effector complement or loop sequences since these can act as transcriptional terminators in expression constructs which use Pol III promoters such as U6 or H1. shRNA design should also take in to account that U6 termination is expected to add a one to five U residues to the 3' end to the shRNA. When designing long hairpin RNAs, it is sometimes advantageous to modify the precise choice of effector sequences (either using sequences from, or adjacent to SEQ ID NOS: 40-78) to maximise the likelihood that Dicer processed effector sequences will include a 5'U or A, thereby encouraging incorporation into AGO2.

The choice of whether to control expression of each [effector sequence-effector complement sequence] pair with individual promoters or a single promoter depends on a number of factors. A single promoter may be utilised to minimise interference between promoters. A ddRNAi construct with only a single promoter is also smaller in size, which can be important in some cases for the stability of the construct, both during production (e.g. replication in *E. coli*) and delivery. In addition, the use of a single promoter avoids the possibility of any homologous recombination between promoters.

In circumstances where a degree of regulation of expression of each effector sequence or complement is required though, it is advantageous to design a ddRNAi construct having multiple promoters, whereby expression of each [effector sequence-effector complement sequence] pair is controlled by a separate promoter. In circumstances where the effector sequences are of a different sequence, the nature of the sequence may mean one sequence is expressed to higher expression levels. When it is desired to ensure more equal expression levels of each effector sequence, the more highly expressed effector sequence can be paired with a weaker promoter and vice versa. Moreover, more efficient expression may be achieved as the length of any one sequence to be transcribed is shorter particularly for pol III promoters. When multiple promoters are used, it is preferable that not all of the promoters are the same to minimise the risk of any homologous recombination between them in the expression cassette. In the case of 2 promoters, each is preferably different. In the case of 3 promoters, at least 2 and optionally all 3 are different from one another.

The DNA sequence encoding the effector sequence is operably linked to the promoter sequence. A sequence is "operably linked" to another nucleotide sequence when it is placed in a functional relationship with another nucleotide sequence. For example, if a coding sequence is operably linked to a promoter sequence, this generally means that the promoter may promote transcription of the coding sequence. Operably linked means that the DNA sequences being linked are typically contiguous and, where necessary to join two protein coding regions, contiguous and in reading frame. However, since enhancers may function when separated from the promoter by several kilobases and intronic sequences may be of variable length, some nucleotide sequences may be operably linked but not contiguous.

A "promoter" or "promoter sequence" or "promoter element" is generally a DNA regulatory region capable of binding RNA polymerase in a cell and initiating transcription of a polynucleotide or polypeptide coding sequence such as mRNA or any kind of RNA transcribed by any class of any RNA polymerase. The promoter and terminator may be taken from different genes, but are typically matched to each other; that is, the promoter and terminator elements are taken from the same gene in which they occur naturally. Promoters also may or may not be modified using molecular techniques, or otherwise, e.g., through modification of regulatory elements, to attain weaker or stronger levels of transcription.

The term "constitutive" when made in reference to a promoter means that the promoter is capable of directing transcription of an operably linked nucleic acid sequence in the absence of a specific stimulus (e.g., heat shock, chemicals, light, etc.). Typically, constitutive promoters are capable of directing expression of a coding sequence in substantially any cell and any tissue. The promoters used to transcribe the ddRNAi agents preferably are constitutive promoters, such as the promoters for ubiquitin, CMV, 3-actin, histone H4, EF-1 alfa or pgk genes controlled by RNA polymerase II, or promoter elements controlled by RNA polymerase I. In other embodiments, a Pol II promoter such as CMV, SV40, U1, hAAT, β-actin or a hybrid Pol II promoter is employed. In other embodiments, promoter elements controlled by RNA polymerase III are used, such as the U6 promoters (e.g. U6-1, U6-8, U6-9), H1 promoter, 7SL promoter, the human Y promoters (hY1, hY3, hY4 (see Maraia et al., (1994)) and hY5 (see Maraia et al., (1994)), the human MRP-7-2 promoter, Adenovirus VA1 promoter, human tRNA promoters, the 5S ribosomal RNA promoters, as well as functional hybrids and combinations of any of these promoters. Variants of all of these promoters may also be utilised, wherein the promoter is modified to decrease or increase its activity. For example, if a strong promoter causes too much expression of the sequence operably linked to it, it can be modified to decrease its activity.

When a U6 promoter is used, it is preferable that the DNA sequence operably linked to the promoter starts with a guanine (G) base; when a H1 promoter is used, it is preferable that the DNA sequence operably linked to the promoter starts with an adenine (A) base. The sequences of the nucleic acids may therefore favour the use of one promoter over another.

Alternatively in some embodiments it may be optimal to select promoters that allow for inducible expression of the multiple ddRNAi agents expressed from the ddRNAi construct. A number of systems for inducible expression using such promoters are known in the art, including but not limited to the tetracycline responsive system and the lac operator-repressor system (see WO 03/022052 A1 Publication; and U.S. Patent Publication 2002/0162126 A1), the ecdyson regulated system, or promoters regulated by glucocorticoids, progestins, estrogen, RU-486, steroids, thyroid hormones, cyclic AMP, cytokines, the calciferol family of regulators, or the metallothionein promoter (regulated by inorganic metals such as zinc or cadmium).

Promoters useful in some embodiments of the present invention may be tissue-specific or cell-specific. The term "tissue-specific" as it applies to a promoter refers to a promoter that is capable of directing selective expression of a nucleotide sequence of interest to a specific type of tissue in the relative absence of expression of the same nucleotide sequence of interest in a different type of tissue (e.g., brain). The term "cell-specific" as applied to a promoter refers to a promoter which is capable of directing selective expression of a nucleotide sequence of interest in a specific type of cell in the relative absence of expression of the same nucleotide sequence of interest in a different type of cell within the same tissue The term "cell-specific" when applied to a promoter also means a promoter capable of promoting selective expression of a nucleotide sequence of interest in a region within a single tissue. Alternatively, promoters may be constitutive or regulatable. Additionally, promoters may be modified so as to possess different specificities.

Examples of cell specific promoters particularly useful in this invention include the RPE cell specific promoter RPE-65 and VMD2, and the choroid endothelial-specific promoters FLT-1 or ICAM2.

As noted above, enhancer elements are optionally included in the ddRNAi constructs of the invention.

When the ddRNAi expression cassette or construct contains more than one terminator sequence or element, the terminator sequences or elements may be the same, or different, or there may be a combination of termination elements represented only once and termination elements represented two times or more within any cassette. Whatever terminator sequences or elements are used they should be selected to ensure that they work appropriately with the liver-specific promoter used. In instances where Pol I, Pol II or Pol III promoters are used, appropriate terminator sequences should be employed. Termination elements useful in the present invention include the U1 termination sequence (U1 box), the synthetic polyA terminator, and the so called minimal PolyA terminator. Transcriptional pause sites, such as MAZ1 and MAZ2, (See Ashfield et al EMBO J 1994 Vol 13 No 23 5656 pp and Yonaha and Proudfoot EMBO J. 2000 Jul. 17; 19(14):3770-7) may be inserted upstream of the polyA terminators to assist in coupling of transcription termination and polyadenylation. For Pol III promoters, the sequences TTTT, TTTTT or TTTTTT are commonly used as terminators. In these instances transcripts are typically terminated by the sequence UU.

ddRNAi Agent Expression Constructs ddRNAi agents may be expressed from a DNA expression cassette inserted into any suitable vector or ddRNAi construct, referred to herein as 'ddRNAi constructs'. A challenge in the past to developing therapeutics for AMD has been efficient and uniform transduction of the correct cells to ensure long term expression without the need for recurring administrations.

When the vector backbone of the construct is compatible with a delivery system, the ddRNAi expression constructs are also delivery constructs. A particularly preferred delivery construct is a viral vector. Use of a viral vector, like an adeno-associated virus (AAV), adenovirus (Ad) or lentivirus (LV) to deliver an expression construct that produces the therapeutic ddRNAi agent from within the cell, avoids an interferon response often caused by direct interactions of nucleic acids with surface-expressed toll-like receptor 3. This is a primary reason for a number of failures of siRNA-based ocular drugs in clinical trials.

In the case of the current invention, the ddRNAi agent of the invention is required to reach the retina pigment epithelial (RPE) cells or other cells deep within the retinal layers. To this effect, the invention utilizes a modified adeno-associated virus (AAV) vector, shown in murine models to be able to penetrate the RPE layer following intravitreal injection. Wildtype, unmodified AAV serotypes have limited ability to transduce more than the adjoining layer of cells when introduced into the eye through this route. For this reason, it is preferred that a modified MV vector is utilised in the invention.

For example, site directed mutagenesis of AAV strains has been used to substitute tyrosine residues, leading to increased transduction (Li Zhong, Baozheng Li, Cathryn S. Mah, (2008) Proc Natl Acad Sci USA. 105(22): 7827-7832). Similar modifications to MV vectors have produced vectors that can transduce across all layers of the retina following intravitral injection (Hilda Petrs-Silva, Astra Dinculescu, Qiuhong Li et al. (2009) Mol Ther. 17(3): 463-471). Likewise, specific serine, threonine or lysine residues in AAV vectors have been modified to avoid the host cellular kinase/ubiquitination/proteasomal machinery and significantly increase transduction efficiency (Gabriel N, Hareendran S, Sen D et al. (2013) Hum Gene Ther Methods. 2013 (2):80-93). Methods that generate libraries of AAV capsid mutants can be screened to isolate variants with the desired properties of increased tissue specificity for a specific target tissue or reduced immunogenicity. Recently, Schaffer et al have been able to show broad transretinal delivery following intravitreal injection of an MV mutated vector in which a 7mer peptide had been inserted into the capsid sequence (Dalkara, D., L. C. Byrne, R. R. Klimczak et al. (2013) Science Translational Medicine, 5:189ra76)

Typically, the genome of MV contains only two genes. The "rep" gene codes for at least four separate proteins utilized in DNA replication. The "cap" gene product is spliced differentially to generate the three proteins that comprise the capsid of the virus. When packaging the genome into nascent virus, only the Inverted Terminal Repeats (ITRs) are obligate sequences; rep and cap can be deleted from the genome and be replaced with heterologous sequences of choice. However, in order to produce the proteins needed to replicate and package the AAV-based heterologous construct into nascent virions, the rep and cap proteins must be provided in trans. The helper functions normally provided by co-infection with the helper virus, such as adenovirus or herpesvirus, can also be provided in trans in the form of one or more DNA expression plasmids. Since the genome normally encodes only two genes it is not surprising that, as a delivery vehicle, AAV is limited by a packaging capacity of 4.5 single stranded kilobases (kb). However, although this size restriction may limit the genes that can be delivered for replacement gene therapies, it does not adversely affect the packaging and expression of shorter sequences such as ddRNAi vectors.

The invention provides a ddRNAi expression construct comprising a ddRNAi expression cassette according for expressing a ddRNAi agent for inhibiting expression of one or more target sequences in an AMD associated gene, the expression cassette comprising (in no particular order)
- one or more promoter sequences
- one or more DNA sequences that encode for one or more effector sequences,
- one or more DNA sequences that encode for one or more effector complement sequences;

and optionally
- one or more terminator sequences
- one or more DNA sequences that encode for loop sequences, spacer sequences, or both
- one or more enhancer sequences, wherein the construct is a viral delivery construct; preferably the viral delivery construct is an MV modified vector.

Preferably the expression cassette further comprises ME sequence so that the ddRNAi agent is expressed as part of or within a miRNA structure.

In a preferred embodiment, the expression cassette of the viral delivery construct comprises two DNA sequences that encode a first effector sequence of any 10 or more contiguous nucleotides within 5' UGUAACAGAUGAGAUG-CUCCA 3' of the AMD-associated gene VEGRF-2 (SEQ ID NO:56) and a second effector sequence of any 10 or more contiguous nucleotides within 5' UAUGUGGGUGGGU-GUGUCUAC 3' of the AMD-associated gene VEGF-A (SEQ ID NO:47).

The expression of the ddRNAi agents of the invention following viral delivery will be durable, potentially up to the life of a patient, from a single administration of the drug. Accordingly, in another aspect of the invention, there is provided a ddRNAi therapeutic comprising a viral vector into which a ddRNAi expression cassette according to the invention is inserted. Preferably the expression cassette encodes for multiple ddRNAi agents, as either long hairpin structures or multiple hairpin structures selected from the combinations and embodiments described throughout the specification. In a preferred embodiment, the effector sequences and the effector complement sequences of the ddRNAi agents are expressed within a miRNA structure.

Typically, in the production of viral vectors, the normal endogenous genes of a virus can be deleted from the genome and be replaced with heterologous sequences of choice. However, in order to produce the proteins needed to replicate and package the virus-based heterologous construct into nascent virion, the viral proteins stripped from the genome must be provided in trans. Generation of the construct can be accomplished using any suitable genetic engineering techniques well known in the art, including without limitation, the standard techniques of PCR, oligonucleotide synthesis, DNA synthesis, restriction endonuclease digestion, ligation, transformation, plasmid purification, and DNA sequencing. The viral construct also may contain genes that allow for replication and propagation of virus, though in preferred embodiments such genes will be supplied in trans. Additionally, the ddRNAi construct may contain genes or genetic sequences from the genome of any known organism incorporated in native form or modified. For example, the preferred viral construct comprises sequences useful for, replication of the construct in bacteria.

After generation of the viral based ddRNAi construct, the construct is packaged into viral particles. Any method known in the art may be used to produce infectious viral particles whose genome comprises a copy of the viral ddRNAi construct. One method utilizes packaging cells that stably express in trans the viral proteins that are required for the incorporation of the viral ddRNAi construct into viral particles, as well as other sequences necessary or preferred for a particular viral delivery system (for example, sequences needed for replication, structural proteins and viral assembly) and either viral-derived or artificial ligands for tissue entry. Following transfection of the viral ddRNAi construct into packaging cells, the packaging cells then replicate viral sequences, express viral proteins and package the ddRNAi expression constructs into infectious viral particles. The packaging cell line may be any cell line that is capable of expressing viral proteins, including but not limited to 293, HeLa, A549, PerC6, D17, MDCK, BHK, bing cherry, phoenix, Cf2Th, or any other line known to or developed by those skilled in the art. One packaging cell line is described, for example, in U.S. Pat. No. 6,218,181.

Alternatively, a cell line that does not stably express necessary viral proteins may be co-transfected with one or more constructs to achieve efficient production of functional particles. One of the constructs is the viral based ddRNAi construct; the other construct comprises nucleic acids encoding the proteins necessary to allow the cells to produce functional virus as well as other helper functions.

The packaging cell line or replication and packaging construct may not express envelope gene products. In these embodiments, the gene encoding the envelope gene can be provided on a separate construct that is co-transfected with the viral based ddRNAi construct. As the envelope protein is responsible, in part, for the host range of the viral particles, the viruses may be pseudotyped. As described supra, a "pseudotyped" virus is a viral particle having an envelope protein that is from a virus other than the virus from which the genome is derived. One with skill in the art can choose an appropriate pseudotype for the viral delivery system used and cell to be targeted.

In addition to conferring a specific host range, a chosen pseudotype may permit the virus to be concentrated to a very high titer. Viruses alternatively can be pseudotyped with ecotropic envelope proteins that limit infection to a specific species (e.g., ecotropic envelopes allow infection of, e.g., murine cells only, where amphotropic envelopes allow infection of, e.g., both human and murine cells). In addition, genetically-modified ligands can be used for cell-specific targeting.

After production in a packaging cell line, the viral particles containing the ddRNAi expression cassettes are purified and quantified (titred). Purification strategies include density gradient centrifugation, or, preferably, column chromatographic methods.

Methods

Administration of ddRNAi agents, ddRNAi constructs of siRNA agents of the invention inhibits expression of genes expressed in cells within the retina. Accordingly, in another aspect of the invention, there is provided a method of treating AMD in an individual comprising the administration of a therapeutically effective amount of a ddRNAi construct to a patient in need of treatment, wherein the ddRNAi agent inhibits expression of one or more target sequences in an AMD-associated gene, preferably a VEGF-A gene. Preferably, the AMD to be treated is wet AMD.

The ddRNAi agent to be administered to the patient may be one or more of:
- ddRNAi agent comprising a first effector sequence; and a first effector complement sequence; wherein the effector sequence is substantially complementary to one or more target regions in a transcript of the one or more target sequences
- ddRNAi agent comprising, in a 5' to 3' direction, a first effector sequence; a second effector sequence; a second effector complement sequence; and a first effector complement sequence, wherein each effector sequence is substantially complementary to one or more target regions in a transcript of the one or more target sequences a ddRNAi agent comprising, in a 5' to 3' direction, a first effector sequence; a second effector sequence; a third effector sequence; a third effector complement sequence; a second effector complement sequence; and a first effector complement sequence wherein each effector sequence is substantially complementary to one or more target regions in a transcript of the one or more target sequences a ddRNAi agent comprising, in a 5' to 3' direction, a first effector sequence; a first effector complement sequence; a second effector sequence; and a second effector complement sequence wherein each effector sequence is substantially complementary to one or more target regions in a transcript of the one or more target sequences a ddRNAi agent comprising, in a 5' to 3' direction, a first effector sequence; a first effector complement sequence; a second effector sequence; a second effector complement sequence; a third effector sequence; and a third effector complement sequence; wherein each effector sequence is substantially complementary to one or more target regions in a transcript of the one or more target sequences a ddRNAi agent comprising, in a 5' to 3' direction, a first effector sequence; a second effector sequence; a loop sequence of 2 to 100 non-self-complementary nucleotides; a second effector complement sequence; and a first effector complement sequence wherein each effector sequence is substantially complementary to one or more target regions in a transcript of the one or more target sequences a ddRNAi agent comprising, in a 5' to 3' direction, a first effector sequence; a loop sequence of 2 to 100 non-self-complementary nucleotides; a first effector complement sequence; a second effector sequence; a loop sequence of 2 to 100 non-self-complementary nucleotides; and a second effector complement sequence wherein each effector sequence is substantially complementary to one or more target regions in a transcript of the one or more target sequences a ddRNAi agent comprising, in a 5' to 3' direction, a first effector sequence; a loop sequence of 2 to 100 non-self-complementary nucleotides; a first effector complement sequence; a spacer sequence of 2 to 100 non-self-complementary nucleotides; a second effector sequence; a loop sequence of 2 to 100 non-self-complementary nucleotides; and a second effector complement sequence wherein each effector sequence is substantially complementary one or more target regions in a transcript of the one or more target sequences a ddRNAi agent comprising, in a 5' to 3' direction, a first effector sequence; a first effector complement sequence; a spacer sequence of 2 to 100 non-self-complementary nucleotides; a second effector sequence; a second effector complement sequence; a spacer sequence of 2 to 100 non-self-complementary nucleotides; a third effector sequence; and a third effector complement sequence any of the above mentioned ddRNAi agents expressed within or as part of an miRNA structure.

As would be understood by one skilled in the art, and as illustrated in the Figures, any particular effector sequence may be swapped in position with its complement in the ddRNAi agent. In particular forms of each of the embodiments described above, each effector sequence is at least 17 nucleotides in length selected from the group consisting of any 10 or more and preferably any 17 or more contiguous nucleotides within a sequence from any one of SEQ ID NOS: 40-78. The effector sequences may all be the same, or may all be different, or may be a combination e.g. 2 effector sequences of at least 10 contiguous nucleotides of SEQ ID NO:47 and 1 effector sequence of at least 10 contiguous nucleotides of (for example) SEQ ID NO: 56.

Preferably, the effector sequence is selected from the group consisting of any contiguous 11, 12, 13, 14, 15 or 16 nucleotides within any one of SEQ ID NOS: 40-78, and most preferably 17 or more contiguous nucleotides within any one of SEQ ID NOS: 40-78. Typically, the effector complement will be the same length, or about the same length (ie ±15% nucleotide length, or 1 to 3 nucleotides different depending on the overall length) as its corresponding effector sequence.

Each of these ddRNAi agents may be administered via a ddRNAi expression cassette in a ddRNAi construct, as described in the earlier sections of the specification. Preferably the ddRNAi construct is the AAV based construct to enable targeting of the construct to the RPE cells in the back of the eye. Multiple targeting may be achieved by delivering two or more ddRNAi expression cassettes or constructs each capable of expressing a single ddRNAi agent, or alternatively, and most preferably, by delivering one ddRNAi expression cassettes or constructs capable of expressing more than one ddRNAi agent.

In alternative embodiments, each of the effector sequences may be 100% complementary to one or more target regions in a transcript of the one or more target sequences, or may only vary by 1, 2, 3, 4 or 5 nucleotides.

The method of treating AMD can optionally include a preliminary step of identifying an individual having symptoms of AMD and requiring treatment. That identification step can include differentially diagnosing the subject as having wet AMD or dry AMD.

For longer term or stable provision of the ddRNAi agents of the invention, the ddRNAi agent is provided via a ddRNAi construct of the invention ie in vivo expression of the ddRNAi agent from a ddRNAi expression cassette inserted into a suitable vector delivered to the cell. The ddRNAi expression cassette comprises:
  one or more promoter sequences
  one or more DNA sequences selected from the group consisting of sequences that encode for any 10 or more contiguous nucleotides within a sequence from SEQ ID NOS: 40-78;
  one or more DNA sequences that encode for one or more effector complement sequences;
  and optionally
  one or more terminator sequences
  one or more DNA sequences that encode for loop sequences, spacer sequences or both
  one or more enhancer sequences.

As outlined earlier in the specification, these components of the ddRNAi expression cassette may have different 5' to 3' arrangements, all of which are suitable for use in the methods of the invention. The expression cassette preferably also includes DNA sequences that encode sequence capable of forming a miRNA structure.

Preferably, the target AMD-associated gene in the methods of the invention is VEGF-A. Accordingly, in one embodiment of the invention, the ddRNAi agent inhibits expression of one or more target sequences in the VEGF-A gene. The DNA sequence that encodes for the first effector sequence is preferably selected from the ddRNAi effector encoding sequences of any 10 or more contiguous nucleotides within a sequence from SEQ ID NOS: 40-49 listed in Table 1. Alternatively, as detailed earlier, the sequence that encodes for the effector sequence may vary from SEQ ID NOS: 40-49 by 1, 2, 3, 4 or 5 nucleotides without effecting the ability of the sequence encoded to base pair with the target sequence and inhibit expression of the VEGF-A target sequence.

Typically, each effector sequence forms a double stranded region with the corresponding effector complement sequence.

In an alternative embodiment, the target AMD-associated gene in the methods of the invention is one or more of VEGFR2, CFB and PDGFR-β.

In an alternative embodiment, the method of treating AMD in an individual comprises the administration of a therapeutically effective amount of a ddRNAi construct that encodes a ddRNAi agent having more than one effector sequence, such as those listed above as SEQ. ID NOS: 40-78, for inhibiting, preventing or reducing expression of one or more target sequences in an AMD associated gene.

In any of the treatment methods of the invention, the patient may also be receiving other treatments, such that the ddRNAi construct administered is an adjunct therapy.

AMD, and wet AMD in particular, is characterised by an abnormal outgrowth of blood vessels from the vasculature situated behind the retina in a process that is often referred to as choroidal neovascularization (CNV). Controlling CNV therefore has a positive effect on patients suffering from wet AMD. Accordingly, another aspect of the invention is a method of treating choroidal neovascularization in an individual comprising the administration of a therapeutically effective amount of a ddRNAi agent, expression cassette or construct of the invention to a patient in need of treatment, wherein the ddRNAi agent inhibits expression of one or more target sequences in one or more of VEGF-A, VEGFR2, CFB and PDGFR-β. Each of these genes is a target of interest by virtue of their role in angiogenesis, neovascularisation or the VEGF pathway.

Another important factor in the pathogenesis of AMD is the formation of extracellular deposits at the base of the eye called drusen. These deposits contribute to distortion of the macular and may also play a role in neovascularisation. CFB is a component of drusen. As such, targeting the CFB gene to inhibit expression of its protein product can reduce the amount of drusen being deposited, therefore having a positive effect on patients suffering from AMD. There is therefore provided a method of reducing drusen deposits in an individual comprising the administration of a therapeutically effective amount of a ddRNAi agent, expression cassette or construct of the invention to a patient in need of treatment, wherein the ddRNAi agent inhibits expression of one or more target sequences in CFB.

Seeking to minimise angiogenesis and therefore CNV, together with seeking to inhibit drusen deposition by way of targeting combinations of VEGF-A, VEGFR2, CFB and PDGFR-β therefore provides a multi-pronged attack strategy for AMD, particularly wet AMD, that has not been previously contemplated in the art, and seeks to not only stop progression of AMD, but to restore visual acuity.

In some instances, it may be preferred to rely on the transient presence of a ddRNAi agent or siRNA agent as opposed to long term expression of ddRNAi agents from integrated or stably maintained ddRNAi constructs. For example, where the patient's tolerance to the treatment is to be determined first. In this instance, a ddRNAi agent or siRNA agent of the invention produced in vitro may be administered.

In a further aspect of the invention there is provided a composition comprising ddRNAi constructs, ddRNAi agents or siRNA agents as an active ingredient for inhibiting, preventing or reducing expression of one or more target sequences in an AMD associated gene, to treat AMD, treat CNV, minimise drusen deposition or alleviate the symptoms of AMD.

In a further aspect of the invention there is provided use of a ddRNAi construct, ddRNAi agent or siRNA agent for inhibiting, preventing or reducing expression of one or more target sequences in an AMD associated gene, to treat AMD, treat CNV, minimise drusen deposition or alleviate the symptoms of AMD. Similarly, there is provided use a ddRNAi construct, ddRNAi agent or siRNA agent in the preparation of a medicament for inhibiting, preventing or reducing expression of one or more target sequences in an AMD associated gene, to treat AMD, treat CNV, minimise drusen deposition or alleviate the symptoms of AMD.

Preferably the AMD is wet AMD.

The one or more effector sequences of the ddRNAi constructs, ddRNAi agents or siRNA agents used in the methods of the invention comprise any 10 or more, preferably any 17 or more, contiguous nucleotides within sequences able to inhibit the expression of the AMD-associated target gene region by at least 70%. Preferably the one or more effector sequence is selected from SEQ ID NOS: 40-78, more preferably SEQ ID NOS: 40-59, and most preferably SEQ ID NOS: 40-49.

In each of the methods of the invention, the ddRNAi agent, ddRNAi expression cassette or ddRNAi expression construct of the invention is preferably delivered to the subject's eye/s by intravitreal injection, although subretinal injection may also be utilised.

Pharmaceutical Compositions

The ddRNAi agents, the siRNA agents or the vectors comprising ddRNAi expression cassettes of the invention can be formulated into pharmaceutical compositions by combination with appropriate, pharmaceutically acceptable carriers or diluents. Accordingly, there is provided a pharmaceutical composition comprising a ddRNAi agent, a ddRNAi expression cassette, a ddRNAi construct or a siRNA agent of the invention for inhibiting, preventing or reducing expression of one or more target sequences in an AMD associated gene, and a pharmaceutically acceptable carrier or diluent.

In another embodiment the invention provides an AMD treatment composition comprising an effective amount of a ddRNAi agent, ddRNAi expression cassette or ddRNAi expression construct of the invention as a main ingredient for inhibiting, preventing or reducing expression of one or more target sequences in an AMD associated gene, optionally with a pharmaceutically acceptable carrier or diluent.

In pharmaceutical dosage forms, the agents or the vectors comprising the ddRNAi expression cassettes may be administered alone or in association or combination with other pharmaceutically active compounds. Those with skill in the art will appreciate readily that dose levels for agents or vectors comprising the ddRNAi expression cassettes will vary as a function of the nature of the delivery vehicle, the relative ease of transduction of the target cells, the expression level of the RNAi agents in the target cells and the like.

The ddRNAi agents, the siRNA agents or the vectors comprising ddRNAi expression cassettes of the invention can be formulated into preparations for injection or administration by dissolving, suspending or emulsifying them in an aqueous or non-aqueous solvent, such as oils, synthetic aliphatic acid glycerides, esters of higher aliphatic acids or propylene glycol; and if desired, with conventional additives such as solubilisers, isotonic agents, suspending agents, emulsifying agents, stabilizers and preservatives.

The most preferred mode of administration of the pharmaceutical composition of the invention to the subject's eye/s is by intravitreal injection. An alternative method of administration is subretinal injection.

Pharmaceutically acceptable carriers or diluents contemplated by the invention include any diluents, carriers, excipients, and stabilizers that are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as plasma albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG).

In general the formulations are prepared by uniformly and intimately bringing into association the active ingredient with liquid carriers or finely divided solid carriers or both, and if necessary, shaping the product. Formulation may be conducted by mixing at ambient temperature at the appropriate pH, and at the desired degree of purity, with physiologically acceptable carriers, i.e., carriers that are non-toxic to recipients at the dosages and concentrations employed.

The one or more effector sequences of the ddRNAi constructs, ddRNAi agents or siRNA agents used in the compositions of the invention comprise any 10 or more, preferably any 17 or more, contiguous nucleotides within sequences able to inhibit the expression of the AMD-associated target gene region by at least 70%. Preferably the one or more effector sequence is selected from SEQ ID NOS: 40-78, more preferably SEQ ID NOS: 40-59, and most preferably SEQ ID NOS: 40-49.

In another embodiment there is provided a kit or article of manufacture including an RNAi agent or pharmaceutical composition as described above.

In other embodiments there is provided a kit for use in a therapeutic application mentioned above, the kit including:
 a container holding a RNAi agent or pharmaceutical composition;
 a label or package insert with instructions for use.

In certain embodiments the kit may contain one or more further active principles or ingredients for treatment of AMD or for treating an AMD-related condition as described above.

The kit or "article of manufacture" may comprise a container and a label or package insert on or associated with the container. Suitable containers include, for example, bottles, vials, syringes, blister pack, etc. The containers may be formed from a variety of materials such as glass or plastic. The container holds an RNAi agent or pharmaceutical composition which is effective for treating the condition and may have a sterile access port (for example the container may be an intravenous solution bag or a vial having a stopper pierceable by a hypodermic injection needle). The label or package insert indicates that the RNAi agent or pharmaceutical composition is used for treating the condition of choice. In one embodiment, the label or package insert includes instructions for use and indicates that the RNAi agent or pharmaceutical composition can be used to treat AMD or for treating a AMD-related condition as described above.

The kit may comprise (a) an RNAi agent or pharmaceutical composition; and (b) a second container with a second active principle or ingredient contained therein. The kit in this embodiment of the invention may further comprise a package insert indicating that the RNAi agent or pharmaceutical composition and other active principle can be used to treat AMD or for treating an AMD-related condition as described above. Alternatively, or additionally, the kit may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

In certain embodiments an RNAi agent or pharmaceutical composition may be provided in the form of a device, disposable or reusable, including a receptacle for holding the RNAi agent or pharmaceutical composition. In one embodiment, the device is a syringe, preferably a syringe suitable for intravitreal injection or subretinal injection. The device may hold 1-2 mL of the RNAi agent or pharmaceutical composition. The RNAi agent or pharmaceutical composition may be provided in the device in a state that is ready for use or in a state requiring mixing or addition of further components.

The invention is now described with reference to the following non-limiting examples.

EXAMPLES

1. Design and Preparation of Constructs to Silence VEGF-A ddRNAi constructs expressing shRNAs targeting VEGF-A were designed, to recognise RNAi target sequences in the VEGF-A mRNA that are well conserved between human and the pre-clinical test species mouse and macaque. 10 ddRNAi constructs (miR-1, miR-2, miR-3, miR-4, miR-5, miR-6, miR-7, miR-8, miR-9 and miR-10) were generated to express the effector sequences listed in Table 2. Oligonucleotides were synthesised (Sigma Aldrich) and assembled to produce BamHI/Hind III fragments that was cloned into the BamHI/Hind III sites of pSilencer 2.1-U6 hygro according to the manufacture's protocol (Invitrogen). These constructs used the human U6 promoter to drive expression of shRNAs. Maps of the vector and an insert for one such construct are shown In FIGS. 2A and 2B. The sequence of the insert and predicted secondary structure of the expressed shRNA for miR-8 are shown in FIGS. 2C and 2D. Sequences of the BamHI/Hind III fragments used to prepare miRs-1 to 10 are listed as SEQ ID NOS: 91-100.

2. Activity and Strand-Specificity of Constructs Targeting VEGF-A

Dual luciferase assays were used to determine the activity of miR constructs. Because firefly luciferase has a relatively short half-life of approximately four hours, measurement of firefly luciferase activity provides a surrogate marker for assessing RNAi inhibitory activity. For these experiments, sensor constructs containing regions of VEGF-A cDNA were cloned into the 3' UTR of a firefly luciferase expression construct pGL3 (Promega). Regions of a VEGF-A cDNA clone, obtained from Open Biosystems (a Thermo-Scientific company), were amplified by PCR using methods well known in the art, to prepare fragments flanked by XbaI and FseI restriction sites; these amplified fragments were then cloned into the XbaI/FseI sites in the 3' UTR of pGL3. Five separate regions of VEGF-A were amplified in this way to prepare reporter constructs that could be used to assay miR 1-10, as shown in Table 3. These five regions (A to E, Table 3) were cloned in both orientations which allowed the strand preference of RISC loading to be determined. "Sense" reporter constructs assayed activity of passenger strands, while reporters termed "antisense" assayed activity of effector strands. ddRNAi constructs with strong effector activity and weak passenger activity are strongly favoured for therapeutic use since, as discussed above, since these are likely to produce less off target effects.

To assay the activity and strand-preference of each of the miR constructs targeting VEGF-A, dual luciferase assays were performed according to manufacturer's (Promega) protocol. Briefly a specific ddRNAi construct was co-transfected along with the appropriate VEGF-A sensor and a *Renilla* luciferase expressing plasmid (pRL: Promega), the latter of which was to normalize for transfection efficiency between wells, into HEK293T cells using Fugene according to manufacturer's (Roche Applied Sciences) protocol. Cells were cultured for 48 hrs and Dual Luciferase assays performed according to manufacturer's (Promega) protocol using a Turner Biosystems Veritas luminometer.

Results of typical experiments are shown in FIG. 4A. These data showed that all 10 ddRNAi constructs showed significant silencing of the antisense target, but differed significantly in activity against the sense target, reflecting marked differences in RISC loading of passenger strands between the different ddRNAi constructs. Based on these data miRs-2, 5 and 8 were chosen for further analyses.

To confirm the activity of these constructs against native VEGF-A, HEK293T cells were co-transfected with an expression plasmid expressing VEGF-A protein along with expression constructs for miR-2, 5 and 8 using Fugene according to manufacturer's (Roche Applied Sciences) protocol. After 48 hrs RNA were isolated using a modified Trizol Protocol (Invitrogen). VEGF-A mRNA levels were determined using RT QPCR Assay on Demand according to manufacturer's protocol (Applied Biosystems Inc). These data (FIG. 4B) show that VEGF-A shMiRs 2, 5 and 8 significantly reduce steady state VEGF-A mRNA levels in the transfected cells.

To further validate the activity of shMiR-8 against endogenously expressed VEGF-A, a spontaneously arising retinal pigment epithelia (RPE) cell line termed ARPE-19 were transduced with an adenovirus construct (MOI=200) that expresses miR-8. RNA and protein were isolated from cells at 24, 48, 72 and 96 hrs. VEGF-A mRNA levels were determined using RTQPCR as described above. Protein levels were determined using an ELISA assay performed with the Human VEGF Quantikine ELISA Kit according to manufacturer's (R&D Systems) protocol. These data (FIG. 4C) showed that miR-8 potently silences VEGF-A expression at both the protein and mRNA level, with levels of knockdown increasing over time.

To quantify levels of shRNA expression from miR-8, a custom RT-QPCR assay was developed. A synthetic RNA standard (Sigma Aldrich) and forward DNA primers (Sigma Aldrich) were used to develop this assay in order to quantify the levels of effector RNA processed from the expressed shRNA of miR-8. The sequences of the synthetic RNA standard and DNA primers were:

Synthetic RNA standard: UGGGUUAUGUGGGUGGGUGUGUCUACCGCCU (SEQ ID NO: 130)

Forward primer (DNA): TATGTGGGTGGGTGTGTCTAC (SEQ ID NO: 131)

Reverse primer (DNA): miScript Universal Primer from kit (Qiagen)

RNAs were reverse transcribed using the miSCRIPT Reverse Transcription Kit according to manufacturer's protocol (Qiagen). Components of this kit polyadenylate RNAs and synthesise cDNA copies via the actions of reverse transcriptase and a clamped oligo dT primer which acts as a primer for cDNA synthesis. cDNAs were amplified and quantified using SYBR green QRT PCR assays, using protocols well known to those familiar with the art. Known amounts of the synthetic RNA standard were reverse transcribed and QPCR amplified to prepare a standard curve. RNAs were isolated from the aforementioned ARPE-19 cells and levels of expressed shRNA were quantified using this assay. FIG. 4B shows that the levels of processed shRNA expressed form miR-8 increased over time and correlated with levels of VEGF-A knockdown at the protein and RNA level. Take together these data showed that miR-8 potently silenced VEGF-A. Note that the VEGF-A target sequences and effector sequences of miRs-2, 5 and 8 show absolute conservation of nucleotide sequences between human and the pre-clinical test species mouse and macaque.

3. Design and Preparation of Constructs to Silence VEGFR2 ddRNAi constructs expressing shRNAs targeting VEGFR2 were designed, using the criteria described above, to recognise target sequences in VEGFR2 mRNA that are conserved between human and the pre-clinical test species mouse and macaque. In most cases, it was difficult to find sequences that were absolutely conserved between human, mouse and monkey species. 10 ddRNAi constructs (miR-V-1, miR-V-2, miR-V-3, miR-V-4, miR-V-5, miR-V-6, miR-V-7, miR-V-8, miR-V-9 and miR-V-10) were constructed. Sequences of the BamHI/HindIII fragments used to prepare these are listed as SEQ ID NOS: 101-110 as summarised in Table 2. Inserts were cloned into pSilencer 2.1-U6 hygro as described in Example 1.

4. Activity and Strand-Specificity of Constructs Targeting VEGFR2

Dual luciferase assays were performed as described above to determine the activity and strand-preference of miR-V-1 through miR-V-10 using the protocol described in Example 2 and the reporter constructs listed in Table 3.

TABLE 3

Reporter constructs used to assay activity and strand specificity of miR constructs.

| Target gene | GB Accession | Reporter code[a] | Positions[b] | miR[c] |
|---|---|---|---|---|
| VEGF-A | NM_001025366 (SEQ ID NO:79) | A-sense | 727-1221 | miR-2 |
| | | B-sense | 1077-1829 | miR-3, 4 & 5 |
| | | C-sense | 1715-2357 | miR-6, 7 & 8 |
| | | D-sense | 3149-3614 | miR-9 & 10 |
| | | E-sense | 299-366 | miR-1 |
| | | A-antisense | 727-1221 | miR-2 |
| | | B-antisense | 1077-1829 | miR-3, 4 & 5 |

TABLE 3-continued

Reporter constructs used to assay activity and strand specificity of miR constructs.

| Target gene | GB Accession | Reporter code[a] | Positions[b] | miR[c] |
|---|---|---|---|---|
| | | C-antisense | 1715-2357 | miR-6, 7 & 8 |
| | | D-antisense | 3149-3608 | miR-9 & 10 |
| | | E-antisense | 299-366 | miR-1 |
| PDGFR-B | NM_002609 (SEQ ID NO:85) | A-sense | 843-1340 | miR-P-1, 2 |
| | | B-sense | 1920-2435 | miR-P-3 |
| | | C-sense | 2672-3212 | miR-P-4, 5, 6, 7, 8 & 9 |
| | | D-sense | 2872-3421 | miR-P-4, 5, 6, 7, 8, 9 & 10 |
| | | A-antisense | 843-1340 | miR-P-1, 2 |
| | | B-antisense | 1920-2435 | miR-P-3 |
| | | C-antisense | 2672-3212 | miR-P-4, 5, 6, 7, 8 & 9 |
| | | D-antisense | 2872-3421 | miR-P-4, 5, 6, 7, 8, 9 & 10 |
| VEGFR-2 | NM_002253 (SEQ ID NO:82) | A-sense | 382-1098 | miR-V1, 2 |
| | | B-sense | 2519-3098 | miR-V-3, 4, & 5 |
| | | C-sense | 3078-3567 | mir-V-6, 7 & 8 |
| | | D-sense | 3549-4108 | mir-V-9 & 10 |
| | | A-antisense | 382-1098 | miR-V1, 2 |
| | | B-antisense | 2520-3098 | miR-V-3, 4, & 5 |
| | | C-antisense | 3078-3567 | mir-V-6, 7 & 8 |
| | | D-antisense | 3549-4108 | mir-V-9 & 10 |
| CFB | NM_001710 (SEQ ID NO:88) | A-sense | 739-1261 | miR-C-1, 2, 3 & 4 |
| | | B-sense | 1361-1901 | miR-C-, 5, 6 & 7 |
| | | C-sense | 2008-2568 | miR-C-8 & 9 |
| | | A-antisense | 739-1261 | miR-C-1, 2, 3 & 4 |
| | | B-antisense | 1361-1901 | miR-C-5, 6 & 7 |
| | | C-antisense | 2008-2568 | miR-C-8 & 9 |

[a]Code describing the particular luc fusion construct used in dual luciferase assays to assay the activity and strand specificity of miR constructs.
[b]Sequences included in luc fusion constructs.
[c]miR constructs assayed with individual reporters.

Results of these experiments are shown in FIG. 5A. These data showed that all 10 constructs could achieve significant silencing of the antisense reporter construct but differed significantly in activity against the sense reporter construct, reflecting marked differences in RISC loading of passenger strands between the different ddRNAi constructs and the resulting consequent propensities for off-target effects. Based on these data, miR-V-2, -3, -7 and -10 were chosen for subsequent analyses.

Figure 5C:
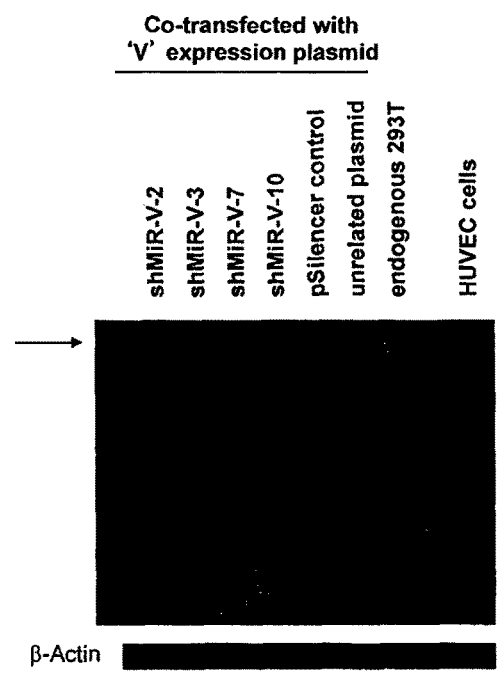

To confirm the activity of these constructs against native VEGFR2 mRNA, HEK 293T cells were co-transfected with plasmids expressing VEGFR2 miRs-V-2, 3, 7 and 10 and an expression plasmid expressing the full length cDNA for VEGFR2 using Fugene according to manufacturer's (Roche Applied Sciences) protocol. After 72 hours RNA were isolated as described above. VEGFR2 mRNA levels were determined using a RT QPCR "Assay on Demand" according to manufacturer's protocol. These data (FIG. 5B) showed that miRs-V-2, 3, 7 and 10 significantly reduced steady state. VEGFR2 mRNA levels compared to controls. FIG. 5C shows that miRs-V-2, 3, 7 and 10 also strongly reduced VEGFR2 protein levels in parallel wells of transfected cells as assessed by Western blot analysis. Take together these data showed that miRs-V-2, 3, 7 and 10 potently silenced VEGFR-2.

5. Design and Preparation of Constructs to Silence PDGFR-β ddRNAi constructs expressing shRNAs targeting PDGFR-B were designed, using the criteria described above, to recognise target sequences in PDGFR-B mRNA that are well conserved between human and the pre-clinical test species mouse and macaque. In most cases, there is a single nucleotide mismatch between the human sequence and the corresponding sequences in both the mouse and monkey models. 10 ddRNAi constructs (miR-P-1, miR-P-2, miR-P-3, miR-P-4, miR-P-5, miR-P-6, miR-P-7, miR-P-8, miR-P-9 and miR-P-10) were made. Sequences of the BamHI/HindIII fragments used to prepare these are listed as SEQ ID NOS: 111-120 as summarised in Table 2. Inserts were cloned into pSilencer 2.1-U6 hygro as described in Example 1.

6. Activity and Strand-Specificity of Constructs Targeting PDGFR-β

Dual luciferase assays were performed as described above and used to determine the activity and strand preference of miR-P-1 through miR-10 using the protocol described in Example 2 with the reporter constructs listed in Table 3. These data showed that all 10 constructs showed significant silencing of the antisense reporter construct. Based on these data miR-P-4 and miR-P-9 were chosen for subsequent analyses.

To confirm the activity of these constructs against native PDGFR-β mRNA, HEK 293T cells were co-transfected with plasmids expressing either PDGFR-β miRs-P-4, or miR-P-9 and a plasmid expressing a full length cDNA of PDGFR-β using Fugene according to manufacturer's (Roche Applied Sciences). After 48 hours RNA was isolated as described above. PDGFR-β mRNA levels were determined using a RT QPCR "Assay on Demand" according to manufacturer's protocol. These data (FIG. 6A) showed that miRs-P-4 and miR-P-9 significantly reduced steady state PDGFR-B mRNA levels compared to controls. FIG. 6B shows that miR-P-4 and miR-P-9 also strongly reduced PDGFR-β protein levels in parallel transfected wells of cells as compared to controls. Take together these data showed that miR-P-4 and miR-P-9 potently silenced PDGFR-β.

7. Design and Preparation of Constructs to Silence CFB ddRNAi constructs expressing shRNAs that target CFB were designed, using the criteria described above, to recognise target sequences in CFB mRNA that are conserved between human and the pre-clinical test species mouse and macaque. In most cases, there is either a single nucleotide mismatch or multiple mismatches between the human sequence and the corresponding sequences in both the mouse and monkey models. 9 ddRNAi constructs (miR-C-1, miR-C-2, miR-C-3, miR-C-4, miR-C-5, miR-C-6, miR-C-7, miR-C-8 and miR-C-9) were made. Sequences of the BamHI/HindIII fragments used to prepare these are listed as SEQ ID NOS: 121-129 as summarised in Table 2. Inserts were cloned into pSilencer 2.1-U6 hygro as described in Example 1.

8. Activity and Strand-Specificity of Constructs Targeting CFB

Dual luciferase assays were used as described above to determine the activity and strand preference of miRs-C-1 to 9 using the protocol described in Example 2 with the reporter constructs listed in Table 3. Results of these experiments are shown in FIG. 7A. These data showed that most of the constructs showed significant silencing of the antisense reporter construct, but differed significantly in activity against the sense reporter construct, reflecting marked differences in RISC loading of passenger strands between the different ddRNAi constructs and consequent potential for off-target effects. Based on these data miR-C-1, miR-C-8 and miR-C-9 were chosen for subsequent analyses.

Figure 7C:
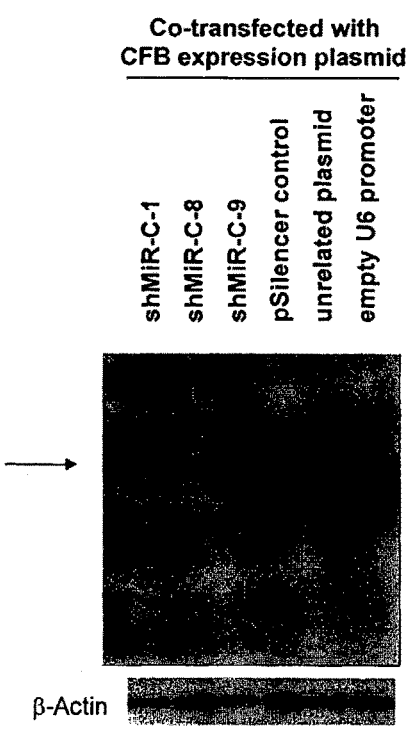

To confirm the activity of these constructs against native CFB mRNA, HEK 293T cells were co-transfected with plasmids expressing either miRs-C-1, miR-C-8 or miR-C-9 and a plasmid expressing the full length cDNA for CFB using the above mentioned methods. After 48 hours RNA was harvested and CFB mRNA levels were determined using a RT QPCR "Assay on Demand". These data (FIG. 7B) showed that miR-C-1, miR-C-8 and miR-C-9 significantly reduced steady state CFB mRNA levels compared to control treated cells. FIG. 7C shows that miRs-C-1, miR-C-8 or miR-C-9 also strongly reduced CFB protein levels parallel transfected cells as compared to controls. As determined by western blot analysis. Taken together these data showed that miRs-C-1, miR-C-8 and miR-C-9 potently silenced CFB.

9. Constructs Targeting VEGF-A

Constructs designed to express therapeutic miR-based shRNAs targeting VEGF-A were prepared. These used either the U6 promoter which would express shRNAs in all cells, or one of four tissue-specific promoters which would express therapeutic shRNAs in appropriate cells. The four tissues-specific promoters were human VDM2 promoter, human ICAM2 promoter, human RPE65 promoter and human FLT promoter.

DNA fragments were synthesised (Blue Herron) that consisted of promoter sequences fused to the miR-7 sequences described in FIG. 2C. These fragments contained flanking restriction sites to allow cloning into AAV vectors; for constructs using pol II promoters the MV vectors contained a minimal polyadenylation site to ensure appropriate transcriptional termination. Maps of these fragments are shown in FIG. 9 and are listed as SEQ ID NOS: 132 through to SEQ ID NOS: 136.

10. Constructs Targeting VEGF-A and VEGFR2

Constructs designed to express therapeutic miR-based shRNAs targeting VEGFF-A and VEGFR2 were prepared. These used either the U6 promoter which would express shRNAs in all cells, or one of the four tissue-specific promoters in Example 9.

DNA fragments were synthesised (Blue Herron) that consisted of promoter sequences fused to the miR-7-miR-V-7 sequences and contained flanking restriction sites to allow cloning into AAV vectors as described in Example 9. Maps of these fragments are shown in FIG. 10 and are listed as SEQ ID NOS: 137 through to SEQ ID NOS: 141.

11. Constructs Targeting VEGFR2, PDGFR-β and CFB

Constructs designed to express therapeutic miR-based shRNAs targeting VEGFR2, PDGFR-β and CFB were prepared. These used either the U6 promoter which would express shRNAs in all cells, or one of the four tissue-specific promoters in Example 9. Each of the hairpins from single constructs miR-V-7, miR-C-8 and miR-P-9 sequences were subcloned into a single vector (in the same order) using a series of restriction enzymes that were engineered into the single vectors. The resultant expression construct also contained flanking restriction sites to allow cloning into AAV vectors as described in Example 9. Promoters reduced to practice used for the expression of these constructs included the human U6 promoter, the FLT promoter, and the ICAM2 promoter which were independently synthesized at Blue Heron. Each of the constructs produced were sequence verified prior to use. Maps of these fragments are shown in FIG. 11 and are listed as SEQ ID NOS: 142 through to SEQ ID NOS: 146.

REFERENCES

Anderson et al, 2010. *Prog Retin Eye Res.* 29: 95-112.
Ashfield et al., 1994. *EMBO J* Vol 13 No 23 5656 Boye et al, 2012. *Human Gene Ther* 23:1101-1115.
Dalkara, D et al. 2013. *Science Translational Medicine*, 5:189ra76
Gregory et al., 2005. *Cell* 18: 631-640
Gu et al, 2012. *Cell* 151: 900-911.
Frank et al., 2010. *Nature.* 465:818-22
Gabriel N et al. 2013. *Hum Gene Ther Methods.* (2):80-93)
Kleinman et al., 2008. *Nature* 452: 591-7
Maraia et al. 1994. *Nucl Acids Res.* 22: 3045-3053
McBride et al, 2008. *PNAS* 105:5868-5873.
Nguyen et al. *Ophthalmology.* 2012 September; 119(9): 1867-73.
Petrs-Silva et al. 2009. *Mol Ther.* 17(3): 463-471
Schwarz et al., 2003. *Cell* 115: 199-208
Stewart M W. *Br J Ophthalmol* (2012). doi:10.1136/bjophthalmol-2011-300654
Wasworth et al. Molecular Therapy vol. 19 no. 2 Feb. 2011; 326-334
Wu et al 2011. *PLoS ONE* 6:e28580
Yonaha and Proudfoot, 2000. *EMBO J.* 19:3770-3777
Zhong et al. 2008. *Proc Natl Acad Sci USA.* 105(22): 7827-7832
Zhu et al, 2010. *Adv Exp Med Biol* 664: 211-216.
U.S. Pat. No. 6,573,099
US 2002/162126US 6218181
WO1999/49020
WO2003/022052

What is claimed is:

1. A DNA-directed RNA interference (ddRNAi) agent for inhibiting expression of one or more target sequences in VEGF-A, the ddRNAi agent comprising:
 a first effector sequence of at least 17 nucleotides in length;
 a first effector complement sequence;
 a second effector sequence of at least 17 nucleotides in length; and
 a second effector complement sequence;
wherein one of the first or second effector sequences is substantially complementary to a region of corresponding length within a transcript of the sequence set forth in SEQ ID NO: 8.

2. A ddRNAi agent according to claim 1 comprising, in a 5' to 3' direction:
 (a) a first effector sequence of at least 17 nucleotides in length;
  a second effector sequence of at least 17 nucleotides in length;
  a second effector complement sequence; and
  a first effector complement sequence; or
 (b) a first effector sequence of at least 17 nucleotides in length;
  a first effector complement sequence;
  a second effector sequence of at least 17 nucleotides in length; and
  a second effector complement sequence;
wherein one of the first or second effector sequences is substantially complementary to a region of corresponding length within a transcript of the sequence set forth in SEQ ID NO: 8.

3. A ddRNAi agent according to claim 1, wherein the effector sequence which is substantially complementary to a region of corresponding length within a transcript of the sequence set forth in SEQ ID NO: 8 is selected from the group consisting of the sequences set forth in SEQ ID NOS: 40-49.

4. A ddRNAi agent according to claim 1, wherein the agent is expressed within a miRNA structure.

5. A ddRNAi expression cassette for expressing a ddRNAi agent according to claim 1, the expression cassette comprising (in no particular order):
one or more promoter sequences;
one or more DNA sequences that encode for one or more effector sequences; and
one or more DNA sequences that encode for one or more effector complement sequences;
and optionally:
one or more terminator sequences;
one or more DNA sequences that encode for loop sequences, spacer sequences, or both;
one or more enhancer sequences; and/or
miRNA encoding (ME) sequences.

6. A ddRNAi expression construct comprising a ddRNAi expression cassette according to claim 5, optionally comprising miRNA encoding (ME) sequences.

7. A ddRNAi expression construct according to claim 6, wherein the construct is a viral delivery construct.

8. A method of treating AMD in a subject comprising administering a therapeutically effective amount of a ddRNAi expression construct of claim 6, optionally wherein the AMD is wet AMD.

9. A method of treating choroidal neovascularisation in a subject comprising administering a therapeutically effective amount of a ddRNAi expression construct of claim 6.

10. A method of reducing drusen deposits in a subject comprising administering a therapeutically effective amount of a ddRNAi expression construct of claim 6.

11. A method according to claim 8, wherein the ddRNAi expression construct is administered to the subject's eye/s by intravitreal injection.

12. A pharmaceutical composition comprising a ddRNAi expression construct of claim 6, and a pharmaceutically acceptable carrier or diluent.

13. A ddRNAi expression cassette for expressing a ddRNAi agent according to claim 1, the expression cassette comprising (in no particular order):
one or more promoter sequences;
one or more DNA sequences that encode for one or more effector sequences; and
one or more DNA sequences that encode for one or more effector complement sequences;
and optionally:
one or more terminator sequences;
one or more DNA sequences that encode for loop sequences, spacer sequences, or both;
one or more enhancer sequences; and/or
miRNA encoding (ME) sequences.

14. A ddRNAi expression construct comprising a ddRNAi expression cassette according to claim 13, optionally comprising miRNA encoding (ME) sequences.

15. A ddRNAi expression construct according to claim 14, wherein the construct is a viral delivery construct.

16. A method of treating AMD in a subject comprising administering a therapeutically effective amount of a ddRNAi expression construct of claim 14.

17. A method according to claim 16 wherein the AMD is wet AMD.

18. A method of treating choroidal neovascularisation in a subject comprising administering a therapeutically effective amount of a ddRNAi expression construct of claim 14.

19. A method of reducing drusen deposits in a subject comprising administering a therapeutically effective amount of a ddRNAi expression construct of claim 14.

20. A method according to claim 16, wherein the ddRNAi expression construct is administered to the subject's eye/s by intravitreal injection.

21. A pharmaceutical composition comprising a ddRNAi expression construct of claim 14, and a pharmaceutically acceptable carrier or diluent.

22. A ddRNAi agent according to claim 1, wherein one of the first or second effector sequences comprises at least 17 contiguous nucleotides of the sequence set forth in SEQ ID NO: 47.

23. A ddRNAi agent according to claim 1, wherein one of the first or second effector sequences comprises the sequence set forth in SEQ ID NO: 47.

\* \* \* \* \*

SEQUENCE LISTING

```
<160> NUMBER OF SEQ ID NOS: 150

<210> SEQ ID NO 1
<211> LENGTH: 21
<212> TYPE: DNA
<213> ORGANISM: Homo sapiens

<400> SEQUENCE: 1
agcaagagct ccagagagaa g                                              21

<210> SEQ ID NO 2
<211> LENGTH: 21
<212> TYPE: DNA
<213> ORGANISM: Homo sapiens
```

```
<400> SEQUENCE: 2
ggcctccgaa accatgaact t                                         21

<210> SEQ ID NO 3
<211> LENGTH: 21
<212> TYPE: DNA
<213> ORGANISM: Homo sapiens

<400> SEQUENCE: 3
cgagaccctg gtggacatct t                                         21

<210> SEQ ID NO 4
<211> LENGTH: 21
<212> TYPE: DNA
<213> ORGANISM: Homo sapiens

<400> SEQUENCE: 4
gcacatagga gagatgagct t                                         21

<210> SEQ ID NO 5
<211> LENGTH: 21
<212> TYPE: DNA
<213> ORGANISM: Homo sapiens

<400> SEQUENCE: 5
tgaatgcaga ccaaagaaag a                                         21

<210> SEQ ID NO 6
<211> LENGTH: 21
<212> TYPE: DNA
<213> ORGANISM: Homo sapiens

<400> SEQUENCE: 6
cagaacagtc cttaatccag a                                         21

<210> SEQ ID NO 7
<211> LENGTH: 21
<212> TYPE: DNA
<213> ORGANISM: Homo sapiens

<400> SEQUENCE: 7
tctgggattc ctgtagacac a                                         21

<210> SEQ ID NO 8
<211> LENGTH: 21
<212> TYPE: DNA
<213> ORGANISM: Homo sapiens

<400> SEQUENCE: 8
gtagacacac ccacccacat a                                         21

<210> SEQ ID NO 9
<211> LENGTH: 21
<212> TYPE: DNA
<213> ORGANISM: Homo sapiens

<400> SEQUENCE: 9
ggtgctactg tttatccgta a                                         21

<210> SEQ ID NO 10
<211> LENGTH: 21
<212> TYPE: DNA
<213> ORGANISM: Homo sapiens
```

```
<400> SEQUENCE: 10
cgagatattc cgtagtacat a                                              21

<210> SEQ ID NO 11
<211> LENGTH: 21
<212> TYPE: DNA
<213> ORGANISM: Homo sapiens

<400> SEQUENCE: 11
ttggactggc tttggcccaa t                                              21

<210> SEQ ID NO 12
<211> LENGTH: 21
<212> TYPE: DNA
<213> ORGANISM: Homo sapiens

<400> SEQUENCE: 12
cccagctaca tgatcagcta t                                              21

<210> SEQ ID NO 13
<211> LENGTH: 21
<212> TYPE: DNA
<213> ORGANISM: Homo sapiens

<400> SEQUENCE: 13
gccatgttct tctggctact t                                              21

<210> SEQ ID NO 14
<211> LENGTH: 21
<212> TYPE: DNA
<213> ORGANISM: Homo sapiens

<400> SEQUENCE: 14
cggaccgtta agcgggccaa t                                              21

<210> SEQ ID NO 15
<211> LENGTH: 21
<212> TYPE: DNA
<213> ORGANISM: Homo sapiens

<400> SEQUENCE: 15
tcatggtgat tgtggaattc t                                              21

<210> SEQ ID NO 16
<211> LENGTH: 21
<212> TYPE: DNA
<213> ORGANISM: Homo sapiens

<400> SEQUENCE: 16
cctgaccttg gagcatctca t                                              21

<210> SEQ ID NO 17
<211> LENGTH: 21
<212> TYPE: DNA
<213> ORGANISM: Homo sapiens

<400> SEQUENCE: 17
tggagcatct catctgttac a                                              21

<210> SEQ ID NO 18
<211> LENGTH: 21
<212> TYPE: DNA
```

<213> ORGANISM: Homo sapiens

<400> SEQUENCE: 18
ggctaagggc atggagttct t                                             21

<210> SEQ ID NO 19
<211> LENGTH: 21
<212> TYPE: DNA
<213> ORGANISM: Homo sapiens

<400> SEQUENCE: 19
accagaaatg taccagacca t                                             21

<210> SEQ ID NO 20
<211> LENGTH: 21
<212> TYPE: DNA
<213> ORGANISM: Homo sapiens

<400> SEQUENCE: 20
accccaaatt ccattatgac a                                             21

<210> SEQ ID NO 21
<211> LENGTH: 21
<212> TYPE: DNA
<213> ORGANISM: Homo sapiens

<400> SEQUENCE: 21
actccaggtg tcatccatca a                                             21

<210> SEQ ID NO 22
<211> LENGTH: 21
<212> TYPE: DNA
<213> ORGANISM: Homo sapiens

<400> SEQUENCE: 22
aggtgtcatc catcaacgtc t                                             21

<210> SEQ ID NO 23
<211> LENGTH: 21
<212> TYPE: DNA
<213> ORGANISM: Homo sapiens

<400> SEQUENCE: 23
ccatgagtac atctacgtgg a                                             21

<210> SEQ ID NO 24
<211> LENGTH: 21
<212> TYPE: DNA
<213> ORGANISM: Homo sapiens

<400> SEQUENCE: 24
ggacctcgtg ggcttcagct a                                             21

<210> SEQ ID NO 25
<211> LENGTH: 21
<212> TYPE: DNA
<213> ORGANISM: Homo sapiens

<400> SEQUENCE: 25
aggcaagctg gtcaagatct g                                             21

<210> SEQ ID NO 26
<211> LENGTH: 21

<212> TYPE: DNA
<213> ORGANISM: Homo sapiens

<400> SEQUENCE: 26
ggagagcatc ttcaacagcc t                                              21

<210> SEQ ID NO 27
<211> LENGTH: 21
<212> TYPE: DNA
<213> ORGANISM: Homo sapiens

<400> SEQUENCE: 27
gcatcttcaa cagcctctac a                                              21

<210> SEQ ID NO 28
<211> LENGTH: 21
<212> TYPE: DNA
<213> ORGANISM: Homo sapiens

<400> SEQUENCE: 28
cccagagctg cccatgaacg a                                              21

<210> SEQ ID NO 29
<211> LENGTH: 21
<212> TYPE: DNA
<213> ORGANISM: Homo sapiens

<400> SEQUENCE: 29
gcagttctac aatgccatca a                                              21

<210> SEQ ID NO 30
<211> LENGTH: 21
<212> TYPE: DNA
<213> ORGANISM: Homo sapiens

<400> SEQUENCE: 30
ccatgcctcc gacgagatct a                                              21

<210> SEQ ID NO 31
<211> LENGTH: 21
<212> TYPE: DNA
<213> ORGANISM: Homo sapiens

<400> SEQUENCE: 31
ctgccaagac tccttcatgt a                                              21

<210> SEQ ID NO 32
<211> LENGTH: 21
<212> TYPE: DNA
<213> ORGANISM: Homo sapiens

<400> SEQUENCE: 32
gaacatctac ctggtgctag a                                              21

<210> SEQ ID NO 33
<211> LENGTH: 21
<212> TYPE: DNA
<213> ORGANISM: Homo sapiens

<400> SEQUENCE: 33
ccgccatgtc atcatcctca t                                              21

<210> SEQ ID NO 34

```
<211> LENGTH: 21
<212> TYPE: DNA
<213> ORGANISM: Homo sapiens

<400> SEQUENCE: 34
ggaggattat ctggatgtct a                                          21

<210> SEQ ID NO 35
<211> LENGTH: 21
<212> TYPE: DNA
<213> ORGANISM: Homo sapiens

<400> SEQUENCE: 35
gcaacatgtg ttcaaagtca a                                          21

<210> SEQ ID NO 36
<211> LENGTH: 21
<212> TYPE: DNA
<213> ORGANISM: Homo sapiens

<400> SEQUENCE: 36
catgtgttca aagtcaagga t                                          21

<210> SEQ ID NO 37
<211> LENGTH: 21
<212> TYPE: DNA
<213> ORGANISM: Homo sapiens

<400> SEQUENCE: 37
caggatatca aagctctgtt t                                          21

<210> SEQ ID NO 38
<211> LENGTH: 21
<212> TYPE: DNA
<213> ORGANISM: Homo sapiens

<400> SEQUENCE: 38
tcggaaggag gtctacatca a                                          21

<210> SEQ ID NO 39
<211> LENGTH: 21
<212> TYPE: DNA
<213> ORGANISM: Homo sapiens

<400> SEQUENCE: 39
gaggatttgg gttttctata a                                          21

<210> SEQ ID NO 40
<211> LENGTH: 21
<212> TYPE: RNA
<213> ORGANISM: Homo sapiens

<400> SEQUENCE: 40
cuucucucug gagcucuugc u                                          21

<210> SEQ ID NO 41
<211> LENGTH: 21
<212> TYPE: RNA
<213> ORGANISM: Homo sapiens

<400> SEQUENCE: 41
aaguucaugg uuucggaggc c                                          21
```

```
<210> SEQ ID NO 42
<211> LENGTH: 21
<212> TYPE: RNA
<213> ORGANISM: Homo sapiens

<400> SEQUENCE: 42
aagaugucca ccagggucuc g                                              21

<210> SEQ ID NO 43
<211> LENGTH: 21
<212> TYPE: RNA
<213> ORGANISM: Homo sapiens

<400> SEQUENCE: 43
aagcucaucu cuccuaugug c                                              21

<210> SEQ ID NO 44
<211> LENGTH: 21
<212> TYPE: RNA
<213> ORGANISM: Homo sapiens

<400> SEQUENCE: 44
ucuuucuuug gucugcauuc a                                              21

<210> SEQ ID NO 45
<211> LENGTH: 21
<212> TYPE: RNA
<213> ORGANISM: Homo sapiens

<400> SEQUENCE: 45
ucuggauuaa ggacuguucu g                                              21

<210> SEQ ID NO 46
<211> LENGTH: 21
<212> TYPE: RNA
<213> ORGANISM: Homo sapiens

<400> SEQUENCE: 46
ugugucuaca ggaaucccag a                                              21

<210> SEQ ID NO 47
<211> LENGTH: 21
<212> TYPE: RNA
<213> ORGANISM: Homo sapiens

<400> SEQUENCE: 47 uauguggggug ggugugucua c                                             21

<210> SEQ ID NO 48
<211> LENGTH: 21
<212> TYPE: RNA
<213> ORGANISM: Homo sapiens

<400> SEQUENCE: 48
uuacggauaa acaguagcac c                                              21

<210> SEQ ID NO 49
<211> LENGTH: 21
<212> TYPE: RNA
<213> ORGANISM: Homo sapiens

<400> SEQUENCE: 49
uauguacuac ggaauaucuc g                                              21
```

```
<210> SEQ ID NO 50
<211> LENGTH: 21
<212> TYPE: RNA
<213> ORGANISM: Homo sapiens

<400> SEQUENCE: 50
auugggccaa agccagucca a                                              21

<210> SEQ ID NO 51
<211> LENGTH: 21
<212> TYPE: RNA
<213> ORGANISM: Homo sapiens

<400> SEQUENCE: 51
auagcugauc auguagcugg g                                              21

<210> SEQ ID NO 52
<211> LENGTH: 21
<212> TYPE: RNA
<213> ORGANISM: Homo sapiens

<400> SEQUENCE: 52
aaguagccag aagaacaugg c                                              21

<210> SEQ ID NO 53
<211> LENGTH: 21
<212> TYPE: RNA
<213> ORGANISM: Homo sapiens

<400> SEQUENCE: 53
auuggcccgc uuaacggucc g                                              21

<210> SEQ ID NO 54
<211> LENGTH: 21
<212> TYPE: RNA
<213> ORGANISM: Homo sapiens

<400> SEQUENCE: 54
agaauuccac aaucaccaug a                                              21

<210> SEQ ID NO 55
<211> LENGTH: 21
<212> TYPE: RNA
<213> ORGANISM: Homo sapiens

<400> SEQUENCE: 55
augagaugcu ccaaggucag g                                              21

<210> SEQ ID NO 56
<211> LENGTH: 21
<212> TYPE: RNA
<213> ORGANISM: Homo sapiens

<400> SEQUENCE: 56
uguaacagau gagaugcucc a                                              21

<210> SEQ ID NO 57
<211> LENGTH: 21
<212> TYPE: RNA
<213> ORGANISM: Homo sapiens

<400> SEQUENCE: 57 aagaaucca ugcccuuagc c                                               21
```

<210> SEQ ID NO 58
<211> LENGTH: 20
<212> TYPE: RNA
<213> ORGANISM: Homo sapiens

<400> SEQUENCE: 58
auggucuggu acauuucugg                                               20

<210> SEQ ID NO 59
<211> LENGTH: 20
<212> TYPE: RNA
<213> ORGANISM: Homo sapiens

<400> SEQUENCE: 59 ugcauaaug gaauuugggg                                                20

<210> SEQ ID NO 60
<211> LENGTH: 21
<212> TYPE: RNA
<213> ORGANISM: Homo sapiens

<400> SEQUENCE: 60
uugauggaug acaccuggag u                                             21

<210> SEQ ID NO 61
<211> LENGTH: 21
<212> TYPE: RNA
<213> ORGANISM: Homo sapiens

<400> SEQUENCE: 61
agacguugau ggaugacacc u                                             21

<210> SEQ ID NO 62
<211> LENGTH: 21
<212> TYPE: RNA
<213> ORGANISM: Homo sapiens

<400> SEQUENCE: 62
uccacguaga uguacucaug g                                             21

<210> SEQ ID NO 63
<211> LENGTH: 21
<212> TYPE: RNA
<213> ORGANISM: Homo sapiens

<400> SEQUENCE: 63
uagcugaagc ccacgagguc c                                             21

<210> SEQ ID NO 64
<211> LENGTH: 21
<212> TYPE: RNA
<213> ORGANISM: Homo sapiens

<400> SEQUENCE: 64
cagaucuuga ccagcuugcc u                                             21

<210> SEQ ID NO 65
<211> LENGTH: 21
<212> TYPE: RNA
<213> ORGANISM: Homo sapiens

<400> SEQUENCE: 65
aggcuguuga agaugcucuc c                                               21

<210> SEQ ID NO 66
<211> LENGTH: 21
<212> TYPE: RNA
<213> ORGANISM: Homo sapiens

<400> SEQUENCE: 66
uguagaggcu guugaagaug c                                               21

<210> SEQ ID NO 67
<211> LENGTH: 21
<212> TYPE: RNA
<213> ORGANISM: Homo sapiens

<400> SEQUENCE: 67
ucguucaugg gcagcucugg g                                               21

<210> SEQ ID NO 68
<211> LENGTH: 21
<212> TYPE: RNA
<213> ORGANISM: Homo sapiens

<400> SEQUENCE: 68
uugauggcau uguagaacug c                                               21

<210> SEQ ID NO 69
<211> LENGTH: 21
<212> TYPE: RNA
<213> ORGANISM: Homo sapiens

<400> SEQUENCE: 69
uagaucucgu cggaggcaug g                                               21

<210> SEQ ID NO 70
<211> LENGTH: 21
<212> TYPE: RNA
<213> ORGANISM: Homo sapiens

<400> SEQUENCE: 70
uacaugaagg agucuuggca g                                               21

<210> SEQ ID NO 71
<211> LENGTH: 21
<212> TYPE: RNA
<213> ORGANISM: Homo sapiens

<400> SEQUENCE: 71
ucuagcacca gguagauguu c                                               21

<210> SEQ ID NO 72
<211> LENGTH: 21
<212> TYPE: RNA
<213> ORGANISM: Homo sapiens

<400> SEQUENCE: 72
augaggauga ugacauggcg g                                               21

<210> SEQ ID NO 73
<211> LENGTH: 21
<212> TYPE: RNA
<213> ORGANISM: Homo sapiens

<400> SEQUENCE: 73
uagacaucca gauaauccuc c                                               21

<210> SEQ ID NO 74
<211> LENGTH: 21
<212> TYPE: RNA
<213> ORGANISM: Homo sapiens

<400> SEQUENCE: 74
uugacuuuga acacauguug c                                               21

<210> SEQ ID NO 75
<211> LENGTH: 21
<212> TYPE: RNA
<213> ORGANISM: Homo sapiens

<400> SEQUENCE: 75
auccuugacu uugaacacau g                                               21

<210> SEQ ID NO 76
<211> LENGTH: 21
<212> TYPE: RNA
<213> ORGANISM: Homo sapiens

<400> SEQUENCE: 76
aaacagagcu uugauauccu g                                               21

<210> SEQ ID NO 77
<211> LENGTH: 21
<212> TYPE: RNA
<213> ORGANISM: Homo sapiens

<400> SEQUENCE: 77
uugauguaga ccuccuuccg a                                               21

<210> SEQ ID NO 78
<211> LENGTH: 21
<212> TYPE: RNA
<213> ORGANISM: Homo sapiens

<400> SEQUENCE: 78
uuauagaaaa cccaaauccu c                                               21

<210> SEQ ID NO 79
<211> LENGTH: 3677
<212> TYPE: DNA
<213> ORGANISM: Homo sapiens

<400> SEQUENCE: 79
tcgcggaggc ttggggcagc cgggtagctc ggaggtcgtg gcgctggggg ctagcaccag      60
cgctctgtcg ggaggcgcag cggttaggtg gaccggtcag cggactcacc ggccagggcg     120
ctcggtgctg gaatttgata ttcattgatc cgggttttat ccctcttctt tttcttaaa     180 cattttttt taaaactgta ttgtttctcg ttttaattta ttttgcttg ccattcccca      240 cttgaatcgg gccgacggct tggggagatt gctctacttc cccaaatcac tgtggatttt     300
ggaaaccagc agaagaggaa aagaggtagc aagagctcca gagagaagtc gaggaagaga     360
gagacggggt cagagagagc gcgcgggcgt gcgagcagcg aaagcgacag gggcaaagtg     420
agtgacctgc ttttgggggt gaccgccgga gcgcggcgtg agccctcccc cttgggatcc     480
cgcagctgac cagtcgcgct gacggacaga cagacagaca ccgcccccag ccccagctac     540

-continued

| | |
|---|---|
| cacctcctcc ccggccggcg gcggacagtg gacgcggcgg cgagccgcgg gcagggccg | 600 |
| gagcccgcgc ccggaggcgg ggtggagggg gtcggggctc gcggcgtcgc actgaaactt | 660 |
| ttcgtccaac ttctgggctg ttctcgcttc ggaggagccg tggtccgcgc ggggaagcc | 720 |
| gagccgagcg gagccgcgag aagtgctagc tcgggccggg aggagccgca gccggaggag | 780 |
| ggggaggagg aagaagagaa ggaagaggag aggggccgc agtggcgact cggcgctcgg | 840 |
| aagccgggct catggacggg tgaggcgcg gtgtgcgcag acagtgctcc agccgcgcgc | 900 |
| gctccccagg ccctggcccg ggcctcgggc cggggaggaa gagtagctcg ccgaggcgcc | 960 |
| gaggagagcg ggccgcccca cagcccgagc cggagaggga gcgcgagccg cgccggcccc | 1020 |
| ggtcgggcct ccgaaaccat gaactttctg ctgtcttggg tgcattggag ccttgccttg | 1080 |
| ctgctctacc tccaccatgc caagtggtcc caggctgcac ccatggcaga aggaggaggg | 1140 |
| cagaatcatc acgaagtggt gaagttcatg gatgtctatc agcgcagcta ctgccatcca | 1200 |
| atcgagaccc tggtggacat cttccaggag taccctgatg agatcgagta catcttcaag | 1260 |
| ccatcctgtg tgcccctgat gcgatgcggg ggctgctgca atgacgaggg cctggagtgt | 1320 |
| gtgcccactg aggagtccaa catcaccatg cagattatgc ggatcaaacc tcaccaaggc | 1380 |
| cagcacatag gagagatgag cttcctacag cacaacaaat gtgaatgcag accaaagaaa | 1440 |
| gatagagcaa gacaagaaaa aaaatcagtt cgaggaaagg gaaaggggca aaaacgaaag | 1500 |
| cgcaagaaat cccggtataa gtcctggagc gtgtacgttg gtgcccgctg ctgtctaatg | 1560 |
| ccctggagcc tccctggccc ccatccctgt gggccttgct cagagcggag aaagcatttg | 1620 |
| tttgtacaag atccgcagac gtgtaaatgt tcctgcaaaa acacagactc gcgttgcaag | 1680 |
| gcgaggcagc ttgagttaaa cgaacgtact tgcagatgtg acaagccgag gcggtgagcc | 1740 |
| gggcaggagg aaggagcctc cctcagggtt tcgggaacca gatctctcac caggaaagac | 1800 |
| tgatacagaa cgatcgatac agaaaccacg ctgccgccac cacaccatca ccatcgacag | 1860 |
| aacagtcctt aatccagaaa cctgaaatga aggaagagga gactctgcgc agagcacttt | 1920 |
| gggtccggag ggcgagactc cggcggaagc attcccgggc gggtgaccca gcacggtccc | 1980 |
| tcttggaatt ggattcgcca tttattttt cttgctgcta aatcaccgag cccggaagat | 2040 |
| tagagagttt tatttctggg attcctgtag acacacccac ccacatacat acatttatat | 2100 |
| atatatatat tatatatata taaaaataaa tatctctatt ttatatatat aaaatatata | 2160 |
| tattcttttt ttaaattaac agtgctaatg ttattggtgt cttcactgga tgtatttgac | 2220 |
| tgctgtggac ttgagttggg aggggaatgt tcccactcag atcctgacag ggaagaggag | 2280 |
| gagatgagag actctggcat gatctttttt ttgtcccact tggtggggcc agggtcctct | 2340 |
| cccctgccca ggaatgtgca aggccagggc atggggcaa atatgaccca gttttgggaa | 2400 |
| caccgacaaa cccagccctg cgcgctgagcc tctctacccc aggtcagacg gacagaaaga | 2460 |
| cagatcacag gtacagggat gaggacaccg gctctgacca ggagtttggg gagcttcagg | 2520 |
| acattgctgt gctttgggga ttccctccac atgctgcacg cgcatctcgc ccccaggggc | 2580 |
| actgcctgga agattcagga gcctgggcgg ccttcgctta ctctcacctg cttctgagtt | 2640 |
| gcccaggaga ccactggcag atgtcccggc gaagagaaga gacacattgt tggaagaagc | 2700 |
| agcccatgac agctccccctt cctgggactc gccctcatcc tcttcctgct cccttcctg | 2760 |
| gggtgcagcc taaaaggacc tatgtcctca caccattgaa accactagtt ctgtcccccc | 2820 |
| aggagacctg gttgtgtgtg tgtgagtggt tgaccttcct ccatccctg gtccttccct | 2880 |
| tcccttcccg aggcacagag agacagggca ggatccacgt gcccattgtg gaggcagaga | 2940 |

-continued

```
aaagagaaag tgttttatat acggtactta tttaatatcc cttttaatt agaaattaaa    3000 acagttaatt taattaaaga gtagggtttt ttttcagtat tcttggttaa tatttaattt    3060 caactatttta tgagatgtat cttttgctct ctcttgctct cttatttgta ccggttttg    3120 tatataaaat tcatgtttcc aatctctctc tccctgatcg gtgacagtca ctagcttatc    3180
ttgaacagat atttaattt gctaacactc agctctgccc tccccgatcc cctggctccc    3240
cagcacacat tcctttgaaa taaggtttca atatacatct acatactata tatatatttg    3300
gcaacttgta tttgtgtgta tatatatata tatatgttta tgtatatatg tgattctgat    3360
aaaatagaca ttgctattct gttttttata tgtaaaaaca aaacaagaaa aaatagagaa    3420
ttctacatac taaatctctc tccttttta attttaatat ttgttatcat ttatttattg    3480
gtgctactgt ttatccgtaa taattgtggg gaaaagatat taacatcacg tctttgtctc    3540
tagtgcagtt tttcgagata ttccgtagta catatttatt tttaaacaac gacaaagaaa    3600
tacagatata tcttaaaaaa aaaaaagcat tttgtattaa agaatttaat tctgatctca    3660
aaaaaaaaaa aaaaaaa                                                   3677
```

<210> SEQ ID NO 80
<211> LENGTH: 3547
<212> TYPE: DNA
<213> ORGANISM: Mus musculus
<400> SEQUENCE: 80

```
agcgcagagg cttggggcag ccgagctgca gcgaggccgc ggcactgggg gcgagctgag      60
cggcggcagc ggagctctgt cgcgagacgc agcgacaagg cagactattc agcggactca     120
ccagcccggg agtctgtgct ctgggatttg atattcaaac ctcttaattt tttttttctta    180 aactgtattg ttttacgctt taatttattt ttgcttccta ttcccctctt aaatcgtgcc     240
aacggtttga ggaggttggt tcttcactcc ctcaaatcac ttcggattgt ggaaatcagc     300
agacgaaaga ggtatcaaga gctccagaga gaagtcaagg aagagagaga gagaccggtc     360
agagagagcg cgctggcgag cgaacagaga gagggacagg ggcaaagtga ctgacctgct     420
tttgggggtg accgccagag cgcggcgtga gccctccccc ttgggatctt gcatcggacc     480
agtcgcgctg acggacagac agacagacac cgccccagc cccagcgccc acctcctcgc      540
cggcgggctg ccgacggtgg acgcggcggc gagccgcgag gaaccgaagc ccgcgcccgg     600
aggcggggtg gagggggtcg gggctcgcgg gattgcacgg aaactttcg tccaacttct      660 gggctcttct cgctccgtag tagccgtggt ctgcgccgca ggagacaaac cgatcggagc     720
tgggagaagt gctagctcgg gcctggagaa gccggggccc gagaagagag gggaggaaga     780
gaaggaagag gagaggggc cgcagtgggc gctcggctct caggagccga gctcatggac      840
gggtgaggcg gccgtgtgcg cagacagtgc tccagccgcg cgcgcgcccc aggccccggc     900
ccgggcctcg gttccagaag ggagaggagc ccgccaaggc gcgcaagaga gcgggctgcc     960
tcgcagtccg agccggagag ggagcgcgag ccgcgccggc cccggacggg cctccgaaac    1020
catgaacttt ctgctctctt gggtgcactg gacctggct ttactgctgt acctccacca     1080
tgccaagtgg tcccaggctg cacccacgac agaaggagag cagaagtccc atgaagtgat    1140
caagttcatg gatgtctacc agcgaagcta ctgccgtccg attgagaccc tggtggacat    1200
cttccaggag taccccgacg agatagagta catcttcaag ccgtcctgtg tgccgctgat    1260
gcgctgtgca ggctgctgta acgatgaagc cctggagtgc gtgcccacgt cagagagcaa    1320
```

```
catcaccatg cagatcatgc ggatcaaacc tcaccaaagc cagcacatag gagagatgag    1380
cttcctacag cacagcagat gtgaatgcag accaaagaaa gacagaacaa agccagaaaa    1440
aaaatcagtt cgaggaaagg gaaagggtca aaacgaaag cgcaagaaat cccggtttaa    1500
atcctggagc gttcactgtg agccttgttc agagcggaga agcatttgt ttgtccaaga    1560
tccgcagacg tgtaaatgtt cctgcaaaaa cacagactcg cgttgcaagg cgaggcagct    1620
tgagttaaac gaacgtactt gcagatgtga caagccaagg cggtgagcca ggctgcagga    1680
aggagcctcc ctcagggttt cgggaaccag acctctcacc ggaaagaccg attaaccatg    1740
tcaccaccac gccatcatcg tcaccgttga cagaacagtc cttaatccag aaagcctgac    1800
atgaaggaag aggagactct tcgaggagca ctttgggtcc ggagggcgag actccggcag    1860
acgcattccc gggcaggtga ccaagcacgg tccctcgtgg gactggattc gccattttct    1920
tatatctgct gctaaatcgc caagcccgga agattagggt tgtttctggg attcctgtag    1980
acacacccac ccacatacac acatatatat atattatata taaataaa tatatatgtt    2040
ttatatataa aatatatata tattcttttt tttaaattaa ctctgctaat gttattggtg    2100
tcttcactgg atatgtttga ctgctgtgga cttgtgttgg gaggaggatg tcctcactcg    2160
gatgccgaca cgggagacaa tgggatgaaa ggcttcagtg tggtctgaga gaggccgaag    2220
tccttttgcc tgccggggag caagcaaggc cagggcacgg gggcacattg gctcacttcc    2280
agaaacacga caaacccatt cctggccctg agtcaagagg acagagagac agatgatgac    2340
agagaaagag ataaagatgc cggttccaac cagaagtttg gggagcctca ggacatggca    2400
tgctttgtgg atccccatga tagtctacaa aagcaccccg cccctctggg cactgcctgg    2460
aagaatcggg agcctggcca gccttcagct cgctcctcca cttctgaggg gcctaggagg    2520
cctcccacag tgtcccggc aagagaagac acggtggtgg aagaagaggc ctggtaatgg    2580
cccctcctcc tgggacccct tcgtcctctc cttaccccac ctcctgggta cagcccagga    2640
ggaccttgtg tgatcagacc attgaaacca ctaattctgt ccccaggaga cttggctgtg    2700
tgtgtgagtg gcttacccct cctcatcttc ccttcccaag gcacagagca atggggcagg    2760
acccgcaagc ccctcacgga ggcagagaaa agagaaagtg ttttatatac ggtacttatt    2820
taatagccct ttttaattag aaattaaaac agttaattta attaaagagt agggtttttt    2880
tcagtattct tggttaatat ttaatttcaa ctatttatga gatgtatctc tcgctctctc    2940
ttatttgtac ttgtgtgtgt gtgtgtgtgt gtgtgtgtgt gtgtgtgtgt gtgtgtatga    3000
aatctgtgtt tccaatctct ctctcccaga tcggtgacag tcactagctt gtcctgagaa    3060
gatatttaat tttgctaaca ctcagctctg ccctcccttg tccccaccac acattccttt    3120
gaaataaggt tcaatatac atttacatac tatatatata tttggcaact tgtgtttgta    3180
tataaatata tatatatata tatatgttta tgtatatatg tgattctgat aaaatagaca    3240
ttgctattct gttttttata tgtaaaaaca aacaagaaa aatagagaat tctacatact    3300
aaatctctct cctttttaa ttttaatatt tgttatcatt tatttattgg tgctactgtt    3360
tatccgtaat aattgtgggg gaaaagata ttaacatcac gtctttgtct ctagagcagt    3420
tttccgagat attccgtagt acatatttat ttttaaacag caacaaagaa atacagatat    3480
atcttaaaaa aaaagcatt ttgtattaaa gaattgaatt ctgatctcaa aaaaaaaaaa    3540
aaaaaaa                                                               3547
```

<210> SEQ ID NO 81
<211> LENGTH: 4090

<212> TYPE: DNA
<213> ORGANISM: Macaca fascicularis

<400> SEQUENCE: 81

```
atgaactatg agtcccatat tgtgctgagg aggggtctgt ggcctgagag gggaagggcc      60
ctggcctctg ccgccctgga aggcaacatc atagccagga atggagcctg ctgctcctac     120
tccttaaccg gtgctcaccc caggcctggc tgtgcctgga aggccttgtt tccatcctgg     180
gccttcactt gccttccccc tgcttattcc tgggcctcca aaaagcttct ctgtgcccca     240
agctctcctc ttccaggaag tcttcctttc ctgtttgaga aggggctccc taacctgcac     300
ccagccaggc cagcggaaca gcccctgtcc acctcctacc ttcctcttgg gcagcttcaa     360
ggagcctgga ggctgcccct gccagccctg ggaactgtg gccccgttct cgagagccag      420
acatccctga ggagctttag acaggagag gaggaagtag ctatgccag ctgtagacca       480
gaccctggca agatccgggt ggacaatcag actgactggt cccactcttc ccacaggcat     540
cagaacccca ctttgttcc ctggagcagc ctggaaatag ccgggtcaga acccagtcag      600
gaattttttcc aagctggttc ctataggcaa gaatgggata ggggcctttg ggagcacttc    660
gggaagatgt ggagagttgg aggaaaaggc agcttggaga ttgctttact tccccaaatc     720
actgtggatt ttggaaacca gcagaaagag gaaagaggta gcaagagctc agagagaag      780
tcgaggaaga gagagacggg gtcagagaga gcgcgcgggc gtgcgagcag cgagagggac     840
aggggcaaag tgagtgacct gcttttgggg gtgaccgccg gagcgcggcg tgagccctcc     900
cccttgggat cccgcagcgg accagtagcg ctgacggaca gacagacaga caccgccccc     960
agccccagcg cccacctcct ccccggccgg cggccgacag tggacgcggc ggcgagccgc    1020
gggcaggggc cggagcccgc gcccggaggc ggggtggagg gggtcgggc tcgcggcgtc     1080
gcactgaaac ttttcgtcca acttctgggc tgttctcgct tcggaggagc cgtggtccgc    1140
gccggggaag ccgagccgag cggagccgcg agaagtgcta gctcgggccg ggaggagccg    1200
cagccggagg aggggagga ggaagaagag aaggaagaag agagggggcc gcggtggcga     1260
ctcggcgctt ggaagccggg ctcatggacg ggtgaggcgg cggtgtgcgc agacagtgct    1320
ccagccgcgc gcgcgcccca ggccctggcc cgggcctcgg ccggggagg aagaggagct     1380
cgccgaggcg ccgaagagag cgggccgccc cacagcccga gccggagagg gagcgcgagc    1440
cgcgccggcc ccggtcgggc ctccgaaacc atgaactttc tgctctcttg ggtgcattgg    1500
agccttgcct tgctgctgta cctccaccat gccaagtggt cccaggctgc acccatggca    1560
gaaggaggag ggcagaatca tcacgaagtg gtgaagttca tggatgtcta tcagcgcagc    1620
tactgccatc caatcgagac cctggtggac atcttccagg agtaccctga tgagattgag    1680
tacatcttca gccatcctg tgtgccctg atgcgatgtg ggggctgctg caatgacgag      1740
ggcctggagt gtgtgcccac tgaggagtcc aacatcacca tgcagattat gcggatcaaa    1800
cctcaccaag gccagcacat aggagagatg agcttcctac agcacaacaa atgtgaatgc    1860
agaccaaaga agatagagc aagacaagaa aaaaatcag ttcgaggaaa gggaaagggg     1920
caaaaacgaa agcgcaagaa atcccggtat aagtcctgga gcgtgtacgt tggtgcccgc    1980
tgctgtctaa ttccctggag cctccctggc ccccatccct gtgggccttg ctcagagcgg    2040
agaaagcatt tgtttgtaca agatccgcag acgtgtaaat gttcctgcaa aaacacagac    2100
tcgcgttgca aggcgaggca gcttgagtta aacgaacgta cttgcagatg tgacaagccg    2160
aggcggtgag ccgggcagga ggaaggagcc tccctcaggg tttcgggaac cagatctctc    2220
```

```
accaggaaag acagatacag aacgatcgat acagaaacca cgctgccgcc accacaccat    2280
caccatcgac agaacagtcc ttaatccaga agcctgaaat gaaggaagag gagactctgc    2340
gcagagcact ttgggtccgg agggcgagac tccggcagaa gcattcccgg cgggtgacc    2400 cagcatggtc cctcttggaa ttggattcgc cattttattt ttcttgctgc taaatcaccg    2460
agcccggaag attagagagt tttatttctg ggattcctgt agacacaccc acccacatac    2520
atacatttat atatatatat atattatata tataaaaata aatatctata ttttatatat    2580
ataaaatata tatattcttt ttttaaatta acagtgctaa tgttattggt gtcttcactg    2640
gatgtatttg actgctgtgg acttgagttg ggaggggggaa tgttcccact cagatcctga    2700
cagggaagag gaggagatga gagactctgg catgatcttt ttttttgtcc cacttggtgg    2760
ggccagggtc ccctcccctg cccaggaacg tgcaaggcca gggtatgggg caaatatga    2820 cccacttttg ggaacaccga caaacccagc cctggcaccg agcctctacc ccgggtcaga    2880
tggacagaaa gacagatgac aggtacaggg acgaggacac tggctctgac taggagtttg    2940
gggagcttca ggacattgct gtgctttggg gattccctcc acatgctgca tgcgcatctt    3000
gcccccaggg gcagcgcctg gaagattcag gagcctgggc ggccttcact tactctcacc    3060
tgcttctgag ttgcccagga ggccactggc agatggcccg gcgaagagaa gagacacatt    3120
gttggaagaa gcagctcatg acagctcccc ttcctgggat tcaccctcgt cctcttcctg    3180
ctccccttcc tggggtgtag cctaaaagga cctgatgtcc tcacaccatt gaaaccacta    3240
gttctgtccc cccaggagac ctggttgtgt gtgtgtgagt ggttgacctt cctccatccc    3300
ctggtccttc ccttcccttc ccgaggcaca gagagacagg gcaggatcca cgtgcccact    3360
gtggaggcag agaaaagaga agtgttttta tatacggtac ttatttaata tccctttta    3420 attagaaatt aaaacagtta atttaattaa aaagtagggt ttttttcagt attcttggtt    3480
aatatttaat ttcaactatt tatgagatgt atcttttgct ctctctcgct ctcttatttg    3540
taccggtttt tgtatataaa attcatgttt ccaatctctc tctccctgat cggtgacagt    3600
cactagctta tcttgaacag atatttaatt ttgctaacac ttagctctgc cctccccgtt    3660
cccctggctc cccagcacac attccttttga aataaggttt caatatacat ctacatacta    3720
tatatatatt tggcaacttg tatttgtgtg tatatatata tatatgttta tgtatatatg    3780
tgattctgat aaaatagaca ttgctattct gttttttata tgtaaaaaca aaacaagaaa    3840
aaatagagaa ttctacatac taaatctctc tcctttttta attttaatat ttgttatcat    3900
ttatttattg gtgctactgt ttatccgtaa taattgtggg gaaagatat taacatcacg    3960 tctttgtctc tagtgcagtt ttttgagata ttccgtagta catatttatt tttaaacaac    4020
aacaaagaaa tacagatata tcttaaaaaa aaaaggattt tgtattaaag aatttaattc    4080
tgatctcaaa                                                          4090
```

<210> SEQ ID NO 82
<211> LENGTH: 6055
<212> TYPE: DNA
<213> ORGANISM: Homo sapiens

<400> SEQUENCE: 82

```
actgagtccc gggaccccgg gagagcggtc aatgtgtggt cgctgcgttt cctctgcctg     60
cgccgggcat cacttgcgcg ccgcagaaag tccgtctggc agcctggata tcctctccta    120
ccggcacccg cagacgcccc tgcagccgcg gtcggcgccc gggctcccta gcctgtgcg    180 ctcaactgtc ctgcgctgcg gggtgccgcg agttccacct ccgcgcctcc ttctctagac    240
```

```
aggcgctggg agaaagaacc ggctcccgag ttctgggcat ttcgcccggc tcgaggtgca    300
ggatgcagag caaggtgctg ctggccgtcg ccctgtgggc ctgcgtggag acccgggccg    360
cctctgtggg tttgcctagt gtttctcttg atctgcccag gctcagcata caaaaagaca    420
tacttacaat taaggctaat acaactcttc aaattacttg caggggacag agggacttgg    480
actggctttg gcccaataat cagagtggca gtgagcaaag ggtggaggtg actgagtgca    540
gcgatggcct cttctgtaag acactcacaa ttccaaaagt gatcggaaat gacactggag    600
cctacaagtg cttctaccgg gaaactgact tggcctcggt catttatgtc tatgttcaag    660
attacagatc tccatttatt gcttctgtta gtgaccaaca tggagtcgtg tacattactg    720
agaacaaaaa caaaactgtg gtgattccat gtctcgggtc catttcaaat ctcaacgtgt    780
cactttgtgc aagataccca gaaaagagat tgttcctga tggtaacaga atttcctggg     840
acagcaagaa gggctttact attcccagct acatgatcag ctatgctggc atggtcttct    900
gtgaagcaaa aattaatgat gaaagttacc agtctattat gtacatagtt gtcgttgtag    960
ggtataggat ttatgatgtg gttctgagtc cgtctcatgg aattgaacta tctgttggag   1020
aaaagcttgt cttaaattgt acagcaagaa ctgaactaaa tgtggggatt gacttcaact   1080
gggaataccc ttcttcgaag catcagcata agaaacttgt aaaccgagac ctaaaaaccc   1140
agtctgggag tgagatgaag aaattttga gcaccttaac tatagatggt gtaacccgga    1200
gtgaccaagg attgtacacc tgtgcagcat ccagtgggct gatgaccaag aagaacagca   1260
catttgtcag ggtccatgaa aacctttgtt tgcttttggg aagtggcatg gaatctctgg   1320
tggaagccac ggtgggggag cgtgtcagaa tccctgcgaa gtaccttggt tacccacccc   1380
cagaaataaa atggtataaa aatgaatac cccttgagtc caatcacaca attaaagcgg    1440
ggcatgtact gacgattatg gaagtgagtg aaagagacac aggaaattac actgtcatcc   1500
ttaccaatcc catttcaaag gagaagcaga gccatgtggt ctctctggtt gtgtatgtcc   1560
caccccagat tggtgagaaa tctctaatct ctcctgtgga ttcctaccag tacggcacca   1620
ctcaaacgct gacatgtacg gtctatgcca ttcctccccc gcatcacatc cactggtatt   1680
ggcagttgga ggaagagtgc gccaacgagc ccagccaagc tgtctcagtg acaaacccat   1740
acccttgtga agaatggaga agtgtggagg acttccaggg aggaaataaa attgaagtta   1800
ataaaaatca atttgctcta attgaaggaa aaaacaaaac tgtaagtacc cttgttatcc   1860
aagcggcaaa tgtgtcagct ttgtacaaat gtgaagcggt caacaaagtc gggagaggag   1920
agagggtgat ctccttccac gtgaccaggg gtcctgaaat tactttgcaa cctgacatgc   1980
agcccactga gcaggagagc gtgtctttgt ggtgcactgc agacagatct acgtttgaga   2040
acctcacatg gtacaagctt ggcccacagc ctctgccaat ccatgtggga gagttgccca   2100
cacctgtttg caagaacttg gatactcttt ggaaattgaa tgccaccatg ttctctaata   2160
gcacaaatga cattttgatc atggagctta agaatgcatc cttgcaggac caaggagact   2220
atgtctgcct tgctcaagac aggaagacca agaaaagaca ttgcgtggtc aggcagctca   2280
cagtcctaga gcgtgtggca cccacgatca caggaaacct ggagaatcag acgacaagta   2340
ttggggaaag catcgaagtc tcatgcacgg catctggaaa tcccctcca cagatcatgt    2400 ggtttaaaga taatgagacc cttgtagaag actcaggcat tgtattgaag gatgggaacc   2460
ggaacctcac tatccgcaga gtgaggaagg aggacgaagg cctctacacc tgccaggcat   2520
gcagtgttct tggctgtgca aaagtggagg cattttttcat aatagaaggt gcccaggaaa   2580
```

```
agacgaactt ggaaatcatt attctagtag gcacggcggt gattgccatg ttcttctggc    2640
tacttcttgt catcatccta cggaccgtta agcgggccaa tggaggggaa ctgaagacag    2700
gctacttgtc catcgtcatg gatccagatg aactcccatt ggatgaacat tgtgaacgac    2760
tgccttatga tgccagcaaa tgggaattcc ccagagaccg gctgaagcta ggtaagcctc    2820
ttggccgtgg tgcctttggc caagtgattg aagcagatgc ctttggaatt gacaagacag    2880
caacttgcag gacagtagca gtcaaaatgt tgaaagaagg agcaacacac agtgagcatc    2940
gagctctcat gtctgaactc aagatcctca ttcatattgg tcaccatctc aatgtggtca    3000
accttctagg tgcctgtacc aagccaggag ggccactcat ggtgattgtg gaattctgca    3060
aatttggaaa cctgtccact tacctgagga gcaagagaaa tgaatttgtc ccctacaaga    3120 ccaaggggc acgattccgt caagggaaag actacgttgg agcaatccct gtggatctga    3180
aacggcgctt ggacagcatc accagtagcc agagctcagc cagctctgga tttgtggagg    3240
agaagtccct cagtgatgta gaagaagagg aagctcctga agatctgtat aaggacttcc    3300
tgaccttgga gcatctcatc tgttacagct tccaagtggc taagggcatg gagttcttgg    3360
catcgcgaaa gtgtatccac agggacctgg cggcacgaaa tatcctctta tcggagaaga    3420
acgtggttaa aatctgtgac tttggcttgg cccgggatat ttataaagat ccagattatg    3480
tcagaaaagg agatgctcgc ctcccttga aatggatggc cccagaaaca ttttttgaca    3540
gagtgtacac aatccagagt gacgtctggt cttttggtgt tttgctgtgg gaaatatttt    3600
ccttaggtgc ttctccatat cctggggtaa agattgatga agaatttgt aggcgattga    3660 aagaaggaac tagaatgagg gcccctgatt atactacacc agaaatgtac cagaccatgc    3720
tggactgctg gcacggggag cccagtcaga gacccacgtt ttcagagttg gtggaacatt    3780
tgggaaatct cttgcaagct aatgctcagc aggatggcaa agactacatt gttcttccga    3840
tatcagagac tttgagcatg gaagaggatt ctggactctc tctgcctacc tcacctgttt    3900
cctgtatgga ggaggaggaa gtatgtgacc ccaaattcca ttatgacaac acagcaggaa    3960
tcagtcagta tctgcagaac agtaagcgaa agagccggcc tgtgagtgta aaaacatttg    4020
aagatatccc gttagaagaa ccagaagtaa aagtaatccc agatgacaac cagacggaca    4080
gtggtatggt tcttgcctca gaagagctga aaactttgga agacagaacc aaattatctc    4140
catcttttgg tggaatggtg cccagcaaaa gcagggagtc tgtggcatct gaaggctcaa    4200
accagacaag cggctaccag tccggatatc actccgatga cacagacacc accgtgtact    4260
ccagtgagga agcagaactt ttaaagctga tagagattgg agtgcaaacc ggtagcacag    4320
cccagattct ccagcctgac tcggggacca cactgagctc tcctcctgtt taaaaggaag    4380
catccacacc cccaactcct ggacatcaca tgagaggtgc tgctcagatt tcaagtgtt    4440 gttctttcca ccagcaggaa gtagccgcat ttgatttca tttcgacaac agaaaaagga    4500
cctcggactg cagggagcca gtcttctagg catatcctgg aagaggcttg tgacccaaga    4560
atgtgtctgt gtcttctccc agtgttgacc tgatcctctt tttcattcat ttaaaaagca    4620
tttatcatgc ccctgctgc gggtctcacc atgggtttag aacaaagacg ttcaagaaat    4680
ggccccatcc tcaaagaagt agcagtacct ggggagctga cacttctgta aaactagaag    4740
ataaaccagg caatgtaagt gttcgaggtg ttgaagatgg aaggatttg cagggctgag    4800 tctatccaag aggctttgtt taggacgtgg gtcccaagcc aagccttaag tgtggaattc    4860
ggattgatag aaaggaagac taacgttacc ttgctttgga gagtactgga gcctgcaaat    4920
gcattgtgtt tgctctggtg gaggtgggca tggggtctgt tctgaaatgt aaagggttca    4980
```

```
gacggggttt ctggttttag aaggttgcgt gttcttcgag ttgggctaaa gtagagttcg    5040
ttgtgctgtt tctgactcct aatgagagtt ccttccagac cgttacgtgt ctcctggcca    5100
agccccagga aggaaatgat gcagctctgg ctccttgtct cccaggctga tcctttattc    5160
agaataccac aaagaaagga cattcagctc aaggctccct gccgtgttga agagttctga    5220
ctgcacaaac cagcttctgg tttcttctgg aatgaatacc ctcatatctg tcctgatgtg    5280
atatgtctga gactgaatgc gggaggttca atgtgaagct gtgtgtggtg tcaaagtttc    5340
aggaaggatt ttacccttt gttcttcccc ctgtccccaa cccactctca ccccgcaacc     5400
catcagtatt ttagttattt ggcctctact ccagtaaacc tgattgggtt tgttcactct    5460
ctgaatgatt attagccaga cttcaaaatt attttatagc ccaaattata acatctattg    5520
tattatttag acttttaaca tatagagcta tttctactga ttttgccct tgttctgtcc     5580
ttttttcaa aaagaaaat gtgttttttg tttggtacca tagtgtgaaa tgctgggaac      5640
aatgactata agacatgcta tggcacatat atttatagtc tgtttatgta gaaacaaatg    5700
taatatatta aagccttata tataatgaac tttgtactat tcacattttg tatcagtatt    5760
atgtagcata acaaaggtca taatgctttc agcaattgat gtcattttat taaagaacat    5820
tgaaaaactt gaaggaatcc ctttgcaagg ttgcattact gtacccatca tttctaaaat    5880
ggaagagggg gtggctgggc acagtggccg cacctaaaa acccagcact ttggggggcc     5940
aaggtgggag gatcgcttga gcccaggagt tcaagaccag tctggccaac atggtcagat    6000
tccatctcaa agaaaaaagg taaaaataaa ataaaatgga gaagaaggaa tcaga          6055

<210> SEQ ID NO 83
<211> LENGTH: 5464
<212> TYPE: DNA
<213> ORGANISM: Mus musculus

<400> SEQUENCE: 83
ctgtgtttcc ttagatcgcg cggaccgcta cccggcagga ctgaaagccc agactgtgtc      60
ccgcagccgg gataacctgg ctgacccgat tccgcggaca ccgctgcagc cgcggctgga    120
gccagggcgc cggtgcccg cgctctcccc ggtcttgcgc tgcgggggcg cataccgcct     180
ctgtgacttc tttgcgggcc agggacggag aaggagtctg tgcctgagaa ctgggctctg    240
tgcccagcgc gaggtgcagg atggagagca aggcgctgct agctgtcgct ctgtggttct    300
gcgtggagac ccgagccgcc tctgtgggtt tgcctggcga ttttctccat ccccccaagc    360
tcagcacaca gaaagacata ctgacaattt tggcaaatac aacccttcag attacttgca    420
ggggacagcg ggacctggac tggctttggc ccaatgctca gcgtgattct gaggaagggg    480
tattggtgac tgaatgcggc ggtggtgaca gtatcttctg caaaacactc accattccca    540
gggtggttgg aaatgatact ggagcctaca agtgctcgta ccgggacgtc gacatagcct    600
ccactgttta tgtctatgtt cgagattaca gatcaccatt catcgcctct gtcagtgacc    660
agcatggcat cgtgtacatc accgagaaca gaacaaaac tgtggtgatc ccctgccgag    720
ggtcgatttc aaacctcaat gtgtctcttt gcgctaggta tccagaaaag agatttgttc    780
cggatggaaa cagaatttcc tgggacacgc agataggctt tactctcccc agttacatga    840
tcagctatgc cggcatggtc ttctgtgagg caaagatcaa tgatgaaacc tatcagtcta    900
tcatgtacat agttgtggtt gtaggatata ggatttatga tgtgattctg agccccccgc    960
atgaaattga gctatctgcc ggagaaaaac ttgtcttaaa ttgtacagcg agaacagagc   1020
```

```
tcaatgtggg gcttgatttc acctggcact ctccaccttc aaagtctcat cataagaaga    1080
ttgtaaaccg ggatgtgaaa ccctttcctg ggactgtggc gaagatgttt ttgagcacct    1140
tgacaataga aagtgtgacc aagagtgacc aaggggaata cacctgtgta gcgtccagtg    1200
gacggatgat caagagaaat agaacatttg tccgagttca cacaaagcct tttattgctt    1260
tcggtagtgg gatgaaatct ttggtggaag ccacagtggg cagtcaagtc cgaatccctg    1320
tgaagtatct cagttaccca gctcctgata tcaaatggta cagaaatgga aggcccattg    1380
agtccaacta cacaatgatt gttggcgatg aactcaccat catggaagtg actgaaagag    1440
atgcaggaaa ctacacggtc atcctcacca accccatttc aatggagaaa cagagccaca    1500
tggtctctct ggttgtgaat gtcccacccc agatcggtga aaagccttg atctcgccta    1560
tggattccta ccagtatggg accatgcaga cattgacatg cacagtctac gccaaccctc    1620
ccctgcacca catccagtgg tactggcagc tagaagaagc ctgctcctac agacccggcc    1680
aaacaagccc gtatgcttgt aaagaatgga gacacgtgga ggatttccag gggggaaaca    1740
agatcgaagt caccaaaaac caatatgccc tgattgaagg aaaaaacaaa actgtaagta    1800
cgctggtcat ccaagctgcc aacgtgtcag cgttgtacaa atgtgaagcc atcaacaaag    1860
cgggacgagg agagagggtc atctccttcc atgtgatcag gggtcctgaa attactgtgc    1920
aacctgctgc ccagccaact gagcaggaga gtgtgtccct gttgtgcact gcagacagaa    1980
atacgtttga gaacctcacg tggtacaagc ttggctcaca ggcaacatcg gtccacatgg    2040
gcgaatcact cacaccagtt tgcaagaact ggatgctct ttggaaactg aatggcacca    2100
tgttttctaa cagcacaaat gacatcttga ttgtggcatt tcagaatgcc tctctgcagg    2160
accaaggcga ctatgtttgc tctgctcaag ataagaagac caagaaaaga cattgcctgg    2220
tcaaacagct catcatccta gagcgcatgg cacccatgat caccgaaat ctggagaatc    2280
agacaacaac cattggcgag accattgaag tgacttgccc agcatctgga atcctaccc    2340
cacacattac atggttcaaa gacaacgaga ccctggtaga agattcaggc attgtactga    2400
gagatgggaa ccggaacctg actatccgca gggtgaggaa ggaggatgga ggcctctaca    2460
cctgccaggc tgcaatgtc cttggctgtg caagagcgga gacgctcttc ataatagaag    2520
gtgcccagga aaagaccaac ttggaagtca ttatcctcgt cggcactgca gtgattgcca    2580
tgttcttctg gctccttctt gtcattgtcc tacggaccgt taagcgggcc aatgaagggg    2640
aactgaagac aggctacttg tctattgtca tggatccaga tgaattgccc ttggatgagc    2700
gctgtgaacg cttgccttat gatgccagca agtgggaatt ccccagggac cggctgaaac    2760
taggaaaacc tcttggccgc ggtgccttcg gccaagtgat tgaggcagac gcttttggaa    2820
ttgacaagac agcgacttgc aaaacagtag ccgtcaagat gttgaaagaa ggagcaacac    2880
acagcgagca tcgagccctc atgtctgaac tcaagatcct catccacatt ggtcaccatc    2940
tcaatgtggt gaacctccta ggcgcctgca ccaagccggg agggcctctc atggtgattg    3000
tggaattctg caagtttgga aacctatcaa cttacttacg gggcaagaga atgaatttg    3060
ttccctataa gagcaaaggg gcacgcttcc gccagggcaa ggactacgtt ggggagctct    3120
ccgtggatct gaaaagacgc ttggacagca tcaccagcag ccagagctct gccagctcag    3180
gctttgttga ggagaaatcg ctcagtgatg tagaggaaga agaagcttct gaagaactgt    3240
acaaggactt cctgaccttg gagcatctca tctgttacag cttccaagtg gctaagggca    3300
tggagttctt ggcatcaagg aagtgtatcc acagggacct ggcagcacga aacattctcc    3360
tatcggagaa gaatgtggtt aagatctgtg acttcggctt ggcccgggac atttataaag    3420
```

```
acccggatta tgtcagaaaa ggagatgccc gactcccttt gaagtggatg gccccggaaa    3480 ccattttga cagagtatac acaattcaga gcgatgtgtg gtctttcggt gtgttgctct      3540
gggaaatatt ttccttaggt gcctccccat accctggggt caagattgat gaagaatttt   3600
gtaggagatt gaaagaagga actagaatgc gggctcctga ctacactacc ccagaaatgt    3660
accagaccat gctggactgc tggcatgagg accccaacca gagaccctcg ttttcagagt    3720
tggtggagca tttgggaaac ctcctgcaag caaatgcgca gcaggatggc aaagactata    3780
ttgttcttcc aatgtcagag acactgagca tggaagagga ttctggactc tccctgccta   3840
cctcacctgt ttcctgtatg gaggaagagg aagtgtgcga ccccaaattc cattatgaca    3900
acacagcagg aatcagtcat tatctccaga acagtaagcg aaagagccgg ccagtgagtg    3960
taaaaacatt tgaagatatc ccattggagg aaccagaagt aaaagtgatc ccagatgaca    4020
gccagacaga cagtgggatg gtccttgcat cagaagagct gaaaactctg gaagacagga    4080
acaaattatc tccatctttt ggtggaatga tgcccagtaa aagcagggag tctgtggcct    4140
cggaaggctc caaccagacc agtggctacc agtctgggta tcactcagat gacacagaca    4200
ccaccgtgta ctccagcgac gaggcaggac ttttaaagat ggtggatgct gcagttcacg    4260
ctgactcagg gaccacactg cgctcacctc ctgtttaaat ggaagtggtc ctgtcccggc    4320
tccgccccca actcctggaa atcacgagag aggtgctgct tagattttca agtgttgttc    4380
tttccaccac ccggaagtag ccacatttga tttcatttt tggaggaggg acctcagact    4440
gcaaggagct tgtcctcagg gcatttccag agaagatgcc catgacccaa gaatgtgttg    4500
actctactct ctttccatt catttaaaag tcctatataa tgtgccctgc tgtggtctca    4560
ctaccagtta aagcaaaaga ctttcaaaca gtggctctgt cctccaagaa gtggcaacgg    4620
cacctctgtg aaactggatc gaatgggcaa tgctttgtgt gttgaggatg ggtgagatgt    4680
cccagggccg agtctgtcta ccttggaggc tttgtggagg atgcgggcta tgagccaagt    4740
gttaagtgtg ggatgtggac tgggaggaag gaaggcgcaa gctcgctcgg agagcggttg    4800
gagcctgcag atgcattgtg ctggctctgg tggaggtggg cttgtggcct gtcaggaaac    4860
gcaaaggcgg ccggcagggt ttggttttgg aaggtttgcg tgctcttcac agtcgggtta    4920
caggcgagtt ccctgtggcg tttcctactc ctaatgagag ttccttccgg actcttacgt    4980
gtctcctggc ctggccccag gaaggaaatg atgcagcttg ctccttcctc atctctcagg   5040
ctgtgcctta attcagaaca ccaaaagaga ggaacgtcgg cagaggctcc tgacggggcc    5100
gaagaattgt gagaacagaa cagaaactca gggtttctgc tgggtggaga cccacgtggc    5160
tgccctggtg gcagtgtctg agggttctct gtcaagtggc ggtaaaggct caggctggtg    5220
ttcttcctct atctccactc ctgtcaggcc cccaagtcct cagtatttta gctttgtggc    5280
ttcctgatgg cagaaaaatc ttaattggtt ggtttgctct ccagataatc actagccaga    5340
tttcgaaatt acttttagc cgaggttatg ataacatcta ctgtatcctt tagaatttta    5400
acctataaaa ctatgtctac tggtttctgc ctgtgtgctt atgttaaaaa aaaaaaaaa    5460 aaaa                                                                 5464
```

<210> SEQ ID NO 84
<211> LENGTH: 5871
<212> TYPE: DNA
<213> ORGANISM: Macaca fascicularis

<400> SEQUENCE: 84

-continued

```
tcccgggacc ccgggagagc aggcggtgtg tggtcactgc gtttcctctg cctgcgccgg      60
gcatcacttg cgcgccgcag agagccagtc tggcagccgg gatatcctct cctactggca     120
tccgcagacg cccctgcagc cgcggtcggc acccgggctc ccaagccgtg tgcgctcaac     180
ggtcctgcgc tgcgcggtgg cgcggattcc gtctccgcgc ctccttctct agacaggcgc     240
tgggagaaag aatcggcttc agagttctgg gcattttgcc cagctcgagg tgcaggatgg     300
cgagcaaggt gctgctggcc gtcgccctgt ggctctgcgt ggagacccgg gccgcctctg     360
tgggtttgcc tagtgtttct cttgatctgc ccaggctcag catacaaaaa gacatactta     420
caattaaggc taatacaact cttcaaatta cttgcagggg acagagggac ttggactggc     480
tttggcccaa taatcagagt ggcagtgagc aaagggtgga ggtgactgag tgcagcgatg     540
gcctcttctg taagacactc acaattccaa aagtgatcgg aaatgacact ggagcctaca     600
agtgcttcta ccgggaaact gacttggcct cggtcattta tgtctatgtt caagattaca     660
gatctccatt tattgcttct gttagtgacc aacatggagt cgtgtacatt actgagaaca     720
aaaacaaaac tgtggtgatt ccatgtctcg gtccatttc aaatctcaac gtgtcacttt      780
gtgcaaggta cccagaaaag agatttgttc ctgatggtaa cagaatttcc tgggacagca     840
agaagggctt tactattccc agctatatga tcagctatgc tggcatggtc ttctgtgaag     900
caaaaattaa tgatgaaagt taccagtcta ttatgtacat agttgtggtt gtagggtata     960
ggatttatga tgtggttctg agtccgtctc atggagttga actatctgtt ggagagaagc    1020
ttgtcttaaa ttgtacagca agaactgaac taaatgtggg gattgacttc aactgggaat    1080 accttcttc gaagcatcag cataagaaac ttgtaaaccg agatctaaaa acccagtctg     1140
ggagtgagat gaagaaattt ttgagcacct aactataga tggtgtaacc cggagtgacc     1200
aaggattgta cacctgtgca gcgtccagtg ggctgatgac caagaagaac agcacatttg    1260
tcagggtcca tgaaaaacct tttgttgctt ttggaagtgg catggaatct ctggtggaag    1320
ccacggtggg ggagcgtgtc agaatccctg tgaagtacct tggttacccg cccccagaaa    1380
taaaatggta taaaaatgga ataccccttg agtccaatca cacagttaaa gtggggcatg    1440
tgctgacgat catggaagtg agcgaaagag acacaggaaa ttacactgtc atccttacca    1500
atcccatttc aaaggagaag cagagtcacg tggtctctct ggttgtgtat gtcccacccc    1560
agattggtga gaaatctctg atctctcctg tggattccta ccagtacggc accactcaaa    1620
cgctgacatg tacggtctac gctattcctc ccccgcatca catccactgg tattggcagt    1680
tggaggaaga gtgccccaac gagcccagcc aagctgtctc agtgacaaac ccataccctt    1740
gtgaagaatg gagaagtgtg gaggacttcc agggaggaaa taaaattgaa gtcaataaaa    1800
atcaatttgc tctaattgaa ggaaaaaaca aaactgtaag taccccttgtt atccaagcgg    1860 caaatgtgtc agctttgtac aaatgtgaag cggtcaacaa agtcgggaga ggagagaggg    1920
tgatctcctt ccatgttacc aggggtcctg aaattacttt gcaacctgac ttgcagccca    1980
ctgaacagga gagcgtgtct ttgtggtgca ctgcagacaa atctacattt gagaacctca    2040
catggtacaa gcttggccca cagcctctgc cagtccacgt gggagagttg cccacacctg    2100
tttgcaagaa cttggatact ctttggaaat tgaatgccac tatattctct aatagcacaa    2160
atgacatttt gatcatggag cttaagaatg catccttgca ggaccaagga gactatgtct    2220
gcgttgctca agacaggaag accaagaaaa gacattgcgt ggtcaggcag ctcacagtcc    2280
tcgagcgcgt ggcacccatg atcacaggaa acctggagaa tcagacgacg agtattgggg    2340
aaaccattga agtctcatgc acggcatctg ggaatccccc tccacagatc atgtggttta    2400
```

```
aagataatga gacccttgta gaagactcag gcattgtatt gaaggatggg aaccggaacc   2460
tcactatccg cagagtgagg aaggaggacg aaggcctcta cacctgccag gcatgcagtg   2520
ttcttggctg tgcaaaagtg gaggcatttt tcataataga aggtgcccag gaaaagacga   2580
acttggaaat cattattcta gtaggcacag cagtgattgc catgttcttc tggctacttc   2640
ttgtcatcat tctacggacc gttaagcggg ccaatggagg ggaactgaag acaggctact   2700
tgtccatcgt catggatcct gatgaactcc cattggatga acactgtgaa cgactgcctt   2760
atgatgccag caaatgggaa ttccccagag accggctgaa gctaggtaag ccgcttggcc   2820
gtggtgcctt tggccaagtg attgaagcag atgcctttgg aattgacaag acagcaactt   2880
gcaggacagt agcagtcaaa atgttgaaag aaggagcgac acacagtgag catcgagccc   2940
tcatgtctga actcaagatc ctcattcata ttggtcacca tctcaatgtg gtcaaccttc   3000
taggtgcctg taccaagcca ggagggccac tcatggtgat tgtggaattc tgcaagtttg   3060
gaaacctatc cacttacctg aggagcaaga gaaatgaatt ttttgttttt tcctttgctt   3120
ttttatagac caaaggggca cgattccgtc aagggaaaga ctatgttgga gcaatccctg   3180
tggatctgaa acggcgcttg gacagcatca ccagtagcca gagctcagcc agctctggat   3240
tgtggagga gaagtccctc agtgatgtag aagaaggagga agctcctgaa gacctgtata   3300
aggacttcct gaccttggag catctcatct gttacagctt ccaagtgct aagggcatgg   3360
agttcttggc atcacgaaag tgtatccaca gggacctggc ggcacgaaat atcctcttat   3420
cggagaagaa cgtggttaaa atctgtgact ttggcttggc ccgggatatt tataaagatc   3480
cagattatgt cagaaaagga gatgctcgcc tcccttttgaa atggatggcc ccagaaacaa   3540
tttttgacag agtgtacaca atccagagtg acgtctggtc ttttggcgtg ttgctgtggg   3600
aaatattttc cttgggtgct tctccatatc ctggggtaaa gattgatgaa gaattttgta   3660
ggcgattgaa agaaggaact agaatgaggg cccccgatta tactacacca gaaatgtacc   3720
agaccatgct ggactgctgg cacggggagc ccagtcagag acccacgttt tcagagttgg   3780
tggaacattt gggaaatctc ttgcaagcta atgctcagca ggacggcaaa gactatattg   3840
ttcttccgat atcagagact ttgagcatgg aagaggattc tggactctct ctgcctacct   3900
cacctgtttc ctgtatggag gaggaggaag tatgtgaccc caaattccat tatgacaaca   3960
cagcaggaat cagtcagtat ctgcagaaca gtaagcgaaa gagccggcct gtgagtgtaa   4020
aaacatttga agacatccca ttagaagaac cagaagtaaa agtaatccca gatgacaacc   4080
agacggacag tggtatggtt cttgcctcag aagagctgaa aactttggaa gacagaacca   4140
aattagctcc atcttttagt ggaatggtgt ccagcaaaag cagggagtct gtggcatctg   4200
agggctcaaa ccagacaagt ggctaccagt ccggatatca ctccgacgac acagacacca   4260
ctgtgtactc cagtgaggaa gcagaacttt taaagctgat agagatcgga gtgcaaaccg   4320
gcagcacagc ccagattctc cagcctgact cggggaccac attgagctcc ctcctgtttt   4380
aaaaggaagc acccacgccc ccaactcctg gacatcacat aagaggtgct gctcagattt   4440
tcaagtgttg ttcttttccac cagcaggaag tagccgcatt tgattttcat ttcaacaaca   4500
aaaaaaggac ctcggactgc agggagctag tcttctaggc atatcctgga agaggcttgt   4560
gacccaagaa tgtgtccgtg tattctccca gtgttaacct gatcctcttt ttcattcatt   4620
taaaaagcat ttatcatgct gcctactgcg ggtctcacca tgggttagaa caaagacgtt   4680
caagaaatgg ccccatcctc aaagaagtag cagtacctgg ggagttgaca cttctgtaaa   4740
```

| | |
|---|---|
| actagaagat aaaccaggca atgtaagtgt ttggggtgtt gcagatggga aggatttgca | 4800 |
| gggctcagtc tatccaagag gctttgttta ggacgtcggt cccaagccaa gccttaagtg | 4860 |
| tggaattcag attgacagaa aggaagacta acattaactt gctctgagag agtactggag | 4920 |
| cctgcaaatg cattgtgttg gctccggtgg aagtgggcat ggggtctgtt ctgaaatgta | 4980 |
| aaggcttcag atggggtttc tggttttaga aggttgcgtg ttcttcgcag ttgggctgaa | 5040 |
| ggagagttcc ttgtgctgtt tccgactcct aatgagagtt ccttccagac ccttacgtgt | 5100 |
| ctcctggcca agccccagga aggaaattat gcagctctgg ctccttgtct ctcaggctga | 5160 |
| tcctttattc agaacaccac aaagtaagga cattcagctc gaggctccct gccgtgttga | 5220 |
| agagttctga ctgcacaaac cagcttctgg tttcttctgg atgaataccc tcatctctat | 5280 |
| cctgatgtga tatgtctgag actgaaggcg ggaggttcaa tgtcaagctg tgtgtagtgt | 5340 |
| caaagcttca ggaaggattt tacccttttg ttcttccccc cgtccccaac ccactctcac | 5400 |
| cccacaaccc atcaggattt tagttatttg gcctctacac tccagtaaac ctctacactc | 5460 |
| cagtaaacaa actccagaga gtttgttcac tctctgaatg attattagcc agacttcaaa | 5520 |
| attactttat agcccaaatt ataacatcta ttgtattgtt tagacttta acatatagag | 5580 |
| ctatttctac tgattttgc ccttttctg tcctttttt caaaaagaa aatgtgtttt | 5640 |
| ttgtttggta ccatagtgtg aaatgctggg aacaatgact ataagacatg ctatggcaca | 5700 |
| tatatttata gtctgtttat gtagaaacaa atgtaatata ttaaagcctt atattatata | 5760 |
| taatgaactt tgtactattc acattttgta tcagtattat gtagcataac aaaggtcata | 5820 |
| atgctttcag caatcgatgt catttttatta aaaacattg aaaaacttga a | 5871 |

<210> SEQ ID NO 85
<211> LENGTH: 5718
<212> TYPE: DNA
<213> ORGANISM: Homo sapiens

<400> SEQUENCE: 85

| | |
|---|---|
| ctcctgaggc tgccagcagc cagcagtgac tgcccgccct atctgggacc caggatcgct | 60 |
| ctgtgagcaa cttggagcca gagaggagat caacaaggag gaggagagag ccggcccctc | 120 |
| agccctgctg cccagcagca gcctgtgctc gccctgccca acgcagacag ccagacccag | 180 |
| ggcggcccct ctggcggctc tgctcctccc gaaggatgct tggggagtga ggcgaagctg | 240 |
| ggccgctcct ctcccctaca gcagcccct tcctccatcc ctctgttctc ctgagccttc | 300 |
| aggagcctgc accagtcctg cctgtccttc tactcagctg ttaccactc tgggaccagc | 360 |
| agtctttctg ataactggga gagggcagta aggaggactt cctggagggg gtgactgtcc | 420 |
| agagcctgga actgtgccca caccagaagc catcagcagc aaggacacca tgcggcttcc | 480 |
| gggtgcgatg ccagctctgg ccctcaaagg cgagctgctg ttgctgtctc tcctgttact | 540 |
| tctggaacca cagatctctc agggcctggt cgtcacaccc cgggggccag agcttgtcct | 600 |
| caatgtctcc agcaccttcg ttctgacctg ctcgggttca gctccggtgg tgtgggaacg | 660 |
| gatgtcccag gagcccccac aggaaatggc caaggcccag gatggcacct tctccagcgt | 720 |
| gctcacactg accaacctca ctgggctaga cacgggagaa tacttttgca cccacaatga | 780 |
| ctcccgtgga ctggagaccg atgagcggaa acggctctac atctttgtgc cagatccac | 840 |
| cgtgggcttc ctccctaatg atgccgagga actattcatc tttctcacgg aaataactga | 900 |
| gatcaccatt ccatgccgag taacagaccc cagctggtg gtgacactgc acgagaagaa | 960 |
| agggggacgtt gcactgcctg tccctatga tcaccaacgt ggcttttctg gtatctttga | 1020 |

-continued

```
ggacagaagc tacatctgca aaaccaccat tggggacagg gaggtggatt ctgatgccta   1080
ctatgtctac agactccagg tgtcatccat caacgtctct gtgaacgcag tgcagactgt   1140
ggtccgccag ggtgagaaca tcaccctcat gtgcattgtg atcgggaatg aggtggtcaa   1200
cttcgagtgg acatacccccc gcaaagaaag tgggcggctg gtggagccgg tgactgactt   1260
cctcttggat atgccttacc acatccgctc catcctgcac atcccagtg ccgagttaga   1320
agactcgggg acctacacct gcaatgtgac ggagagtgtg aatgaccatc aggatgaaaa   1380
ggccatcaac atcaccgtgg ttgagagcgg ctacgtgcgg ctcctgggag aggtgggcac   1440
actacaattt gctgagctgc atcggagccg gacactgcag gtagtgttcg aggcctaccc   1500
accgcccact gtcctgtggt tcaaagacaa ccgcaccctg ggcgactcca gcgctggcga   1560
aatcgccctg tccacgcgca acgtgtcgga gacccggtat gtgtcagagc tgacactggt   1620
tcgcgtgaag gtggcagagg ctggccacta ccaccatgcgg gccttccatg aggatgctga   1680
ggtccagctc tccttccagc tacagatcaa tgtccctgtc cgagtgctgg agctaagtga   1740
gagccaccct gacagtgggg aacagacagt ccgctgtcgt ggccggggca tgccccagcc   1800
gaacatcatc tggtctgcct gcagagacct caaaaggtgt ccacgtgagc tgccgcccac   1860
gctgctgggg aacagttccg aagaggagag ccagctggag actaacgtga cgtactggga   1920
ggaggagcag gagtttgagg tggtgagcac actgcgtctg cagcacgtgg atcggccact   1980
gtcggtgcgc tgcacgctgc gcaacgctgt gggccaggac acgcaggagg tcatcgtggt   2040
gccacactcc ttgccccttta aggtggtggt gatctcagcc atcctggccc tggtggtgct   2100
caccatcatc tcccttatca tcctcatcat gctttggcag aagaagccac gttacgagat   2160
ccgatggaag gtgattgagt ctgtgagctc tgacggccat gagtacatct acgtggaccc   2220
catgcagctg ccctatgact ccacgtggga gctgccgcgg gaccagcttg tgctgggacg   2280
caccctcggc tctggggcct ttgggcaggt ggtggaggcc acggctcatg gcctgagcca   2340
ttctcaggcc acgatgaaag tggccgtcaa gatgcttaaa tccacagccc gcagcagtga   2400
gaagcaagcc cttatgtcgg agctgaagat catgagtcac cttgggcccc acctgaacgt   2460
ggtcaacctg ttgggggcct gcaccaaagg aggacccatc tatatcatca ctgagtactg   2520
ccgctacgga gacctggtgg actacctgca ccgcaacaaa cacaccttcc tgcagcacca   2580
ctccgacaag cgccgcccgc ccagcgcgga gctctacagc aatgctctgc ccgttgggct   2640
cccccctgccc agccatgtgt ccttgaccgg ggagagcgac ggtggctaca tggacatgag   2700
caaggacgag tcggtggact atgtgcccat gctggacatg aaaggagacg tcaaatatgc   2760
agacatcgag tcctccaact acatggcccc ttacgataac tacgttccct ctgcccctga   2820
gaggacctgc cgagcaactt tgatcaacga gtctccagtg ctaagctaca tggacctcgt   2880
gggcttcagc taccaggtgg ccaatggcat ggagtttctg gcctccaaga actgcgtcca   2940
cagagacctg gcggctagga acgtgctcat ctgtgaaggc aagctggtca agatctgtga   3000
ctttggcctg gctcgagaca tcatgcggga ctcgaattac atctccaaag gcagcacctt   3060
tttgcctttta aagtggatgg ctccggagag catcttcaac agcctctaca ccaccctgag   3120
cgacgtgtgg tccttcggga tcctgctctg ggagatcttc accttgggtg gcaccccctta   3180
cccagagctg cccatgaacg agcagttcta caatgccatc aaacgggggtt accgcatggc   3240
ccagcctgcc catgcctccg acgagatcta tgagatcatg cagaagtgct gggaagagaa   3300
gtttgagatt cggccccccct tctcccagct ggtgctgctt ctcgagagac tgttgggcga   3360
```

```
aggttacaaa aagaagtacc agcaggtgga tgaggagttt ctgaggagtg accacccagc    3420
catccttcgg tcccaggccc gcttgcctgg gttccatggc ctccgatctc ccctggacac    3480
cagctccgtc ctctatactg ccgtgcagcc caatgagggt gacaacgact atatcatccc    3540
cctgcctgac cccaaacccg aggttgctga cgagggccca ctggagggtt cccccagcct    3600
agccagctcc accctgaatg aagtcaacac ctcctcaacc atctcctgtg acagccccct    3660
ggagccccag gacgaaccag agccagagcc ccagcttgag ctccaggtgg agccggagcc    3720
agagctggaa cagttgccgg attcggggtg ccctgcgcct cgggcggaag cagaggatag    3780
cttcctgtag ggggctggcc cctaccctgc cctgcctgaa gctcccccc tgccagcacc     3840
cagcatctcc tggcctggcc tgaccgggct tcctgtcagc caggctgccc ttatcagctg    3900
tcccttctg gaagctttct gctcctgacg tgttgtgccc caaaccctgg ggctggctta     3960
ggaggcaaga aaactgcagg ggccgtgacc agccctctgc ctccagggag gccaactgac    4020
tctgagccag ggttccccca gggaactcag ttttcccata tgtaagatgg gaaagttagg    4080
cttgatgacc cagaatctag gattctctcc ctggctgaca ggtggggaga ccgaatccct    4140
ccctgggaag attcttggag ttactgaggt ggtaaattaa cttttttctg ttcagccagc    4200
tacccctcaa ggaatcatag ctctctcctc gcacttttat ccacccagga gctagggaag    4260
agaccctagc ctccctggct gctggctgag ctagggccta gccttgagca gtgttgcctc    4320
atccagaaga aagccagtct cctccctatg atgccagtcc ctgcgttccc tggcccgagc    4380
tggtctgggg ccattaggca gcctaattaa tgctggaggc tgagccaagt acaggacacc    4440
cccagcctgc agcccttgcc cagggcactt ggagcacacg cagccatagc aagtgcctgt    4500
gtccctgtcc ttcaggccca tcagtcctgg ggctttttct ttatcaccct cagtcttaat    4560
ccatccacca gagtctagaa ggccagacgg gccccgcatc tgtgatgaga atgtaaatgt    4620
gccagtgtgg agtggccacg tgtgtgtgcc agtatatggc cctggctctg cattggacct    4680
gctatgaggc tttggaggaa tccctcaccc tctctgggcc tcagtttccc cttcaaaaaa    4740
tgaataagtc ggacttatta actctgagtg ccttgccagc actaacattc tagagtattc    4800
caggtggttg cacatttgtc cagatgaagc aaggccatat accctaaact tccatcctgg    4860
gggtcagctg ggctcctggg agattccaga tcacacatca cactctgggg actcaggaac    4920
catgcccctt ccccaggccc ccagcaagtc tcaagaacac agctgcacag gccttgactt    4980
agagtgacag ccggtgtcct ggaaagcccc cagcagctgc cccagggaca tgggaagacc    5040
acgggacctc tttcactacc cacgatgacc tccgggggta tcctgggcaa aagggacaaa    5100
gagggcaaat gagatcacct cctgcagccc accactccag cacctgtgcc gaggtctgcg    5160
tcgaagacag aatggacagt gaggacagtt atgtcttgta aaagacaaga agcttcagat    5220
gggtacccca agaaggatgt gagaggtggg cgctttggag gtttgcccct cacccaccag    5280
ctgccccatc cctgaggcag cgctccatgg gggtatggtt ttgtcactgc ccagacctag    5340
cagtgacatc tcattgtccc cagcccagtg ggcattggag gtgccagggg agtcagggtt    5400
gtagccaaga cgcccccgca cggggagggt tgggaagggg gtgcaggaag ctcaacccct    5460
ctgggcacca accctgcatt gcaggttggc accttacttc cctgggatcc ccagagttgg    5520
tccaaggagg gagagtgggt tctcaatacg gtaccaaaga tataatcacc taggtttaca    5580
aatattttta ggactcacgt taactcacat ttatacagca gaaatgctat tttgtatgct    5640
gttaagtttt tctatctgtg tactttttt taagggaaag attttaatat taaacctggt    5700
gcttctcact cacaaaaaa                                                 5718
```

<210> SEQ ID NO 86
<211> LENGTH: 5413
<212> TYPE: DNA
<213> ORGANISM: Mus musculus

<400> SEQUENCE: 86

| | | | | | |
|---|---|---|---|---|---|
| ggggcagaga | aagcccacag | tggtgtgagc | tctggggctg | tctgtggcca | cagtcccggc | 60 |
| taccctatct | gggacctagg | attgctctgg | gagtaacttt | gagagagagg | agaacagaga | 120 |
| ggaaacagtc | cagagccaga | gcgggcccag | accagtcgtc | agtctcctgc | ctgccagcta | 180 |
| gacctagggc | ggcccctcgg | gctgctccgc | tcctcccgga | ggatgctttt | ggagtgagga | 240 |
| ggggccgggc | tgcttctcac | ccctgagcac | cctctccatt | cccctgattc | tctcagggtt | 300 |
| ttccgcaatc | aggccagccc | ttctactgct | gtccgttttt | tgggtccagc | aaaataacag | 360 |
| aagacagcga | ggtggacttc | ctggaggggg | tgatagctca | catcagaagc | catctgtagc | 420 |
| ccggacacca | tggggcttcc | aggagtgata | ccagctttag | tcctcagagg | ccagttgttg | 480 |
| ctgtccgtgt | tatggctcct | gggaccgcag | acctcccggg | gcctagtcat | cacgcccccct | 540 |
| gggccagagt | ttgttctcaa | catctccagc | acctttgttc | tgacctgctc | gggctcagct | 600 |
| ccggtgatgt | gggaacagat | gtcccaggtg | ccctggcaag | aagcggccat | gaatcaggac | 660 |
| ggcaccttct | ccagtgtgct | gacactgacc | aatgtcactg | gggagacac | tggggaatac | 720 |
| ttttgtgtct | acaacaactc | actagggccg | gagctcagtg | agaggaagcg | tatctatatc | 780 |
| tttgtgccag | atcccaccat | gggcttcctc | cctatggact | ccgaggacct | gttcattttt | 840 |
| gtcacggatg | tcactgagac | gacaattccg | tgccgagtga | cagaccccca | gctggaggtg | 900 |
| acgctacatg | agaagaaagt | ggatatcccc | ctacacgtac | cctacgacca | ccagcgaggt | 960 |
| ttcactggta | cttttgagga | caagacttac | atttgcaaaa | ccaccattgg | ggacagggaa | 1020 |
| gtggactccg | atacttacta | cgtctacagc | ctccaggtgt | catccatcaa | cgtctctgtg | 1080 |
| aatgccgtgc | agactgtggt | ccgccagggc | gagagcatca | ccatccggtg | cattgtgatg | 1140 |
| ggcaatgatg | tggtgaactt | ccaatggacg | tacccccgca | tgaagagtgg | gcggctggtg | 1200 |
| gagccagtga | cagactacct | ctttggagtg | ccctcccgca | ttggctccat | cctgcatatc | 1260 |
| cccacggctg | agctgagtga | ttcgggcacc | tatacttgca | acgtgtcagt | gagtgtgaac | 1320 |
| gaccatggcg | atgagaaagc | catcaacatc | tctgtgatcg | agaatggcta | cgtgcggctg | 1380 |
| ctggagacac | tgggagatgt | agaaattgct | gagctgcacc | ggagtcggac | gctgcgggtg | 1440 |
| gtgttcgagg | cttatccgat | gccttctgtc | ctgtggctca | aggacaaccg | taccttgggt | 1500 |
| gactccggcg | ctggcgagtt | agttttgtct | actcgcaaca | tgtctgagac | ccggtacgtg | 1560 |
| tcagaactga | tcctggtacg | tgtgaaggtg | tcagaagcgg | gctactatac | tatgcgagcc | 1620 |
| ttccacgagg | acgatgaggt | ccagctctcc | ttcaagctgc | aggtcaatgt | ccccgtccgt | 1680 |
| gtgctggagc | tgagtgagag | tcaccctgcc | aatgggagc | agacaatccg | ctgtcgtggc | 1740 |
| cggggcatgc | ctcagccaaa | tgtcacctgg | tctacctgca | gagacctcaa | aagtaggtgt | 1800 |
| ccacgaaaac | tgtcacccac | acccttgggg | aatagttcca | aggaggagag | ccagctagaa | 1860 |
| acgaatgtga | ctttctggga | ggaagatcag | gaatacgagg | tggtgagcac | actgcgcctg | 1920 |
| cgccacgtgg | atcagccact | gtccgtacgc | tgcatgctgc | agaactccat | gggtggagat | 1980 |
| tcgcaggagg | tcaccgtggt | cccacattcc | ttgcccttca | aagtggtggt | gatctcagcc | 2040 |
| atcctggcct | tagtggtcct | taccgtcatc | tctctcatca | tcctcatcat | gctgtggcag | 2100 |

-continued

```
aagaagccac gctatgagat ccgatggaag gtcattgagt ctgtgagctc tgacggtcat    2160
gagtacatct acgtggaccc tgtgcagttg ccttacgact ccacctggga gctgccacgg    2220
gaccagcttg ttctgggacg cactcttggc tctggggctt tcggacaggt ggtggaggcc    2280
acagctcacg gtctgagcca ttcgcaggcc accatgaaag tggctgtcaa gatgctgaaa    2340
tcgacagcca gaagtagcga gaagcaagcc ttaatgtccg agctgaagat tatgagtcat    2400
cttggacccc acctgaacgt ggtcaacctg ctgggggcct gcaccaaagg agggcccatc    2460
tacatcatca cggaatactg ccgatacggt gatctggtgg actacctgca ccggaacaaa    2520
cacaccttct tgcagcgaca ctccaacaag cattgtccgc ccagtgctga gctctacagc    2580
aacgccctgc cagtggggtt ctccctaccc agccacttga acctgactgg ggagagtgac    2640
ggtggctaca tggatatgag caaggatgaa tctatagatt acgtgcccat gttggacatg    2700
aaaggagaca tcaaatacgc agacattgag tcccccagct acatggcccc ttatgataac    2760
tatgtcccat ctgcccctga aaggacctat cgcgccacct taatcaacga ctcaccagtg    2820
ctcagctaca cagacctcgt gggcttcagc taccaagtgg ccaacggcat ggacttctta    2880
gcctctaaga actgtgttca cgagacttg gcggccagga atgtgctcat ctgcgagggc    2940
aagctggtca gatctgtga cttcggcctg gctcgagaca tcatgaggga ctcaaactac    3000
atctccaaag gcagcacctt cctgcctctg aagtggatgg ccccagagag catcttcaac    3060
agcctctaca ccactttgag tgatgtctgg ctttttggga tcctactctg ggagatcttc    3120
acactgggtg gcaccccta cccagagctg cccatgaacg accagttcta caatgccatc    3180 aagagggggct accgcatggc ccagcctgct catgcctccg acgagatcta tgagatcatg    3240
cagaaatgct gggaagaaaa gtttgagact cgaccccct tctcccagct ggtgctgctc    3300
ctggagaggc ttctgggtga aggctataaa aagaagtacc agcaggtaga tgaggagttc    3360
ctgaggagtg accatcctgc catcctgagg tcccaagccc gctttccggg gatccacagc    3420
ctccgatccc ctctggacac cagctctgtt ctctacactg ccgtgcagcc caatgagagt    3480
gacaatgact acatcatccc cttacctgac cccaagcctg acgttgctga tgaaggtctc    3540
ccagaggggt cccccagcct tgccagttcc accttgaatg aagtcaacac ttcctccacc    3600
atctcctgcg acagtcccct ggagctccaa gaagagccac agcaagcaga gcctgaggca    3660
caactggagc agccacagga ttcaggctgc ccaggacctc tggctgaagc agaggacagc    3720
ttcctgtagg aactgacatc actccatttt gcccgaatct cccttctgcc tcccagaacc    3780
caaccctctt ggcctggcct ggcctggcct ggctcccag cagctacact gccacaagct    3840
gtcccctcga ggaaagccct tggtttgcag cactcaaggt ccagggaccc agcttagctt    3900
aggaggcaag agaactctgc ctcgggaagg tcatgggact ctgaaccagg gttcctccag    3960
gggactcagt ttccccaaat gtaagaggaa gagttgtact tggctacagg acaggtctgg    4020
agcccggatt cctgcagaaa tccacgactg tacggtggtg tgttcatatc ctcctgtgta    4080
gcagctgccc ctcagctgga ttgctctact ttgatcttcc taagaatcag gcaaggacct    4140
ggtgtctggc tcctggccaa actgtaacca gccttggaca aggtcttttc attcagagcc    4200 cacctccct ggtcttagct ttcccaggcc cgagctggtc tggggccagc catgcttaat    4260
gaatgctgtt agtggtgaag gtaggccgag tacagaatgc tctggcctgc agccctgcct    4320
gggcactcag ggcacacctg gccacaggaa gcacccactc ctttcagccc caccagtcct    4380
agaatagtcc ccaggtcact ctcagctgac ccacccacca gagtctgcag ggccattgtc    4440
cacgcctgtg ataggctaag catctgcctg aagtgtgtac ctaccactag gagccctggc    4500
```

-continued

```
tctgcgctgg acctgctatg agaccttggg ggctttcctt gttctctctg gggaccagtt      4560
ttctttcccc tttgaaaagc aagttggaca catagactct gagtaccctg tcaatagtac      4620
aattcttgta tgttctggga gtttgctctt gtcccgagga agcagggtca agtccttaaa      4680
ctgatctttc taggggtcag ctgagctctt ggaagatccc tgatacactt cacactctgg      4740
gggttcagga accgagcctc ttcttcaagt ctccaagtgc aactgcccag accttgactt      4800
ggagtgacag tgagtgtcct aggaaacccc cttacagctg tcctgaggac acagaagaga      4860
ccacgagacc cttttttcat atcatgaagc cagcaagagt ggcagagaag gcaagccagg      4920
ttacctcggg ccactgtcac cagcagcgtg tggacagaca tgatgacag tgaggacaga      4980 cgtcccatgc aggacaagag acttgagatg gcaatgaga ggaagatgct gacgggatta      5040
ccacctcaac tgccagctgc cccgtcccc agggagcacc ccacagaaac agttctaacc      5100
ctgaaccaat gaacattgca agtgcctggg gactagggag tgggggaag tcagcctttc      5160 tggggaccct ccctgctagc tggttggcta gctggcatct ccccgcttgg agcagcagag      5220
gctggggagt actgctcaca atggtaccaa agatagaatc cctaggtttt acaagtactt      5280
gtaggactcg agataaccca catttagaca ccggaagtgc tattttatat gctgttaagt      5340
tttcctatct gtactttttt tttaaatggg aaagatttta atattaaact tggtgcttct      5400
cactgaataa ccg      5413
```

<210> SEQ ID NO 87
<211> LENGTH: 5693
<212> TYPE: DNA
<213> ORGANISM: Macaca fascicularis

<400> SEQUENCE: 87

```
ctcctgaggc tgccagcagc cagcagtgac tgcccgccct atctgggacc aggatcgct       60 ctgtgagcaa cttggagcca gagaggagat caacaacgag gaggagagag ccggcccctc      120
agcccagctg cccagcagca gcctgcgctc gccctgccca acgcagacag ccagacccag      180
ggcggcccct ctgcggctc tgctcctccc gaaggatgct tggggagtga ggcgaagctg      240
ggccgctcct cttccctgca gcagtcccct ccctccatcc ctccgttctc ctgagccttc      300
aggagcctgc aacggtcctg cctggccttc tacccagctg ttacccactc tgggaccagc      360
agtctttctg ataacagaaa ctccaaactt gataacaggc agagggcagt aaggaggact      420
tcctggaggg ggtgactgtc cagagcctgg aactctgccc acaccagaag ccatcagcag      480
caaggacacc atgcggcttc cgggtgcgat gccagctctg ccctcaaag gccagctgct      540 gttgctgccc ctgctgttac tgctggaacc gcaggtctct cagggcctgg tcatcacacc      600 cccgggggcca gagcttatcc tcaatgtctc cagcaccttt gttctgacct gctcgggttc      660
agctcccgtg gtgtgggagc ggatgtccca ggagctccca caggaaatgg ccaaggccca      720
ggacaatacc ttctccagtg tgctgacact gaccaacctc actgggctag acacgggaga      780
atacttttgc acctacaatg actcccgtgg actggagcct gatgagcgga acggctcta       840 catctttgtg ccagatccca ccatgggctt cctccctaat gacgccgagg aactattcat      900
ctttcttacg gaaataactg agatcaccat tccatgccga gtaacagacc cacaactggt      960
ggtgacactg cacgagaaga aagggggacat tgcactgcct gtcccctacg atcaccagcg     1020
tggcttttct ggtatctttg aggacagaag ctacatctgc aaaaccacca ttggggacag     1080
ggaggtggat tccgacgcct actatgtcta cagactccag gtgtcatcca tcaacgtctc     1140
```

```
cgtgaatgca gtgcagacgg tggtccgcca gggtgagaac attaccctca tgtgcattgt    1200
gatcgggaat gaggtggtca acttcgagtg gatgtacccc cgcaaagaaa gtgggcggct    1260
ggtggagccg gtgaccgact tcctcttgga tatgccttac cacatccgct ccatcctgca    1320
catccccagt gccgagttag aagactcggg gacctacacc tgcaatgtga cagagagtgt    1380
gaatgaccat caggatgaaa aggccatcaa catcactgtg gttgagagtg gctacgtgcg    1440
gctcctggga gaggtgggag cactacaatt tgctgagctg caccggagcc ggacactgca    1500
ggtagtgttc gaggcctacc ctccgcccac cgtcctgtgg ttcaaagaca accgcacctt    1560
gggcgactcc agcgcaggcg agatcgccct gtccacgcgc aacgtgtcag agaccaggta    1620
tgtgtcagag ctgacactcg ttcgggtgaa ggtggcagag gctggccact acaccatgcg    1680
ggccttccat gaggacgctg aggtccagct ctccttccag ctacagatca atgtccctgt    1740
ccgcgtgctg gagctaagtg agagccaccc agacagcggg gaacagacag tccgctgtcg    1800
tggccggggc atgccccagc cgaacatcat ctggtctgcc tgcagagacc tcaaaaggtg    1860
tccacgcgag ctgccgccca tgctgctggg gaacagttct gaagaggaga gccagctgga    1920
gacgaacgtg acatactggg aggaggagca ggagtttgag gtggtgagca cactgcgtct    1980
gcagcacgtg gatcggccac tgtcggtgcg ctgcacgctg cgcaacgctg tgggccagga    2040
catgcaggag gtcatcgtgg tgccacactc tttgcccttc aaggcagtgg tgatctcagc    2100
catcctggcc ctggtggtcc tcaccatcat ctccctatc atcctcatca tgctttggca    2160
gaagaagcca cgttacgaga tccgatggaa ggtgattgag tctgtgagct ctgatggcca    2220
tgagtacatc tacgtggacc ccatgcagct gccctatgac tccacgtggg agctgccgcg    2280
ggaccagctt gtgctgggac gcaccctcgg ctctgggggcc tttgggcagg tggtggaggc    2340
cacggctcat ggcctgagcc attctcaggc cacgatgaaa gtggccgtca agatgcttaa    2400
atccacagcc cgcagcagtg agaagcaagc cctcatgtcg gagctgaaga tcatgagtca    2460
ccttgggccc caccctgaacg tggtcaacct gttgggggcc tgcaccaaag gaggacccat    2520
ctatatcatc actgagtact gccgctacgg agacctggtg gactacctgc accgcaacaa    2580
gcacacgttc ctgcagcacc attccgacaa gcgccgcccg cccagcgcgg agctctacag    2640
caatgcgctg cccgttgggc tcccctgcc cagccacgtg tccctgactg gggagagcga    2700
tggtggctac atggacatga gcaaggacga gtcggtggac tacgtgccca tgctggacat    2760
gaaaggagat gtcaaatatg ccgacatcga gtcctccaac tacatggccc cctacgataa    2820
ctacgttccc tctgccctg agaggacctg tcgggcaact ttaatcaatg agtctccggt    2880
gctaagctac atggaccttg tgggcttcag ctaccaggtg gccaatggca tggagttcct    2940
ggcctccaag aactgcgtgc accgagacct ggcggccagg aacgtgctca tctgcgaggg    3000
caagctggtc aagatctgtg actttggcct ggctcgagac atcatgcggg attcgaatta    3060
catctccaaa ggcagtacct ttttgccttt gaagtggatg gctccagaga gcatcttcaa    3120
cagcctctac accaccctga gcgacgtgtg gtccttcggg atcctgctct gggagatctt    3180
cactttgggt ggcacccctt acccagagct gcccatgaat gagcagttct acaatgccat    3240
caaacggggt taccgcatgg cccagcctgc ccacgcctcc gacgagatct atgagatcat    3300
gcagaagtgc tgggaagaga gtttgagat tcggccccct ttctcccagc tggtgctgct    3360
tctcgagaga ctgttgggcg aaggttacaa aaagaagtac cagcaggtgg atgaggagtt    3420
tctgaggagt gaccacccag ccatccttcg gtcccaggcc cgcttgcctg ggttccatgg    3480
cctccgatct cccctggaca gcagctccgt cctctatacc gccgtgcagc ccaatgaggg    3540
```

-continued

```
tgacaacgac tatatcatcc ccctgcctga ccccaaaccc gaggttgctg acgagggccc    3600
actggagggt tccccagcc tagccagctc caccctgaat gaagtcaaca cctcctcgac    3660
catctcctgt gacagccctc tggagcccca ggaggaacca gagccagagc cccagcttga    3720
gcgccaggtg gaaccagagc cagagctgga acagctgccg gattcagggt gccccgcgcc    3780
tcgagcggaa gcagaggaca gcttcctgta gggggctggc ccccaccctg ccctgcccaa    3840
agcttcccct ctgccagcac ccagcacctc tggcctggc cgggtctcct gtcagccagg     3900
ctgcccttat cagctgtccc cttctggaag ctttctgctc ctgacgtgtt gtgccccaaa    3960
ccctggggct ggcttaggag gcaagaaaac tgcaggggcc atgaccagcc ctgtgcctcc    4020
agggaggcta actgactctg agccaggggtt ccgcccaggg gactccgttt tcccatatgt   4080
aagatggtaa agttgggctt gatgcccaga atctaggatt ctctccctgg ctgataggta    4140
gggaggtcaa atccctccct ggaaagattc ttggggttat tgaggtggta aattaacttt    4200
tttctgttca gccagctacc cctcaaggaa tcatagctct ctcctcgcac ttttatccac    4260
ccaggagcta ggaaagggac cctagcatcc ctggctgctg cctgagctgg ggcctagcct    4320
tgggcagtgt tgcctcatcc agaagaaagc cagtctcctc cctatgatgc cagtccctgc    4380
tttccctggc ccaagctggt ctggggccat taggcagcct aattaatgct ggaggctgag    4440
ccaagtacag gacaccccca gcctgcagcc cctgcccagg gcacttggag cacatgtggc    4500
catagcaagt gcccgtgtcc ctgtccttca ggcccatcag tcctggagct ttttctttat    4560
caccctcagt cttaatccat ccaccagagt ctggaaggcc agacgggccc cgcatctgtg    4620
atgagaatgt aaatgtgcca gtgtggagtg gccacatgtg tgttccaata tatggccctg    4680
gctctgcact ggatctgcta tgagactttg gaggaatccc tcgccctctc tgggcctcag    4740 ttttccccctt gaaaaaatga acaagtcgga cttattaact ccaagtgcct tgccagcact    4800
aacattctag aatattccag gtggtcgcac atttgtccag atgaagcaag gtcatatacc    4860
ctaaacttcc atcctggggg gtcagctggg ctcctgggag attccagatc acacatcaca    4920
ctctggggac acaggaacca tgcccttcc ccaggcctcc agcaagtctc aagaacgcag     4980
ctgtccaggc cttgacttaa gaatgacagc cggtgtcttg gaaagccccc agcagctgcc    5040
ccagggacat gggaagacca cgggacctct ttcactaccc ccgatgacct ctgagggtat    5100
cccgggcaaa agagacagag ggcaaatgag atcacctcct gcagcccacc actccagcac    5160
ctgcgccgag gtctgcgtca gttatgtctt gtaaaggaca agaagcttca gatgggtact    5220
ccaagaagga tatgagaggt gggcgctttg gaggtttcct cctcaaccac cagctgcccc    5280
atccctgagg cagcactccg tgggggtatg gttttgtcac tgcccagacc tagcagtgac    5340
atctcattgt ccccagccca gtgagcattg gaggtgccag gggagtcggt tgtagccaag    5400
gcgtcccagc acggggaggg ttgggaaggg ggtgcaggaa gggcaccagc cctgcattgc    5460
aggttggcac cttacttccc tgagatcccc aaagttggtc caaggaggga gagtgggctc    5520
tcaatacggt accaaagata taatcaccta ggtttacaaa tatttttagg actcacgtta    5580
actcacattt atacagcaga agtgctattt tgtatgctgt taagttttc tatctgtgta     5640 cttttttaa gggaaagatt ttaatattaa acctggtgct tctcactcac aga            5693
```

<210> SEQ ID NO 88
<211> LENGTH: 2646
<212> TYPE: DNA
<213> ORGANISM: Homo sapiens

```
<400> SEQUENCE: 88
gacttctgca gtttctgttt ccttgactgg cagctcagcg gggccctccc gcttggatgt    60
tccgggaaag tgatgtgggt aggacaggcg gggcgagccg caggtgccag aacacagatt   120
gtataaaagg ctgggggctg gtggggagca ggggaaggga atgtgaccag gtctaggtct   180
ggagtttcag cttggacact gagccaagca gacaagcaaa gcaagccagg acacaccatc   240
ctgccccagg cccagcttct ctcctgcctt ccaacgccat ggggagcaat ctcagccccc   300
aactctgcct gatgcccttt atcttgggcc tcttgtctgg aggtgtgacc accactccat   360
ggtctttggc ccggcccag ggatcctgct ctctggaggg ggtagagatc aaaggcggct   420
ccttccgact tctccaagag ggccaggcac tggagtacgt gtgtccttct ggcttctacc   480
cgtaccctgt gcagacacgt acctgcagat ctacggggtc ctggagcacc ctgaagactc   540
aagaccaaaa gactgtcagg aaggcagagt gcagagcaat ccactgtcca agaccacacg   600
acttcgagaa cggggaatac tggccccggt ctccctacta caatgtgagt gatgagatct   660
ctttccactg ctatgacggt tacactctcc ggggctctgc caatcgcacc tgccaagtga   720
atggccgatg gagtgggcag acagcgatct gtgacaacgg agcggggtac tgctccaacc   780
cgggcatccc cattggcaca aggaaggtgg gcagccagta ccgccttgaa gacagcgtca   840
cctaccactg cagccggggg cttaccctgc gtggctccca gcggcgaacg tgtcaggaag   900
gtggctcttg gagcgggacg gagccttcct gccaagactc cttcatgtac gacacccctc   960
aagaggtggc cgaagctttc ctgtcttccc tgacagagac catagaagga gtcgatgctg  1020
aggatgggca cggcccaggg gaacaacaga agcggaagat cgtcctggac ccttcaggct  1080
ccatgaacat ctacctggtg ctagatggat cagacagcat tggggccagc aacttcacag  1140
gagccaaaaa gtgtcagtc aacttaattg agaaggtggc aagttatggt gtgaagccaa  1200
gatatggtct agtgacatat gccacatacc ccaaaatttg ggtcaaagtg tctgaagcag  1260
acagcagtaa tgcagactgg gtcacgaagc agctcaatga aatcaattat gaagaccaca  1320
agttgaagtc agggactaac accaagaagg ccctccaggc agtgtacagc atgatgagct  1380
ggccagatga cgtccctcct gaaggctgga accgcacccg ccatgtcatc atcctcatga  1440
ctgatggatt gcacaacatg ggcggggacc caattactgt cattgatgag atccgggact  1500
tgctatacat tggcaaggat cgcaaaaaacc caagggagga ttatctggat gtctatgtgt  1560 ttgggggtcgg gcctttggtg aaccaagtga acatcaatgc tttggcttcc aagaaagaca  1620
atgagcaaca tgtgttcaaa gtcaaggata tggaaaacct ggaagatgtt ttctaccaaa  1680
tgatcgatga aagccagtct ctgagtctct gtggcatggt ttgggaacac aggaagggta  1740
ccgattacca caagcaacca tggcaggcca agatctcagt cattcgccct tcaaagggac  1800
acgagagctg tatgggggct gtggtgtctg agtactttgt gctgacagca gcacattgtt  1860
tcactgtgga tgacaaggaa cactcaatca aggtcagcgt aggaggggag aagcgggacc  1920
tggagataga agtagtccta tttcacccca actacaacat taatgggaaa aaagaagcag  1980
gaattcctga attttatgac tatgacgttg ccctgatcaa gctcaagaat aagctgaaat  2040
atggccagac tatcaggccc atttgtctcc cctgcaccga gggaacaact cgagctttga  2100
ggcttcctcc aactaccact tgccagcaac aaaaggaaga gctgctccct gcacaggata  2160
tcaaagctct gttttgtgtct gaggaggaga aaagctgac tcggaaggag gtctacatca  2220
agaatgggga taagaaaggc agctgtgaga gagatgctca atatgcccca ggctatgaca  2280
aagtcaagga catctcagag gtggtcaccc ctcggttcct ttgtactgga ggagtgagtc  2340
```

```
cctatgctga ccccaatact tgcagaggtg attctggcgg cccccttgata gttcacaaga   2400 gaagtcgttt cattcaagtt ggtgtaatca gctggggagt agtggatgtc tgcaaaaacc   2460
agaagcggca aaagcaggta cctgctcacg cccgagactt tcacatcaac ctctttcaag   2520
tgctgccctg gctgaaggag aaactccaag atgaggattt gggttttcta taagggtttt   2580
cctgctggac aggggcgtgg gattgaatta aaacagctgc gacaacaaaa aaaaaaaaa   2640 aaaaaa                                                               2646

<210> SEQ ID NO 89
<211> LENGTH: 2763
<212> TYPE: DNA
<213> ORGANISM: Mus musculus

<400> SEQUENCE: 89
gctccatcac acagtccatg gaaagactga tcttttaaat tgggggtagt ggaggtggtg     60
gtctgtgctt gttaggaggg gtctgggggc taagagggag ctttgaaagg gaagttctgg    120
cccttggtca gtcaagggtg gggctcacat agtttctgtt tcctcagttg gcagttcagc    180
tggggccctc cttcatgaat gttccggaaa gcagtggctg cgtgcgcagg gtaggctggc    240
caggctgcag atgccagagc agattgcata aaaggttagg ggacagtggg aaagggggtgt   300 agccagatcc agcatttggg tttcagtttg gacaggaggt caaataggca cccagagtga    360
cctggagagg gctttgggcc actggactct ctggtgcttt ccatgacaat ggagagcccc    420
cagctctgcc tcgtcctctt ggtcttaggc ttctcctctg gaggtgtgag cgcaactcca    480
gtgcttgagg cccggcccca agtctcctgc tctctggagg gagtagagat caaaggcggc    540
tcctttcaac ttctccaagg cggtcaggcc ctggagtacc tatgtccctc tggcttctac    600 ccatacccccg tgcagactcg aacctgcaga tccacaggct cctggagcga cctgcagacc    660
cgagaccaaa agattgtcca gaaggcggaa tgcagagcaa tacgctgccc acgaccgcag    720
gactttgaaa atggggaatt ctggccccgg tccccccttct acaacctgag tgaccagatt    780
tcttttcaat gctatgatgg ttacgttctc cggggctctg ctaatcgcac ctgccaagag    840
aatggccggt gggatgggca acagcaatt tgtgatgatg gagctggata ctgtcccaat    900
cccggtattc ctattgggac aaggaaggtg ggtagccaat accgccttga agacattgtt    960
acttaccact gcagccgggg acttgtcctg cgtggctccc agaagcgaaa gtgtcaagaa   1020
ggtggctcat ggagtgggac agagccttcc tgccaagatt ccttcatgta tgacagccct   1080
caagaagtgg ccgaagcatt cctatcctcc ctgacagaga ccatcgaagg agccgatgct   1140
gaggatgggc acagcccagg agaacagcag aagaggaaga ttgtcctaga cccctcgggc   1200
tccatgaata tctacctggt gctagatgga tcagacagca tcggaagcag caacttcaca   1260
ggggctaagc ggtgcctcac caacttgatt gagaaggtgg cgagttacgg ggtgaggcca   1320
cgatatggtc tcctgacata tgctacagtc cccaaagtgt tggtcagagt gtctgatgag   1380
aggagtagcg atgccgactg ggtcacagag aagctcaacc aaatcagtta tgaagaccac   1440
aagctgaagt cagggaccaa caccaagagg gctctccagg ctgtgtatag catgatgagc   1500
tgggcagggg atgccccgcc tgaaggctgg aatagaaccc gccatgtcat catcattatg   1560
actgatggct tgcacaacat gggtggaaac cctgtcactg tcattcagga catccgagcc   1620
ttgctggaca tcggcaggga tcccaaaaat cccaggagg attacctgga tgtgtatgtg   1680 tttgggtcg ggcctctggt ggactccgtg aacatcaatg ccttagcttc caaaaggac    1740
```

```
aatgagcatc atgtgtttaa agtcaaggat atggaagacc tggagaatgt tttctaccaa    1800
atgattgatg aaaccaaatc tctgagtctc tgtggcatgg tgtgggagca taaaaaaggc    1860
aacgattatc ataagcaacc atggcaagcc aagatctcag tcactcgccc tctgaaagga    1920
catgagacct gtatgggggc cgtggtgtct gagtacttcg tgctgacagc agcgcactgc    1980
ttcatggtgg atgatcagaa acattccatc aaggtcagcg tgggggtca gaggcgggac     2040 ctggagattg aagaggtcct gttccacccc aaatacaata ttaatgggaa aaaggcagaa    2100
gggatccctg agttctatga ttatgatgtg ccctagtca agctcaagaa caagctcaag     2160
tatggccaga ctctcaggcc catctgtctc ccctgcacgg agggaaccac acgagccttg    2220
aggcttcctc agacagccac ctgcaagcag cacaaggaac agttgctccc tgtgaaggat    2280
gtcaaagctc tgtttgtatc tgagcaaggg aagagcctga ctcggaagga ggtgtacatc    2340
aagaatgggg acaagccagt tgtgagagag atgctacaaa ggcccaaggc tatgagaagg    2400
tcaaagatgc ctctgaggtg gtcactccac ggttcctctg cacaggaggg gtggatccct    2460
atgctgaccc caacacatgc aaaggagatt ccggggggccc tctcattgtt cacaagagaa    2520
gccgcttcat tcaagttggt gtgattagct ggggagtagt agatgtctgc agagaccaga    2580
ggcggcaaca gctggtaccc tcttatgccc gggacttcca catcaacctc ttccaggtgc    2640
tgccctggct aaaggacaag ctcaaagatg aggatttggg ttttctataa agagcttcct    2700
gcagggagag tgtgaggaca gattaaagca gttacaataa caaaaaaaaa aaaaaaaaa    2760 aaa                                                                   2763

<210> SEQ ID NO 90
<211> LENGTH: 4086
<212> TYPE: DNA
<213> ORGANISM: Macaca fascicularis

<400> SEQUENCE: 90
atagatatat tagcatcagg gagacagggc aaaggttcca cccttcagct cagtccccag     60
tccctgctta ttatttccct aacagaagac catccccctt gccactccct gggttttctt    120
ctctggcagc aatgaagcag ctgctgagcc agctctggtt ttcgggaagt cagatgacct    180
tttccctccc gcggctctct gcctctcgct gtccctaggg aggacaccat ggacccactg    240
atggttcttt tttgcctgct gttcctgtac ccaggtccgg cagactcggc tacctcctgc    300
cctcagaacg tgaatatctc tggtggcacc ttcaccctca gccatggctg ggcccctggg    360
agccttctca tctactcctg tccccagggc ctgtacccat ccccagcgtc acggctgtgc    420
aagagcagcg acagtggca gaccccaaga gccacccggt ctctgactaa ggcggtctgc    480
aaacctggcc actgccccaa ccccggcatt tcgctgggcg cggtgcggac aggctcccgc    540
tttggtcatg gggacaaggt ccgctatcgc tgctcctcga tcttgtgct cacggggtct    600 gcggagcggg agtgccaggg caacggggtc tggagtggaa cggagcccat ctgccgccag    660
ccctactctt atgacttccc tgaggacgtg gcccctgccc tgggcacctc cttctcccac    720
atgcttgggg ccaccaatcc cacccagagg acaaaggatc atgaaaatgg aactgggact    780
aacacctatg cagccctaaa cagtgtctat ctcatgatga caatcaaat gcaactcctt    840 ggcatgaaaa cgatggcctg gcaggaaatc cgacatgcca tcatccttct gacagatgga    900
aagtccaata tgggtggctc tcccaaaaca gctgttgacc aaatcagaga gatcttgaat    960
atcaaccaga gaggaatga ctatctggac atctatgcca tcggggtggg caagctggat    1020
gtggactgga gagaactgaa tgagctgggg tccaagaagg atggcgagag gcatgccttc    1080
```

-continued

```
attctgcagg acacaaaggc tctgcaccag gtctttgaac atatgctgga tgtctccaag      1140
ctcacagaca ccatctgcgg ggtggggaac atgtcagcaa acgcctctga ccaagagagg      1200
acaccctggc atgtcactat taagcccaag agccaagaga cctgccgggg agccctcatc      1260
tccgaccaat gggtcctgac agcggctcac tgcttccgcg atggcaacga ccactcccta      1320
tggagggtca atgtgggaga ccccaaatcc cagtgggggca aagaattcct tattgagaag      1380
gcagtgattt ccccaggatt tgatgtcttt gccaaaaaga accagggaat cctggagttc      1440
tatggtgatg acatcgccct gctgaagctg gcccagaaag taaagatgtc cacccatgcc      1500
aggcccatct gccttccctg caccatggag gccaatctgg ctctgcggag acctcaaggc      1560
agcacctgta gggaccatga gaatgaactg ctgaacaaac agagtgttcc tgctcatttt      1620
gtcgccttga tgggagcaa actgaacatt aaccttaaga tgggagtgga gtggacaagc       1680
tgtgccgagg tcgtctccca agaaaaaacc atgttcccca acttgacaga tgtcagggag      1740
gtggtgacag accagtttct atgcagtggg acccaggagg atgagagtcc ctgcaagggt      1800
gtgaccacca ctccattgtc ttcggcccag cctcaaggat cctgctctct ggagggggta      1860
gagatcaaag gtggctcctt ccgacttctc caagagggcc aggcactgga atacgtgtgt      1920
ccttctggct tctacccgta ccctgtgcag acacgtacct gcagatccac ggggtcctgg      1980
agcaccctgc agactcaaga tcgaaaaact gtcaagaagg cagagtgcag agcaatccgc      2040
tgtccacgac cacaggactt cgagaacggg gaataccggc cccggtctcc ctactacaat      2100
gtgagtgatg agatctcttt ccactgctat gacggttaca ctctccgggg ctctgccaat      2160
cgcacctgcc aagtgaatgg ccggtggagt gggcagacag cgatctgtga caacggagcg      2220
gggtactgct ccaacccagg catccccatt ggcacaagga aggtgggcag ccggtaccgc      2280
cttgaagaca gcgtcaccta ccactgcagc cgggggctta ccctgcgtgg ctcccagcgg      2340
cgaacatgtc aggaaggtgg ctcttggagc gggacggagc cttcctgcca agactccttc      2400
atgtacgaca cccctcaaga ggtggccgaa gctttcctgt cttccctgac ggagaccata      2460
gaaggagtcg atgccgagga tgggcacagc ccagggggaac aacagaagcg gaggatcatc      2520
ctagaccctt caggctccat gaacatctac ctggtgctag atggatcaga cagcattggg      2580
gccggcaact tcacaggagc caaaaagtgt ctagtcaact taattgagaa ggtggcaagt      2640
tatggtgtga agccaagata tgctctagta acatatgcca cataccccag aatttgggtc      2700
aaagtgtctg accaagagag cagcaatgca gactgggtca cgaagaagct cagtgaaatc      2760
aattatgaag accacaagtt gaagtcaggg actaacacca gagggccct ccaggcagtg       2820
tacagcatga tgagttggcc agaggacatc cctcctgaag gctggaaccg cacccgccat      2880
gtcatcatcc tcatgaccga tggattgcac aacatgggcg gggacccaat tactgtcatt      2940
gatgagatcc gggacttgtt atacatcggc aaggatcgta aaacccgag ggaggattat       3000
ctggatgtct atgtgtttgg ggttggacct tggtgggacc aagtgaacat caatgctttg      3060
gcttccaaga aagacaatga gcaacatgtg ttcaaagtca aggatatgga aaacctggaa      3120
gacgttttct tccaaatgat tgatgaaagc cagtctctga gtctctgtgg catggtttgg      3180
gaacacagca agggtaccga ttaccacaag caaccatggc aggccaagat ctcagtcact      3240
cgccccttcga agggacatga gagctgtatg gggctgtgg tgtctgagta ctttgtgctg       3300
acagcagcac attgttttac tgtggacgac aaggaacact caatcaaggt cagcgtggga      3360
gggaagaagc gggacctgga gatagaaaaa gtcctatttc accccgacta caacattagc      3420
```

| | |
|---|---|
| gagaaaaaag aagcaggaat tcctgaattt tatgactatg acgttgccct gatcaagctc | 3480 |
| aagaataagt tgaattatga cccgactatc aggcccattt gtctcccctg caccgaggga | 3540 |
| acaactcgag ctttgaggct tcctccaact accacttgcc agcaacagaa ggaagagctg | 3600 |
| ctccctgcac aggatatcaa agctctgttt gtgtctgagg aggagaagaa gctgactcgg | 3660 |
| aaggaggtct acatcaagaa tggggataag aaaggcagct gtgagagaga tgctcaatat | 3720 |
| gccccaggct atgacaaagt caaggacatc tcggaggtgg tcacccctcg gttcctttgt | 3780 |
| actggaggag tgagtcccta tgctgacccc aatacttgca gaggtgattc tggcggcccc | 3840 |
| ttgatagttc acaagagaag tcgtttcatt caagttggtg tcatcagctg gggagtagtg | 3900 |
| gatgtctgca aaaaccagaa gcggcaaaag caggtacctg ctcacgcccg agactttcac | 3960 |
| gtcaacctct tccaagtgct gccctggctg aaggagaaac tccaagatga ggatttgggt | 4020 |
| tttctctaag gggttttcctg ctggacaggg gcgcgggatt gaattaaaac agctgcgaca | 4080 |
| acactt | 4086 |

```
<210> SEQ ID NO 91
<211> LENGTH: 136
<212> TYPE: DNA
<213> ORGANISM: Artificial Sequence
<220> FEATURE:
<223> OTHER INFORMATION: miR-1 structure

<400> SEQUENCE: 91
```

| | |
|---|---|
| ggatccggta tattgctgtt gacagtgagc gtgcaagagc tccagagaga agactgtgaa | 60 |
| gcagatgggt cttctctctg gagctcttgc tcgcctactg cctcggactt caagctagcg | 120 |
| gtacctttt aagctt | 136 |

```
<210> SEQ ID NO 92
<211> LENGTH: 136
<212> TYPE: DNA
<213> ORGANISM: Artificial Sequence
<220> FEATURE:
<223> OTHER INFORMATION: miR-12 structure

<400> SEQUENCE: 92
```

| | |
|---|---|
| ggatccggta tattgctgtt gacagtgagc gagcctccga aaccatgaac ttactgtgaa | 60 |
| gcagatgggt aagttcatgg tttcggaggc ccgcctactg cctcggactt caagctagcg | 120 |
| gtacctttt aagctt | 136 |

```
<210> SEQ ID NO 93
<211> LENGTH: 136
<212> TYPE: DNA
<213> ORGANISM: Artificial Sequence
<220> FEATURE:
<223> OTHER INFORMATION: miR-3 structure

<400> SEQUENCE: 93
```

| | |
|---|---|
| ggatccggta tattgctgtt gacagtgagc gagagaccct ggtggacatc ttactgtgaa | 60 |
| gcagatgggt aagatgtcca ccagggtctc gcgcctactg cctcggactt caagctagcg | 120 |
| gtacctttt aagctt | 136 |

```
<210> SEQ ID NO 94
<211> LENGTH: 136
<212> TYPE: DNA
<213> ORGANISM: Artificial Sequence
<220> FEATURE:
<223> OTHER INFORMATION: miR-4 structure
```

<400> SEQUENCE: 94
ggatccggta tattgctgtt gacagtgagc gacacatagg agagatgagc ttactgtgaa    60
gcagatgggt aagctcatct ctcctatgtg ccgcctactg cctcggactt caagctagcg   120
gtaccttttt aagctt                                                    136

<210> SEQ ID NO 95
<211> LENGTH: 136
<212> TYPE: DNA
<213> ORGANISM: Artificial Sequence
<220> FEATURE:
<223> OTHER INFORMATION: miR-5 structure

<400> SEQUENCE: 95
ggatccggta tattgctgtt gacagtgagc gagaatgcag accaaagaaa gaactgtgaa    60
gcagatgggt tctttctttg gtctgcattc acgcctactg cctcggactt caagctagcg   120
gtaccttttt aagctt                                                    136

<210> SEQ ID NO 96
<211> LENGTH: 136
<212> TYPE: DNA
<213> ORGANISM: Artificial Sequence
<220> FEATURE:
<223> OTHER INFORMATION: miR-6 structure

<400> SEQUENCE: 96
ggatccggta tattgctgtt gacagtgagc gaagaacagt ccttaatcca gaactgtgaa    60
gcagatgggt tctggattaa ggactgttct gcgcctactg cctcggactt caagctagcg   120
gtaccttttt aagctt                                                    136

<210> SEQ ID NO 97
<211> LENGTH: 136
<212> TYPE: DNA
<213> ORGANISM: Artificial Sequence
<220> FEATURE:
<223> OTHER INFORMATION: miR-7 structure

<400> SEQUENCE: 97
ggatccggta tattgctgtt gacagtgagc gactgggatt cctgtagaca caactgtgaa    60
gcagatgggt tgtgtctaca ggaatcccag acgcctactg cctcggactt caagctagcg   120
gtaccttttt aagctt                                                    136

<210> SEQ ID NO 98
<211> LENGTH: 136
<212> TYPE: DNA
<213> ORGANISM: Artificial Sequence
<220> FEATURE:
<223> OTHER INFORMATION: miR-8 structure

<400> SEQUENCE: 98
ggatccggta tattgctgtt gacagtgagc gatagacaca cccacccaca taactgtgaa    60
gcagatgggt tatgtgggtg ggtgtgtcta ccgcctactg cctcggactt caagctagcg   120
gtaccttttt aagctt                                                    136

<210> SEQ ID NO 99
<211> LENGTH: 136
<212> TYPE: DNA
<213> ORGANISM: Artificial Sequence
<220> FEATURE:

<223> OTHER INFORMATION: miR-9 structure

<400> SEQUENCE: 99
ggatccggta tattgctgtt gacagtgagc gagtgctact gtttatccgt aaactgtgaa    60
gcagatgggt ttacggataa acagtagcac ccgcctactg cctcggactt caagctagcg   120
gtaccttttt aagctt                                                   136

<210> SEQ ID NO 100
<211> LENGTH: 136
<212> TYPE: DNA
<213> ORGANISM: Artificial Sequence
<220> FEATURE:
<223> OTHER INFORMATION: miR-10 structure

<400> SEQUENCE: 100
ggatccggta tattgctgtt gacagtgagc gagagatatt ccgtagtaca taactgtgaa    60
gcagatgggt tatgtactac ggaatatctc gcgcctactg cctcggactt caagctagcg   120
gtaccttttt aagctt                                                   136

<210> SEQ ID NO 101
<211> LENGTH: 136
<212> TYPE: DNA
<213> ORGANISM: Artificial Sequence
<220> FEATURE:
<223> OTHER INFORMATION: miR-V-1 structure

<400> SEQUENCE: 101
ggatccggta tattgctgtt gacagtgagc gatggactgg ctttggccca atactgtgaa    60
gcagatgggt attgggccaa agccagtcca acgcctactg cctcggactt caagctagcg   120
gtaccttttt aagctt                                                   136

<210> SEQ ID NO 102
<211> LENGTH: 136
<212> TYPE: DNA
<213> ORGANISM: Artificial Sequence
<220> FEATURE:
<223> OTHER INFORMATION: miR-V-2 structure

<400> SEQUENCE: 102
ggatccggta tattgctgtt gacagtgagc gaccagctac atgatcagct atactgtgaa    60
gcagatgggt atagctgatc atgtagctgg gcgcctactg cctcggactt caagctagcg   120
gtaccttttt aagctt                                                   136

<210> SEQ ID NO 103
<211> LENGTH: 136
<212> TYPE: DNA
<213> ORGANISM: Artificial Sequence
<220> FEATURE:
<223> OTHER INFORMATION: miR-V-3 structure

<400> SEQUENCE: 103
ggatccggta tattgctgtt gacagtgagc gaccatgttc ttctggctac ttactgtgaa    60
gcagatgggt aagtagccag aagaacatgg ccgcctactg cctcggactt caagctagcg   120
gtaccttttt aagctt                                                   136

<210> SEQ ID NO 104
<211> LENGTH: 136
<212> TYPE: DNA
<213> ORGANISM: Artificial Sequence
<220> FEATURE:
<223> OTHER INFORMATION: miR-V-4 structure

<400> SEQUENCE: 104
ggatccggta tattgctgtt gacagtgagc gaggaccgtt aagcgggcca atactgtgaa    60
gcagatgggt attggcccgc ttaacggtcc gcgcctactg cctcggactt caagctagcg   120
gtaccttttt aagctt                                                   136

<210> SEQ ID NO 105
<211> LENGTH: 136
<212> TYPE: DNA
<213> ORGANISM: Artificial Sequence
<220> FEATURE:
<223> OTHER INFORMATION: miR-V-5 structure

<400> SEQUENCE: 105
ggatccggta tattgctgtt gacagtgagc gacatggtga ttgtggaatt ctactgtgaa    60
gcagatgggt agaattccac aatcaccatg acgcctactg cctcggactt caagctagcg   120
gtaccttttt aagctt                                                   136

<210> SEQ ID NO 106
<211> LENGTH: 136
<212> TYPE: DNA
<213> ORGANISM: Artificial Sequence
<220> FEATURE:
<223> OTHER INFORMATION: miR-V-6 structure

<400> SEQUENCE: 106
ggatccggta tattgctgtt gacagtgagc gactgacctt ggagcatctc atactgtgaa    60
gcagatgggt atgagatgct ccaaggtcag gcgcctactg cctcggactt caagctagcg   120
gtaccttttt aagctt                                                   136

<210> SEQ ID NO 107
<211> LENGTH: 136
<212> TYPE: DNA
<213> ORGANISM: Artificial Sequence
<220> FEATURE:
<223> OTHER INFORMATION: miR-V-7 structure

<400> SEQUENCE: 107
ggatccggta tattgctgtt gacagtgagc gaggagcatc tcatctgtta caactgtgaa    60
gcagatgggt tgtaacagat gagatgctcc acgcctactg cctcggactt caagctagcg   120
gtaccttttt aagctt                                                   136

<210> SEQ ID NO 108
<211> LENGTH: 136
<212> TYPE: DNA
<213> ORGANISM: Artificial Sequence
<220> FEATURE:
<223> OTHER INFORMATION: miR-V-8 structure

<400> SEQUENCE: 108
ggatccggta tattgctgtt gacagtgagc gagctaaggg catggagttc ttactgtgaa    60
gcagatgggt aagaactcca tgcccttagc ccgcctactg cctcggactt caagctagcg   120
gtaccttttt aagctt                                                   136

<210> SEQ ID NO 109
<211> LENGTH: 136
<212> TYPE: DNA

```
<213> ORGANISM: Artificial Sequence
<220> FEATURE:
<223> OTHER INFORMATION: miR-V-9 structure

<400> SEQUENCE: 109
ggatccggta tattgctgtt gacagtgagc gaccagaaat gtaccagacc atactgtgaa      60
gcagatgggt atggtctggt acatttctgg acgcctactg cctcggactt caagctagcg     120
gtaccttttt aagctt                                                     136

<210> SEQ ID NO 110
<211> LENGTH: 136
<212> TYPE: DNA
<213> ORGANISM: Artificial Sequence
<220> FEATURE:
<223> OTHER INFORMATION: miR-V-10 structure

<400> SEQUENCE: 110
ggatccggta tattgctgtt gacagtgagc gaccccaaat tccattatga caactgtgaa      60
gcagatgggt tgtcataatg gaatttgggg acgcctactg cctcggactt caagctagcg     120
gtaccttttt aagctt                                                     136

<210> SEQ ID NO 111
<211> LENGTH: 136
<212> TYPE: DNA
<213> ORGANISM: Artificial Sequence
<220> FEATURE:
<223> OTHER INFORMATION: miR-P-1 structure

<400> SEQUENCE: 111
ggatccggta ccggtatatt gctgttgaca gtgagcgtct ccaggtgtca tccatcaaac      60
tgtgaagcag atgggtttga tggatgacac ctggagtcgc ctactgcctc ggacttcaac     120
aattgttttt aagctt                                                     136

<210> SEQ ID NO 112
<211> LENGTH: 136
<212> TYPE: DNA
<213> ORGANISM: Artificial Sequence
<220> FEATURE:
<223> OTHER INFORMATION: miR-P-2 structure

<400> SEQUENCE: 112
ggatccggta ccggtatatt gctgttgaca gtgagcgtgg tgtcatccat caacgtctac      60
tgtgaagcag atgggtagac gttgatggat gacacctcgc ctactgcctc ggacttcaac     120
aattgttttt aagctt                                                     136

<210> SEQ ID NO 113
<211> LENGTH: 136
<212> TYPE: DNA
<213> ORGANISM: Artificial Sequence
<220> FEATURE:
<223> OTHER INFORMATION: miR-P-3 structure

<400> SEQUENCE: 113
ggatccggta ccggtatatt gctgttgaca gtgagcgaca tgagtacatc tacgtggaac      60
tgtgaagcag atgggttcca cgtagatgta ctcatggcgc ctactgcctc ggacttcaac     120
aattgttttt aagctt                                                     136

<210> SEQ ID NO 114
<211> LENGTH: 136
```

<212> TYPE: DNA
<213> ORGANISM: Artificial Sequence
<220> FEATURE:
<223> OTHER INFORMATION: miR-P-4 structure

<400> SEQUENCE: 114
ggatccggta ccggtatatt gctgttgaca gtgagcgaga cctcgtgggc ttcagctaac    60
tgtgaagcag atgggttagc tgaagcccac gaggtcccgc ctactgcctc ggacttcaac   120
aattgttttt aagctt                                                  136

<210> SEQ ID NO 115
<211> LENGTH: 136
<212> TYPE: DNA
<213> ORGANISM: Artificial Sequence
<220> FEATURE:
<223> OTHER INFORMATION: miR-P-5 structure

<400> SEQUENCE: 115
ggatccggta ccggtatatt gctgttgaca gtgagcgtgg caagctggtc aagatctgac    60
tgtgaagcag atgggtcaga tcttgaccag cttgcctcgc ctactgcctc ggacttcaac   120
aattgttttt aagctt                                                  136

<210> SEQ ID NO 116
<211> LENGTH: 136
<212> TYPE: DNA
<213> ORGANISM: Artificial Sequence
<220> FEATURE:
<223> OTHER INFORMATION: miR-P-6 structure

<400> SEQUENCE: 116
ggatccggta ccggtatatt gctgttgaca gtgagcgaga gagcatcttc aacagcctac    60
tgtgaagcag atgggtaggc tgttgaagat gctctcccgc ctactgcctc ggacttcaac   120
aattgttttt aagctt                                                  136

<210> SEQ ID NO 117
<211> LENGTH: 136
<212> TYPE: DNA
<213> ORGANISM: Artificial Sequence
<220> FEATURE:
<223> OTHER INFORMATION: miR-P-7 structure

<400> SEQUENCE: 117
ggatccggta ccggtatatt gctgttgaca gtgagcgaca tcttcaacag cctctacaac    60
tgtgaagcag atgggttgta gaggctgttg aagatgccgc ctactgcctc ggacttcaac   120
aattgttttt aagctt                                                  136

<210> SEQ ID NO 118
<211> LENGTH: 136
<212> TYPE: DNA
<213> ORGANISM: Artificial Sequence
<220> FEATURE:
<223> OTHER INFORMATION: miR-P-8 structure

<400> SEQUENCE: 118
ggatccggta ccggtatatt gctgttgaca gtgagcgacc agagctgccc atgaacgaac    60
tgtgaagcag atgggttcgt tcatgggcag ctctggcgc ctactgcctc ggacttcaac    120
aattgttttt aagctt                                                  136

<210> SEQ ID NO 119

```
<211> LENGTH: 124
<212> TYPE: DNA
<213> ORGANISM: Artificial Sequence
<220> FEATURE:
<223> OTHER INFORMATION: miR-P-9 structure

<400> SEQUENCE: 119
ggtaccggta tattgctgtt gacagtgagc gacagttcta caatgccatc aaactgtgaa      60
gcagatgggt ttgatggcat tgtagaactg ccgcctactg cctcggactt caacaattgt     120
tttt                                                                  124

<210> SEQ ID NO 120
<211> LENGTH: 136
<212> TYPE: DNA
<213> ORGANISM: Artificial Sequence
<220> FEATURE:
<223> OTHER INFORMATION: miR-P-10 structure

<400> SEQUENCE: 120
ggatccggta ccggtatatt gctgttgaca gtgagcgaca tgcctccgac gagatctaac      60
tgtgaagcag atgggttaga tctcgtcgga ggcatggcgc ctactgcctc ggacttcaac     120
aattgttttt aagctt                                                     136

<210> SEQ ID NO 121
<211> LENGTH: 136
<212> TYPE: DNA
<213> ORGANISM: Artificial Sequence
<220> FEATURE:
<223> OTHER INFORMATION: miR-C-1

<400> SEQUENCE: 121
ggatccgcta gcggtatatt gctgttgaca gtgagcgatg ccaagactcc ttcatgtaac      60
tgtgaagcag atgggttaca tgaaggagtc ttggcagcgc ctactgcctc ggacttcaag     120
gtaccttttt aagctt                                                     136

<210> SEQ ID NO 122
<211> LENGTH: 136
<212> TYPE: DNA
<213> ORGANISM: Artificial Sequence
<220> FEATURE:
<223> OTHER INFORMATION: miR-C-2 structure

<400> SEQUENCE: 122
ggatccgcta gcggtatatt gctgttgaca gtgagcgaaa catctacctg gtgctagaac      60
tgtgaagcag atgggttcta gcaccaggta gatgttccgc ctactgcctc ggacttcaag     120
gtaccttttt aagctt                                                     136

<210> SEQ ID NO 123
<211> LENGTH: 136
<212> TYPE: DNA
<213> ORGANISM: Artificial Sequence
<220> FEATURE:
<223> OTHER INFORMATION: miR-C-3 structure

<400> SEQUENCE: 123
ggatccgcta gcggtatatt gctgttgaca gtgagcgagg tgctagatgg atcagacaac      60
tgtgaagcag atgggttgtc tgatccatct agcaccacgc ctactgcctc ggacttcaag     120
gtaccttttt aagctt                                                     136
```

<210> SEQ ID NO 124
<211> LENGTH: 136
<212> TYPE: DNA
<213> ORGANISM: Artificial Sequence
<220> FEATURE:
<223> OTHER INFORMATION: miR-C-4 structure

<400> SEQUENCE: 124
ggatccgcta gcggtatatt gctgttgaca gtgagcgact agatggatca gacagcatac    60
tgtgaagcag atgggtatgc tgtctgatcc atctagccgc ctactgcctc ggacttcaag   120
gtaccttttt aagctt                                                   136

<210> SEQ ID NO 125
<211> LENGTH: 136
<212> TYPE: DNA
<213> ORGANISM: Artificial Sequence
<220> FEATURE:
<223> OTHER INFORMATION: miR-C-5 structure

<400> SEQUENCE: 125
ggatccgcta gcggtatatt gctgttgaca gtgagcgaga ggattatctg gatgtctaac    60
tgtgaagcag atgggttaga catccagata atcctcccgc ctactgcctc ggacttcaag   120
gtaccttttt aagctt                                                   136

<210> SEQ ID NO 126
<211> LENGTH: 136
<212> TYPE: DNA
<213> ORGANISM: Artificial Sequence
<220> FEATURE:
<223> OTHER INFORMATION: miR-C-6 structure

<400> SEQUENCE: 126
ggatccgcta gcggtatatt gctgttgaca gtgagcgatc tctgagtctc tgtggcatac    60
tgtgaagcag atgggtatgc cacagagact cagagaccgc ctactgcctc ggacttcaag   120
gtaccttttt aagctt                                                   136

<210> SEQ ID NO 127
<211> LENGTH: 136
<212> TYPE: DNA
<213> ORGANISM: Artificial Sequence
<220> FEATURE:
<223> OTHER INFORMATION: miR-C-7 structure

<400> SEQUENCE: 127
ggatccgcta gcggtatatt gctgttgaca gtgagcgagc tgtggtgtct gagtacttac    60
tgtgaagcag atgggtaagt actcagacac cacagcccgc ctactgcctc ggacttcaag   120
gtaccttttt aagctt                                                   136

<210> SEQ ID NO 128
<211> LENGTH: 136
<212> TYPE: DNA
<213> ORGANISM: Artificial Sequence
<220> FEATURE:
<223> OTHER INFORMATION: miR-C-8 structure

<400> SEQUENCE: 128
ggatccgcta gcggtatatt gctgttgaca gtgagcgaag gatatcaaag ctctgtttac    60
tgtgaagcag atgggtaaac agagctttga tatcctgcgc ctactgcctc ggacttcaag   120
gtaccttttt aagctt                                                   136

```
<210> SEQ ID NO 129
<211> LENGTH: 136
<212> TYPE: DNA
<213> ORGANISM: Artificial Sequence
<220> FEATURE:
<223> OTHER INFORMATION: miR-C-9 structure

<400> SEQUENCE: 129
ggatccgcta gcggtatatt gctgttgaca gtgagcgacg aaggaggtc tacatcaaac    60 tgtgaagcag atgggtttga tgtagacctc cttccgacgc ctactgcctc ggacttcaag   120 gtacctttt aagctt                                                   136

<210> SEQ ID NO 130
<211> LENGTH: 31
<212> TYPE: RNA
<213> ORGANISM: Artificial Sequence
<220> FEATURE:
<223> OTHER INFORMATION: Artificial primer (qRT PCR RNA)

<400> SEQUENCE: 130
uggguuaugu ggugggugu gucuaccgcc u                                   31

<210> SEQ ID NO 131
<211> LENGTH: 21
<212> TYPE: DNA
<213> ORGANISM: Artificial Sequence
<220> FEATURE:
<223> OTHER INFORMATION: Artificial primer (qRT PCR)

<400> SEQUENCE: 131
tatgtgggtg ggtgtgtcta c                                             21

<210> SEQ ID NO 132
<211> LENGTH: 470
<212> TYPE: DNA
<213> ORGANISM: Artificial Sequence
<220> FEATURE:
<223> OTHER INFORMATION: U6-miR-7 - DNA construct

<400> SEQUENCE: 132
cctaaggccc agtggaaaga cgcgcaggca aaacgcacca cgtgacggag cgtgaccgcg    60
cgccgagcgc gcgccaaggt cgggcaggaa gagggcctat ttcccatgat tccttcatat   120
ttgcatatac gatacaaggc tgttagagag ataattagaa ttaatttgac tgtaaacaca   180
aagatattag tacaaaatac gtgacgtaga aagtaataat ttcttgggta gtttgcagtt   240
ttaaaattat gttttaaaat ggactatcat atgcttaccg taacttgaaa gtatttcgat   300 ttcttggtt tatatatctt gtggaaagga cgcgggatcc ggtatattgc tgttgacagt   360
gagcgactgg gattcctgta gacacaactg tgaagcagat gggttgtgtc tacaggaatc   420
ccagacgcct actgcctcgg acttcaagct agcggtacct ttttaagctt              470

<210> SEQ ID NO 133
<211> LENGTH: 604
<212> TYPE: DNA
<213> ORGANISM: Artificial Sequence
<220> FEATURE:
<223> OTHER INFORMATION: VDM2-miR-7 - DNA construct

<400> SEQUENCE: 133
cctaaggcat tctttccata gcccacaggg ctgtcaaaga ccccagggcc tagtcagagg    60
ctcctccttc ctggagagtt cctggcacag aagttgaagc tcagcacagc ccctaaccc   120
```

```
ccaactctct ctgcaaggcc tcaggggtca gaacactggt ggagcagatc ctttagcctc      180 tggatttttag ggccatggta gagggggtgt tgccctaaat tccagccctg gtctcagccc     240
aacaccctcc aagaagaaat tagagggcc atggccaggc tgtgctagcc gttgcttctg      300
agcagattac aagaagggac taagacaagg actcctttgt ggaggtcctg gcttagggag      360
tcaagtgacg gcggctcagc actcacgtgg gcagtgccag cctctaagag tgggcagggg     420
cactggccac agagtcccag ggagtcccac cagcctagtc gccagaccgg atccggtata     480
ttgctgttga cagtgagcga ctgggattcc tgtagacaca actgtgaagc agatgggttg     540
tgtctacagg aatcccagac gcctactgcc tcggacttca agctagcggt accttttttaa    600 gctt                                                                 604
```

<210> SEQ ID NO 134
<211> LENGTH: 477
<212> TYPE: DNA
<213> ORGANISM: Artificial Sequence
<220> FEATURE:
<223> OTHER INFORMATION: ICAM2-miR-7 - DNA construct

<400> SEQUENCE: 134

```
cctaaggatg ggatttgggg ttccccagat ctggggcttg taggcctgac tctcccctgt       60
gcacacgtct catacacgca tgcgtgcacc cattgcctgc cccgcccctt gcacagggag      120
tcagcaggga ggactgggtt atgccctgct tatcagcagc ttcccagctt cctctgcctg      180
gattcttaga ggcctggggt cctagaacga gctggtgcac gtggcttccc aaagatctct      240
cagataatga gaggaaatgc agtcatcagt ttgcagaagg ctagggattc tgggccatag      300
ctcagacctg cgcccaccat ctccctccag gcagcccttg gggatccggt atattgctgt      360
tgacagtgag cgactgggat tcctgtagac acaactgtga agcagatggg ttgtgtctac      420
aggaatccca gacgcctact gcctcggact tcaagctagc ggtacctttt taagctt        477
```

<210> SEQ ID NO 135
<211> LENGTH: 984
<212> TYPE: DNA
<213> ORGANISM: Artificial Sequence
<220> FEATURE:
<223> OTHER INFORMATION: RPE65-miR-7 - DNA construct

<400> SEQUENCE: 135

```
cctaaggttc caaggacttc tttgggcagt accttgtctg tgctggcaag caactgagac       60
ttaatgaaag agtattggag atatgaatga attgatgctg tatactctca gagtgccaaa      120
catataccaa tggacaagaa ggtgaggcag agagcagaca ggcattagtg acaagcaaag      180
atatgcagaa tttcattctc agcaaatcaa aagtcctcaa cctggttgga agaatattgg      240
cactgaatgg tatcaataag gttgctagag agggttagag gtgcacaatg tgcttccata      300
acattttata cttctccaat cttagcacta atcaaacatg gttgaatact ttgtttacta      360
taactcttac agagttataa gatctgtgaa gacagggaca gggacaatac ccatctctgt      420
ctggttcata ggtggtatgt aatagatatt tttaaaaata agtgagttaa tgaatgaggg     480
tgagaatgaa ggcacagagg tattagggggg aggtgggccc cagagaatgg tgccaaggtc    540
cagtggggtg actgggatca gctcaggcct gacgctggcc actcccacct agctcctttc     600
tttctaatct gttctcattc tccttgggaa ggattgaggt ctctggaaaa cagccaaaca     660
actgttatgg gaacagcaag cccaaataaa gccaagcatc aggggggatct gagagctgaa    720
```

```
agcaacttct gttccccctc cctcagctga aggggtgggg aagggctccc aaagccataa    780
ctccttttaa gggatttaga aggcataaaa aggcccctgg ctgagaactt ccttcttcat    840
tctgcagtgg atccggtata ttgctgttga cagtgagcga ctgggattcc tgtagacaca    900
actgtgaagc agatgggttg tgtctacagg aatcccagac gcctactgcc tcggacttca    960
agctagcggt acctttttaa gctt                                           984
```

```
<210> SEQ ID NO 136
<211> LENGTH: 426
<212> TYPE: DNA
<213> ORGANISM: Artificial Sequence
<220> FEATURE:
<223> OTHER INFORMATION: FLT-miR-7 - DNA construct

<400> SEQUENCE: 136
cctaagggcg ctcccgggcc cgcgtcgcca gcacctcccc acgcgcgctc ggccccgggc     60
cacccgccct cgtcggcccc cgcccctctc cgtagccgca gggaagcgag cctgggagga    120
agaagagggt aggtggggag gcggatgagg ggtggggac cccttgacgt caccagaagg    180
aggtgccggg gtaggaagtg ggctgggaa aggttataaa tcgcccccgc cctcggctgc    240
tcttcatcga ggtccgcggg aggctcggag gcgccaggc ggacactcct ggatccggta    300
tattgctgtt gacagtgagc gactgggatt cctgtagaca caactgtgaa gcagatgggt    360
tgtgtctaca ggaatcccag acgcctactg cctcggactt caagctagcg gtaccttttt    420
aagctt                                                                426
```

```
<210> SEQ ID NO 137
<211> LENGTH: 577
<212> TYPE: DNA
<213> ORGANISM: Artificial Sequence
<220> FEATURE:
<223> OTHER INFORMATION: U6-miR-7-MiR-V-7 - DNA construct

<400> SEQUENCE: 137
cctaaggccc agtggaaaga cgcgcaggca aaacgcacca cgtgacggag cgtgaccgcg     60
cgccgagcgc gcgccaaggt cgggcaggaa gagggcctat ttcccatgat tccttcatat    120
ttgcatatac gatacaaggc tgttagagag ataattgaa ttaatttgac tgtaaacaca    180
aagatattag tacaaaatac gtgacgtaga agtaataat ttcttgggta gtttgcagtt    240
ttaaaattat gttttaaaat ggactatcat atgcttaccg taacttgaaa gtatttcgat    300
ttcttgggtt tatatatctt gtggaaagga cgcgggatcc ggtatattgc tgttgacagt    360
gagcgactgg gattcctgta gacacaactg tgaagcagat gggttgtgtc tacaggaatc    420
ccagacgcct actgcctcgg acttcaagct agcggtaccg gtatattgct gttgacagtg    480
agcgaggagc atctcatctg ttacaactgt gaagcagatg ggttgtaaca gatgagatgc    540
tccacgccta ctgcctcgga cttcaatttt taagctt                              577
```

```
<210> SEQ ID NO 138
<211> LENGTH: 705
<212> TYPE: DNA
<213> ORGANISM: Artificial Sequence
<220> FEATURE:
<223> OTHER INFORMATION: VDM2-miR-7-miR-V-7 - DNA construct

<400> SEQUENCE: 138
cctaaggcat tctttccata gcccacaggg ctgtcaaaga ccccagggcc tagtcagagg     60
ctcctccttc ctggagagtt cctggcacag aagttgaagc tcagcacagc ccctaacccc    120
```

| | |
|---|---|
| ccaactctct ctgcaaggcc tcaggggtca gaacactggt ggagcagatc ctttagcctc | 180 |
| tggattttag ggccatggta gagggggtgt tgccctaaat tccagccctg gtctcagccc | 240 |
| aacaccctcc aagaagaaat tagaggggcc atggccaggc tgtgctagcc gttgcttctg | 300 |
| agcagattac aagaagggac taagacaagg actcctttgt ggaggtcctg gcttagggag | 360 |
| tcaagtgacg gcggctcagc actcacgtgg gcagtgccag cctctaagag tgggcagggg | 420 |
| cactggccac agagtcccag ggagtcccac cagcctagtc gccagaccga tccggtatat | 480 |
| tgctgttgac agtgagcgac tgggattcct gtagacacaa ctgtgaagca gatgggttgt | 540 |
| gtctacagga atcccagacg cctactgcct cggacttcaa gctagcggta ccggtatatt | 600 |
| gctgttgaca gtgagcgagg agcatctcat ctgttacaac tgtgaagcag atgggttgta | 660 |
| acagatgaga tgctccacgc ctactgcctc ggacttcaaa agctt | 705 |

<210> SEQ ID NO 139
<211> LENGTH: 578
<212> TYPE: DNA
<213> ORGANISM: Artificial Sequence
<220> FEATURE:
<223> OTHER INFORMATION: ICAM2-miR-7-miR-V-7 - DNA construct

<400> SEQUENCE: 139

| | |
|---|---|
| cctaaggatg ggatttgggg ttccccagat ctggggcttg taggcctgac tctcccctgt | 60 |
| gcacacgtct catacacgca tgcgtgcacc cattgcctgc cccgcccctt gcacagggag | 120 |
| tcagcaggga ggactgggtt atgccctgct tatcagcagc ttcccagctt cctctgcctg | 180 |
| gattcttaga ggcctggggt cctagaacga gctggtgcac gtggcttccc aaagatctct | 240 |
| cagataatga gaggaaatgc agtcatcagt ttgcagaagg ctagggattc tgggccatag | 300 |
| ctcagacctg cgcccaccat ctccctccag gcagcccttg ggatccggta tattgctgtt | 360 |
| gacagtgagc gactgggatt cctgtagaca caactgtgaa gcagatgggt tgtgtctaca | 420 |
| ggaatcccag acgcctactg cctcggactt caagctagcg gtaccggtat attgctgttg | 480 |
| acagtgagcg aggagcatct catctgttac aactgtgaag cagatgggtt gtaacagatg | 540 |
| agatgctcca cgcctactgc ctcggacttc aaaagctt | 578 |

<210> SEQ ID NO 140
<211> LENGTH: 1085
<212> TYPE: DNA
<213> ORGANISM: Artificial Sequence
<220> FEATURE:
<223> OTHER INFORMATION: RPE65-miR-7-miR-V-7 - DNA construct

<400> SEQUENCE: 140

| | |
|---|---|
| cctaaggttc caaggacttc tttgggcagt accttgtctg tgctggcaag caactgagac | 60 |
| ttaatgaaag agtattggag atatgaatga attgatgctg tatactctca gagtgccaaa | 120 |
| catataccaa tggacaagaa ggtgaggcag agagcagaca ggcattagtg acaagcaaag | 180 |
| atatgcagaa tttcattctc agcaaatcaa aagtcctcaa cctggttgga agaatattgg | 240 |
| cactgaatgg tatcaataag gttgctagag agggttagag gtgcacaatg tgcttccata | 300 |
| acattttata cttctccaat cttagcacta atcaaacatg gttgaatact ttgtttacta | 360 |
| taactcttac agagttataa gatctgtgaa gacagggaca gggacaatac ccatctctgt | 420 |
| ctggttcata ggtggtatgt aatagatatt tttaaaaata agtgagttaa tgaatgaggg | 480 |
| tgagaatgaa ggcacagagg tattagggg aggtgggccc cagagaatgg tgccaaggtc | 540 |

```
cagtggggtg actgggatca gctcaggcct gacgctggcc actcccacct agctcctttc    600
tttctaatct gttctcattc tccttgggaa ggattgaggt ctctggaaaa cagccaaaca    660
actgttatgg gaacagcaag cccaaataaa gccaagcatc aggggggatct gagagctgaa   720 agcaacttct gttcccctc cctcagctga aggggtgggg aagggctccc aaagccataa    780
ctccttttaa gggatttaga aggcataaaa aggcccctgg ctgagaactt ccttcttcat    840
tctgcagtga tccggtatat tgctgttgac agtgagcgac tgggattcct gtagacacaa    900
ctgtgaagca gatgggttgt gtctacagga atcccagacg cctactgcct cggacttcaa    960
gctagcggta ccggtatatt gctgttgaca gtgagcgagg agcatctcat ctgttacaac   1020
tgtgaagcag atgggttgta acagatgaga tgctccacgc ctactgcctc ggacttcaaa   1080
agctt                                                              1085
```

<210> SEQ ID NO 141
<211> LENGTH: 421
<212> TYPE: DNA
<213> ORGANISM: Artificial Sequence
<220> FEATURE:
<223> OTHER INFORMATION: FLT-miR-7-miR-V-7 - DNA construct

<400> SEQUENCE: 141

```
cctaagggcg ctcccgggcc cgcgtcgcca gcacctcccc acgcgcgctc ggccccgggc     60
cacccgccct cgtcggcccc cgcccctctc cgtagccgca gggaagcgag cctgggagga    120
agaagagggt aggtggggag gcggatgagg ggtgggggac cccttgacgt caccagaagg    180
aggtgccggg gtaggaagtg ggctggggaa aggttataaa tcgcccccgc cctcggctgc    240
tcttcatcga ggtccgcggg aggctcggag cgcgccaggc ggacactcct ggatccggta    300
tattgctgtt gacagtgagc gactgggatt cctgtagaca caactgtgaa gcagatgggt    360
tgtgtctaca ggaatcccag acgcctactg cctcggactt caagctagcg gtaccaagct    420
t                                                                   421
```

<210> SEQ ID NO 142
<211> LENGTH: 690
<212> TYPE: DNA
<213> ORGANISM: Artificial Sequence
<220> FEATURE:
<223> OTHER INFORMATION: U6-miR-V-7-miR-C-8-miR-P9 - DNA construct

<400> SEQUENCE: 142

```
cctaaggccc agtggaaaga cgcgcaggca aaacgcacca cgtgacggag cgtgaccgcg     60
cgccgagcgc gcgccaaggt cgggcaggaa gagggcctat ttcccatgat tccttcatat    120
ttgcatatac gatacaaggc tgttagagag ataattagaa ttaatttgac tgtaaacaca    180
aagatattag tacaaaatac gtgacgtaga aagtaataat ttcttgggta gtttgcagtt    240
ttaaaattat gttttaaaat ggactatcat atgcttaccg taacttgaaa gtatttcgat    300 ttcttggggtt tatatatctt gtggaaagga cgcgggatcc ggtatattgc tgttgacagt    360
gagcgaggag catctcatct gttacaactg tgaagcagat gggttgtaac agatgagatg    420
ctccacgcct actgcctcgg acttcaagct agcggtatat tgctgttgac agtgagcgaa    480
ggatatcaaa gctctgttta ctgtgaagca gatgggtaaa cagagctttg atatcctgcg    540
cctactgcct cggacttcaa ggtaccggta tattgctgtt gacagtgagc gacagttcta    600
caatgccatc aaactgtgaa gcagatgggt tgatggcat gtagaactg ccgcctactg    660 cctcggactt caacaattgt ttttaagctt                                     690
```

<210> SEQ ID NO 143
<211> LENGTH: 824
<212> TYPE: DNA
<213> ORGANISM: Artificial Sequence
<220> FEATURE:
<223> OTHER INFORMATION: VDM2-miR-V-7-miR-C-8-miR-P-9 - DNA construct

<400> SEQUENCE: 143

```
cctaaggcat tctttccata gcccacaggg ctgtcaaaga ccccagggcc tagtcagagg      60
ctcctccttc ctggagagtt cctggcacag aagttgaagc tcagcacagc cccctaaccc     120
ccaactctct ctgcaaggcc tcaggggtca gaacactggt ggagcagatc ctttagcctc     180
tggattttag ggccatggta gaggggtgt  tgccctaaat tccagccctg gtctcagccc     240
aacaccctcc aagaagaaat tagaggggcc atggccaggc tgtgctagcc gttgcttctg     300
agcagattac aagaagggac taagacaagg actcctttgt ggaggtcctg gcttagggag     360
tcaagtgacg gcggctcagc actcacgtgg gcagtgccag cctctaagag tgggcagggg     420
cactggccac agagtcccag ggagtcccac cagcctagtc gccagaccgg atccggtata     480
ttgctgttga cagtgagcga ggagcatctc atctgttaca actgtgaagc agatgggttg     540
taacagatga gatgctccac gcctactgcc tcggacttca agctagcggt atattgctgt     600
tgacagtgag cgaaggatat caaagctctg tttactgtga agcagatggg taaacagagc     660
tttgatatcc tgcgcctact gcctcggact tcaaggtacc ggtatattgc tgttgacagt     720
gagcgacagt tctacaatgc catcaaactg tgaagcagat gggtttgatg gcattgtaga     780
actgccgcct actgcctcgg acttcaacaa ttgtttttaa gctt                      824
```

<210> SEQ ID NO 144
<211> LENGTH: 697
<212> TYPE: DNA
<213> ORGANISM: Artificial Sequence
<220> FEATURE:
<223> OTHER INFORMATION: ICAM2-miR-V-7-miR-C-8-miR-P-9 - DNA construct

<400> SEQUENCE: 144

```
cctaaggatg ggatttgggg ttccccagat ctggggcttg taggcctgac tctccctgt      60
gcacacgtct catacacgca tgcgtgcacc cattgcctgc cccgcccctt gcacagggag    120
tcagcaggga ggactgggtt atgccctgct tatcagcagc ttcccagctt cctctgcctg    180
gattcttaga ggcctggggt cctagaacga gctggtgcac gtggcttccc aaagatctct    240
cagataatga gaggaaatgc agtcatcagt ttgcagaagg ctagggattc tgggccatag    300
ctcagacctg cgcccaccat ctccctccag gcagcccttg gggatccggt atattgctgt    360
tgacagtgag cgaggagcat ctcatctgtt acaactgtga agcagatggg ttgtaacaga    420
tgagatgctc cacgcctact gcctcggact tcaagctagc ggtatattgc tgttgacagt    480
gagcgaagga tatcaaagct ctgtttactg tgaagcagat gggtaaacag agctttgata    540
tcctgcgcct actgcctcgg acttcaaggt accggtatat tgctgttgac agtgagcgac    600
agttctacaa tgccatcaaa ctgtgaagca gatgggtttg atggcattgt agaactgccg    660
cctactgcct cggacttcaa caattgtttt taagctt                             697
```

<210> SEQ ID NO 145
<211> LENGTH: 1204
<212> TYPE: DNA
<213> ORGANISM: Artificial Sequence
<220> FEATURE:

<223> OTHER INFORMATION: RPE65-miR-V-7-miR-C-8-miR-P-9 - DNA construct

<400> SEQUENCE: 145

```
cctaaggttc caaggacttc tttgggcagt accttgtctg tgctggcaag caactgagac      60
ttaatgaaag agtattggag atatgaatga attgatgctg tatactctca gagtgccaaa     120
catataccaa tggacaagaa ggtgaggcag agagcagaca ggcattagtg acaagcaaag     180
atatgcagaa tttcattctc agcaaatcaa aagtcctcaa cctggttgga agaatattgg     240
cactgaatgg tatcaataag gttgctagag agggttagag gtgcacaatg tgcttccata     300
acattttata cttctccaat cttagcacta atcaaacatg gttgaatact ttgtttacta     360
taactcttac agagttataa gatctgtgaa gacagggaca gggacaatac ccatctctgt     420
ctggttcata ggtggtatgt aatagatatt tttaaaaata agtgagttaa tgaatgaggg     480
tgagaatgaa ggcacagagg tattaggggg aggtgggccc cagagaatgg tgccaaggtc     540
cagtggggtg actgggatca gctcaggcct gacgctggcc actcccacct agctcctttc     600
tttctaatct gttctcattc tccttgggaa ggattgaggt ctctgaaaaa cagccaaaca     660
actgttatgg gaacagcaag cccaaataaa gccaagcatc aggggatct gagagctgaa     720
agcaacttct gttcccctc cctcagctga aggggtgggg aagggctccc aaagccataa     780
ctccttttaa gggatttaga aggcataaaa aggcccctgg ctgagaactt ccttcttcat     840
tctgcagtgg atccggtata ttgctgttga cagtgagcga ggagcatctc atctgttaca     900
actgtgaagc agatgggttg taacagatga gatgctccac gcctactgcc tcggacttca     960
agctagcggt atattgctgt tgacagtgag cgaaggatat caaagctctg tttactgtga    1020
agcagatggg taaacagagc tttgatatcc tgcgcctact gcctcggact tcaaggtacc    1080
ggtatattgc tgttgacagt gagcgacagt tctacaatgc catcaaactg tgaagcagat    1140
gggtttgatg gcattgtaga actgccgcct actgcctcgg acttcaacaa ttgttttttaa    1200
gctt                                                                 1204
```

<210> SEQ ID NO 146
<211> LENGTH: 646
<212> TYPE: DNA
<213> ORGANISM: Artificial Sequence
<220> FEATURE:
<223> OTHER INFORMATION: FLT-miR-V-7-miR-C-8-miR-P-9 - DNA construct

<400> SEQUENCE: 146

```
cctaagggcg ctcccgggcc cgcgtcgcca gcacctcccc acgcgcgctc ggccccgggc      60
caccgccct cgtcggcccc cgcccctctc cgtagccgca gggaagcgag cctgggagga     120
agaagagggt aggtggggag gcggatgagg ggtgggggac cccttgacgt caccagaagg     180
aggtgccggg gtaggaagtg ggctggggaa aggttataaa tcgccccgc cctcggctgc     240
tcttcatcga ggtccgcggg aggctcggag gcgccaggc ggacactcct ggatccggta     300
tattgctgtt gacagtgagc gaggagcatc tcatctgtta caactgtgaa gcagatgggt     360
tgtaacagat gagatgctcc acgcctactg cctcggactt caagctagcg gtatattgct     420
gttgacagtg agcgaaggat atcaaagctc tgtttactgt gaagcagatg ggtaaacaga     480
gctttgatat cctgcgccta ctgcctcgga cttcaaggta ccggtatatt gctgttgaca     540
gtgagcgaca gttctacaat gccatcaaac tgtgaagcag atgggtttga tggcattgta     600
gaactgccgc ctactgcctc ggacttcaac aattgttttt aagctt                    646
```

```
<210> SEQ ID NO 147
<211> LENGTH: 121
<212> TYPE: RNA
<213> ORGANISM: Artificial Sequence
<220> FEATURE:
<223> OTHER INFORMATION: miR-8 structure

<400> SEQUENCE: 147
gguauauugc uguugacagu gagcgauaga cacacccacc cacauaacug ugaagcagau      60
ggguuaugug gguggugug ucuaccgccu acugccucgg acuucaagcu agcgguaccu     120
u                                                                    121

<210> SEQ ID NO 148
<211> LENGTH: 52
<212> TYPE: DNA
<213> ORGANISM: Artificial Sequence
<220> FEATURE:
<223> OTHER INFORMATION: Chemically synthesized

<400> SEQUENCE: 148
ggtatattgc tgttgacagt gagcgaggta tattgctggg gacagtgagc cc             52

<210> SEQ ID NO 149
<211> LENGTH: 61
<212> TYPE: DNA
<213> ORGANISM: Artificial Sequence
<220> FEATURE:
<223> OTHER INFORMATION: Chemically synthesized

<400> SEQUENCE: 149
ggtatattgc tgttgacagt gagcgaattg ccatgggtat attgctgggg acagtgagcc     60
c                                                                    61

<210> SEQ ID NO 150
<211> LENGTH: 52
<212> TYPE: DNA
<213> ORGANISM: Artificial Sequence
<220> FEATURE:
<223> OTHER INFORMATION: ME sequence

<400> SEQUENCE: 150
ggtatattgc tgttgacagt gagcgaggta tattgctggg gacagtgagc cc             52
```